United States Patent
Burstein

(10) Patent No.: US 11,718,664 B2
(45) Date of Patent: *Aug. 8, 2023

(54) METHODS FOR REDUCING MIGRAINE FREQUENCY IN A SUBJECT IN NEED THEREOF

(71) Applicant: Beth Israel Deaconess Medical Center, Inc., Boston, MA (US)

(72) Inventor: Rami Burstein, Chesnut Hill, MA (US)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 311 days.

This patent is subject to a terminal disclaimer.

(21) Appl. No.: 16/996,581

(22) Filed: Aug. 18, 2020

(65) Prior Publication Data

US 2020/0385449 A1    Dec. 10, 2020

Related U.S. Application Data

(63) Continuation of application No. 15/909,895, filed on Mar. 1, 2018, now Pat. No. 10,766,952.

(60) Provisional application No. 62/516,406, filed on Jun. 7, 2017, provisional application No. 62/514,346, filed on Jun. 2, 2017, provisional application No. 62/490,953, filed on Apr. 27, 2017, provisional application No. 62/466,158, filed on Mar. 2, 2017.

(51) Int. Cl.
| | | |
|---|---|---|
| *A61K 39/395* | (2006.01) | |
| *C07K 16/18* | (2006.01) | |
| *C07K 16/28* | (2006.01) | |
| *A61P 25/06* | (2006.01) | |
| *A61K 9/00* | (2006.01) | |
| *A61P 43/00* | (2006.01) | |
| *A61P 29/00* | (2006.01) | |
| *A61K 39/00* | (2006.01) | |

(52) U.S. Cl.
CPC ............ *C07K 16/18* (2013.01); *A61K 9/0019* (2013.01); *A61K 39/3955* (2013.01); *A61P 25/06* (2018.01); *A61P 29/00* (2018.01); *A61P 43/00* (2018.01); *A61K 2039/505* (2013.01); *A61K 2039/54* (2013.01); *A61K 2039/545* (2013.01); *C07K 2317/24* (2013.01); *C07K 2317/51* (2013.01); *C07K 2317/515* (2013.01); *C07K 2317/55* (2013.01); *C07K 2317/56* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 8,586,045 B2 | 11/2013 | Zeller et al. |
| 9,102,731 B2 | 8/2015 | Boone et al. |
| 10,766,952 B2 | 9/2020 | Burstein |
| 2011/0305711 A1 | 12/2011 | Allan et al. |
| 2012/0294797 A1 | 11/2012 | Kovacevich et al. |
| 2015/0307607 A1 | 10/2015 | Poulsen et al. |
| 2016/0311913 A1 | 10/2016 | Sun et al. |
| 2016/0347810 A1 | 12/2016 | Xie et al. |
| 2019/0135927 A1 | 5/2019 | Levin |
| 2021/0309725 A1 | 10/2021 | Cady et al. |

FOREIGN PATENT DOCUMENTS

| | | |
|---|---|---|
| CN | 102946905 A | 2/2013 |
| CN | 103421114 A | 12/2013 |
| CN | 103596593 A | 2/2014 |
| CN | 103702685 A | 4/2014 |
| CN | 104292332 A | 1/2015 |
| CN | 106456759 A | 2/2017 |
| CN | 107206057 A | 9/2017 |
| EP | 2987451 A1 | 2/2016 |
| WO | WO-2016/171742 A1 | 10/2016 |

OTHER PUBLICATIONS

Ashkenazi et el., "Identifying cutaneous allodynia in chronic migraine using a practical clinical method," Cephalalgia, 27(2): 111-117 (2007).
Walter et al., "TEV-48125: a Review of a Monoclonal CGRP Antibody in Development for the Preventative Treatment of Migraine," Curr Pain Headache Rep., 19:6 (2015).
International Search Report for Russian Application No. 2019130867, dated Jul. 2021 (3 pages).
Office Action for Russian Application No. 2019130867, dated Jul. 2021 (9 pages).
Negro et al., "A two years open-label prospective study of OnabotulinumtoxinA 195 U in medication overuse headahce: a real-world experience," J Headache Pain. 17:1 (2016) (9 pages).
Communication pursuant to Article 94(3) EPC for European Patent Application No. 18710741.2 dated Mar. 1, 2022 (6 pages).
Bigal et al., "Safety, tolerability, and efficacy of TEV-48125 for preventive treatment of chronic migraine: a multicentre, randomised, double-blind, placebo-controlled, phase 2b study," Lancet Neurol. 14(11):1091-1100 (2015).
Bigal et al., "Therapeutic antibodies against CGRP or its receptor," Br J Clin Pharmacol. 79(6):886-895 (2015).
Bree et al., "Development of CGRP-dependent pain and headache related behaviours in a rat model of concussion: Implications for mecahnisms of post-traumatic headache," available in PMC Apr. 9, 2019, published in final edited form as: Cephalalgia. 38(2):246-258 (2018) (24 pages).

(Continued)

*Primary Examiner* — Christine J Saoud
*Assistant Examiner* — Jon M Lockard
(74) *Attorney, Agent, or Firm* — Clark & Elbing LLP

(57) ABSTRACT

The present invention relates to methods for selecting a headache patient responsive to treatment with an anti-CGRP antibody and to methods for reducing headache frequency in the selected patient comprising administering an anti-CGRP antibody.

20 Claims, 53 Drawing Sheets

Specification includes a Sequence Listing.

(56) References Cited

OTHER PUBLICATIONS

Dodick et al., "Safety and efficacy of ALD403, an antibody to calcitonin gene-related peptide, for the prevention of frequent episodic migraine: a randomised, double-blind, placebo-controlled, exploratory phase 2 trial," Lancet Neurol. 13(11):1100-1107 (2014).
Goldberg et al., "Targeting CGRP: A New Era for Migraine Treatment," CNS Drugs. 29(6):443-452 (2015).
International Preliminary Report on Patentability for International Application No. PCT/US2018/020536, dated Sep. 3, 2019 (10 pages).
International Search Report and Written Opinion for International Application No. PCT/US2018/020536, dated Jun. 18, 2018 (14 pages).
Melo-Carrillo et al., "Fremanezumab—A Humanized Monoclonal Anti-CGRP Antibody—Inhibits Thinly Myelinated (A-delta) But Not Unmyelinated (C) Meningeal Nociceptors," J Neurosci. 37(44):10587-10596 (2017).
Melo-Carrillo et al., "Selective Inhibition of Trigeminovascular Neurons by Fremanezumab: A Humanized Monoclonal Anti-CGRP Antibody," J Neurosci. 37(30):7149-7163 (2017).
Bigal et al., "Safety, tolerability, and efficacy of TEV-48125 for preventive treatment of high-frequency episodic migraine: a multicentre, randomised, double-blind, placebo-controlled, phase 2b study," Lancet Neurol. 14(11):1081-90 (2015).
Notice of Reasons for Rejection and English Translation for Japanese Patent Application No. 2019-547512, dated Feb. 16, 2022 (10 pages).
Edvinsson et al., "CGRP Receptor Antagonism and Migraine," Neurotherapeutics. 7(2):164-75 (2010) (12 pages).
Office Action for Chinese Patent Application No. 201880029375.7 dated Feb. 16, 2023 (8 pages).
Lian et al., "Nitric oxide and calcitonin gene-related peptide contents in human-being during migraine attached, and the possible pathogenetic investigation," Chin J. Neurol. 32(2):94-95 (1999) (2 pages) (with English Abstract).
Wang, "The underlying mechanism of the role of acupuncture for alleviating migraine of the rat through CGRP in the trigeminal pathway," China Academy of Chinese Medical Services, Doctoral Dissertation (2019) (144 pages) (with English Abstract).

| Fab | $K_D(nM)$ 1-37 (WT) | $K_D(nM)$ 19-37[a] | $K_D(nM)$ 25-37[a] | F27A | V28A | P29A | T30A | N31A | V32A | G33A | S34A | K35A | F37A |
|---|---|---|---|---|---|---|---|---|---|---|---|---|---|
| 7EP | 1.0 | 1.1±0.8 | 0.14±0.05 | 1.0 | 1.0 | 26 | 7 | 9 | 41 | 1256 | 6.9 | 4 | 3508 |
| 8B6 | 1.1 | 1.5±1.2 | 0.45±0.08 | 1.0 | 1.0 | 9 | 2.2 | 3 | 5 | 496 | 2.6 | 3 | 2527 |
| 10A8 | 2.1 | 2.4±1.4 | 1.0±0.2 | 1.0 | 1.0 | 9 | 4 | 4 | 11 | 36 | 82 | 13 | 2152 |
| 7D11 | 4.4 | 10±7 | 3.4±0.4 | 1.1 | 1.0 | 7 | 4 | 5 | 5 | 86 | 18 | 1.4 | 420 |
| 6H2 | 9.3 | 7.8±0.2 | 8.5±0.5 | 0.9 | 0.8 | 1.0 | 0.8 | 4 | 11 | 14 | 0.5 | 1.0 | |
| 4901 | 60.5 | 52±12 | 296±115 | 0.8 | 0.8 | 0.2 | 0.2 | 0.3 | 0.9 | 1.3 | 0.8 | 0.3 | |
| 14E10 | 79.7 | 91±3 | 117.4±0.7 | 0.8 | 0.7 | 11 | 3 | 18 | 2 | 1 | 3 | 0.4[b] | |
| 9B8 | 84.7 | 76±20 | 96±28 | 0.8 | 0.7 | 0.6 | 0.6 | 0.7 | 0.6 | 1.3 | 4 | 0.4[b] | |
| 13C2 | 94.4 | 86±13 | 137±5 | 0.7 | 0.7 | 0.5 | 0.4 | 0.6 | 0.2 | 0.9 | 1.1 | 0.4[b] | |
| 14A9 | 148.4 | 219±114 | 246±20 | 0.8 | 0.7 | 0.7 | 0.5 | 0.8 | 0.7 | 1.6 | 1.3 | 0.4[b] | |
| 6D5 | 209.9 | 207±26 | 378±22 | 0.8 | 0.7 | 0.5 | 0.4 | 0.6 | 0.5 | 3 | 1.1 | 6 | |
| 1C5 | 296.4 | 223±51 | 430±173 | 0.8 | 0.8 | 0.6 | 0.4 | 0.6 | 0.6 | 1.1 | 1.1 | 5 | |

$K_D$(mutant/parent)

FIG. 1

Bold = Kabat CDR
Underline = Chothia CDR

G1 Heavy chain (SEQ ID NO: 1)

```
  1               5              10              15              20              25          H1  30
  E   V   Q   L   V   E   S   G   G   G   L   V   Q   P   G   G   S   L   R   L   S   C   A   A   S   G   F   T   F   S
 31                              35                              40                              45              H2  50                              55                              60
  N   Y   W   I   S   W   V   R   Q   A   P   G   K   G   L   E   W   V   A   E   I   R   S   E   S   D   A   S   A   T
 61                              65                              70                              75                              80                              85                              90
  H   Y   A   E   A   V   K   G   R   F   T   I   S   R   D   N   A   K   N   S   L   Y   L   Q   M   N   S   L   R   A
 91                              95                             100                             105      H3                 110                             115                             120
  E   D   T   A   V   Y   Y   C   L   A   Y   F   D   Y   G   L   A   I   Q   N   Y   W   G   Q   G   T   L   V   T   V
121 122
  S   S
```

G1 Light chain (SEQ ID: 2)

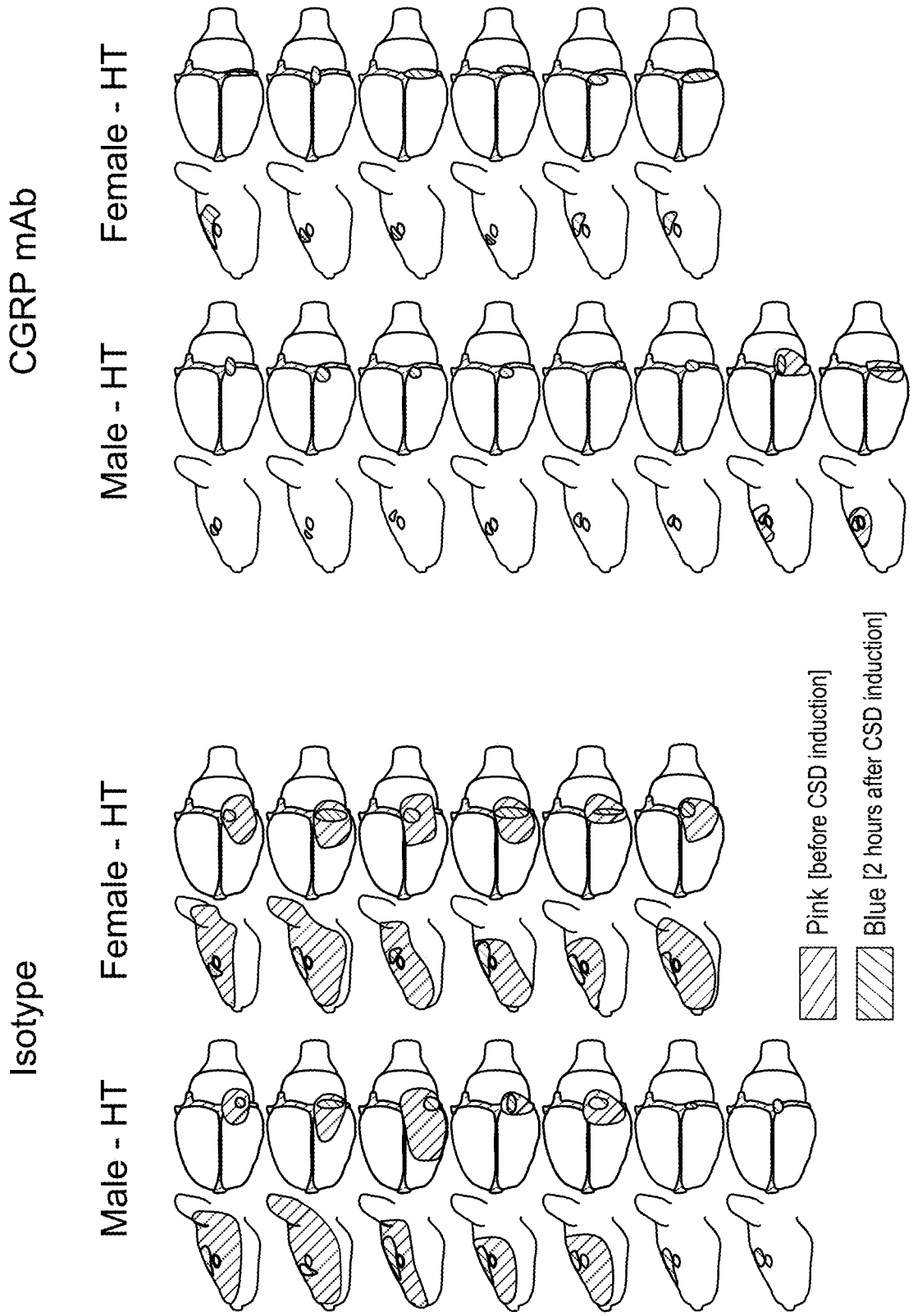

|  | Naive state | | | | Post-CSD state | | | |
|---|---|---|---|---|---|---|---|---|
|  | Male | | Female | | Male | | Female | |
| Spontaneous Activity | HT | WDR | HT | WDR | HT | WDR | HT | WDR |
| CGRP-mAb | Inhibition | No inhibition | No inhibition | No inhibition | Prevention | No prevention | Prevention | No prevention |
| Isotype | No inhibition | No inhibition | No inhibition | No inhibition | Activation/sensitization | Partial activation | Activation/sensitization | Partial activation |
| Von Frey Hair | HT | WDR | HT | WDR | HT | WDR | HT | WDR |
| CGRP-mAb | Inhibition | No inhibition | Inhibition | No inhibition | Prevention | No sensitization | Prevention | No sensitization |
| Isotype | No inhibition | No inhibition | No inhibition | No inhibition | Sensitization | No sensitization | Sensitization | No sensitization |
| Brush | HT | WDR | HT | WDR | HT | WDR | HT | WDR |
| CGRP-mAb | No inhibition | No inhibition | No inhibition | No inhibition | Prevention | No sensitization | Prevention | No sensitization |
| Isotype | No inhibition | No inhibition | No inhibition | No inhibition | Sensitization | No sensitization | Sensitization | No sensitization |
| Pressure | HT | WDR | HT | WDR | HT | WDR | HT | WDR |
| CGRP-mAb | No inhibition | No inhibition | No inhibition | No inhibition | Prevention | No sensitization | Prevention | No sensitization |
| Isotype | No inhibition | No inhibition | No inhibition | No inhibition | Sensitization | No sensitization | Sensitization | No sensitization |
| Pinch | HT | WDR | HT | WDR | HT | WDR | HT | WDR |
| CGRP-mAb | No inhibition | No inhibition | No inhibition | No inhibition | No sensitization | No sensitization | Prevention | No sensitization |
| Isotype | No inhibition | No inhibition | No inhibition | No inhibition | No sensitization | No sensitization | Sensitization | No sensitization |
| Cornea | HT | WDR | HT | WDR | HT | WDR | HT | WDR |
| CGRP-mAb | No inhibition | No inhibition | No inhibition | No inhibition | No sensitization | No sensitization | Prevention | No sensitization |
| Isotype | No inhibition | No inhibition | No inhibition | No inhibition | No sensitization | No sensitization | Sensitization | No sensitization |

FIG. 17

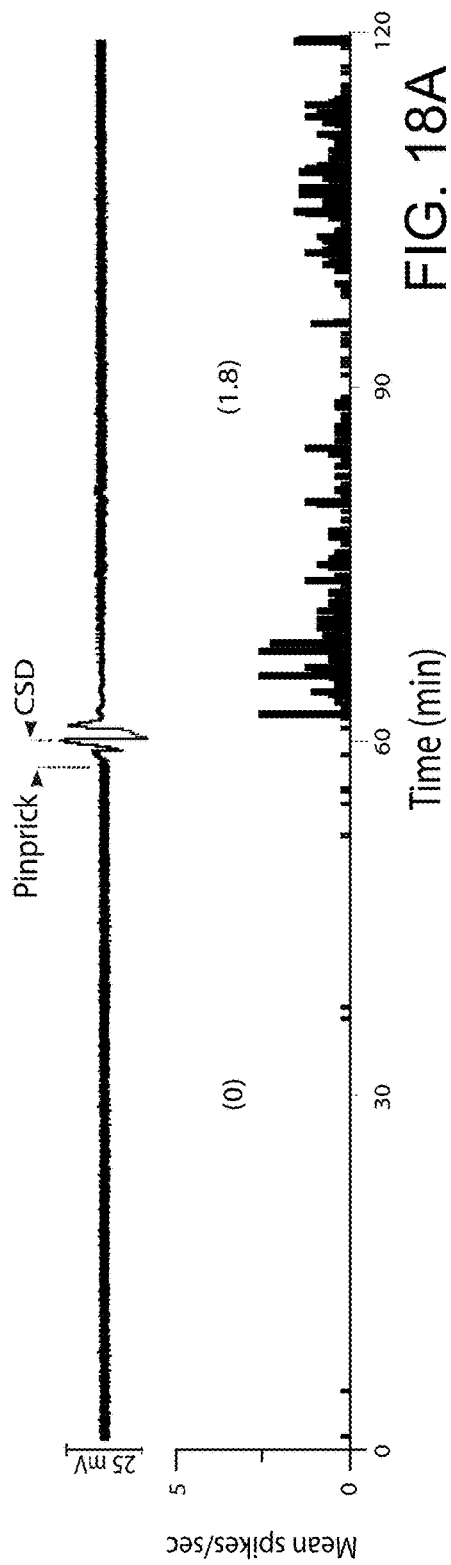
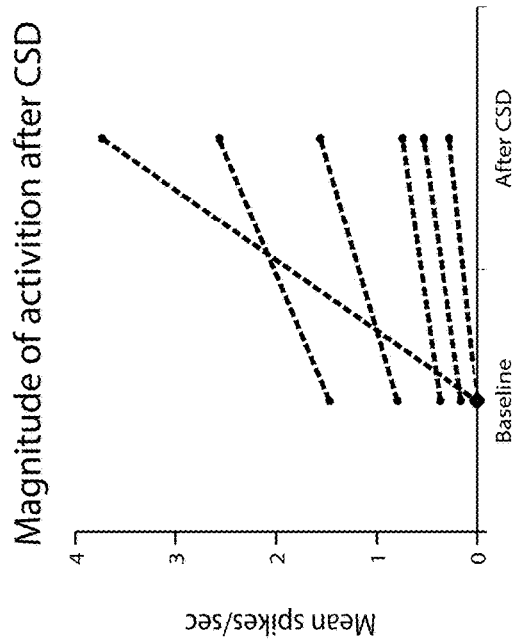
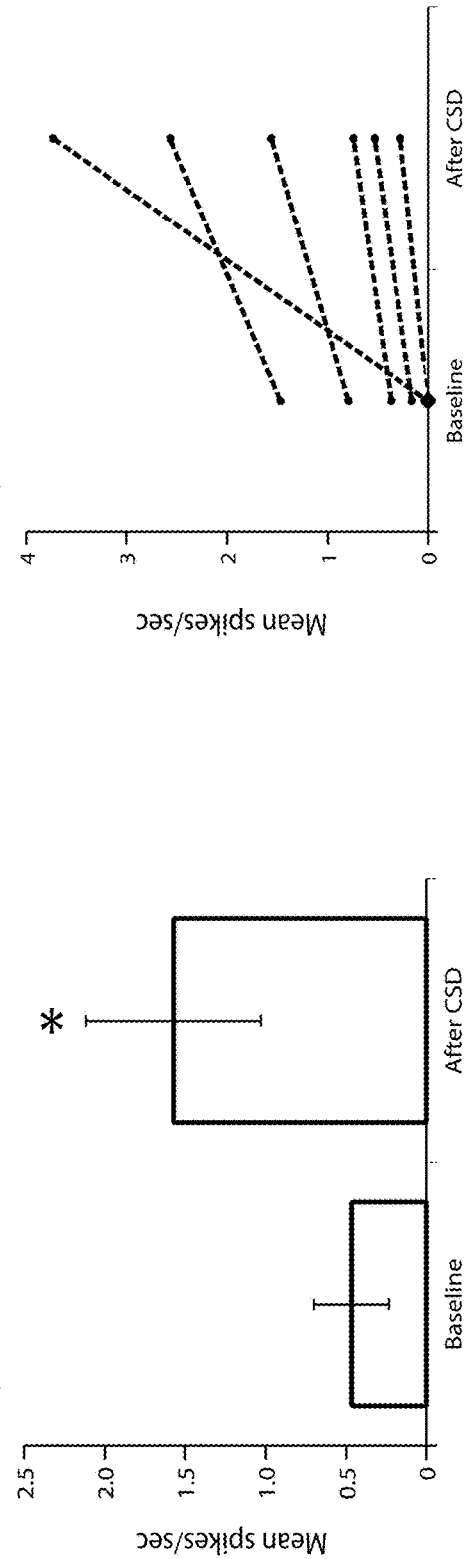
FIG. 18A
FIG. 18B
FIG. 18C

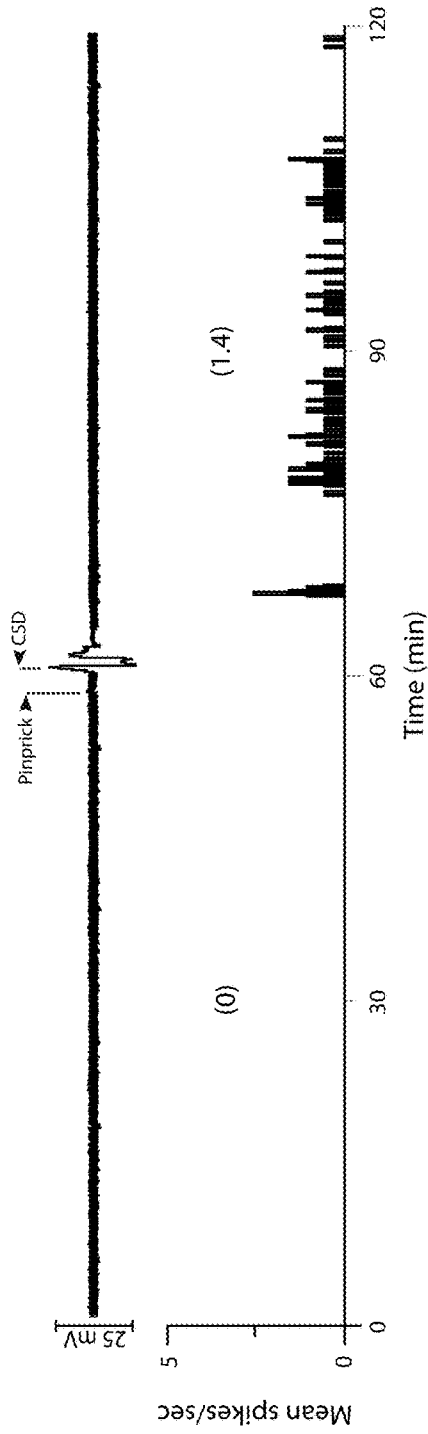
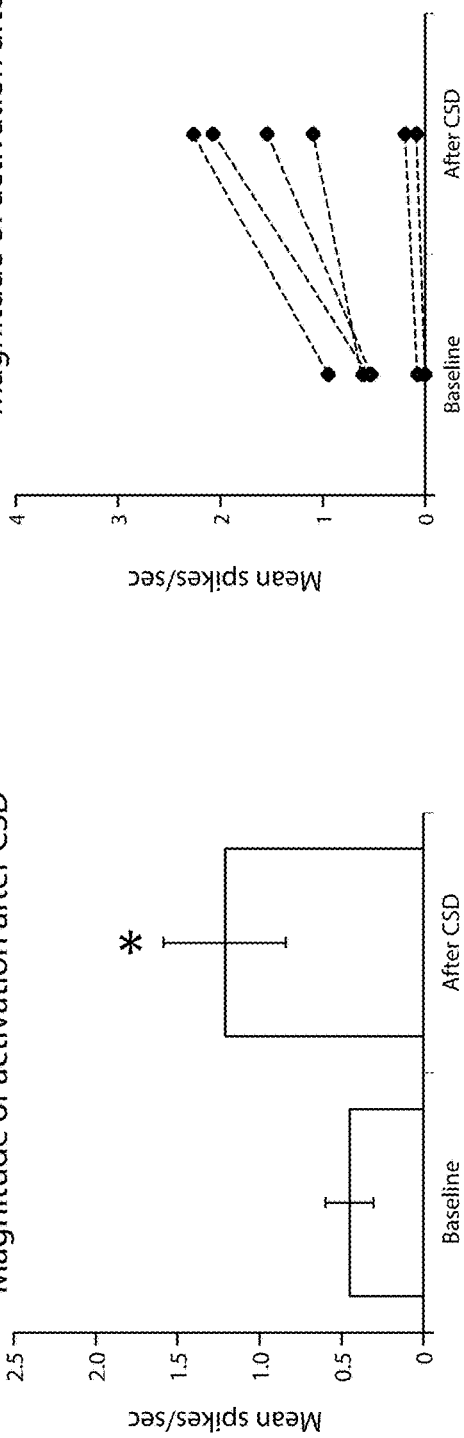
FIG. 19A
FIG. 19B
FIG. 19C

| A delta fibers | | | |
|---|---|---|---|
| | Activated by CSD | Not activated | Percentage |
| Isotype | 6 | 5 | 54% |
| CGRP-mAb | 1 | 6 | 14% |
| Z test p = .001 | | | |

FIG. 21A

| C fibers | | | |
|---|---|---|---|
| | Activated by CSD | Not activated | Percentage |
| Isotype | 6 | 13 | 31% |
| CGRP-mAb | 3 | 10 | 23% |
| Z test p > 0.05 | | | |

FIG. 21B

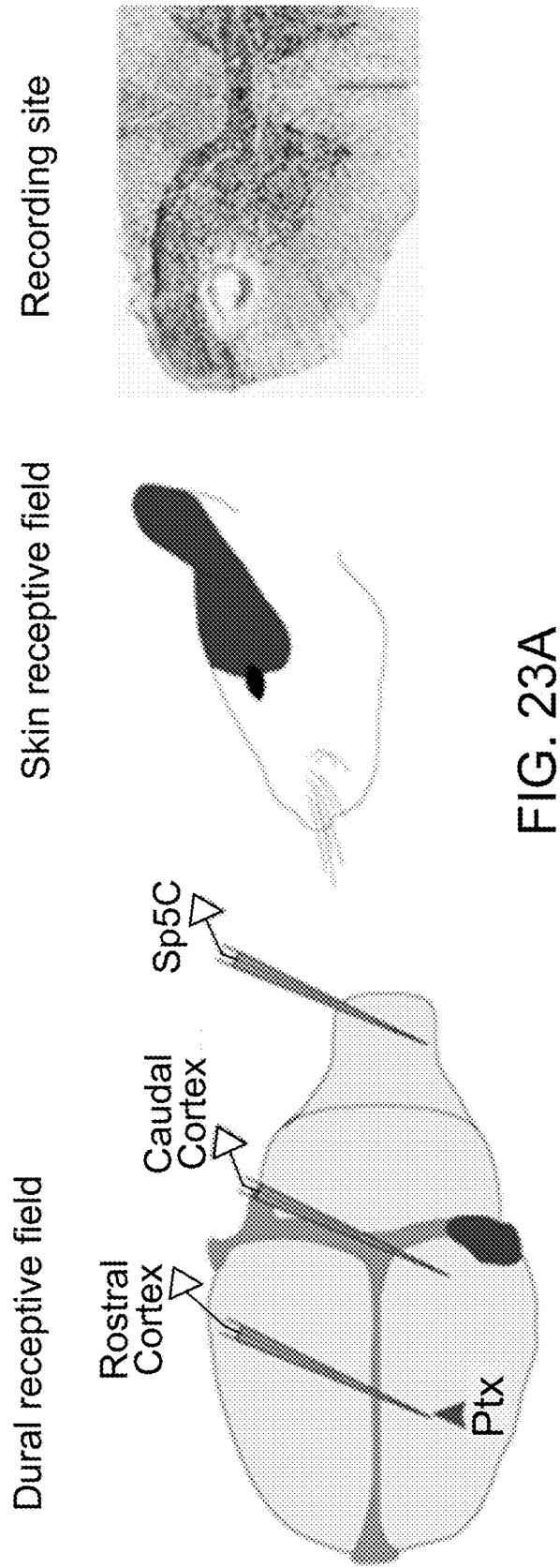
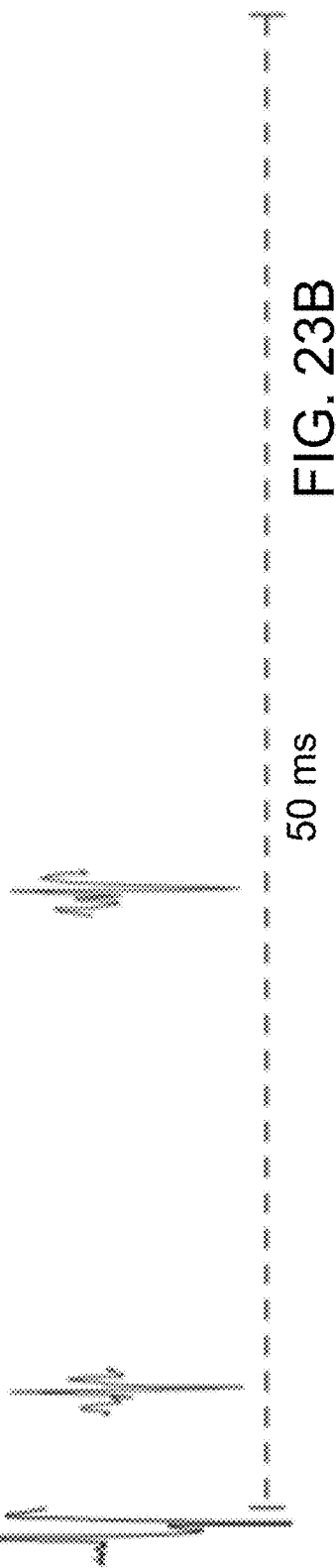
FIG. 23A
FIG. 23B

Mechanical stimulation on Dura

Mechanical stimulation on Skin

METHODS FOR REDUCING MIGRAINE FREQUENCY IN A SUBJECT IN NEED THEREOF

SEQUENCE LISTING

The instant application contains a Sequence Listing which has been submitted electronically in ASCII format and is hereby incorporated by reference in its entirety. The ASCII copy, created on Aug. 18, 2020, is named 01948-265007_Sequence_Listing_8.18.20_ST25 and is 77,274 bytes in size.

BACKGROUND

Humanized anti-calcitonin gene-related peptide (CGRP) monoclonal antibodies have been found to be effective in reducing the frequency of chronic migraine (Dodick D W et al. (2014) *Lancet Neurol.* 13:1100-1107; Dodick D W et al. (2014) *Lancet Neurol.* 13:885-892; Bigal M E et al. (2015) *Lancet Neurol.* 14:1081-1090; Bigal M E et al. (2015) *Lancet Neurol.* 14:1091-1100; and Sun H et al. (2016) *Lancet Neurol.* 15:382-390). However, while anti-CGRP antibodies have been found effective in treating certain headaches, patients can respond in varying ways. For example, an anti-CGRP antibody can be totally effective, partially effective, or not effective at all in treating the headache or preventing the occurrence of a headache. It could benefit patient care, conserve physician time, and prevent unnecessary use of a particular course of treatment if it could be determined prior to treatment with an anti-CGRP antibody whether use of that antibody will be effective to treat a headache and/or to prevent development of a headache.

Therefore methods for determining whether treatment comprising an anti-CGRP antibody will be effective in the treatment of a patient who has headache or who is susceptible to headache are needed.

SUMMARY

The present invention relates to methods for selecting a headache patient responsive to treatment with an anti-CGRP antibody and to methods for reducing headache frequency in the selected patient with an anti-CGRP antibody.

In an aspect, provided herein is a method for reducing headache frequency in a patient, comprising: a) selecting a patient whose headache is mediated by activation and sensitization of high-threshold (HT) neurons; and b) administering to the patient a monoclonal antibody that modulates (e.g., blocks, inhibits, suppresses or reduces) the CGRP pathway in an amount sufficient to reduce headache frequency in the patient.

In another aspect, provided herein is a method for reducing headache frequency in a patient, comprising: a) selecting a patient who exhibits hyperalgesia reducible by administering a first monoclonal antibody that modulates (e.g., blocks, inhibits, suppresses or reduces) the CGRP pathway; and b) administering to the patient a second monoclonal antibody that modulates the CGRP pathway in an amount sufficient to reduce headache frequency in the patient.

In yet another aspect, provided herein is a method for reducing headache frequency in a patient, comprising: a) selecting a patient whose headaches are primarily experienced in a portion of the head (e.g., one-side periorbital, one-side temporal, or one eye); and b) administering to the patient a monoclonal antibody that modulates (e.g., blocks, inhibits, suppresses or reduces) the CGRP pathway in an amount sufficient to reduce headache frequency in the patient.

In another aspect, provided herein is a method for reducing headache frequency in a patient, comprising: a) selecting a patient who exhibits elimination of hyperalgesia and allodynia by administering a first monoclonal antibody that blocks, inhibits, suppresses, or reduces the CGRP pathway; and b) administering to the patient a second monoclonal antibody that blocks, inhibits, suppresses, or reduces the CGRP pathway in an amount sufficient to reduce headache frequency in the patient.

In an embodiment of any of the methods provided herein, the patient is a migraine patient.

In a further embodiment of any of the methods provided herein, the patient is a chronic or episodic migraine patient.

In an embodiment of any of the methods provided herein, the patient has meningitis, an epidural bleed, a subdural bleed, a sub-arachnoid bleed, or a brain tumor.

In an embodiment of any of the methods provided herein, the headache is of intracranial origin.

In an embodiment of any of the methods provided herein, the headache is migraine. In another embodiment of any of the methods provided herein, the headache is migraine with aura.

In an embodiment of any of the methods provided herein, the headache is attributed to meningitis, an epidural bleed, a subdural bleed, a sub-arachnoid bleed, or a brain tumor.

In another embodiment of any of the methods provided herein, the monoclonal antibody is administered to the patient intravenously or subcutaneously.

In another embodiment, the methods provided herein further comprise administration one or more additional doses of the monoclonal antibody to the patient.

In another embodiment of any of the methods provided herein, the monoclonal antibody is an anti-CGRP antagonist antibody. In another embodiment of any of the methods provided herein, the monoclonal antibody is an anti-CGRP receptor antibody.

In an embodiment of any of the methods provided herein, the monoclonal antibody is human or humanized.

In an embodiment of any of the methods provided herein, the monoclonal antibody is an IgG1, IgG2, IgG3, or IgG4 antibody.

In an embodiment of any of the methods provided herein, the patient is a human.

In yet another embodiment, the monoclonal antibody is administered while the patient is migraine-free. In another embodiment, the monoclonal antibody is administered while the patient has a headache (e.g., a migraine).

In another embodiment, the monoclonal antibody of the methods provided herein are administered to the patient from or using a pre-filled syringe, pre-filled syringe with a needle safety device, injection pen, or auto-injector.

In embodiments of the methods provided herein, the monoclonal antibody comprises a CDR H1 as set forth in SEQ ID NO:3; a CDR H2 as set forth in SEQ ID NO:4; a CDR H3 as set forth in SEQ ID NO:5; a CDR L1 as set forth in SEQ ID NO:6; a CDR L2 as set forth in SEQ ID NO:7; and a CDR L3 as set forth in SEQ ID NO:8. In some embodiments, the monoclonal antibody comprises a heavy chain variable region comprising or consisting of the amino acid sequence as set forth in SEQ ID NO:1, and a light chain variable region comprising or consisting of the amino acid sequence as set forth in SEQ ID NO:2. In some embodiments, the monoclonal antibody comprises a heavy chain comprising or consisting of the amino acid sequence as set forth in SEQ ID NO:11, and a light chain comprising or consisting of the amino acid sequence as set forth in SEQ ID NO:12. In a particular embodiment, the monoclonal antibody is fremanezumab (also referred to herein as "G1").

In an embodiment, the monoclonal antibody is administered at a dose of from about 225 to about 900 mg, e.g., at a dose of about 225 mg, at a dose of about 675 mg, at a dose of about 900 mg. These doses may be administered to the patient monthly or quarterly. Further, any of these doses (e.g., about 225, about 675, or about 900 mg) may be administered intravenously or subcutaneously. In a particular embodiment, the dosing regimen comprises an initial dose (e.g., 675 mg), and further comprises administering to the patient an additional dose of about 225 mg of the monoclonal antibody once per month in each of the two months (or three months, four months, five months, six months, or twelve months) subsequent to the month in which the initial dose is administered to the patient.

In an embodiment, the monoclonal antibody is administered as a formulation comprising the antibody at a concentration of at least about 150 mg/mL. In another embodiment, the monoclonal antibody is administered in a volume of less than 2 mL (e.g., about 1.8 mL, about 1.7 mL, about 1.6 mL, about 1.5 mL, about 1.4 ml, about 1.3 mL, about 1.2 mL, about 1.1 mL, about 1.0 ml, about 0.9 mL, about 0.8 mL, about 0.7 mL, about 0.6 mL, about 0.5 mL, or less). In some embodiments, the monoclonal antibody is preferably administered in a volume of about 1.5 mL.

In an embodiment, the monoclonal antibody comprises a CDR H1 as set forth in SEQ ID NO:87; a CDR H2 as set forth in SEQ ID NO:88; a CDR H3 as set forth in SEQ ID NO:89; a CDR L1 as set forth in SEQ ID NO:84; a CDR L2 as set forth in SEQ ID NO:85; and a CDR L3 as set forth in SEQ ID NO:86. In some embodiments, the monoclonal antibody comprises a heavy chain variable region comprising or consisting of the amino acid sequence as set forth in SEQ ID NO:82, and a light chain variable region comprising or consisting of the amino acid sequence as set forth in SEQ ID NO:80. In some embodiments, the monoclonal antibody comprises a heavy chain comprising or consisting of the amino acid sequence as set forth in SEQ ID NO:83, and a light chain comprising or consisting of the amino acid sequence as set forth in SEQ ID NO:81.

In a further embodiment, the monoclonal antibody is eptinezumab. Eptinezumab may be administered at a dose of about 100 mg, about 300 mg, or about 1000 mg. Any of these doses (e.g., about 100 mg, about 300 mg, or about 1000 mg) may be administered intravenously or subcutaneously.

In another embodiment, the monoclonal antibody comprises a CDR H1 as set forth in SEQ ID NO:93; a CDR H2 as set forth in SEQ ID NO:94; a CDR H3 as set forth in SEQ ID NO:95; a CDR L1 as set forth in SEQ ID NO:91; a CDR L2 as set forth in SEQ ID NO:92; and a CDR L3 as set forth in SEQ ID NO:90. In some embodiments, the monoclonal antibody comprises a heavy chain variable region comprising or consisting of the amino acid sequence as set forth in SEQ ID NO:97, and a light chain variable region comprising or consisting of the amino acid sequence as set forth in SEQ ID NO:96. In some embodiments, the monoclonal antibody comprises a heavy chain comprising or consisting of the amino acid sequence as set forth in SEQ ID NO:99, and a light chain comprising or consisting of the amino acid sequence as set forth in SEQ ID NO:98.

In a further embodiment, the monoclonal antibody is galcanezumab. Galcanezumab may be administered at a dose of about 120 mg or about 240 mg. Further, the 120 mg dose may be administered in a volume of about 1.5 mL and the 240 mg dose may be administered in a volume of about 3 mL. Any of these doses (e.g., about 120 mg or 240 mg) may be administered intravenously or subcutaneously.

In another embodiment, the monoclonal antibody comprises a CDR H1 as set forth in SEQ ID NO:103; a CDR H2 as set forth in SEQ ID NO:104; a CDR H3 as set forth in SEQ ID NO:105; a CDR L1 as set forth in SEQ ID NO:100; a CDR L2 as set forth in SEQ ID NO:101; and a CDR L3 as set forth in SEQ ID NO:102. In some embodiments, the monoclonal antibody comprises a heavy chain variable region comprising or consisting of the amino acid sequence as set forth in SEQ ID NO:107, and a light chain variable region comprising or consisting of the amino acid sequence as set forth in SEQ ID NO:106. In some embodiments, the monoclonal antibody comprises a heavy chain comprising or consisting of the amino acid sequence as set forth in SEQ ID NO:109, and a light chain comprising or consisting of the amino acid sequence as set forth in SEQ ID NO:108.

In a further embodiment, the monoclonal antibody is erenumab. Erenumab may be administered at a dose of about 70 mg or about 140 mg. Further, the 70 mg does may be administered in a volume of about 1 mL. The 140 mg dose may be administered in a volume of about 2 mL. Any of these doses (e.g., about 70 or 140 mg) may be administered intravenously or subcutaneously.

In an aspect, provided herein is a use of a monoclonal antibody that modulates (e.g., blocks, inhibits, suppresses or reduces) the CGRP pathway, for the manufacture of a medicament for headache frequency reduction in a patient whose headache is mediated by the activation and sensitization of high-threshold (HT) neurons.

In an aspect, provided herein is a use of a monoclonal antibody that modulates (e.g., blocks, inhibits, suppresses or reduces) the CGRP pathway, for the manufacture of a medicament for headache frequency reduction in a patient who exhibits hyperalgesia reducible by administration of a monoclonal antibody that modulates (e.g., blocks, inhibits, suppresses or reduces) the CGRP pathway.

In an aspect, provided herein is a use of a monoclonal antibody that modulates (e.g., blocks, inhibits, suppresses or reduces) the CGRP pathway, for the manufacture of a medicament for headache frequency reduction in a patient whose headaches are primarily experienced in a portion of the head (e.g., one-side periorbital, one-side temporal, or one eye).

In an embodiment of any of the uses provided herein, the monoclonal antibody comprises a CDR H1 as set forth in SEQ ID NO:3; a CDR H2 as set forth in SEQ ID NO:4; a CDR H3 as set forth in SEQ ID NO:5; a CDR L1 as set forth in SEQ ID NO:6; a CDR L2 as set forth in SEQ ID NO:7; and a CDR L3 as set forth in SEQ ID NO:8. In some embodiments of any of the uses provided herein, the monoclonal antibody comprises a heavy chain variable region comprising or consisting of the amino acid sequence as set forth in SEQ ID NO:1, and a light chain variable region comprising or consisting of the amino acid sequence as set forth in SEQ ID NO:2. In some embodiments of any of the uses provided herein, the monoclonal antibody comprises a heavy chain comprising or consisting of the amino acid sequence as set forth in SEQ ID NO:11, and a light chain comprising or consisting of the amino acid sequence as set forth in SEQ ID NO:12.

In another embodiment of any of the uses provided herein, the monoclonal antibody comprises a CDR H1 as set forth in SEQ ID NO:87; a CDR H2 as set forth in SEQ ID NO:88; a CDR H3 as set forth in SEQ ID NO:89; a CDR L1 as set forth in SEQ ID NO:84; a CDR L2 as set forth in SEQ ID NO:85; and a CDR L3 as set forth in SEQ ID NO:86. In some embodiments of any of the uses described herein, the monoclonal antibody comprises a heavy chain variable region comprising or consisting of the amino acid sequence as set forth in SEQ ID NO:82, and a light chain variable region comprising or consisting of the amino acid sequence as set forth in SEQ ID NO:80. In some embodiments of any of the uses described herein, the monoclonal antibody comprises a heavy chain comprising or consisting of the amino acid sequence as set forth in SEQ ID NO:83, and a light chain comprising or consisting of the amino acid sequence as set forth in SEQ ID NO:81.

In another embodiment of any of the uses provided herein, the monoclonal antibody comprises a CDR H1 as set forth in SEQ ID NO:93; a CDR H2 as set forth in SEQ ID NO:94; a CDR H3 as set forth in SEQ ID NO:95; a CDR L1 as set forth in SEQ ID NO:91; a CDR L2 as set forth in SEQ ID NO:92; and a CDR L3 as set forth in SEQ ID NO:90. In some embodiments of any of the uses described herein, the monoclonal antibody comprises a heavy chain variable region comprising or consisting of the amino acid sequence as set forth in SEQ ID NO:97, and a light chain variable region comprising or consisting of the amino acid sequence as set forth in SEQ ID NO:96. In some embodiments of any of the uses described herein, the monoclonal antibody comprises a heavy chain comprising or consisting of the amino acid sequence as set forth in SEQ ID NO:99, and a light chain comprising or consisting of the amino acid sequence as set forth in SEQ ID NO:98.

In another embodiment of any of the uses provided herein, the monoclonal antibody comprises a CDR H1 as set forth in SEQ ID NO:103; a CDR H2 as set forth in SEQ ID NO:104; a CDR H3 as set forth in SEQ ID NO:105; a CDR L1 as set forth in SEQ ID NO:100; a CDR L2 as set forth in SEQ ID NO:101; and a CDR L3 as set forth in SEQ ID NO:102. In some embodiments of any of the uses provided herein, the monoclonal antibody comprises a heavy chain variable region comprising or consisting of the amino acid sequence as set forth in SEQ ID NO:107, and a light chain variable region comprising or consisting of the amino acid sequence as set forth in SEQ ID NO:106. In some embodiments of any of the uses provided herein, the monoclonal antibody comprises a heavy chain comprising or consisting of the amino acid sequence as set forth in SEQ ID NO:109, and a light chain comprising or consisting of the amino acid sequence as set forth in SEQ ID NO:108. In an aspect, provided herein is a kit comprising: a pre-filled syringe, pre-filled syringe with a needle safety device, injection pen, or auto-injector comprising a dose of a monoclonal antibody that modulates (e.g., blocks, inhibits, suppresses or reduces) the CGRP pathway; and instructions to determine whether a patient's headaches are mediated by the activation and sensitization of high-threshold (HT) neurons.

In an aspect, provided herein is a monoclonal antibody that blocks, inhibits, suppresses or reduces the calcitonin gene related peptide (CGRP) pathway for use in the reduction of headache frequency in a patient, wherein the patient is one whose headaches are mediated by activation and sensitization of high-threshold (HT) neurons. In some embodiments, the patient has been determined to have headaches mediated by activation and sensitization of high-threshold (HT) neurons.

In another aspect, provided herein is a monoclonal antibody that blocks, inhibits, suppresses or reduces the calcitonin gene related peptide (CGRP) pathway for use in the reduction of headache frequency in a patient, wherein the patient is one who exhibits hyperalgesia reducible by administration of a monoclonal antibody that blocks, inhibits, suppresses or reduces the CGRP pathway. In some embodiments, the patient has been determined to exhibit hyperalgesia. In some embodiments, the patient has been determined to have hyperalgesia which is reducible by administration of a monoclonal antibody that blocks, inhibits, suppresses or reduces the CGRP pathway.

In yet another aspect, provided herein is a monoclonal antibody that blocks, inhibits, suppresses or reduces the calcitonin gene related peptide (CGRP) pathway for use in the reduction of headache frequency in a patient, wherein the patient is one whose headaches are primarily experienced in a portion of the head. In some embodiments, the patient has been determined to primarily experience headaches in a portion of the head.

In some embodiments, the antibody comprises a CDR H1 as set forth in SEQ ID NO:3; a CDR H2 as set forth in SEQ ID NO:4; a CDR H3 as set forth in SEQ ID NO:5; a CDR L1 as set forth in SEQ ID NO:6; a CDR L2 as set forth in SEQ ID NO:7; and a CDR L3 as set forth in SEQ ID NO:8. In some embodiments, the antibody comprises a heavy chain variable region comprising the amino acid sequence as set forth in SEQ ID NO:1, and a light chain variable region comprising the amino acid sequence as set forth in SEQ ID NO:2. In some embodiments, the antibody comprises a heavy chain comprising the amino acid sequence as set forth in SEQ ID NO:11, and a light chain comprising the amino acid sequence as set forth in SEQ ID NO:12.

In some embodiments, the antibody comprises a CDR H1 as set forth in SEQ ID NO:87; a CDR H2 as set forth in SEQ ID NO:88; a CDR H3 as set forth in SEQ ID NO:89; a CDR L1 as set forth in SEQ ID NO:84; a CDR L2 as set forth in SEQ ID NO:85; and a CDR L3 as set forth in SEQ ID NO:86. In some embodiments, the antibody comprises a heavy chain variable region comprising the amino acid sequence as set forth in SEQ ID NO:82, and a light chain variable region comprising the amino acid sequence as set forth in SEQ ID NO:80. In some embodiments, the antibody comprises a heavy chain comprising the amino acid sequence as set forth in SEQ ID NO:83, and a light chain comprising the amino acid sequence as set forth in SEQ ID NO:81.

In some embodiments, the antibody comprises a CDR H1 as set forth in SEQ ID NO:93; a CDR H2 as set forth in SEQ ID NO:94; a CDR H3 as set forth in SEQ ID NO:95; a CDR L1 as set forth in SEQ ID NO:91; a CDR L2 as set forth in SEQ ID NO:92; and a CDR L3 as set forth in SEQ ID NO:90. In some embodiments, the antibody comprises a heavy chain variable region comprising the amino acid sequence as set forth in SEQ ID NO:97, and a light chain variable region comprising the amino acid sequence as set forth in SEQ ID NO:96. In some embodiments, the antibody comprises a heavy chain comprising the amino acid sequence as set forth in SEQ ID NO:99, and a light chain comprising the amino acid sequence as set forth in SEQ ID NO:98.

In some embodiments, the antibody comprises a CDR H1 as set forth in SEQ ID NO:103; a CDR H2 as set forth in SEQ ID NO:104; a CDR H3 as set forth in SEQ ID NO:105; a CDR L1 as set forth in SEQ ID NO:100; a CDR L2 as set forth in SEQ ID NO:101; and a CDR L3 as set forth in SEQ ID NO:102. In some embodiments, the antibody comprises a heavy chain variable region comprising the amino acid sequence as set forth in SEQ ID NO:107, and a light chain variable region comprising the amino acid sequence as set forth in SEQ ID NO:106. In some embodiments, the antibody comprises a heavy chain comprising the amino acid sequence as set forth in SEQ ID NO:109, and a light chain comprising the amino acid sequence as set forth in SEQ ID NO:108.

In an aspect, provided herein is a kit comprising: a pre-filled syringe, pre-filled syringe with a needle safety device, injection pen, or auto-injector comprising a dose of a monoclonal antibody that modulates (e.g., blocks, inhibits, suppresses or reduces) the CGRP pathway; and instructions to determine whether a patient exhibits hyperalgesia, reducible by administering a monoclonal antibody that modulates (e.g., blocks, inhibits, suppresses or reduces) the CGRP pathway.

In another aspect, provided herein is a kit comprising: a pre-filled syringe, pre-filled syringe with a needle safety device, injection pen, or auto-injector comprising a dose of a monoclonal antibody that blocks, inhibits, suppresses or reduces the CGRP pathway; and instructions to determine whether a patient's headaches are primarily experienced in a portion of the head (e.g., one-side periorbital, one-side temporal, or one eye).

BRIEF DESCRIPTION OF THE DRAWINGS

FIG. 1 is a table showing binding affinities of 12 murine antibodies for different alanine substituted human α-CGRP fragments. Binding affinities were measured at 25° C. using Biacore by flowing Fabs across CGRPs on the chip. The boxed values represent the loss in affinity of alanine mutants relative to parental fragment, 25-37 (italic), except K35A, which was derived from a 19-37 parent. "$^a$" indicates affinities for 19-37 and 25-37 fragments are the mean average±standard deviation of two independent measurements on different sensor chips. "$^b$" indicates these interactions deviated from a simple bimolecular interaction model due to a biphasic off rate, so their affinities were determined using a conformational change model. Grey-scale key: white (1.0) indicates parental affinity; light grey (less than 0.5) indicates higher affinity than parent; dark grey (more than 2) indicates lower affinity than parent; and black indicates that no binding was detected.

FIG. 5 shows the amino acid sequence of the heavy chain variable region (SEQ ID NO:1) and light chain variable region (SEQ ID NO:2) of antibody G1. The Kabat CDRs are in bold text, and the Chothia CDRs are underlined. The amino acid residues for the heavy chain and light chain variable region are numbered sequentially.

FIGS. 7A and 7F show recording sites plotted on a representative transverse section through the first cervical segment. The circles represent HT and WDR neurons, as indicated. FIGS. 7B, 7D, 7G, and 7I show the most sensitive regions of cutaneous (i.e., where brush, pressure and pinch were applied) and corneal receptive fields. FIGS. 7C, 7E, 7H, and 7J show the mechanically sensitive receptive fields on the dura, which were all on or around the transverse sinus. The portion of the dura shown in the receptive field drawings is outlined by the dashed line in the inset in FIG. 7H. All dural and facial receptive fields were ipsilateral to the recorded neuron. Abbreviations: HT, high-threshold; WDR, wide-dynamic range.

FIGS. 8A, 8D, and 8F are plots of spontaneous discharge rate recorded at baseline (BL) and at 1-4 hours following CGRP-mAb (FIG. 8A) or isotype-conAb (FIG. 8E) administration to HT neurons. Numbers in parentheses show the mean discharge rate for the 15-minute sampling period at each time point. Bin width=1 sec. FIGS. 8B and 8C are histograms showing mean (±S.E.) spontaneous discharge of HT and WDR neurons recorded at baseline and 1-4 hours following CGRP-mAb administration in male (FIG. 8B) and female (FIG. 8C) rats. FIGS. 8F and 8G are histograms showing mean (±S.E.) spontaneous discharge of HT and WDR neurons recorded at baseline and 1-4 hours following isotype-conAb administration in male (FIG. 8F) and female (FIG. 8G) rats. * $p<0.05$ compared to baseline. Numbers in parentheses in FIGS. 8B, 8C, 8F, and 8G depict the number of neurons in each group.

FIGS. 9A and 9D are graphs showing the responses to indentation of the dura with a von Frey hair (VFH, 4.19 g) at baseline (BL) and at 1-4 hours following CGRP-mAb (FIG. 9A) or isotype control antibody (isotype-conAb) (FIG. 9D) administration to HT neurons. Numbers in parentheses show the mean discharge rate during the stimulus. Bin width=1 sec. FIGS. 9B and 9C are graphs showing the mean (±S.E.) discharge rates in response to dural stimulation at baseline and 1-4 hours following drug administration for the entire sample of neurons that received CGRP-mAb in male (FIG. 9B) and female (FIG. 9C) rats. FIGS. 9E and 9F are graphs showing the mean (±S.E.) discharge rates in response to dural stimulation at baseline and 1-4 hours following drug administration for the entire sample of neurons that received isotype-conAb in male (FIG. 9E) and female (FIG. 9F) rats. * p<0.05 compared to baseline. Numbers in parentheses in FIGS. 9B, 9C, 9E, and 9F depict number of neurons in each group.

FIGS. 10A, 10B, 10E, and 10F are graphs showing the responses to mechanical stimulation of the cutaneous receptive fields of HT (FIGS. 10A and 10E) and WDR (FIGS. 10B and 10F) with brush, pressure, and pinch, at baseline (BL) and at 1-4 hours following CGRP-mAb or isotype-conAb administration. Numbers in parentheses show the mean discharge rate during each stimulus. Bin width=1 sec. FIGS. 10C and 10D are graphs showing the mean (±S.E.) discharge rates in response to cutaneous stimulation at baseline and 1-4 hours following drug administration for the entire sample of neurons that received CGRP-mAb in male (FIG. 10C) and female (FIG. 10D) rats. FIGS. 10G and 10H are graphs showing the mean (±S.E.) discharge rates in response to cutaneous stimulation at baseline and 1-4 hours following drug administration for the entire sample of neurons that received isotype-conAb in male (FIG. 10G) and female (FIG. 10H) rats. Numbers in parentheses in FIGS. 10C, 10D, 10G, and 10H depict number of neurons in each group.

FIGS. 11A and 11D are graphs showing the responses to mechanical stimulation of the cornea by gentle brushing, at baseline (BL) and at 1-4 hours following CGRP-mAb (FIG. 11A) or isotype-conAb (FIG. 11D) administration to HT neurons. Numbers in parentheses show the mean discharge rate during each stimulus. Bin width=1 sec. FIGS. 11B and 11C are graphs showing the mean (±S.E.) discharge rates in response to cornea stimulation at baseline and 1-4 hours following drug administration for the entire sample of neurons that received CGRP-mAb in male (FIG. 11B) and female (FIG. 11C) rats. FIGS. 11E and 11F are graphs showing the mean (±S.E.) discharge rates in response to cornea stimulation at baseline and 1-4 hours following drug administration for the entire sample of neurons that received isotype-conAb in male (FIG. 11E) and female (FIG. 11F) rats. Numbers in parentheses in FIGS. 11B, 11C, 11E, and 11F depict number of neurons in each group.

FIGS. 12A and 12D are graphs show the discharge of trigeminovascular neurons prior to CSD induction (top), during CSD induction (middle), and 2 hours post-CSD (bottom), in two HT neurons that received CGRP-mAb (FIG. 12A) or isotype-conAb (FIG. 12D) 4 hours before CSD induction. Bin width=1 sec. FIGS. 12B and 12C are graphs showing the mean (±S.E.) discharge rates for the entire sample of HT and WDR trigeminovascular neurons tested for CSD responses after isotype-conAb administration in male (FIG. 12B) and female (FIG. 12C) rats. FIGS. 12E and 12F are graphs showing the mean (±S.E.) discharge rates for the entire sample of HT and WDR trigeminovascular neurons tested for CSD responses after CGRP-mAb administration in male (FIG. 12E) and female (FIG. 12F) rats. Discharge is shown at baseline (4 hours post-drug treatment, prior to CSD induction) and 2 hours post-CSD. * p<0.05 compared to baseline. Numbers in parentheses in FIGS. 12B, 12C, 12E, and 12F depict number of neurons in each group.

FIGS. 13A and 13B depict the expansion of dural and cutaneous receptive fields following occurrence of CSD in male and female rats. Blue (upper left to lower right diagonal lines) and pink (upper right to lower left diagonal lines) illustrate dural and cutaneous receptive fields before, and 2 hours after CSD induction, respectively, in isotype-conAb (FIG. 13A) and CGRP-mAb (FIG. 13B) treated rats.

FIGS. 14A and 14D are graphs showing the responses to indentation of the dura prior to CSD induction (BL) and 2 hours post-CSD, in two HT neurons that received treatment with CGRP-mAb (FIG. 14A) or isotype-conAb (FIG. 14D) 4 hours prior to CSD induction. Numbers in parentheses show the mean discharge rate during each stimulus. Bin width=1 sec. FIGS. 14B, 14C, 14E, and 14F are graphs showing the mean (±S.E.) discharge in response to dural indentation prior to CSD induction (Baseline) and 2 hours post-CSD, in neurons that received treatment with isotype-conAb (FIGS. 14B and 14C) or CGRP-mAb (FIGS. 14E and 14F). Neurons recorded in males are shown in FIGS. 14B and 14E; neurons recorded in females are shown in FIGS. 14C and 14F. * p<0.05 compared to baseline. Numbers in parentheses in FIGS. 14B, 14C, 14E, and 14F depict number of neurons in each group.

FIGS. 15A and 15D are graphs showing the responses to mechanical stimulation of the cutaneous receptive fields with brush, pressure, and pinch, prior to CSD induction (BL) and 2 hours post-CSD, for two HT neurons that received CGRP-mAb (FIG. 15A) or isotype-conAb (FIG. 15D) 4 hours before CSD induction. Numbers in parentheses show the mean discharge rate during each stimulus. Bin width=1 sec. FIGS. 15B, 15C, 15E, and 15F are graphs showing the mean (±S.E.) discharge in response to cutaneous stimulation prior to (Baseline) and 2 hours post-CSD induction, in HT neurons that received treatment with isotype-conAb or CGRP-mAb 4 hours prior to CSD induction. Neurons recorded in males are shown in FIGS. 15B and 15E; neurons recorded in females are shown in FIGS. 15C and 15F. * p<0.05 compared to baseline.

FIGS. 16A and 16D are graphs showing the responses to corneal stimulation (gentle brush) prior to CSD induction (BL) and 2 hours post-CSD, in two HT neurons that received treatment with isotype-conAb (FIG. 16A) or CGRP-mAb (FIG. 16D) 4 hours prior to CSD induction. Bin width=1 sec. FIGS. 16B, 16C, 16E, and 16F are graphs showing the mean (±S.E.) discharge in response to corneal stimulation prior to CSD induction (Baseline) and 2 hours post-CSD, in neurons that received treatment with isotype-conAb (FIGS. 16B and 16C) or CGRP-mAb (FIGS. 16E and 16F) 4 hours prior to CSD induction. Neurons recorded in males are shown in FIGS. 16B and 16E; neurons recorded in females are shown in FIGS. 16C and 16F. * p<0.05 compared to baseline.

FIG. 17 are tables showing the results of the studies (as described in Example 5) of spontaneous activity of the HT and WDR neurons in male and female rats in a naïve state and post-CSD state upon application of the indicated stimuli.

FIGS. 18A, 18B and 18C are graphs showing the activation of a-delta meningeal nociceptors by CSD. FIG. 18A are graphs showing an exemplary individual a-delta fiber response to CSD. The baseline spontaneous activity of the neuron is shown from 0 to 60 min whereas the firing rate of the neuron after CSD is shown from 60 to 120 min. FIG. 18B is a bar graph showing the mean (±SE) response magnitude of the six a-delta fibers that were activated by CSD (p<0.05). FIG. 18C is a graph showing the changes in response frequency of all six a-delta neurons.

FIGS. 19A, 19B, and 19C are graphs showing the activation of C-type meningeal nociceptors by CSD. FIG. 19A are graphs showing an exemplary individual C-type fiber response to CSD. The baseline spontaneous activity of the neuron is shown from 0 to 60 min whereas the firing rate of the neuron after CSD is shown from 60 to 120 min. FIG. 19B shows the mean (±SE) response magnitude of the six C-type fibers that were activated by CSD (p<0.05). FIG. 19C shows the changes in response frequency of all six C-type neurons.

FIG. 20A shows an individual example of fremanezumab treated a-delta fiber showing no change in spontaneous activity after CSD.

FIG. 20B shows examples of responses of two C-type meningeal nociceptors to CSD after treatment with fremanezumab. Note that the upper neuron was not activated by CSD whereas the lower neuron was activated by CSD.

FIGS. 21A and 21B are tables showing the incidence of activation of A-delta or C-type meningeal nociceptors by CSD.

FIG. 23A shows an experimental setup showing locations of ECG recording in the parietal cortex, neuronal recording in lamina I of the upper cervical dorsal horn, and the neuron's dural and facial receptive fields.

FIG. 23B is a graph showing electrical stimulation on dura.

DETAILED DESCRIPTION

Figure 2A:
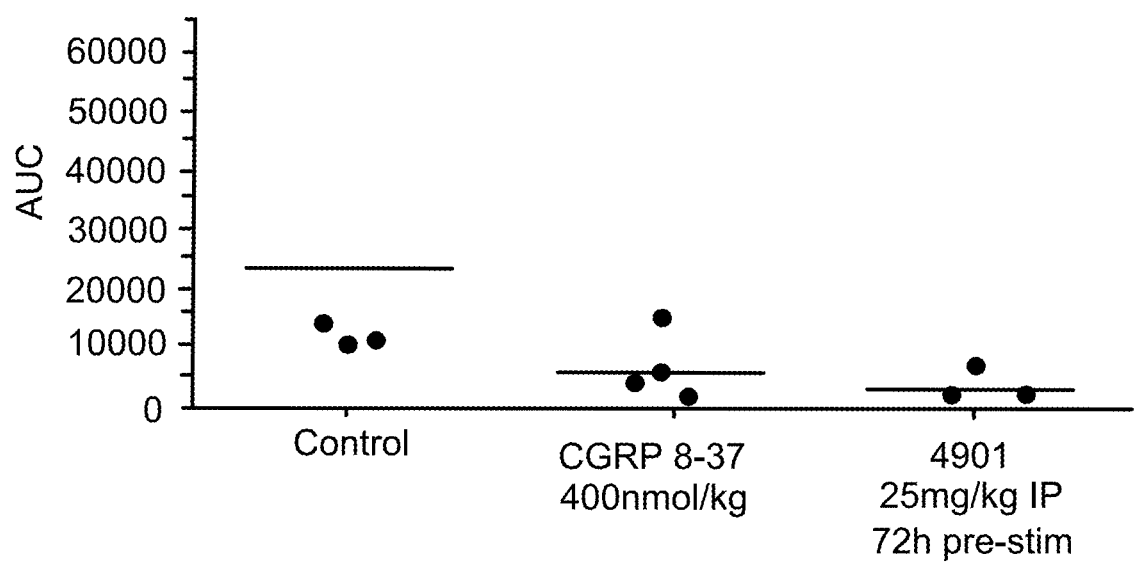
FIGS. 2A and 2B show the effect of administering CGRP 8-37 (400 nmol/kg), antibody 4901 (25 mg/kg), and antibody 7D11 (25 mg/kg) on skin blood flow measured as blood cell flux after electrical pulse stimulation for 30 seconds. CGRP 8-37 was administered intravenously (iv) 3-5 min before electrical pulse stimulation. Antibodies were administered intraperitoneal (IP) 72 hours before electrical pulse stimulation. Each point in the graphs represents AUC of one rat treated under the conditions as indicated. Each line in the graphs represents average AUC of rats treated under the condition as indicated. AUC (area under the curve) equals to Δflux×Δtime. "Δflux" represents the change of flux units after the electrical pulse stimulation; and "Δtime" represents the time period taken for the blood cell flux level to return to the level before the electrical pulse stimulation.

Provided herein is a method for reducing headache frequency, comprising a) selecting a patient whose headache is mediated by activation and sensitization of high-threshold neurons; and b) administering to the patient a monoclonal antibody that modulates (e.g., blocks, inhibits, suppresses or reduces) the calcitonin gene related peptide (CGRP) pathway in an amount sufficient to reduce headache frequency in the patient. In an embodiment, the sensitization of the high-threshold neurons depends on incoming pain signals from the meninges.

A large body of evidence supports an important role for CGRP in the pathophysiology of migraine. This evidence gave rise to a global effort to develop a new generation of therapeutics that reduces the availability of CGRP in migraineurs. Recently, humanized monoclonal anti-CGRP antibodies, among them fremanezumab (TEV-48125), were found to be effective in reducing the frequency of chronic or episodic migraine.

Single-unit extracellular recording techniques were used to determine the effects of TEV-48125 (30 mg/kg IV) and its isotype (control) on spontaneous and evoked activity in naïve and CSD-sensitized central trigeminovascular neurons in the medullary and upper cervical dorsal horn in anesthetized male and female rats (see, e.g., Example 5).

The study described herein demonstrates that the anti-CGRP antibody fremanezumab (TEV-48125) inhibits naïve high-threshold (HT) but not wide dynamic range (WDR) trigeminovascular neurons, that the inhibitory effects are limited to their activation from the intracranial dura but not facial skin or cornea, and that when given sufficient time, this drug prevents activation and sensitization of HT but not WDR neurons by cortical spreading depression. This inhibition was similar in male and female rats.

For patients whose chronic and episodic migraines are relieved by anti-CGRP antibodies, such as fremanezumab, the findings raise the possibility that HT neurons play a critical previously-unrecognized role in the initiation and chronification of the perception of headache, whereas WDR neurons contribute to the associated allodynia and central sensitization (see Example 5). Clinically, the findings may help explain the therapeutic effects of anti-CGRP antibodies in reducing headaches of intracranial origin such as migraine, and headaches attributed to meningitis, an epidural bleed, a subdural bleed, a sub-arachnoid bleed, and certain brain tumors. This finding also explains why this therapeutic approach may not be effective for every headache patient.

Definitions

As used herein, "about" when used in reference to numerical ranges, cutoffs, or specific values is used to indicate that the recited values may vary by up to as much as 10% from the listed value. Thus, the term "about" is used to encompass variations of ±10% or less, variations of ±5% or less, variations of ±1% or less, variations of ±0.5% or less, or variations of ±0.1% or less from the specified value.

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also fragments thereof (such as Fab, Fab', F(ab')2, Fv), single chain (ScFv), mutants thereof, fusion proteins comprising an antibody portion (such as domain antibodies), and any other modified configuration of the immunoglobulin molecule that comprises an antigen recognition site. An antibody includes an antibody of any class, such as IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1, and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

As used herein, "monoclonal antibody" or "mAb" refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to polyclonal antibody preparations, which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein, 1975, *Nature*, 256:495, or may be made by recombinant DNA methods such as described in U.S. Pat. No. 4,816,567. The monoclonal antibodies may also be isolated from phage libraries generated using the techniques described in McCafferty et al., 1990, *Nature*, 348:552-554, for example.

As used herein, "humanized" antibodies refer to forms of non-human (e.g., murine) antibodies that are specific chimeric immunoglobulins, immunoglobulin chains, or fragments thereof (such as Fv, Fab, Fab', F(ab')2 or other antigen-binding subsequences of antibodies) that contain minimal sequence derived from non-human immunoglobulin. For the most part, humanized antibodies are human immunoglobulins (recipient antibody) in which residues from a complementarity determining region (CDR) of the recipient are replaced by residues from a CDR of a non-human species (donor antibody) such as mouse, rat, or rabbit having the desired specificity, affinity, and, biological activity. In some instances, Fv framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Antibodies may have Fc regions modified as described in WO 99/58572. Other forms of humanized antibodies have one or more CDRs (one, two, three, four, five, six) which are altered with respect to the original antibody, which are also termed one or more CDRs "derived from" one or more CDRs from the original antibody.

As used herein, "human antibody" means an antibody having an amino acid sequence corresponding to that of an antibody produced by a human and/or has been made using any of the techniques for making human antibodies known in the art or disclosed herein. This definition of a human antibody includes antibodies comprising at least one human heavy chain polypeptide or at least one human light chain polypeptide. One such example is an antibody comprising murine light chain and human heavy chain polypeptides. Human antibodies can be produced using various techniques known in the art. In one embodiment, the human antibody is selected from a phage library, where that phage library expresses human antibodies (Vaughan et al., 1996, *Nat. Biotechnol.*, 14:309-314; Sheets et al., 1998, *PNAS*, (USA) 95:6157-6162; Hoogenboom and Winter, 1991, *J. Mol. Biol.*, 227:381; Marks et al., 1991, *J. Mol. Biol.*, 222:581). Human antibodies can also be made by introducing human immunoglobulin loci into transgenic animals, e.g., mice in which the endogenous immunoglobulin genes have been partially or completely inactivated. This approach is described in U.S. Pat. Nos. 5,545,807; 5,545,806; 5,569, 825; 5,625,126; 5,633,425; and 5,661,016. Alternatively, the human antibody may be prepared by immortalizing human B lymphocytes that produce an antibody directed against a target antigen (such B lymphocytes may be recovered from an individual or may have been immunized in vitro). See, e.g., Cole et al., *Monoclonal Antibodies and Cancer Therapy*, Alan R. Liss, p. 77 (1985); Boerner et al., 1991, *J. Immunol.*, 147 (1):86-95; and U.S. Pat. No. 5,750,373.

As used herein, the term "calcitonin gene-related peptide" and "CGRP" refers to any form of calcitonin gene-related peptide and variants thereof that retain at least part of the activity of CGRP. For example, CGRP may be α-CGRP or β-CGRP. As used herein, CGRP includes all mammalian species of native sequence CGRP, e.g., human, canine, feline, equine, and bovine.

As used herein, an "anti-CGRP antibody" refers to an antibody that modulates CGRP biological activity, or the CGRP pathway, including downstream pathways mediated by CGRP signaling, such as receptor binding and/or elicitation of a cellular response to CGRP. For example, an anti-CGRP antibody may block, inhibit, suppress or reduce the calcitonin gene related peptide (CGRP) pathway. The term anti-CGRP antibody encompasses both "anti-CGRP antagonist antibodies" and "anti-CGRP receptor antibodies." In some embodiments, the anti-CGRP antibody is a monoclonal antibody (i.e., an anti-CGRP monoclonal antibody).

An "anti-CGRP antagonist antibody" refers to an antibody that is able to bind to CGRP and thereby inhibit CGRP biological activity and/or downstream pathway(s) mediated by CGRP signaling. An anti-CGRP antagonist antibody encompasses antibodies that modulate, block, antagonize, suppress or reduce CGRP biological activity, or otherwise antagonize the CGRP pathway, including downstream pathways mediated by CGRP signaling, such as receptor binding and/or elicitation of a cellular response to CGRP. In some embodiments, an anti-CGRP antagonist antibody binds CGRP and prevents CGRP binding to a CGRP receptor. In other embodiments, an anti-CGRP antagonist antibody binds CGRP and prevents activation of a CGRP receptor. Examples of anti-CGRP antagonist antibodies are provided herein.

An "anti-CGRP receptor antibody" refers to an antibody that is able to bind to a CGRP receptor and thereby modulate the CGRP pathway. Examples of anti-CGRP receptor antibodies are provided herein (e.g., erenumab).

As used herein, the terms "G1," "antibody G1," "TEV-48125," and "fremanezumab" are used interchangeably to refer to an anti-CGRP antagonist antibody produced by expression vectors having deposit numbers of ATCC PTA-6867 and ATCC PTA-6866. The amino acid sequence of the heavy chain and light chain variable regions are shown in FIG. 5. The CDR portions of antibody G1 (including Chothia and Kabat CDRs) are diagrammatically depicted in FIG. 5. The polynucleotides encoding the heavy and light chain variable regions are shown in SEQ ID NO:9 and SEQ ID NO:10. The G1 heavy chain full length amino acid sequence is shown in SEQ ID NO:11. The G1 light chain full length amino acid sequence is shown in SEQ ID NO:12. The characterization and processes for making antibody G1 (and variants thereof) are described in Examples 1-4 infra, as well as PCT Publication No. WO 2007/054809 and *WHO Drug Information* 30(2): 280-1 (2016), which are hereby incorporated by reference in its entirety The terms "ALD403," and "eptinezumab" refer to an anti-CGRP antagonist antibody, which is a humanized IgG1 monoclonal antibody from a rabbit precursor. Characterization and processes for making eptinezumab can be found in U.S. Publication No. US 2012/0294797 and WHO Drug Information 30(2): 274-5 (2016), which are incorporated by reference in its entirety.

The terms "LY2951742," and "galcanezumab" refer to an anti-CGRP antagonist antibody, which is a humanized IgG4 monoclonal antibody from a murine precursor. Characterization and processes for making galcanezumab can be found in U.S. Publication No. US 2011/0305711 and *WHO Drug Information* 29(4): 526-7 (2015), which are incorporated by reference in its entirety. Dosing and formulations associated with galcanezumab can be found in PCT Publication No. WO 2016/205037, which is also incorporated by reference in its entirety.

The terms "AMG334," and "erenumab" refer to an anti-CGRP receptor antibody, which is a fully humanized IgG2 antibody. Characterization and processes for making erenumab can be found in U.S. Publication No. US 2010/0172895, U.S. Pat. No. 9,102,731, and *WHO Drug Information* 30(2): 275-6 (2016), each of which are incorporated by reference in their entireties. Dosing and formulations associated with erenumab can be found in PCT Publication No. WO 2016/171742, which is also incorporated by reference in its entirety.

The terms "polypeptide," "oligopeptide," "peptide," and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of this invention are based upon an antibody, the polypeptides can occur as single chains or associated chains.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after polymerization, such as by conjugation with a labeling component. Other types of modifications include, for example, "caps," substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), (O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

Diagnosis or assessment of headache is well-established in the art. References such as the International Classification of Headache Disorders, 3$^{rd}$ edition (ICHD-III beta version; *Cephalalgia* (2013) 33(9): 629-808) can be used by a skilled practitioner to assess the type of headache experienced by a patient. Headaches within the scope of the instant invention include headaches of intracranial origin. Non-limiting examples of headaches of intracranial origin include migraine (e.g., chronic and episodic) and headache attributed to meningitis, an epidural bleed, a subdural bleed, a sub-arachnoid bleed, and certain brain tumors (wherein headache results from increased pressure in the skull).

For example, "chronic migraine" refers to headache occurring on 15 or more days per month for more than three months, which has the features of migraine headache on at least 8 days per month. Diagnostic criteria for chronic migraine according to ICHD-III beta version, 2013 is as follows:

A. Headache (tension-type-like and/or migraine-like) on ≥15 days per month for >3 months and fulfilling criteria B and C (below).
B. Occurring in a patient who has had at least five attacks fulfilling certain criteria for migraine without aura and/or certain criteria for migraine with aura
C. On ≥8 days per month for >3 months, fulfilling any of the following:
  1. certain criteria for migraine without aura
  2. certain criteria for migraine with aura
  3. believed by the patient to be migraine at onset and relieved by a triptan or ergot derivative
D. Not better accounted for by another headache diagnosis.

Skilled practitioners will be readily able to recognize a subject with any of the types of migraine headache described herein. Assessment may be performed based on subjective measures, such as patient characterization of symptoms. For example, migraine may be diagnosed based on the following criteria: 1) episodic attacks of headache lasting 4 to 72 hours; 2) with two of the following symptoms: unilateral pain, throbbing, aggravation on movement, and pain of moderate or severe intensity; and 3) one of the following symptoms: nausea or vomiting, and photophobia or phonophobia (Goadsby et al., *N. Engl. J. Med.* 346:257-270, 2002). In some embodiments, assessment of headache (e.g., migraine) may be via headache hours, as described elsewhere herein. For example assessment of headache (e.g., migraine) may be in terms of daily headache hours, weekly headache hours, monthly headache hours and/or yearly headache hours. In some cases, headache hours may be as reported by the subject.

As used herein, "treatment" is an approach for obtaining beneficial or desired clinical results. For purposes of this invention, beneficial or desired clinical results include, but are not limited to, one or more of the following: improvement in any aspect of headache, including lessening severity, alleviation of pain intensity, and other associated symptoms, reducing frequency of recurrence, increasing the quality of life of those suffering from the headache, and decreasing dose of other medications required to treat the headache. Using migraine as an example, other associated symptoms include, but are not limited to, nausea, vomiting, and sensitivity to light, sound, and/or movement. The terms "patient" and "subject" are used interchangeably herein. In some embodiments, the patient is a human. As used herein, "preventing" is an approach to stop headache from occurring or existing in a subject, who is susceptible to the development of headache. For example, the patient may been previously diagnosed with chronic or episodic migraine. In other examples, the patient may have been diagnosed with meningitis, an epidural bleed, a subdural bleed, a sub-arachnoid bleed, or a brain tumor.

"Reducing headache incidence" or "reducing headache frequency" means any of reducing severity (which can include reducing need for and/or amount of (e.g., exposure to) other drugs and/or therapies generally used for this headache condition), duration, and/or frequency (including, for example, delaying or increasing time to next headache attack in an individual). As is understood by those skilled in the art, individuals may vary in terms of their response to treatment, and, as such, for example, a "method of reducing frequency of headache in an individual" reflects administering the anti-CGRP antagonist antibody based on a reasonable expectation that such administration may likely cause such a reduction in headache incidence in that particular individual.

"Ameliorating" headache or one or more symptoms of headache means a lessening or improvement of one or more symptoms of headache as compared to not administering an anti-CGRP antagonist antibody. "Ameliorating" also includes shortening or reduction in duration of a symptom.

As used herein, "controlling headache" refers to maintaining or reducing severity or duration of one or more symptoms of headache or frequency of headache (e.g., migraine) attacks in an individual (as compared to the level before treatment). For example, the duration or severity of head pain, or frequency of attacks is reduced by at least about any of 10%, 20%, 30%, 40%, 50%, 60%, 70%, 80%, 90% or more, in the individual as compared to the duration or severity of head pain, or frequency of attacks before treatment.

As used herein, a "headache hour" refers to an hour during which a subject experiences headache. Headache hours can be expressed in terms of whole hours (e.g., one headache hour, two headache hours, three headache hours, etc.) or in terms of whole and partial hours (e.g., 0.5 headache hours, 1.2 headache hours, 2.67 headache hours, etc.). One or more headache hours may be described with respect to a particular time interval. For example, "daily headache hours" may refer to the number of headache hours a subject experiences within a day interval (e.g., a 24-hour period). In another example, "weekly headache hours" may refer to the number of headache hours a subject experiences within a week interval (e.g., a 7-day period). As can be appreciated, a week interval may or may not correspond to a calendar week. In another example, "monthly headache hours" may refer to the number of headache hours a subject experiences within a month interval. As can be appreciated, a month interval (e.g., a period of 28, 29, 30, or 31 days) may vary in terms of number of days depending upon the particular month and may or may not correspond to a calendar month. In yet another example, "yearly headache hours" may refer to the number of headache hours a subject experiences within a year interval. As can be appreciated, a year interval (e.g., a period of 365 or 366 days) may vary in terms of number of days depending upon the particular year and may or may not correspond to a calendar year.

As used herein, a "headache day" refers to a day during which a subject experiences headache. Headache days can be expressed in terms of whole days (e.g., one headache day, two headache days, three headache days, etc.) or in terms of whole and partial days (e.g., 0.5 headache days, 1.2 headache days, 2.67 headache days, etc.). One or more headache days may be described with respect to a particular time interval. For example, "weekly headache days" may refer to the number of headache days a subject experiences within a week interval (e.g., a 7-day period). As can be appreciated, a week interval may or may not correspond to a calendar week. In another example, "monthly headache days" may refer to the number of headache days a subject experiences within a month interval. As can be appreciated, a month interval (e.g., a period of 28, 29, 30, or 31 days) may vary in terms of number of days depending upon the particular month and may or may not correspond to a calendar month. In yet another example, "yearly headache days" may refer to the number of headache days a subject experiences within a year interval. As can be appreciated, a year interval (e.g., a period of 365 or 366 days) may vary in terms of number of days depending upon the particular year and may or may not correspond to a calendar year.

As used therein, "delaying" the development of headache means to defer, hinder, slow, retard, stabilize, and/or postpone progression of the disease. This delay can be of varying lengths of time, depending on the history of the disease and/or individuals being treated. As is evident to one skilled in the art, a sufficient or significant delay can, in effect, encompass prevention, in that the individual does not develop headache. A method that "delays" development of the symptom is a method that reduces probability of developing the symptom in a given time frame and/or reduces extent of the symptoms in a given time frame, when compared to not using the method. Such comparisons are typically based on clinical studies, using a statistically significant number of subjects.

"Development" or "progression" of headache means initial manifestations and/or ensuing progression of the disorder. Development of headache can be detectable and assessed using standard clinical techniques as well known in the art. However, development also refers to progression that may be undetectable. For purpose of this disclosure, development or progression refers to the biological course of the symptoms. "Development" includes occurrence, recurrence, and onset. As used herein "onset" or "occurrence" of headache includes initial onset and/or recurrence.

As used herein, an "effective dosage" or "effective amount" of drug, compound, or pharmaceutical composition is an amount sufficient to effect beneficial or desired results. For prophylactic use, beneficial or desired results include results such as eliminating or reducing the risk, lessening the severity, or delaying the onset of the disease, including biochemical, histological and/or behavioral symptoms of the disease, its complications and intermediate pathological phenotypes presenting during development function of the disease. For therapeutic use, beneficial or desired results include clinical results such as reducing pain intensity, duration, or frequency of headache attack, and decreasing one or more symptoms resulting from headache (biochemical, histological and/or behavioral), including its complications and intermediate pathological phenotypes presenting during development of the disease, increasing the quality of life of those suffering from the disease, decreasing the dose of other medications required to treat the disease, enhancing effect of another medication, and/or delaying the progression of the disease of patients. An effective dosage can be administered in one or more administrations. For purposes of this disclosure, an effective dosage of drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

As used herein, "allodynia" refers to pain experienced by a patient and due to a stimulus that does not normally elicit pain (International Association for the Study of Pain, 2014-2015, "Allodynia and Hyperalgesia in Neuropathic Pain").

As used herein, "hyperalgesia" refers to an increase in pain experienced by a patient from a stimulus that normally provokes pain (International Association for the Study of Pain, 2014-2015, "Allodynia and Hyperalgesia in Neuropathic Pain").

Both allodynia and hyperalgesia can be distinguished and quantified by one of skill in the art by methods such as, for example, quantitative sensory testing (QST) (Rolke (2006) et al. Pain 123: 231-243). Rolke et al. teaches QST reference data for obtaining the full somatosensory phenotype of a patient, in both relative and absolute terms. For example, Rolke et al. describes a test for mechanical pain sensitivity (MPS) as a means for detecting pinprick hyperalgesia. In such a test, MPS can be assessed using a set of pinprick stimuli to obtain a stimulus-response function for pinprick-evoked pain (where the strongest pinprick force is about eight-times the mean mechanical pain threshold). Subjects can be asked to give the pain a rating for each stimulus on a '0-100' scale, wherein '0' indicates no pain and '100' indicates highest pain. A certain number of pinpricks are delivered to the subject at certain time intervals to avoid wind-up. After each pinprick, the subject provides numerical pain ratings. MPS is then calculated as the geometric mean (compound measure) of all numerical ratings for pinprick stimuli (Rolke et al. at p. 233).

As used herein, "sensitization" is the process whereby the strength of the stimulus that is needed to generate a response decrease over time, while the amplitude of the response increases.

The phrase "headache primarily experienced in a portion of the head" refers to description by the patient of having headache (experienced as, e.g., pain) in an identified part of the head. Examples of "portions of the head" include one-side periorbital, one-side temporal, one eye, a small area in the back of the head (e.g., just lateral to the midline), a small area on the top of the head, a small area in the middle of the forehead, a 'dot' (e.g., 10×10 mm) where the supraorbital nerve exits the skull (i.e., in the medial end of the eyebrow)

and a small area across the forehead. One of skill in the art would be able to assess whether a patient is experiencing headache in a portion of the head based on the patient's description (Noseda, R. et al. (2016) *Brain.* 139 (7): 1971-1986).

A. Methods and Uses of Anti-CGRP Antibodies for Reducing Headache Frequency

Provided herein is a method for reducing headache (e.g., migraine) frequency in a patient. The method includes selecting a patient experiencing headache mediated by the activation and sensitization of high-threshold (HT) neurons (e.g., by cortical spreading depression (CSD), in response to any vascular dilatation in the meninges, or incoming pain signals from the meninges). The patient is then treated with an anti-CGRP antibody.

Selecting the patient includes determining whether the patient's headache is mediated by HT neurons. Skilled practitioners will appreciate that such a determination can be made in any number of ways described herein, such as by observation of HT neuron activity and/or administering a monoclonal antibody that modulates the CGRP pathway to the patient and determining whether the antibody reduces hyperalgesia (as measured, for example, by QST), and/or determining that the patient's headache pain is localized (e.g., experienced most intensely or primarily) in a portion of the head.

Example 5 describes the means by which neurons could be identified and selected (HT v. WDR neurons) in a rat. This example further describes the observations made in connection with the activation and sensitization of each of these types of neurons after induction of CSD.

Patients who experience hyperalgesia, wherein the hyperalgesia is reduced (e.g., reversed or eliminated) upon administration of a monoclonal antibody that modulates (e.g., blocks, inhibits, suppresses or reduces) the CGRP pathway, are likely to respond to a course of treatment comprising a monoclonal antibody that modulates (e.g., blocks, inhibits, suppresses or reduces) the CGRP pathway, e.g., a longer course and/or higher dose course of treatment with an anti-CGRP antibody. If the anti-CGRP antibody reduces the headache in hyperalgesic patients, it confirms that the headache was mediated by the HT neurons because the anti-CGRP antibody does not inhibit the other class of nociceptive neurons, the WDR, as shown in Example 5. Example 6 describes the experimental design of QST that is useful in determining whether a patient experiences hyperalgesia, and whether it is reduced upon treatment with an anti-CGRP antibody.

Likewise, a patient who experiences allodynia, wherein the allodynia is reduced (e.g., reversed or eliminated) upon administration of a monoclonal antibody that modulates (e.g., blocks, inhibits, suppresses or reduces) the CGRP pathway, is likely to respond to a course of treatment comprising a monoclonal antibody that modulates (e.g., blocks, inhibits, suppresses or reduces) the CGRP pathway, e.g., a longer course and/or higher dose course of treatment with an anti-CGRP antibody.

Thus, a patient that responds to treatment with an anti-CGRP antibody may experience a reduction, reversal, or elimination of both hyperalgesia and allodynia after a first course of treatment.

Further, it is known that high-threshold neurons exhibit small receptive fields, while wide dynamic range neurons exhibit large receptive fields. Thus, headache pain localized (or primarily experienced) in a portion of the head may identify a patient who will respond favorably to treatment with a monoclonal antibody that modulates the CGRP pathway.

Accordingly, one treatment strategy includes: a) selecting a patient who exhibits hyperalgesia reducible by administering a first monoclonal antibody that modulates the CGRP pathway; and b) administering to the patient a second monoclonal antibody that blocks, inhibits, suppresses or reduces the CGRP pathway in an amount sufficient to reduce headache frequency in the patient. In such treatments, the first and second monoclonal antibodies administered to the patient may be the same type of anti-CGRP antibody or different types of anti-CGRP antibodies, and each one may be administered to the patient intravenously or subcutaneously, or both. For example, the first and second monoclonal antibodies can each independently be selected from an anti-CGRP antagonist antibody and an anti-CGRP receptor antibody. In some treatment regimens, the first and second monoclonal antibodies may be anti-CGRP antagonist antibodies. In others, the first monoclonal antibody may be an anti-CGRP antagonist antibody, while the second monoclonal antibody may be an anti-CGRP receptor antibody. The first and second monoclonal antibodies can be human or humanized. The first and/or second monoclonal antibodies can each independently be selected from IgG1, IgG2, IgG3, and IgG4 antibodies.

In some instances, the first and/or second monoclonal antibodies are administered while the patient is headache-free (e.g., migraine-free). In other embodiments, the first and/or second monoclonal antibody are administered while the patient is experiencing headache (e.g., migraine).

In instances when the patient is experiencing migraine, administration preferably occurs soon after onset of the migraine. For example, administration can occur while the patient is experiencing prodromes (i.e., symptoms that precede the headache such as aura), but before the headache phase.

In yet other embodiment, the patient is or was previously diagnosed as having episodic or chronic migraine. In such a patient, the first and/or second monoclonal antibody can be administered while the patient is free of migraine, or experiencing the early stages of migraine or mild migraine.

In another embodiment, the patient is or was previously diagnosed as having meningitis, an epidural bleed, a subdural bleed, a sub-arachnoid bleed, or a brain tumor. In these instances, the headache may be attributed to meningitis, an epidural bleed, a subdural bleed, a sub-arachnoid bleed, or a brain tumor.

Skilled practitioners will appreciate that the antibody(ies) can be administered to the patient using any method known in the art. For example, the antibody(ies) can be administered to the patient using a pre-filled syringe, a pre-filled syringe with a needle safety device, an injection pen, an auto-injector, or any combination thereof.

Particularly useful as first and/or second monoclonal antibodies are anti-CGRP antibodies that include a) a CDR H1 as set forth in SEQ ID NO:3; a CDR H2 as set forth in SEQ ID NO:4; a CDR H3 as set forth in SEQ ID NO:5; a CDR L1 as set forth in SEQ ID NO:6; a CDR L2 as set forth in SEQ ID NO:7; and a CDR L3 as set forth in SEQ ID NO:8 or b) a variant of an antibody according to (a) as shown in Table 5. In some embodiments, the first and/or second monoclonal antibodies comprise a heavy chain variable region comprising or consisting of the amino acid sequence as set forth in SEQ ID NO:1, and a light chain variable region comprising or consisting of the amino acid sequence as set forth in SEQ ID NO:2. In some embodiments, the first and/or second monoclonal antibodies comprise a heavy chain comprising or consisting of the amino acid sequence as set forth in SEQ ID NO:11, and a light chain comprising or consisting of the amino acid sequence as set forth in SEQ ID NO:12. An exemplary monoclonal antibody is fremanezumab (also referred to herein as "G1").

Following selection of the patient, the first and/or second monoclonal antibody can be administered at a dose of from about 225 mg to about 900 mg, e.g., a dose of about 225 mg, about 250 mg, about 275 mg, about 300 mg, about 325 mg, about 350 mg, about 375 mg, about 400 mg, about 425 mg, about 450 mg, about 475 mg, about 500 mg, about 500 mg, about 525 mg, about 550 mg, about 550 mg, about 575 mg, about 600 mg, about 625 mg, about 650 mg, about 675 mg, about 700 mg, about 725 mg, about 750 mg, about 775 mg, about 800 mg, about 825 mg, about 850 mg, about 875 mg, or about 900 mg. These doses may be administered to the patient monthly or quarterly. In one exemplary treatment, the dosing regimen can include an initial dose (e.g., 675 mg), and further include administering to the patient an additional 225 mg dose of the monoclonal antibody once per month in each of the two months (or three months, four months, five months, six months, or twelve months) subsequent to the month in which the patient receives the initial dose.

The first and/or second monoclonal antibody can be administered as part of any useful formulation and in any formulation volume. Particularly useful is a formulation comprising the antibody at a concentration of at least about 150 mg/mL (e.g., about 175 mg/mL, about 200 mg/mL, about 225 mg/mL, about 250 mg/mL, about 275 mg/mL, about 300 mg/mL, about 325 mg/mL, about 350 mg/mL, about 375 mg/mL, about 400 mg/mL, about 425 mg/mL, about 450 mg/mL or more). Also useful are formulations wherein the monoclonal antibody can be administered in a volume of less than 2 mL (e.g., about 1.8 mL, about 1.7 mL, about 1.6 mL, about 1.5 mL, about 1.4 ml, about 1.3 mL, about 1.2 mL, about 1.1 mL, about 1.0 ml, about 0.9 mL, about 0.8 mL, about 0.7 mL, about 0.6 mL, about 0.5 mL, or less). In some embodiments, the monoclonal antibody is preferably administered in a volume of about 1.5 mL. Any of the doses provided herein (e.g., about 225 mg, about 675 mg, or about 900 mg) may be administered intravenously or subcutaneously. For example, fremanezumab may be administered at a dose of about 225 mg monthly or quarterly, and be administered subcutaneously.

Also useful in treatment methods described herein are first and/or second monoclonal antibodies that include a CDR H1 as set forth in SEQ ID NO:87; a CDR H2 as set forth in SEQ ID NO:88; a CDR H3 as set forth in SEQ ID NO:89; a CDR L1 as set forth in SEQ ID NO:84; a CDR L2 as set forth in SEQ ID NO:85; and a CDR L3 as set forth in SEQ ID NO:86. In some embodiments, the first and/or second monoclonal antibodies comprise a heavy chain variable region comprising or consisting of the amino acid sequence as set forth in SEQ ID NO:82, and a light chain variable region comprising or consisting of the amino acid sequence as set forth in SEQ ID NO:80. In some embodiments, the first and/or second monoclonal antibodies comprise a heavy chain comprising or consisting of the amino acid sequence as set forth in SEQ ID NO:83, and a light chain comprising or consisting of the amino acid sequence as set forth in SEQ ID NO:81. Exemplary of such an antibody would be eptinezumab. This antibody may be administered at a dose of about 100 mg, about 150 mg, about 200 mg, about 250 mg, about 300 mg, about 350 mg, about 400 mg, about 450 mg, about 500 mg, about 600 mg, about 700 mg, about 800 mg, about 900 mg, or about 1000 mg. Any of the doses provided herein (e.g., about 100 mg, about 300 mg, or about 1000 mg) may be administered intravenously or subcutaneously.

Also useful are first and/or second monoclonal antibodies that include a CDR H1 as set forth in SEQ ID NO:93; a CDR H2 as set forth in SEQ ID NO:94; a CDR H3 as set forth in SEQ ID NO:95; a CDR L1 as set forth in SEQ ID NO:91; a CDR L2 as set forth in SEQ ID NO:92; and a CDR L3 as set forth in SEQ ID NO:90. In some embodiments, the first and/or second monoclonal antibodies comprise a heavy chain variable region comprising or consisting of the amino acid sequence as set forth in SEQ ID NO:97, and a light chain variable region comprising or consisting of the amino acid sequence as set forth in SEQ ID NO:96. In some embodiments, the first and/or second monoclonal antibodies comprise a heavy chain comprising or consisting of the amino acid sequence as set forth in SEQ ID NO:99, and a light chain comprising or consisting of the amino acid sequence as set forth in SEQ ID NO:98. Exemplary of such an antibody would be galcanezumab. This antibody may be administered at a dose of about 100 mg, about 120 mg, about 150 mg, about 200 mg, about 240 mg, about 250 mg, about 300 mg, about 350 mg, about 360 mg, about 400 mg, about 450 mg, about 480 mg, about 500 mg, about 600 mg, about 700 mg, about 800 mg, about 900 mg, or about 1000 mg. Further, the 120 mg dose may be administered in a volume of about 1.5 mL and the 240 mg dose may be administered in a volume of about 3 mL. Any of the doses provided herein (e.g., about 120 mg or about 240 mg) may be administered intravenously or subcutaneously.

Also useful are first and/or second monoclonal antibodies that include a CDR H1 as set forth in SEQ ID NO:103; a CDR H2 as set forth in SEQ ID NO:104; a CDR H3 as set forth in SEQ ID NO:105; a CDR L1 as set forth in SEQ ID NO:100; a CDR L2 as set forth in SEQ ID NO:101; and a CDR L3 as set forth in SEQ ID NO:102. In some embodiments, the first and/or second monoclonal antibodies comprise a heavy chain variable region comprising or consisting of the amino acid sequence as set forth in SEQ ID NO:107, and a light chain variable region comprising or consisting of the amino acid sequence as set forth in SEQ ID NO:106. In some embodiments, the first and/or second monoclonal antibodies comprise a heavy chain comprising or consisting of the amino acid sequence as set forth in SEQ ID NO:109, and a light chain comprising or consisting of the amino acid sequence as set forth in SEQ ID NO:108. Exemplary of such an antibody would be erenumab. Erenumab may be administered at a dose of about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg. Further, the 70 mg does may be administered in a volume of about 1 mL. The 140 mg dose may be administered in a volume of about 2 mL. Any of the doses provided herein (e.g., about 70 mg or about 140 mg) may be administered intravenously or subcutaneously.

Accordingly, in certain methods described herein, a monoclonal antibody to be used in the methods described herein may be selected from the group consisting of fremanezumab, eptinezumab, galcanezumab, erenumab, and bioequivalents thereof.

Administration of an anti-CGRP antibody can be by any means known in the art, including: orally, intravenously, subcutaneously, intraarterially, intramuscularly, intranasally (e.g., with or without inhalation), intracardially, intraspinally, intrathoracically, intraperitoneally, intraventricularly, sublingually, transdermally, and/or via inhalation. Administration may be systemic, e.g., intravenously, or localized. In some embodiments, an initial dose and one or more additional doses are administered via same route, i.e., subcutaneously or intravenously. In some embodiments, the one or more additional doses are administered via a different route than the initial dose, i.e., the initial dose may be administered intravenously and the one or more additional doses may be administered subcutaneously.

In some instances, methods described herein can further include administering to the patient a second agent simultaneously or sequentially with the monoclonal antibody. The second agent can be non-steroidal anti-inflammatory drugs (NSAID) and/or triptans and/or a 5 hydroxytryptamine 1F receptor agonist (i.e., a serotonin receptor agonist). In some instances, the second agent is an agent that is administered to the patient prophylactically.

Non-limiting examples of NSAIDs that can be used in combination with an anti-CGRP antibody include aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, nabumetone, naproxen, oxaprozin, phenylbutazone, piroxicam, sulindac, tolmetin or zomepirac, cyclooxygenase-2 (COX-2) inhibitors, celecoxib, rofecoxib, meloxicam, JTE-522, L-745,337, NS398, or a pharmaceutically acceptable salt thereof.

Non-limiting examples of triptans that can be used in combination with an anti-CGRP antibody include sumatriptan, zolmitriptan, naratriptan, rizatriptan, eletriptan, almotriptan, and afrovatriptan.

A non-limiting example of a 5 hydroxytryptamine 1F receptor agonist is lasmiditan.

The preventing, treating, or reducing of the methods provided herein can comprise reducing the number of headache hours of any severity, reducing the number of migraine hours of any severity, reducing the number of monthly headache days of any severity, reducing the number of monthly migraine days of any severity, reducing the use of any acute headache medications, reducing a 6-item Headache Impact Test (HIT-6) disability score, improving 12-Item Short Form Health Survey (SF-12) score (Ware et al., *Med. Care* 4:220-233, 1996), reducing Patient Global Impression of Change (PGIC) score (Hurst et al., *J. Manipulative Physiol. Ther.* 27:26-35, 2004), improving Sport Concussion Assessment tool 3 (SCAT-3) score (McCrory et al. *British J. Sport. Med.* 47:263-266, 2013), or any combination thereof. In some embodiments, the number of monthly headache or migraine days can be reduced for at least seven days after a single administration.

In some embodiments, monthly headache or migraine hours experienced by the subject after said administering is reduced by 40 or more hours (e.g., 45, 50, 55, 60, 65, 70, 75, 80, or more) from a pre-administration level in the subject. Monthly headache or migraine hours may be reduced by more than 60 hours. In some embodiments, monthly headache or migraine hours experienced by the subject after said administering are reduced by 25% or more (e.g., 30%, 35%, 40%, 45%, 50%, or more) relative to a pre-administration level in the subject. Monthly headache or migraine hours may be reduced by 40% or more. In some embodiments, monthly headache or migraine days experienced by the subject after said administering is reduced by three or more days (e.g., 3, 4, 5, 6, 7, 8, 9, 10, 11, 12, 13, 14, 15, 16, 17, 18, 19, 20, or more days) from a pre-administration level in the subject. In some embodiments, the number of monthly headache or migraine days can be reduced by at least about 50% from a pre-administration level in the subject. Thus, in some aspects, the number of monthly headache or migraine days can be reduced by at least about 50%, at least about 55%, at least about 60%, at least about 65%, at least about 70%, at least about 75%, at least about 80%, or at least about 90%.

B. Anti-CGRP Antibodies for Use in Treatment Methods

In some embodiments, the methods provided herein use an antibody, which can be an anti-CGRP antagonist antibody. An anti-CGRP antagonist antibody can refer to any antibody molecule that modulates (e.g., blocks, suppresses or reduces, including significantly) CGRP biological activity, including downstream pathways mediated by CGRP signaling, such as receptor binding and/or elicitation of a cellular response to CGRP.

An anti-CGRP antagonist antibody can exhibit any one or more of the following characteristics: (a) bind to CGRP; (b) block CGRP from binding to its receptor(s); (c) block or decrease CGRP receptor activation (including, but not limited to, cAMP activation); (d) inhibit CGRP biological activity or downstream pathways mediated by CGRP signaling function; (e) prevent, ameliorate, or treat any aspect of migraine; (f) increase clearance of CGRP; and (g) inhibit (reduce) CGRP synthesis, production or release. Anti-CGRP antagonist antibodies are known in the art. See e.g., Tan et al., *Clin. Sci.* (Lond). 89:565-73, 1995; Sigma (Missouri, US), product number C7113 (clone #4901); Plourde et al., *Peptides* 14:1225-1229, 1993.

In some embodiments, the antibody reacts with CGRP in a manner that inhibits CGRP, and/or the CGRP pathway, including downstream pathways mediated by the CGRP signaling function. In some embodiments, the anti-CGRP antagonist antibody recognizes human CGRP. In some embodiments, the anti-CGRP antagonist antibody binds to both human α-CGRP and β-CGRP. In some embodiments, the anti-CGRP antagonist antibody binds human and rat CGRP. In some embodiments, the anti-CGRP antagonist antibody binds the C-terminal fragment having amino acids 25-37 of CGRP. In some embodiments, the anti-CGRP antagonist antibody binds a C-terminal epitope within amino acids 25-37 of CGRP. The anti-CGRP antibodies useful in the present invention can encompass monoclonal antibodies, polyclonal antibodies, antibody fragments (e.g., Fab, Fab', F(ab')2, Fv, Fc, etc.), chimeric antibodies, bispecific antibodies, heteroconjugate antibodies, single chain (ScFv), mutants thereof, fusion proteins comprising an antibody portion (e.g., a domain antibody), humanized antibodies, and any other modified configuration of the immunoglobulin molecule that comprises an antigen recognition site of the required specificity, including glycosylation variants of antibodies, amino acid sequence variants of antibodies, and covalently modified antibodies. The antibodies may be murine, rat, human, or any other origin (including chimeric or humanized antibodies).

In some embodiments, the anti-CGRP antagonist antibody is a monoclonal antibody. In some embodiments, the anti-CGRP antagonist antibody is humanized. In some embodiments, the antibody is human. In some embodiments, the anti-CGRP antagonist antibody is antibody G1 (as described herein). In some embodiments, the anti-CGRP antagonist antibody comprises one or more CDR(s) (such as one, two, three, four, five, or, in some embodiments, all six CDRs) of antibody G1 or variants of G1 shown in Table 5. In still other embodiments, the anti-CGRP antagonist antibody comprises the amino acid sequence of the heavy chain variable region shown in FIG. 5 (SEQ ID NO:1) and the amino acid sequence of the light chain variable region shown in FIG. 5 (SEQ ID NO:2). In still other embodiments, the anti-CGRP antagonist antibody comprises a heavy chain full length amino acid sequence shown in SEQ ID NO:11, and a light chain full length amino acid sequence shown if SEQ ID NO:12.

In some embodiments, the antibody comprises a light chain variable region (LCVR) and a heavy chain variable region (HCVR) selected from the groups consisting of: (a) LCVR17 (SEQ ID NO:58) and HCVR22 (SEQ ID NO:59); (b) LCVR18 (SEQ ID NO:60) and HCVR23 (SEQ ID NO:61); (c) LCVR19 (SEQ ID NO:62) and HCVR24 (SEQ ID NO:63); (d) LCVR20 (SEQ ID NO:64) and HCVR25 (SEQ ID NO:65); (e) LCVR21 (SEQ ID NO:66) and HCVR26 (SEQ ID NO:67); (f) LCVR27 (SEQ ID NO:68) and HCVR28 (SEQ ID NO:69); (g) LCVR29 (SEQ ID NO:70) and HCVR30 (SEQ ID NO:71); (h) LCVR31 (SEQ ID NO:72) and HCVR32 (SEQ ID NO:73); (i) LCVR33 (SEQ ID NO:74) and HCVR34 (SEQ ID NO:75); (j) LCVR35 (SEQ ID NO:76) and HCVR36 (SEQ ID NO:77); and (k) LCVR37 (SEQ ID NO:78) and HCVR38 (SEQ ID NO:79). Sequences of these regions are provided herein. Other examples of anti-CGRP antibodies are described in U.S. Patent Publication Nos. US 2011/0305711 (SEQ ID NOs:5, 6, 7, 12, 16, 19, 24, 29, 34, and 39), US 2012/0294802, US 2012/0294797 (SEQ ID NOs:51-60), which are hereby incorporated by reference in their entireties. For example, antibodies with any of the following sequences may be used.

```
Ab6 Variable region Light chain (humanized)
protein sequence (US20120294797)
                                       (SEQ ID NO: 80)
QVLTQSPSSLSASVGDRVTINCQASQSVYHNTYLAWYQQKPGKVPKQLIY

DASTLASGVPSRFSGSGSGTDFTLTISSLQPEDVATYYCLGSYDCTNGDC

FVFGGGTKVEIKR

Ab6 Light chain (humanized) Full length protein
sequence (US20120294797)
                                       (SEQ ID NO: 81)
QVLTQSPSSLSASVGDRVTINCQASQSVYHNTYLAWYQQKPGKVPKQLIY

DASTLASGVPSRFSGSGSGTDFTLTISSLQPEDVATYYCLGSYDCTNGDC

FVFGGGTKVEIKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC

Ab6 Variable region heavy chain (humanized)
protein sequence (US20120294797)
                                       (SEQ ID NO: 82)
EVQLVESGGGLVQPGGSLRLSCAVSGIDLSGYYMNWVRQAPGKGLEWVGV

IGINGATYYASWAKGRFTISRDNSKTTVYLQMNSLRAEDTAVYFCARGDI

WGQGTLVTVSS

Ab6 Heavy chain (humanized) Full length protein
sequence - yeast produced (US20120294797)
                                       (SEQ ID NO: 83)
EVQLVESGGGLVQPGGSLRLSCAVSGIDLSGYYMNWVRQAPGKGLEWVGV

IGINGATYYASWAKGRFTISRDNSKTTVYLQMNSLRAEDTAVYFCARGDI

WGQGTLVTVSSASTKGPSVFPLAPSSKSTSGGTAALGCLVKDYFPEPVTV

SWNSGALTSGVHTFPAVLQSSGLYSLSSVVTVPSSSLGTQTYICNVNHKP

SNTKVDARVEPKSCDKTHTCPPCPAPELLGGPSVFLFPPKPKDTLMISRT

PEVTCVVVDVSHEDPEVKFNWYVDGVEVHNAKTKPREEQYASTYRVVSVL

TVLHQDWLNGKEYKCKVSNKALPAPIEKTISKAKGQPREPQVYTLPPSRE

EMTKNQVSLTCLVKGFYPSDIAVEWESNGQPENNYKTTPPVLDSDGSFFL

YSKLTVDKSRWQQGNVFSCSVMHEALHNHYTQKSLSLSPGK

Ab6 Variable region Light chain (humanized)
protein sequence CDR1 (US20120294797)
                                       (SEQ ID NO: 84)
QASQSVYHNTYLA Ab6 Variable region Light chain (humanized)
protein sequence CDR2 (US20120294797)
                                       (SEQ ID NO: 85)
DASTLAS Ab6 Variable region Light chain (humanized)
protein sequence CDR3 (US20120294797)
                                       (SEQ ID NO: 86)
LGSYDCTNGDCFV Ab6 Variable region heavy chain (humanized)
protein sequence CDR1 (US20120294797)
                                       (SEQ ID NO: 87)
GYYMN Ab6 Variable region heavy chain (humanized)
protein sequence CDR2 (US20120294797)
                                       (SEQ ID NO: 88)
IGINGATYYASWAKG Ab6 Variable region heavy chain (humanized)
protein sequence CDR3 (US20120294797)
                                       (SEQ ID NO: 89)
GDI Light chain variable region protein sequence CDR3
(US20110305711)
                                       (SEQ ID NO: 90)
QQGDALPPT Light chain variable region protein sequence CDR1
(US20110305711)
                                       (SEQ ID NO: 91)
RASKDISKYL Light chain variable region protein sequence CDR2
(US20110305711)
                                       (SEQ ID NO: 92)
YTSGYHS Heavy chain variable region protein sequence CDR1
(US20110305711)
                                       (SEQ ID NO: 93)
GYTFGNYWMQ Heavy chain variable region protein sequence CDR2
(US20110305711)
                                       (SEQ ID NO: 94)
AIYEGTGKTVYIQKFAD Heavy chain variable region protein sequence CDR3
(US20110305711)
                                       (SEQ ID NO: 95)
LSDYVSGFGY Light chain variable region protein sequence
(US20110305711)
                                       (SEQ ID NO: 96)
DIQMTQSPSSLSASVGDRVTITCRASKDISKYLNWYQQKPGKAPKLLIYY

TSGYHSGVPSRFSGSGSGTDFTLTISSLQPEDFATYYCQQGDALPPTFGG

GTKVEIK
```

Heavy chain variable region protein sequence
(US20110305711)
(SEQ ID NO: 97)
QVQLVQSGAEVKKPGSSVKVSCKASGYTFGNYWMQWVRQAPGQGLEWMGA

IYEGTGKTVYIQKFADRVTITADKSTSTAYMELSSLRSEDTAVYYCARLS

DYVSGFGYWGQGTTVTVSS

Light chain protein sequence (US20110305711)
(SEQ ID NO: 98)
DIQMTQSPSSLSASVGDRVTITCRASKDISKYLNWYQQKPGKAPKLLIYY

TSGYHSGVPSRFSGSGSGTDFTLTISSLQPEDFATYYCQQGDALPPTFGG

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

Heavy chain protein sequence (US20110305711)
(SEQ ID NO: 99)
QVQLVQSGAEVKKPGSSVKVSCKASGYTFGNYWMQWVRQAPGQGLEWMGA

IYEGTGKTVYIQKFADRVTITADKSTSTAYMELSSLRSEDTAVYYCARLS

DYVSGFGYWGQGTTVTVSSASTKGPSVFPLAPCSRSTSESTAALGCLVKD

YFPEPVTVSWNSGALTSGVHTFPAVLQSSGLYSLSSVVTVPSSSLGTKTY

TCNVDHKPSNTKVDKRVESKYGPPCPPCPAPEAAGGPSVFLFPPKPKDTL

MISRTPEVTCVVVDVSQEDPEVQFNWYVDGVEVHNAKTKPREEQFNSTYR

VVSVLTVLHQDWLNGKEYKCKVSNKGLPSSIEKTISKAKGQPREPQVYTL

PPSQEEMTKNQVSLTCLVKGFYPSDIAVEWESNGQPENNYKTTPPVLDSD

GSFFLYSRLTVDKSRWQEGNVFSCSVMHEALHNHYTQKSLSLSLG

In some embodiments, the antibody comprises a modified constant region, such as a constant region that is immunologically inert described herein.

The binding affinity ($K_D$) of an anti-CGRP antagonist antibody to CGRP (such as human α-CGRP) can be about 0.02 to about 200 nM. In some embodiments, the binding affinity is any of about 200 nM, about 100 nM, about 50 nM, about 10 nM, about 1 nM, about 500 pM, about 100 pM, about 60 pM, about 50 pM, about 20 pM, about 15 pM, about 10 pM, about 5 pM, or about 2 pM. In some embodiments, the binding affinity is less than any of about 250 nM, about 200 nM, about 100 nM, about 50 nM, about 10 nM, about 1 nM, about 500 pM, about 100 pM, or about 50 pM.

In some embodiments, an anti-CGRP receptor antibody can be used in any of the methods described herein. For example, anti-CGRP receptor antibodies, as described in U.S. Patent Publication Nos. US 2010/0172895 and U.S. Pat. No. 9,102,731, which are hereby incorporated by reference in their entireties, may be used. Therefore, antibodies with any of the following sequences may be used.

Light chain variable region protein sequence CDR1
(U.S. Pat. No. 9,102,731)
(SEQ ID NO: 100)
SGSSSNIGNNYVS Light chain variable region protein sequence CDR2
(U.S. Pat. No. 9,102,731)
(SEQ ID NO: 101)
DNNKRPS Light chain variable region protein sequence CDR3
(U.S. Pat. No. 9,102,731)
(SEQ ID NO: 102)
GTWDSRLSAVV Heavy chain variable region protein sequence CDR1
(U.S. Pat. No. 9,102,731)
(SEQ ID NO: 103)
SFGMH Heavy chain variable region protein sequence CDR2
(U.S. Pat. No. 9,102,731)
(SEQ ID NO: 104)
VISFDGSIKYSVDSVKG Heavy chain variable region protein sequence CDR3
(U.S. Pat. No. 9,102,731)
(SEQ ID NO: 105)
DRLNYYDSSGYYHYKYYGMAV Light chain variable region protein sequence (U.S. Pat. No. 9,102,731)
(SEQ ID NO: 106)
QSVLTQPPSVSAAPGQKVTISCSGSSSNIGNNYVSWYQQLPGTAPKLLIY

DNNKRPSGIPDRFSGSKSGTSTTLGITGLQTGDEADYYCGTWDSRLSAVV

FGGGTKLTVL

Heavy chain variable region protein sequence (U.S. Pat. No. 9,102,731)
(SEQ ID NO: 107)
QVQLVESGGGVVQPGRSLRLSCAASGFTFSSFGMHWVRQAPGKGLEWVAV

ISFDGSIKYSVDSVKGRFTISRDNSKNTLFLQMNSLRAEDTAVYYCARDR

LNYYDSSGYYHYKYYGMAVWGQGTTVTVSS

Light chain protein sequence (U.S. Pat. No. 9,102,731)
(SEQ ID NO: 108)
MDMRVPAQLLGLLLLWLRGARCQSVLTQPPSVSAAPGQKVTISCSGSSSN

IGNNYVSWYQQLPGTAPKLLIYDNNKRPSGIPDRFSGSKSGTSTTLGITG

LQTGDEADYYCGTWDSRLSAVVFGGGTKLTVLGQPKANPTVTLFPPSSEE

LQANKATLVCLISDFYPGAVTVAWKADGSPVKAGVETTKPSKQSNNKYAA

SSYLSLTPEQWKSHRSYSCQVTHEGSTVEKTVAPTECS

Heavy chain protein sequence (U.S. Pat. No. 9,102,731)
(SEQ ID NO: 109)
MDMRVPAQLLGLLLLWLRGARCQVQLVESGGGVVQPGRSLRLSCAASGFT

FSSFGMHWVRQAPGKGLEWVAVISFDGSIKYSVDSVKGRFTISRDNSKNT

LFLQMNSLRAEDTAVYYCARDRLNYYDSSGYYHYKYYGMAVWGQGTTVTV

SSASTKGPSVFPLAPCSRSTSESTAALGCLVKDYFPEPVTVSWNSGALTS

GVHTFPAVLQSSGLYSLSSVVTVPSSNFGTQTYTCNVDHKPSNTKVDKTV

ERKCCVECPPCPAPPVAGPSVFLFPPKPKDTLMISRTPEVTCVVVDVSHE

DPEVQFNWYVDGVEVHNAKTKPREEQFNSTFRVVSVLTVVHQDWLNGKEY

KCKVSNKGLPAPIEKTISKTKGQPREPQVYTLPPSREEMTKNQVSLTCLV

KGFYPSDIAVEWESNGQPENNYKTTPPMLDSDGSFFLYSKLTVDKSRWQQ

GNVFSCSVMHEALHNHYTQKSLSLSPGK

C. Antibody G1 and Related Antibodies, Polypeptides, Polynucleotides, Vectors and Host Cells Provided herein are methods of reducing headache frequency in a patient, including using compositions (e.g., pharmaceutical compositions), comprising antibody G1 and its variants shown in Table 5 or polypeptide derived from antibody G1 and its variants shown in Table 5; and polynucleotides comprising sequences encoding G1 and its variants or the polypeptide. In some embodiments, the compositions used in the methods provided herein comprise one or more antibodies or polypeptides (which may or may not be an antibody) that bind to CGRP, and/or one or more polynucleotides comprising sequences encoding one or more antibodies or polypeptides that bind to CGRP. These compositions may further comprise suitable excipients, such as pharmaceutically acceptable excipients including buffers, which are well known in the art.

Anti-CGRP antagonist antibodies and polypeptides useful in the methods described herein may be characterized by any (one or more) of the following characteristics: (a) ability to bind to CGRP; (b) ability to block CGRP from binding to its receptor(s); (c) ability to block or decrease CGRP receptor activation (including cAMP activation); (d) ability to inhibit CGRP biological activity or downstream pathways mediated by CGRP signaling function; (e) ability to prevent, ameliorate, or treat any aspect of headache (e.g., migraine); (f) ability to increase clearance of CGRP; and (g) ability to inhibit (reduce) CGRP synthesis, production or release.

Useful in the methods described herein are any of the following, or compositions (including pharmaceutical compositions) comprising any of the following: (a) antibody G1 or its variants shown in Table 5; (b) a fragment or a region of antibody G1 or its variants shown in Table 5; (c) a light chain of antibody G1 or its variants shown in Table 5; (d) a heavy chain of antibody G1 or its variants shown in Table 5; (e) one or more variable region(s) from a light chain and/or a heavy chain of antibody G1 or its variants shown in Table 5; (f) one or more CDR(s) (one, two, three, four, five or six CDRs) of antibody G1 or its variants shown in Table 5; (g) CDR H3 from the heavy chain of antibody G1; (h) CDR L3 from the light chain of antibody G1 or its variants shown in Table 5; (i) three CDRs from the light chain of antibody G1 or its variants shown in Table 5; (j) three CDRs from the heavy chain of antibody G1 or its variants shown in Table 5; (k) three CDRs from the light chain and three CDRs from the heavy chain, of antibody G1 or its variants shown in Table 5; and (1) an antibody comprising any one of (b) through (k). In some instances, the methods include using polypeptides comprising any one or more of the above.

The CDR portions of antibody G1 (including Chothia and Kabat CDRs) are diagrammatically depicted in FIG. 5. Determination of CDR regions is well within the skill of the art. Skilled practitioners will appreciate that CDRs can be a combination of the Kabat and Chothia CDR (also termed "combined CDRs" or "extended CDRs"). In some instances, the CDRs are the Kabat CDRs, and in others the CDRs are the Chothia CDRs. In other words, in some instances where more than one CDR are useful, the CDRs may be any of Kabat, Chothia, combination CDRs, or combinations thereof.

Methods described herein can employ a polypeptide (which may or may not be an antibody) which comprises at least one CDR, at least two, at least three, or at least four, at least five, or all six CDRs that are substantially identical to at least one CDR, at least two, at least three, at least four, at least five or all six CDRs of G1 or its variants shown in Table 5. The methods can include using antibodies which have at least two, three, four, five, or six CDR(s) that are substantially identical to at least two, three, four, five or six CDRs of G1 or derived from G1. In some instances, the at least one, two, three, four, five, or six CDR(s) are at least about 85%, 86%, 87%, 88%, 89%, 90%, 95%, 96%, 97%, 98%, or 99% identical to at least one, two, three, four, five or six CDRs of G1 or its variants shown in Table 5.

Methods provided herein can utilize a polypeptide (which may or may not be an antibody) which comprises an amino acid sequence of G1 or its variants shown in Table 5 that has any of the following: at least 5 contiguous amino acids, at least 8 contiguous amino acids, at least about 10 contiguous amino acids, at least about 15 contiguous amino acids, at least about 20 contiguous amino acids, at least about 25 contiguous amino acids, at least about 30 contiguous amino acids of a sequence of G1 or its variants shown in Table 5, wherein at least 3 of the amino acids are from a variable region of G1 (FIG. 5) or its variants shown in Table 5. For example, the variable region can be from a light chain of G1 or a heavy chain of G1. An exemplary polypeptide has contiguous amino acid (lengths described above) from both the heavy and light chain variable regions of G1. In another embodiment, the 5 (or more) contiguous amino acids are from a complementarity determining region (CDR) of G1 shown in FIG. 5. In some embodiments, the contiguous amino acids are from a variable region of G1.

The binding affinity ($K_D$) of an anti-CGRP antagonist antibody and polypeptide to CGRP, as used in the methods provided herein, (such as human α-CGRP) can be about 0.06 to about 200 nM. For example, the binding affinity can be any of about 200 nM, 100 nM, about 50 nM, about 10 nM, about 1 nM, about 500 pM, about 100 pM, about 60 pM, about 50 pM, about 20 pM, about 15 pM, about 10 pM, about 5 pM, or about 2 pM. In other examples, the binding affinity is less than any of about 250 nM, about 200 nM, about 100 nM, about 50 nM, about 10 nM, about 1 nM, about 500 pM, about 100 pM, or about 50 pM.

The methods provided herein may use single chain variable region fragments ("scFv") of antibodies described herein, such as G1. Single chain variable region fragments are made by linking light and/or heavy chain variable regions by using a short linking peptide. Bird et al. (1988) *Science* 242:423-426.

Humanized antibody comprising one or more CDRs of antibody G1 or its variants shown in Table 5, or one or more CDRs derived from antibody G1 or its variants shown in Table 5 can be made using any methods known in the art.

In some instances, methods described herein can employ using antibody G1 comprising modifications such as those shown in Table 5, including functionally equivalent antibodies which do not significantly affect their properties and variants which have enhanced or decreased activity and/or affinity. For example, the amino acid sequence of antibody G1 or its variants shown in Table 5 may be mutated to obtain an antibody with the desired binding affinity to CGRP. Examples of modified polypeptides include polypeptides with conservative substitutions of amino acid residues, one or more deletions or additions of amino acids which do not significantly deleteriously change the functional activity, or use of chemical analogs.

Modifications also include glycosylated and nonglycosylated polypeptides, as well as polypeptides with other post-translational modifications, such as, for example, glycosylation with different sugars, acetylation, and phosphorylation. Techniques to achieve this type of modification are well known in the art.

Compositions (such as a pharmaceutical compositions) comprising polynucleotides encoding polypeptides described herein can be used in the presently described methods. In some instances, the composition can include an expression vector comprising a polynucleotide encoding a G1 antibody and/or any of the antibodies or polypeptides described herein. For example, the composition can include either or both of the polynucleotides shown in SEQ ID NO:9 and SEQ ID NO:10. Useful expression vectors, and methods of administering polynucleotide compositions are known in the art and further described herein.

D. Compositions

In some embodiments, compositions used in a method provided herein comprise an effective amount of an anti-CGRP antibody or an antibody-derived polypeptide described herein. A composition (e.g., a medicament or therapeutic formulation) can further comprise pharmaceutically acceptable carriers, excipients, or stabilizers (Remington: The Science and practice of Pharmacy 20th Ed. (2000) Lippincott Williams and Wilkins, Ed. K. E. Hoover). Acceptable carriers, excipients, or stabilizers are nontoxic to recipients at the dosages and concentrations employed.

An antibody (e.g., an anti-CGRP antagonist or an anti-CGRP receptor antibody) and compositions thereof provided herein can also be used in conjunction with other agents that serve to enhance and/or complement the effectiveness of the antibody.

E. Kits

Also provided herein are kits for use in the instant methods. Kits can include one or more containers comprising an antibody described herein (e.g., an anti-CGRP antagonist antibody (such as a humanized antibody)) or polypeptide described herein, and instructions for use in accordance with any of the methods described herein. Generally, these instructions comprise a description of administration of the antibody to select and treat a patient according to any of the methods described herein. For example, the kit may comprise a description of how to select a patient suitable for treatment based on identifying whether that patient has headache (e.g., a headache of intracranial origin) mediated by activation and sensitization of HT neurons. In still other embodiments, the instructions include a description of how to administer a monoclonal antibody (e.g., anti-CGRP antagonist antibody) to the patient to reduce the frequency of headache.

Accordingly, a kit can include, e.g., a pre-filled syringe, pre-filled syringe with a needle safety device, injection pen, or auto-injector comprising a dose of a monoclonal antibody that modulates the calcitonin gene related peptide (CGRP) pathway; and instructions to determine whether a patient's headache is mediated by the activation of high-threshold (HT) neurons. Alternatively or in addition, the instructions may instruct to determine whether a patient exhibits hyperalgesia, reducible by administering a monoclonal antibody that modulates (e.g., blocks, inhibits, suppresses or reduces) the CGRP pathway, and/or to determine whether a patient's headaches are primarily experienced in a portion of the head (e.g., one-side periorbital, one-side temporal, or one eye).

Another exemplary kit may comprise a monoclonal antibody that modulates the CGRP pathway and detailed instructions on how to administer QST to a patient or instructions on conducting a patient questionnaire and analyzing the responses to determine whether the patients headache is primarily experienced in a portion of the head (e.g., one-side periorbital, one-side temporal, or one eye).

In addition to instructions relating to the identification of responders, the kits may further comprise instructions for further treatment with a monoclonal antibody (e.g., anti-CGRP antagonist or receptor antibody), including information relating to dosage, dosing schedule, and route of administration for the intended treatment (e.g., instructions to achieve reduction in headache frequency once a patient is identified as a responder according to the instructions of the kit).

In a kit provided herein, a monoclonal antibody provided in a kit can include a CDR H1 as set forth in SEQ ID NO:3; a CDR H2 as set forth in SEQ ID NO:4; a CDR H3 as set forth in SEQ ID NO:5; a CDR L1 as set forth in SEQ ID NO:6; a CDR L2 as set forth in SEQ ID NO:7; and a CDR L3 as set forth in SEQ ID NO:8. In some embodiments, a monoclonal antibody provided in a kit comprises a heavy chain variable region comprising or consisting of the amino acid sequence as set forth in SEQ ID NO:1, and a light chain variable region comprising or consisting of the amino acid sequence as set forth in SEQ ID NO:2. In some embodiments, a monoclonal antibody provided in a kit comprises a heavy chain comprising or consisting of the amino acid sequence as set forth in SEQ ID NO:11, and a light chain comprising or consisting of the amino acid sequence as set forth in SEQ ID NO:12.

Alternatively or in addition, a monoclonal antibody provided in a kit can include a CDR H1 as set forth in SEQ ID NO:87; a CDR H2 as set forth in SEQ ID NO:88; a CDR H3 as set forth in SEQ ID NO:89; a CDR L1 as set forth in SEQ ID NO:84; a CDR L2 as set forth in SEQ ID NO:85; and a CDR L3 as set forth in SEQ ID NO:86. In some embodiments, a monoclonal antibody provided in a kit comprises a heavy chain variable region comprising or consisting of the amino acid sequence as set forth in SEQ ID NO:82, and a light chain variable region comprising or consisting of the amino acid sequence as set forth in SEQ ID NO:80. In some embodiments, a monoclonal antibody provided in a kit comprises a heavy chain comprising or consisting of the amino acid sequence as set forth in SEQ ID NO:83, and a light chain comprising or consisting of the amino acid sequence as set forth in SEQ ID NO:81.

Alternatively or in addition, a monoclonal antibody provided in a kit can include a CDR H1 as set forth in SEQ ID NO:93; a CDR H2 as set forth in SEQ ID NO:94; a CDR H3 as set forth in SEQ ID NO:95; a CDR L1 as set forth in SEQ ID NO:91; a CDR L2 as set forth in SEQ ID NO:92; and a CDR L3 as set forth in SEQ ID NO:90. In some embodiments, a monoclonal antibody provided in a kit comprises a heavy chain variable region comprising or consisting of the amino acid sequence as set forth in SEQ ID NO:97, and a light chain variable region comprising or consisting of the amino acid sequence as set forth in SEQ ID NO:96. In some embodiments, a monoclonal antibody provided in a kit comprises a heavy chain comprising or consisting of the amino acid sequence as set forth in SEQ ID NO:99, and a light chain comprising or consisting of the amino acid sequence as set forth in SEQ ID NO:98.

Alternatively or in addition, a monoclonal antibody provided in a kit can include a CDR H1 as set forth in SEQ ID NO:103; a CDR H2 as set forth in SEQ ID NO:104; a CDR H3 as set forth in SEQ ID NO:105; a CDR L1 as set forth in SEQ ID NO:100; a CDR L2 as set forth in SEQ ID NO:101; and a CDR L3 as set forth in SEQ ID NO:102. In some embodiments, a monoclonal antibody provided in a kit comprises a heavy chain variable region comprising or consisting of the amino acid sequence as set forth in SEQ ID NO:107, and a light chain variable region comprising or consisting of the amino acid sequence as set forth in SEQ ID NO:106. In some embodiments, a monoclonal antibody provided in a kit comprises a heavy chain comprising or consisting of the amino acid sequence as set forth in SEQ ID NO:109, and a light chain comprising or consisting of the amino acid sequence as set forth in SEQ ID NO:108.

A monoclonal antibody provided in a kit can be fremanezumab, eptinezumab, galcanezumab, erenumab, or any bioequivalent thereof. Skilled practitioners will appreciate that a kit can include a combination of any of the foregoing antibodies The kits of this invention can be provided in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is an anti-CGRP antagonist antibody and/or a monoclonal antibody that modulates the CGRP pathway. The container may further comprise a second pharmaceutically active agent.

Kits may optionally provide additional components such as buffers and interpretive information. Normally, the kit comprises a container and a label or package insert(s) on or associated with the container.

The following Examples are provided to illustrate but not limit the invention. It is understood that the examples and embodiments described herein are for illustrative purposes only and that various modifications or changes in light thereof will be suggested to persons skilled in the art and are to be included within the spirit and purview of this application. All publications, patents, and patent applications cited herein are hereby incorporated by reference in their entirety for all purposes to the same extent as if each individual publication, patent or patent application were specifically and individually indicated to be so incorporated by reference.

EXAMPLES

Example 1: Generation and Characterization of Monoclonal Antibodies Directed Against CGRP Generation of anti-CGRP antibodies. To generate anti-CGRP antibodies that have cross-species reactivity for rat and human CGRP, mice were immunized with 25-100 μg of human α-CGRP or β-CGRP conjugated to KLH in adjuvant (50 μl per footpad, 100 μl total per mouse) at various intervals. Immunization was generally performed as described in Geerligs H J et al., 1989, *J. Immunol. Methods* 124:95-102; Kenney J S et al., 1989, *J. Immunol. Methods* 121:157-166; and Wicher K et al., 1989, *Int. Arch. Allergy Appl. Immunol.* 89:128-135. Mice were first immunized with 50 μg of human α-CGRP or β-CGRP conjugated to KLH in CFA (complete Freund's adjuvant). After 21 days, mice were secondly immunized with 25 μg of human β-CGRP (for mice first immunized with human α-CGRP) or α-CGRP (for mice first immunized with human (3-CGRP) conjugated to KLH in IFA (incomplete Freund's adjuvant). Twenty-three days later after the second immunization, third immunization was performed with 25 μg of rat α-CGRP conjugated to KLH in IFA. Ten days later, antibody titers were tested using ELISA. Forth immunization was performed with 25 μg of the peptide (rat α-CGRP-KLH) in IFA 34 days after the third immunization. Final booster was performed with 100 μg soluble peptide (rat α-CGRP) 32 days after the forth immunization.

Splenocytes were obtained from the immunized mouse and fused with NSO myeloma cells at a ratio of 10:1, with polyethylene glycol 1500. The hybrids were plated out into 96-well plates in DMEM containing 20% horse serum and 2-oxaloacetate/pyruvate/insulin (Sigma), and hypoxanthine/aminopterin/thymidine selection was begun. On day 8, 100 μl of DMEM containing 20% horse serum was added to all the wells. Supernatants of the hybrids were screened by using antibody capture immunoassay. Determination of antibody class was done with class-specific second antibodies.

A panel of monoclonal antibody-producing cell lines was selected based on their binding to human and rat CGRP for further characterization. These antibodies and characteristics are shown below in Tables 1 and 2.

Purification and Fab fragment preparation. Monoclonal antibodies selected for further characterization were purified from supernatants of hybridoma cultures using protein A affinity chromatography. The supernatants were equilibrated to pH 8. The supernatants were then loaded to the protein A column MabSelect (Amersham Biosciences #17-5199-02) equilibrated with PBS to pH 8. The column was washed with 5 column volumes of PBS, pH 8. The antibodies were eluted with 50 mM citrate-phosphate buffer, pH 3. The eluted antibodies were neutralized with 1 M Phosphate Buffer, pH 8. The purified antibodies were dialyzed with PBS, pH 7.4. The antibody concentrations were determined by SDS-PAGE, using a murine monoclonal antibody standard curve.

Fabs were prepared by papain proteolysis of the full antibodies using Immunopure Fab kit (Pierce #44885) and purified by flow through protein A chromatography following manufacturer instructions. Concentrations were determined by ELISA and/or SDS-PAGE electrophoresis using a standard Fab of known concentration (determined by amino acid analysis), and by A280 using 1OD=0.6 mg/ml (or theoretical equivalent based on the amino acid sequence).

Affinity determination of the Fabs. Affinities of the anti-CGRP monoclonal antibodies were determined at either 25° C. or 37° C. using the BIACORE3000$^3$ surface plasmon resonance (SPR) system (Biacore, INC, Piscataway N.J.) with the manufacture's own running buffer, HBS-EP (10 mM HEPES pH 7.4, 150 mM NaCl, 3 mM EDTA, 0.005% v/v polysorbate P20). Affinity was determined by capturing N-terminally biotinylated CGRP peptides (custom ordered from GenScript Corporation, New Jersey or Global Peptide Services, Colorado) via pre-immobilized streptavidin on SA chip and measuring binding kinetics of antibody Fab titrated across the CGRP surface. Biotinylated CGRP was diluted into HBS-EP and injected over the chip at a concentration of less than 0.001 mg/ml. Using variable flow time across the individual chip channels, two ranges of antigen density were achieved: <50 response units (RU) for detailed kinetic studies and about 800 RU for concentration studies and screening. Two- or three-fold serial dilutions typically at concentrations spanning 1 μM-0.1 nM (aimed at 0.1-10× estimated K$_D$) of purified Fab fragments were injected for 1 minute at 100 μL/min and dissociation times of 10 minutes were allowed. After each binding cycle, surfaces were regenerated with 25 mM NaOH in 25% v/v ethanol, which was tolerated over hundreds of cycles. Kinetic association rate (k$_{on}$) and dissociation rate (k$_{off}$) were obtained simultaneously by fitting the data to a 1:1 Langmuir binding model (Karlsson et al. (1994). *Methods Enzymology* 6. 99-110) using the BIAevaluation program. Global equilibrium dissociation constants (K$_D$) or "affinities" were calculated from the ratio $K_D = k_{off}/k_{on}$. Affinities of the murine Fab fragments are shown in Tables 1 and 2.

Epitope mapping of the murine anti-CGRP antibodies. To determine the epitope that anti-CGRP antibodies bind on human α-CGRP, binding affinities of the Fab fragments to various CGRP fragments were measured as described above by capturing N-terminally biotinylated CGRP fragments amino acids 19-37 and amino acids 25-37 on a SA sensor chip. FIG. 1 shows their binding affinities measured at 25° C. As shown in FIG. 1, all antibodies, except antibody 4901, bind to human α-CGRP fragments 19-37 and 25-37 with affinity similar to their binding affinity to full length human α-CGRP (1-37). Antibody 4901 binds to human α-CGRP fragment 25-37 with six-fold lower affinity than binding to full length human α-CGRP fragment, due mainly to a loss in off-rate. The data indicate that these anti-CGRP antibodies generally bind to the C-terminal end of CGRP.

Alanine scanning was performed to further characterize amino acids in human α-CGRP involved in binding of anti-CGRP antibodies. Different variants of human α-CGRP with single alanine substitutions were generated by peptide synthesis. Their amino acid sequences are shown in Table 3 along with all the other peptides used in the Biacore analysis. Affinities of Fab fragments of the anti-CGRP antibodies to these variants were determined using Biacore as described above. As shown in FIG. 1, all 12 antibodies target a C-terminal epitope, with amino acid F37 being the most crucial residue. Mutation of F37 to alanine significantly lowered the affinity or even completely knocked out binding of the anti-CGRP antibodies to the peptide. The next most important amino acid residue is G33, however, only the high affinity antibodies (7E9, 8B6, 10A8, and 7D11) were affected by alanine replacement at this position. Amino acid residue S34 also plays a significant, but lesser, role in the binding of these four high affinity antibodies.

TABLE 1

Characteristics of the anti-CGRP monoclonal antibodies' binding to human α-CGRP and their antagonist activity

| Antibodies | $K_D$ to human α-CGRP at 25° C. (nM) | $K_D$ to human α-CGRP at 37° C. (nM) | Cell-based blocking human α-CGRP binding to its receptor at 25° C. (measured by cAMP activation) | $IC_{50}$ (nM binding sites) at 25° C. (room temp.) measured in radioligand binding assay. |
|---|---|---|---|---|
| 7E9 | 1.0 | 0.9 | Yes | 2.5 |
| 8B6 | 1.1 | 1.2 | Yes | 4.0 |
| 10A8 | 2.1 | 3.0 | Yes | n.d. |
| 7D11 | 4.4 | 5.4 | Yes | n.d. |
| 6H2 | 9.3 | 42 | Yes | 12.9 |
| 4901 | 61 | 139 | Yes | 58 |
| 14E10 | 80 | 179 | Yes | n.d. |
| 9B8 | 85 | 183 | No | n.d. |
| 13C2 | 94 | 379 | No | n.d. |
| 14A9 | 148 | 581 | No | n.d. |
| 6D5 | 210 | 647 | No | n.d. |
| 1C5 | 296 | 652 | No | n.d. |

Note:
Antibody 4901 is commercially available (Sigma, Product No. C7113).
n.d. = not determined

TABLE 2

Characteristics of the anti-CGRP monoclonal antibodies' binding to rat α-CGRP and antagonist activity

| Antibodies | $K_D$ to rat α-CGRP at 37° C. (nM) | Cell-based blocking of binding of rat α-CGRP to its receptor at 25° C. (measured by cAMP activation) | In vivo blocking in saphenous nerve assay |
|---|---|---|---|
| 4901 | 3.4 | Yes | Yes |
| 7E9 | 47 | Yes | Yes |
| 6H2 | 54 | No | No |
| 8B6 | 75 | Yes | Yes |
| 7D11 | 218 | Yes | Yes |
| 10A8 | 451 | No | n.d. |
| 9B8 | 876 | No | n.d. |
| 14E10 | 922 | No | n.d. |
| 13C2 | >1000 | No | n.d. |
| 14A9 | >1000 | No | n.d. |
| 6D5 | >1000 | No | n.d. |
| 1C5 | >1000 | No | n.d. |

"n.d." indicates no test was performed for the antibody.

TABLE 3

Amino acid sequences of human α-CGRP fragments (SEQ ID NOS: 15-40) and related peptides (SEQ ID NOS: 41-47). All peptides are C-terminally amidated except SEQ ID NOS: 36-40. Residues in bold indicate point mutations.

| CGRP | Amino acid sequence | SEQ ID NO |
|---|---|---|
| 1-37 (WT) | ACDTATCVTHRLAGLLSRSGGVVKNNFVPTNVGSKAF | 15 |
| 8-37 | VTHRLAGLLSRSGGVVKNNFVPTNVGSKAF | 16 |
| 19-37 | SGGVVKNNFVPTNVGSKAF | 17 |
| P29A (19-37) | SGGVVKNNFVATNVGSKAF | 18 |

TABLE 3-continued

Amino acid sequences of human α-CGRP fragments (SEQ ID NOS: 15-40) and related peptides (SEQ ID NOS: 41-47). All peptides are C-terminally amidated except SEQ ID NOS: 36-40. Residues in bold indicate point mutations.

| CGRP | Amino acid sequence | SEQ ID NO |
|---|---|---|
| K35A (19-37) | SGGVVKNNFVPTNVGSAAF | 19 |
| K35E (19-37) | SGGVVKNNFVPTNVGSEAF | 20 |
| K35M (19-37) | SGGVVKNNFVPTNVGSMAF | 21 |
| K35Q (19-37) | SGGVVKNNFVPTNVGSQAF | 22 |
| F37A (19-37) | SGGVVKNNFVPTNVGSKAA | 23 |
| 25-38A | NNFVPTNVGSKAFA | 24 |
| 25-37 | NNFVPTNVGSKAF | 25 |
| F27A (25-37) | NNAVPTNVGSKAF | 26 |
| V28A (25-37) | NNFAPTNVGSKAF | 27 |
| P29A (25-37) | NNFVATNVGSKAF | 28 |
| T30A (25-37) | NNFVPANVGSKAF | 29 |
| N31A (25-37) | NNFVPTAVGSKAF | 30 |
| V32A (25-37) | NNFVPTNAGSKAF | 31 |
| G33A (25-37) | NNFVPTNVASKAF | 32 |
| S34A (25-37) | NNFVPTNVGAKAF | 33 |
| F37A (25-37) | NNFVPTNVGSKAA | 34 |
| 26-37 | NFVPTNVGSKAF | 35 |
| 19-37-COOH | SGGVVKNNFVPTNVGSKAF | 36 |
| 19-36-COOH | SGGVVKNNFVPTNVGSKA | 37 |
| 1-36-COOH | ACDTATCVTHRLAGLLSRSGGVVKNNFVPTNVGSKA | 38 |
| 1-19-COOH | ACDTATCVTHRLAGLLSRS | 39 |
| 1-13-COOH | ACDTATCVTHRLA | 40 |
| rat α (1-37) | SCNTATCVTHRLAGLLSRSGGVVKDNFVPTNVGSEAF | 41 |
| rat α (19-37) | SGGVVKDNFVPTNVGSEAF | 42 |
| human β (1-37) | ACNTATCVTHRLAGLLSRSGGMVKSNFVPTNVGSKAF | 43 |
| rat β (1-37) | SCNTATCVTHRLAGLLSRSGGVVKDNFVPTNVGSKAF | 44 |
| Human calcitonin (1-32) | CGNLSTCMLGTYTQDFNKFHTFPQTAIGVGAP | 45 |
| Human amylin (1-37) | KCNTATCATQRLANFLVHSSNNFGAILSSTNVGSNTY | 46 |
| Human adrenomedullin (1-52) | YRQSMNNFQGLRSFGCRFGTCTVQKLAHQIYQFTDKDKDNVAPRSKISPQGY | 47 |

Example 2: Screening of Anti-CGRP Antagonist Antibodies Using In Vitro Assays Murine anti-CGRP antibodies were further screened for antagonist activity in vitro using cell based cAMP activation assay and binding assay.

Antagonist activity measured by cAMP assay. Five microliters of human or rat α-CGRP (final concentration 50 nM) in the presence or absence of an anti-CGRP antibody (final concentration 1-3000 nM), or rat α-CGRP or human α-CGRP (final concentration 0.1 nM-10 μM; as a positive control for c-AMP activation) was dispensed into a 384-well plate (Nunc, Cat. No. 264657). Ten microliters of cells (human SK-N-MC if human α-CGRP is used, or rat L6 from ATCC if rat α-CGRP is used) in stimulation buffer (20 mM HEPES, pH 7.4, 146 mM NaCl, 5 mM KCl, 1 mM $CaCl_2$), 1 mM $MgCl_2$, and 500 μM 3-Isobutyl-1-methylxanthine (IBMX)) were added into the wells of the plate. The plate was incubated at room temperature for 30 minutes.

After the incubation, cAMP activation was performed using HitHunter™ Enzyme Fragment Complementation Assay (Applied Biosystems) following manufacture's instruction. The assay is based on a genetically engineered β-galactosidase enzyme that consists of two fragments-termed Enzyme Acceptor (EA) and Enzyme Donor (ED). When the two fragments are separated, the enzyme is inactive. When the fragments are together they can recombine spontaneously to form active enzyme by a process called complementation. The EFC assay platform utilizes an ED-cAMP peptide conjugate in which cAMP is recognized by anti-cAMP. This ED fragment is capable of reassociation with EA to form active enzyme. In the assay, anti-cAMP antibody is optimally titrated to bind ED-cAMP conjugate and inhibit enzyme formation. Levels of cAMP in cell lysate samples compete with ED-cAMP conjugate for binding to the anti-cAMP antibody. The amount of free ED conjugate in the assay is proportional to the concentration of cAMP. Therefore, cAMP is measured by the formation of active enzyme that is quantified by the turnover of β-galactosidase luminescent substrate. The cAMP activation assay was performed by adding 10 μl of lysis buffer and anti-cAMP antibody (1:1 ratio) following by incubation at room temperature for 60 min. Then 10 μl of ED-cAMP reagent was added into each well and incubated for 60 minutes at room temperature. After the incubation, 20 μl of EA reagent and CL mixture (containing the substrate) (1:1 ratio) was added into each well and incubated for 1-3 hours or overnight at room temperature. The plate was read at 1 second/well on PMT instrument or 30 seconds/place on imager. The antibodies that inhibit activation of cAMP by α-CGRP were identified (referred to as "yes") in Tables 1 and 2 above. Data in Tables 1 and 2 indicate that antibodies that demonstrated antagonist activity in the assay generally have high affinity. For example, antibodies having $K_D$ (determined at 25° C.) of about 80 nM or less to human α-CGRP or having $K_D$ (determined at 37° C.) of about 47 nM or less to rat α-CGRP showed antagonist activity in this assay.

Radioligand binding assay. Binding assay was performed to measure the $IC_{50}$ of anti-CGRP antibody in blocking the CGRP from binding to the receptor as described previously. Zimmermann et al., *Peptides* 16:421-4, 1995; Mallee et al., *J. Biol. Chem.* 277:14294-8, 2002. Membranes (25 μg) from SK-N-MC cells were incubated for 90 min at room temperature in incubation buffer (50 mM Tris-HCl, pH 7.4, 5 mM $MgCl_2$, 0.1% BSA) containing 10 pM $^{125}$I-human α-CGRP in a total volume of 1 mL. To determine inhibition concentrations ($IC_{50}$), antibodies or unlabeled CGRP (as a control), from a about 100 fold higher stock solution were dissolved at varying concentrations in the incubation buffer and incubated at the same time with membranes and 10 pM $^{125}$I-human α-CGRP. Incubation was terminated by filtration through a glass microfiber filter (GF/B, 1 μm) which had been blocked with 0.5% polyethylemimine. Dose response curves were plotted and $K_i$ values were determined by using the equation: $K_i = IC_{50}/(1+([ligand]/K_D))$; where the equilibrium dissociation constant $K_D=8$ pM for human α-CGRP to CGRP1 receptor as present in SK-N-MC cells, and $B_{max}=0.025$ pmol/mg protein. The reported $IC_{50}$ value (in terms of IgG molecules) was converted to binding sites (by multiplying it by 2) so that it could be compared with the affinities ($K_D$) determined by Biacore (see Table 1).

Table 1 shows the $IC_{50}$ of murine antibodies 7E9, 8B6, 6H2 and 4901. Data indicate that antibody affinity generally correlates with $IC_{50}$: antibodies with higher affinity (lower $K_D$ values) have lower $IC_{50}$ in the radioligand binding assay.

Example 3: Effect of Anti-CGRP Antagonist Antibodies on Skin Vasodilatation Induced by Stimulation of Rat Saphenous Nerve To test antagonist activity of anti-CGRP antibodies, effect of the antibodies on skin vasodilatation by stimulation of rat saphenous nerve was tested using a rat model described previously. Escott et al., *Br. J. Pharmacol.* 110:772-776, 1993. In this rat model, electrical stimulation of saphenous nerve induces release of CGRP from nerve endings, resulting in an increase in skin blood flow. Blood flow in the foot skin of male Sprague Dawley rats (170-300 g, from Charles River Hollister) was measured after saphenous nerve stimulation. Rats were maintained under anesthesia with 2% isoflurane. Bretylium tosylate (30 mg/kg, administered i.v.) was given at the beginning of the experiment to minimize vasoconstriction due to the concomitant stimulation of sympathetic fibers of the saphenous nerve. Body temperature was maintained at 37° C. by the use of a rectal probe thermostatically connected to a temperature controlled heating pad. Compounds including antibodies, positive control (CGRP 8-37), and vehicle (PBS, 0.01% Tween 20) were given intravenously through the right femoral vein, except for the experiment shown in FIG. 3, the test compound and the control were injected through tail vein, and for experiments shown in FIGS. 2A and 2B, antibodies 4901 and 7D11 were injected intraperitoneally (IP). Positive control compound CGRP 8-37 (vasodilatation antagonist), due to its short half-life, was given 3-5 min before nerve stimulation at 400 nmol/kg (200 μl). Tan et al., *Clin. Sci.* 89:656-73, 1995. The antibodies were given in different doses (1 mg/kg, 2.5 mg/kg, 5 mg/kg, 10 mg/kg, and 25 mg/kg).

Figure 2B:
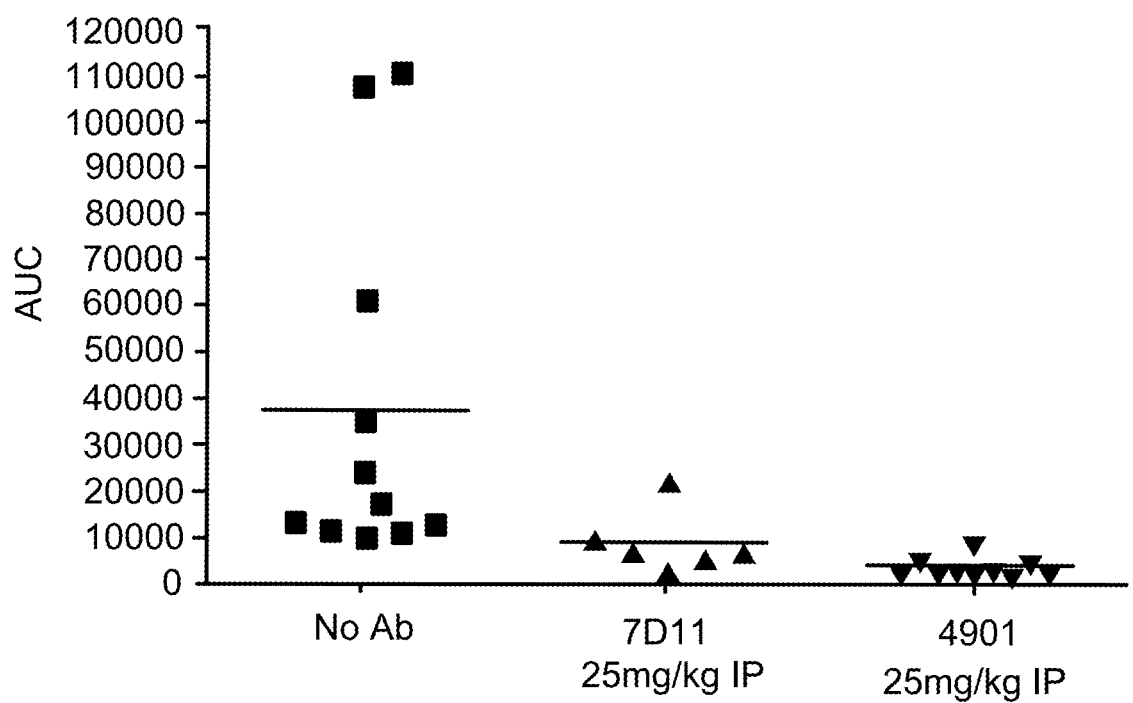

For experiments shown in FIGS. 2A and 2B, antibody 4901 (25 mg/kg), antibody 7D11 (25 mg/kg), or vehicle control (PBS with 0.01% Tween 20) was administered intraperitoneally (IP) 72 hours before the electrical pulse stimulation. For experiment shown in FIG. 3, antibody 4901 (1 mg/kg, 2.5 mg/kg, 5 mg/kg, or 25 mg/kg) or vehicle control (PBS with 0.01% Tween 20) was administered intravenously 24 hours before the electrical pulse stimulation. After administration of the antibodies or vehicle control, the saphenous nerve of the right hindlimb was exposed surgically, cut proximally and covered with plastic wrap to prevent drying. A laser Doppler probe was placed over the medio-dorsal side of the hindpaw skin, which is the region innervated by the saphenous nerve. Skin blood flow, measured as blood cell flux, was monitored with a laser Doppler flow meter. When a stable base-line flux (less than 5% variation) was established for at least 5 minutes, the nerve was placed over platinum bipolar electrodes and electrically stimulated with 60 pulses (2 Hz, 10 V, 1 ms, for 30 seconds) and then again 20 minutes later. Cumulative change in skin blood flow was estimated by the area under the flux-time curve (AUC, which is equal to change in flux multiplied by change in time) for each flux response to electrical pulse stimulation. The average of the blood flow response to the two stimulations was taken. Animals were kept under anesthesia for a period of one to three hours.

Figure 3:
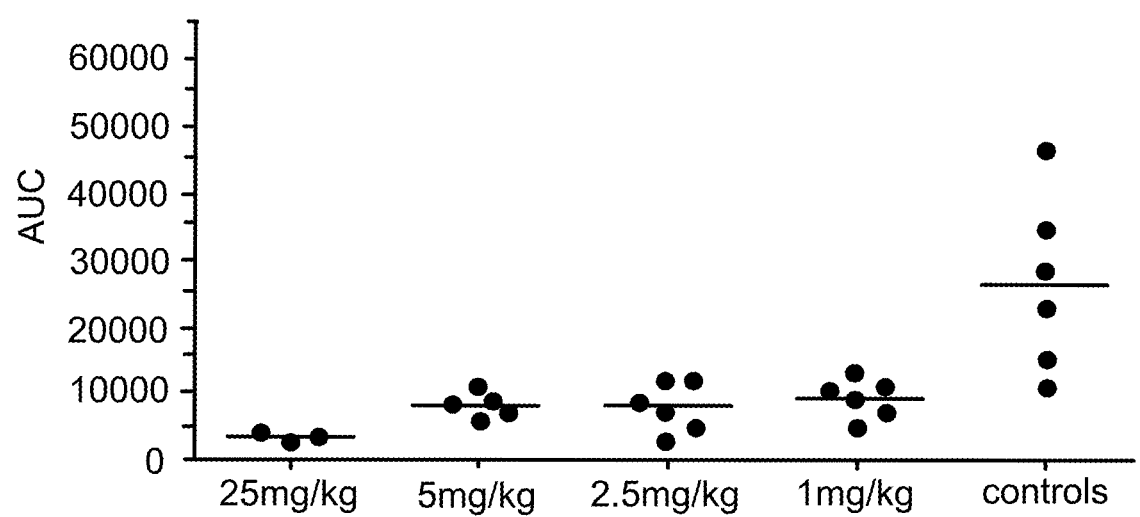
FIG. 3 shows the effect of administering different dosages of antibody 4901 (25 mg/kg, 5 mg/kg, 2.5 mg/kg, or 1 mg/kg) on skin blood flow measured as blood cell flux after electrical pulse stimulation for 30 seconds. Antibodies were administered intravenously (IV) 24 hours before electrical pulse stimulation. Each point in the graph represents AUC of one rat treated under the conditions as indicated. The line in the graph represents average AUC of rats treated under the condition as indicated.

As shown in FIG. 2A and FIG. 2B, blood flow increase stimulated by applying electronic pulses on saphenous nerve was inhibited by the presence of CGRP 8-37 (400 nmol/kg, administered i.v.), antibody 4901 (25 mg/kg, administered ip), or antibody 7D11 (25 mg/kg, administered ip) as compared to the control. CGRP 8-37 was administered 3-5 minutes before the saphenous nerve stimulation; and antibodies were administered 72 hours before the saphenous nerve stimulation. As shown in FIG. 3, blood flow increase stimulated by applying electronic pulses on saphenous nerve was inhibited by the presence of antibody 4901 at different doses (1 mg/kg, 2.5 mg/kg, 5 mg/kg, and 25 mg/kg) administered intravenously at 24 hours before the saphenous nerve stimulation.

Figure 4A:
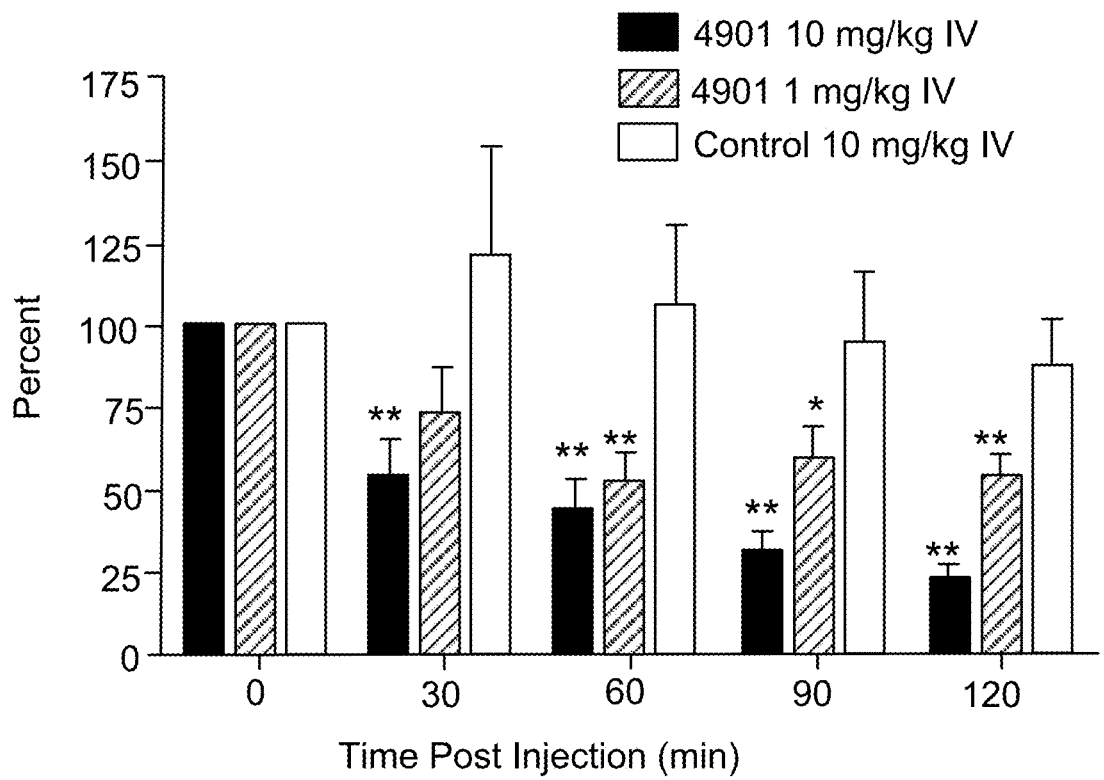
FIGS. 4A and 4B show the effect of administering antibody 4901 (1 mg/kg or 10 mg/kg, i.v.), antibody 7E9 (10 mg/kg, i.v.), and antibody 8B6 (10 mg/kg, i.v.) on skin blood flow measured as blood cell flux after electrical pulse stimulation for 30 seconds. Antibodies were administered intravenously (i.v.) followed by electrical pulse stimulation at 30 min, 60 min, 90 min, and 120 min after antibody administration. Y axis represents percent of AUC as compared to level of AUC when no antibody was administered (time 0). X axis represents time (minutes) period between the administration of antibodies and electrical pulse stimulation. "*" indicates $P<0.05$, and "**" indicates $P<0.01$, as compared to time 0. Data were analyzed using one-way ANOVA with a Dunnett's Multiple comparison test.
Figure 4B:
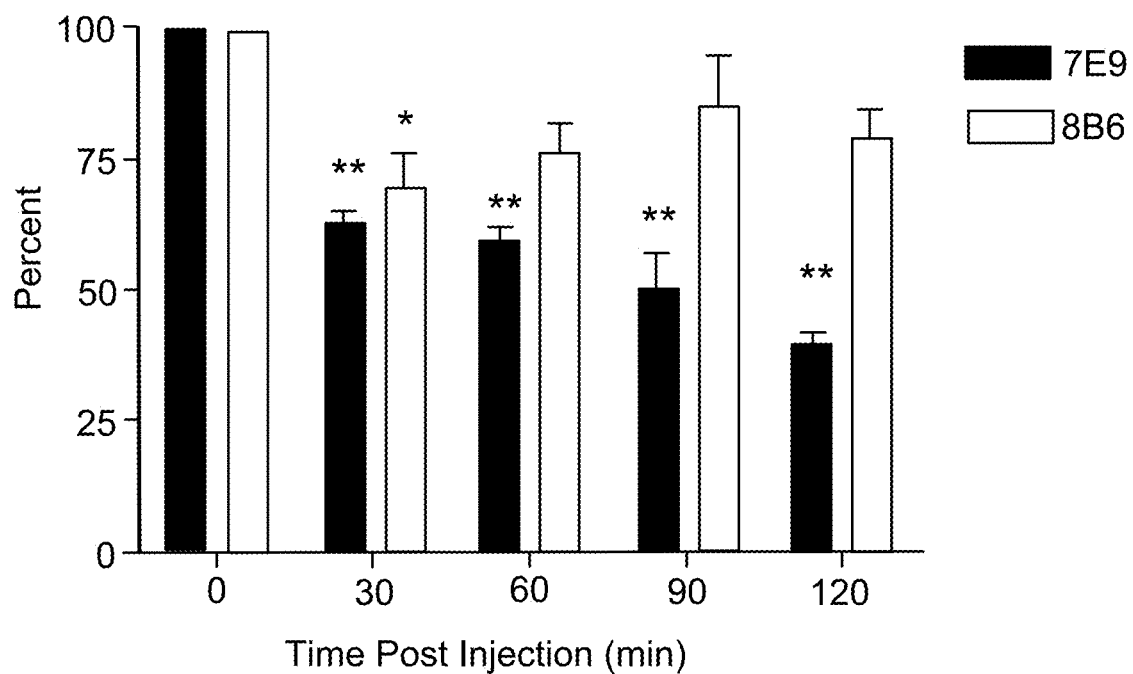

For experiments shown in FIGS. 4A and 4B, saphenous nerve was exposed surgically before antibody administration. The saphenous nerve of the right hindlimb was exposed surgically, cut proximally and covered with plastic wrap to prevent drying. A laser Doppler probe was placed over the medio-dorsal side of the hindpaw skin, which is the region innervated by the saphenous nerve. Skin blood flow, measured as blood cell flux, was monitored with a laser Doppler flow meter. Thirty to forty-five minutes after bretylium tosylate injection, when a stable base-line flux (less than 5% variation) was established for at least 5 minutes, the nerve was placed over platinum bipolar electrodes and electrically stimulated (2 Hz, 10V, 1 ms, for 30 seconds) and again 20 minutes later. The average of the blood flow flux response to these two stimulations was used to establish the baseline response (time 0) to electrical stimulation. Antibody 4901 (1 mg/kg or 10 mg/kg), antibody 7E9 (10 mg/kg), antibody 8B6 (10 mg/kg), or vehicle (PBS with 0.01% Tween 20) were then administered intravenously (i.v.). The nerve was subsequently stimulated (2 Hz, 10V, 1 ms, for 30 sec) at 30 minutes, 60 minutes, 90 minutes, and 120 minutes after antibody or vehicle administration. Animals were kept under anesthesia for a period of approximately three hours. Cumulative change in skin blood flow was estimated by the area under the flux-time curve (AUC, which is equal to change in flux multiplied by change in time) for each flux response to electrical pulse stimulations.

As shown in FIG. 4A, blood flow increase stimulated by applying electronic pulses on saphenous nerve was significantly inhibited by the presence of antibody 4901 1 mg/kg administered i.v., when electronic pulse stimulation was applied at 60 minutes, 90 minutes, and 120 minutes after the antibody administration, and blood flow increase stimulated by applying electronic pulses on saphenous nerve was significantly inhibited by the presence of antibody 4901 10 mg/kg administered i.v., when electronic pulse stimulation was applied at 30 minutes, 60 minutes, 90 minutes, and 120 minutes after the antibody administration. FIG. 4B shows that blood flow increase stimulated by applying electronic pulses on saphenous nerve was significantly inhibited by the presence of antibody 7E9 (10 mg/kg, administered i.v.) when electronic pulse stimulation was applied at 30 min, 60 min, 90 min, and 120 min after antibody administration, and by the presence of antibody 8B6 (10 mg/kg, administered i.v.) when electronic pulse stimulation was applied at 30 min after antibody administration.

These data indicate that antibodies 4901, 7E9, 7D11, and 8B6 are effective in blocking CGRP activity as measured by skin vasodilatation induced by stimulation of rat saphenous nerve.

Example 4. Characterization of Anti-CGRP Antibody G1 and its Variants

Amino acid sequences for the heavy chain variable region and light chain variable region of anti-CGRP antibody G1 are shown in FIG. 5. The following methods were used for expression and characterization of antibody G1 and its variants.

Expression vector used. Expression of the Fab fragment of the antibodies was under control of an IPTG inducible lacZ promoter similar to that described in Barbas (2001) Phage display: a laboratory manual, Cold Spring Harbor, N.Y., Cold Spring Harbor Laboratory Press pg. 2.10. Vector pComb3x), however, modifications included addition and expression of the following additional domains: the human Kappa light chain constant domain and the CH1 constant domain of IgG2 human immunoglobulin, Ig gamma-2 chain C region, protein accession number P01859; Immunoglobulin kappa light chain (*Homo sapiens*), protein accession number CAA09181.

Small scale Fab preparation. From *E. coli* transformed (either using electroporation-competent TG1 cells or chemically-competent Top 10 cells) with a Fab library, single colonies were used to inoculate both a master plate (agar LB+carbenicillin (50 µg/mL)+2% glucose) and a working plate (2 mL/well, 96-well/plate) where each well contained 1.5 mL LB+carbenicillin (50 µg/mL)+2% glucose. A gas permeable adhesive seal (ABgene, Surrey, UK) was applied to the plate. Both plates were incubated at 30° C. for 12-16 hours; the working plate was shaken vigorously. The master plate was stored at 4° C. until needed, while the cells from the working plate were pelleted (4000 rpm, 4° C., 20 minutes) and resuspended in 1.0 mL LB+carbenicillin (50 µg/mL)+0.5 mM IPTG to induce expression of Fabs by vigorous shaking for 5 hours at 30° C. Induced cells were centrifuges at 4000 rpm, 4° C. for 20 minutes and resuspended in 0.6 mL Biacore HB-SEP buffer (10 mM HEPES pH 7.4, 150 mM NaCl, 3 mM EDTA, 0.005% v/v P20). Lysis of HB-SEP resuspended cells was accomplished by freezing (−80° C.) and then thawing at 37° C. Cell lysates were centrifuged at 4000 rpm, 4° C. for 1 hour to separate the debris from the Fab-containing supernatants, which were subsequently filtered (0.2 µm) using a Millipore MultiScreen Assay System 96-Well Filtration Plate and vacuum manifold. Biacore was used to analyze filtered supernatants by injecting them across CGRPs on the sensor chip. Affinity-selected clones expressing Fabs were rescued from the master plate, which provided template DNA for PCR, sequencing, and plasmid preparation.

Large scale Fab preparation. To obtain kinetic parameters, Fabs were expressed on a larger scale as follows. Erlenmeyer flasks containing 150 mL LB+carbenicillin (50 µg/mL)+2% glucose were inoculated with 1 mL of a "starter" overnight culture from an affinity-selected Fab-expressing *E. coli* clone. The remainder of the starter culture (~3 mL) was used to prepare plasmid DNA (QIAprep mini-prep, Qiagen kit) for sequencing and further manipulation. The large culture was incubated at 30° C. with vigorous shaking until an $OD_{600\ nm}$ of 1.0 was attained (typically 12-16 h). The cells were pelleted by centrifuging at 4000 rpm, 4° C. for 20 minutes, and resuspended in 150 mL LB+carbenicillin (50 µg/mL)+0.5 mM IPTG. After 5 hours expression at 30° C., cells were pelleted by centrifuging at 4000 rpm, 4° C. for 20 minutes, resuspended in 10 mL Biacore HBS-EP buffer, and lysed using a single freeze (−80° C.)/thaw (37° C.) cycle. Cell lysates were pelleted by centrifuging at 4000 rpm, 4° C. for one hour, and the supernatant was collected and filtered (0.2 um). Filtered supernatants were loaded onto Ni-NTA superflow sepharose (Qiagen, Valencia, Calif.) columns equilibrated with PBS, pH 8, then washed with 5 column volumes of PBS, pH 8. Individual Fabs eluted in different fractions with PBS (pH 8)+300 mM Imidazole. Fractions containing Fabs were pooled and dialyzed in PBS, then quantified by ELISA prior to affinity characterization.

Full antibody preparation. For expression of full antibodies, heavy and light chain variable regions were cloned in mammalian expression vectors and transfected using lipofectamine into HEK 293 cells for transient expression. Antibodies were purified using protein A using standard methods.

Vector pDb.CGRP.hFcGI is an expression vector comprising the heavy chain of the G1 antibody, and is suitable for transient or stable expression of the heavy chain. Vector pDb.CGRP.hFcGI has nucleotide sequences corresponding to the following regions: the murine cytomegalovirus promoter region (nucleotides 7-612); a synthetic intron (nucleotides 613-1679); the DHFR coding region (nucleotides 688-1253); human growth hormone signal peptide (nucleotides 1899-1976); heavy chain variable region of G1 (nucleotides 1977-2621); human heavy chain IgG2 constant region containing the following mutations: A330P331 to S330S331 (amino acid numbering with reference to the wildtype IgG2 sequence; see Eur. J. Immunol. (1999) 29:2613-2624). Vector pDb.CGRP.hFcGI was deposited at the ATCC on Jul. 15, 2005, and was assigned ATCC Accession No. PTA-6867.

Vector pEb.CGRP.hKGI is an expression vector comprising the light chain of the G1 antibody, and is suitable for transient expression of the light chain. Vector pEb.CGRP.hKGI has nucleotide sequences corresponding to the following regions: the murine cytomegalovirus promoter region (nucleotides 2-613); human EF-1 intron (nucleotides 614-1149); human growth hormone signal peptide (nucleotides 1160-1237); antibody G1 light chain variable region (nucleotides 1238-1558); human kappa chain constant region (nucleotides 1559-1882). Vector pEb.CGRP.hKGI was deposited at the ATCC on Jul. 15, 2005, and was assigned ATCC Accession No. PTA-6866.

Biacore assay for affinity determination. Affinities of G1 monoclonal antibody and its variants were determined at either 25° C. or 37° C. using the BIACORE3000³ surface plasmon resonance (SPR) system (Biacore, INC, Piscataway N.J.). Affinity was determined by capturing N-terminally biotinylated CGRP or fragments via pre-immobilized streptavidin (SA sensor chip) and measuring the binding kinetics of antibody G1 Fab fragments or variants titrated across the CGRP or fragment on the chip. All Biacore assays were conducted in HBS-EP running buffer (10 mM HEPES pH 7.4, 150 mM NaCl, 3 mM EDTA, 0.005% v/v polysorbate P20). CGRP surfaces were prepared by diluting the N-biotinylated CGRP to a concentration of less than 0.001 mg/mL into HBS-EP buffer and injecting it across the SA sensor chip using variable contact times. Low capacity surfaces, corresponding to capture levels <50 response units (RU) were used for high-resolution kinetic studies, whereas high capacity surfaces (about 800 RU of captured CGRP) were used for concentration studies, screening, and solution affinity determinations. Kinetic data were obtained by diluting antibody G1 Fab serially in two- or three-fold increments to concentrations spanning 1 uM-0.1 nM (aimed at 0.1-10× estimated $K_D$). Samples were typically injected for 1 minute at 100 µL/min and dissociation times of at least 10 minutes were allowed. After each binding cycle, surfaces were regenerated with 25 mM NaOH in 25% v/v ethanol, which was tolerated over hundreds of cycles. An entire titration series (typically generated in duplicate) was fit globally to a 1:1 Langmuir binding model using the BIAevaluation program. This returned a unique pair of association and dissociation kinetic rate constants (respectively, $k_{on}$ and $k_{off}$) for each binding interaction, whose ratio gave the equilibrium dissociation constant ($K_D = k_{off}/k_{on}$). Affinities ($K_D$ values) determined in this way are listed in Tables 5 and 6.

High-resolution analysis of binding interactions with extremely slow offrates. For interactions with extremely slow offrates (in particular, antibody G1 Fab binding to human □-CGRP on the chip at 25° C.), affinities were obtained in a two-part experiment. The protocol described above was used with the following modifications. The association rate constant ($k_{on}$) was determined by injecting a 2-fold titration series (in duplicate) spanning 550 nM-1 nM for 30 seconds at 100 µL/min and allowing only a 30 second dissociation phase. The dissociation rate constant ($k_{off}$) was determined by injecting three concentrations (high, medium, and low) of the same titration series in duplicate for 30 seconds and allowing a 2-hour dissociation phase. The affinity ($K_D$) of each interaction was obtained by combining the $k_{on}$ and $k_{off}$ values obtained in both types of experiments, as shown in Table 4.

Determining solution affinity by Biacore. The solution affinity of antibody G1 for rat α-CGRP and F37A (19-37) human α-CGRP was measured by Biacore at 37° C. A high capacity CGRP chip surface was used (the high-affinity human α-CGRP was chosen for detection purposes) and HBS-EP running buffer was flowed at 5 µL/min. Antibody G1 Fab fragment at a constant concentration of 5 nM (aimed to be at or below the expected $K_D$ of the solution-based interaction) was pre-incubated with competing peptide, either rat α-CGRP or F37A (19-37) human α-CGRP, at final concentrations spanning 1 nM to 1 µM in 3-fold serial dilutions. Antibody G1 Fab solutions in the absence or presence of solution-based competing peptide, were injected across CGRP on the chip and the depletion of binding responses detected at the chip surface as a result of solution competition was monitored. These binding responses were converted to "free Fab concentrations" using a calibration curve, which was constructed by titrating antibody G1 Fab alone (5, 2.5, 1.25, 0.625, 0.325 and 0 nM) across the CGRP on the chip. "Free Fab concentrations" were plotted against the concentration of competing solution-based peptide used to generate each data point and fit to a solution affinity model using the BIAevaluation software. The solution affinities determined (indirectly) in this way are shown in Tables 4 and 6 and were used to validate the affinities obtained when Fabs are injected directly across N-biotinylated CGRPs on a SA chip. The close agreement between the affinities determined by these two methods confirms that tethering an N-biotinylated version of the CGRP to the chip does not alter its native solution binding activity.

Table 4 below shows the binding affinities of antibody G1 to human α-CGRP, human β-CGRP, rat α-CGRP, and rat β-CGRP determined by Biacore, by flowing Fab fragments across N-biotinylated CGRPs on a SA chip. To better resolve the affinities of binding interactions with extremely slow offrates, affinities were also determined in a two-part experiment to complement this assay orientation, the solution affinity of the rat α-CGRP interaction was also determined (as described above). The close agreement of the affinities measured in both assay orientations confirms that the binding affinity of the native rat α-CGRP in solution is not altered when it is N-biotinylated and tethered to a SA chip.

TABLE 4

Binding affinities of antibody G1 Fabs titrated across CGRPs on the chip

| CGRP on chip | Temp. (° C.) | $k_{on}$ (1/Ms) | $k_{off}$ (1/s) | $K_D$ (nM) |
|---|---|---|---|---|
| Human α-CGRP | 25 | $1.86 \times 10^5$ | $7.80 \times 10^{-6}$ | 0.042 (7%, n = 4)* |
| Human α-CGRP | 37 | $5.78 \times 10^5$ | $3.63 \times 10^{-5}$ | 0.063 (4%, n = 2)* |
| Human β-CGRP | 37 | $4.51 \times 10^5$ | $6.98 \times 10^{-5}$ | 0.155 |
| Rat α-CGRP | 25 | $5.08 \times 10^4$ | $6.18 \times 10^{-5}$ | 1.22 (12%, n = 2)* |
| Rat α-CGRP | 37 | $1.55 \times 10^5$ | $3.99 \times 10^{-4}$ | 2.57* (Solution $K_D$ = 10 50%, n = 4)** |
| Rat β-CGRP | 37 | $5.16 \times 10^5$ | $7.85 \times 10^{-5}$ | 0.152 |

*Affinities for α-CGRPS (rat and human) were determined in a high-resolution two-part experiment, in which the dissociation phase was monitored for 2 hours (the values for $k_{on}$, $k_{off}$, and $K_D$ represent the average of n replicate experiments with the standard deviation expressed as a percent variance). Affinities for β-CGRPs (rat and human) were determined by global analysis using only a 20-min dissociation phase, which was not accurate enough to quantify their extremely off-rates (their off-rates are likely slower than stated here and therefore their affinities are likely even higher). Antibody G1 Fab dissociated extremely slowly from all CGRPs (except α-rat CGRP) with off-rates that approached the resolution limit of the Biacore assay (especially at 25°C.).

**Solution affinity determined by measuring the depletion of binding responses detected at CGRP on the chip for antibody G1 Fab pre-incubated with solution-based rat α-CGRP competitor.

Table 5 below shows antibodies having the amino acid sequence variation as compared to antibody G1 and their affinities to both rat α-CGRP and human α-CGRP. All amino acid substitutions of the variants shown in Table 5 are described relative to the sequence of G1. The binding affinities of Fab fragments were determined by Biacore by flowing them across CGRPs on a SA chip.

TABLE 5

Amino acid sequences and binding affinity data for antibody G1 variants determined at 37° C. by Biacore.

| Clone | L1 | L2 | H2 | HC-FW3 | α-rat $k_{off}$ (1/s) | α-rat $K_D$ (nM) | α-human $k_{off}$ (1/s) | α-human $K_D$ (nM) |
|---|---|---|---|---|---|---|---|---|
| G1 | | | | | $3.99 \times 10^{-4}$ | 2.57 | $3.63 \times 10^{-5}$ | 0.063 |
| M1 | | | | A100L | $1.10 \times 10^{-3}$ | | $1.73 \times 10^{-4}$ | |
| M2 | | | | L99A A100R | $2.6 \times 10^{-3}$ | 58 | $3.1 \times 10^{-4}$ | 3 |
| M3 | | | | L99A A100S | $2.0 \times 10^{-3}$ | 61 | $2.1 \times 10^{-4}$ | 1.7 |
| M4 | | | | L99A A100V | $1.52 \times 10^{-3}$ | 84.4 | $6.95 \times 10^{-5}$ | 0.43 |
| M5 | | | | L99A A100Y | $7.35 \times 10^{-4}$ | 40.8 | $3.22 \times 10^{-5}$ | 0.20 |
| M6 | | | | L99N | $7.84 \times 10^{-4}$ | 43.6 | $1.33 \times 10^{-4}$ | 0.83 |
| M7 | | | | L99N A100C | $9.18 \times 10^{-4}$ | 51.0 | $2.43 \times 10^{-4}$ | 1.52 |
| M8 | | | | L99N A100G | $7.45 \times 10^{-4}$ | 41.4 | $9.20 \times 10^{-5}$ | 0.58 |
| M9 | | | | L99N A100Y | n.d. | n.d. | $1.00 \times 10^{-5}$ | 0.06 |
| M10 | | | | L99S A100S | $1.51 \times 10^{-3}$ | 83.9 | $1.73 \times 10^{-4}$ | 1.08 |
| M11 | | | | L99S A100T | $4.83 \times 10^{-3}$ | 268.3 | $2.83 \times 10^{-4}$ | 1.77 |
| M12 | | | | L99S A100V | $1.94 \times 10^{-3}$ | 107.8 | $1.01 \times 10^{-4}$ | 0.63 |
| M13 | | | | L99T A100G | $1.84 \times 10^{-3}$ | 102.2 | $1.86 \times 10^{-4}$ | 1.16 |
| M14 | | | | L99T A100K | n.d. | n.d. | $1.00 \times 10^{-5}$ | 0.06 |
| M15 | | | | L99T A100P | $1.15 \times 10^{-3}$ | 63.9 | $1.58 \times 10^{-5}$ | 0.10 |
| M16 | | | | L99T A100S | $9.96 \times 10^{-4}$ | 55.3 | $1.65 \times 10^{-4}$ | 1.03 |
| M17 | | | | L99T A100V | $2.06 \times 10^{-3}$ | 114.4 | $1.85 \times 10^{-4}$ | 1.16 |
| M18 | | | | L99V A100G | $1.22 \times 10^{-3}$ | 67.8 | $7.03 \times 10^{-5}$ | 0.44 |
| M19 | | | | L99V A100R | n.d. | n.d. | $1.00 \times 10^{-5}$ | 0.06 |
| M20 | R28W | | | L99R A100L | $1.44 \times 10^{-3}$ | 80.0 | $1.36 \times 10^{-4}$ | 0.85 |
| M21 | R28W | | | L99S | $6.95 \times 10^{-4}$ | 15.2 | $1.42 \times 10^{-4}$ | 1.23 |
| M22 | R28W | | | L99T | $1.10 \times 10^{-3}$ | 61.1 | $1.16 \times 10^{-4}$ | 0.73 |
| M23 | R28G | | | L99T A100V | $7.99 \times 10^{-4}$ | 44.4 | $1.30 \times 10^{-4}$ | 0.81 |

TABLE 5-continued

Amino acid sequences and binding affinity data for antibody G1 variants determined at 37° C. by Biacore.

| Clone | L1 | L2 | H2 | HC-FW3 | α-rat $k_{off}$ (1/s) | α-rat $K_D$ (nM) | α-human $k_{off}$ (1/s) | α-human $K_D$ (nM) |
|---|---|---|---|---|---|---|---|---|
| M24 | R28L | | | L99T A100V | $1.04 \times 10^{-3}$ | 57.8 | $1.48 \times 10^{-4}$ | 0.93 |
| M25 | R28N | | | L99T A100V | $\underline{1.4 \times 10^{-3}}$ | $\underline{76}$ | $\underline{1.4 \times 10^{-4}}$ | $\underline{1.3}$ |
| M26 | R28N | | A57G | L99T A100V | $9.24 \times 10^{-4}$ | 51.3 | $1.48 \times 10^{-4}$ | 0.93 |
| M27 | R28N T30A | | | L99T A100V | $3.41 \times 10^{-3}$ | 189.4 | $3.57 \times 10^{-4}$ | 2.23 |
| M28 | R28N T30D | | E54R A57N | L99T A100V | $1.25 \times 10^{-3}$ | 69.4 | $9.96 \times 10^{-5}$ | 0.62 |
| M29 | R28N T30G | | | L99T A100V | $3.59 \times 10^{-3}$ | 199.4 | $3.80 \times 10^{-4}$ | 2.38 |
| M30 | R28N T30G | | E54K A57E | L99T A100V | $6.38 \times 10^{-3}$ | 354.4 | $5.90 \times 10^{-4}$ | 3.69 |
| M31 | R28N T30G | | E54K A57G | L99T A100V | $3.61 \times 10^{-3}$ | 200.6 | $3.47 \times 10^{-4}$ | 2.17 |
| M32 | R28N T30G | | E54K A57H | L99T A100V | $2.96 \times 10^{-3}$ | 164.4 | $2.71 \times 10^{-4}$ | 1.69 |
| M33 | R28N T30G | | E54K A57N S58G | L99T A100V | $9.22 \times 10^{-3}$ | 512.2 | $7.50 \times 10^{-4}$ | 4.69 |
| M34 | R28N T30G | | E54K A57N S58T | L99T A100V | $2.17 \times 10^{-3}$ | 120.6 | $6.46 \times 10^{-4}$ | 4.04 |
| M35 | R28N T30G | | E54K A57S | L99T A100V | $3.99 \times 10^{-3}$ | 221.7 | $3.39 \times 10^{-4}$ | 2.12 |
| M36 | R28N T30R | | | L99T A100V | $4.79 \times 10^{-3}$ | 266.1 | $2.39 \times 10^{-4}$ | 1.49 |
| M37 | R28N T30S | | A57G | L99T A100V | $1.45 \times 10^{-3}$ | 80.6 | $2.26 \times 10^{-4}$ | 1.41 |
| M38 | R28N T30W | | | L99T A100V | $5.11 \times 10^{-3}$ | 283.9 | $2.18 \times 10^{-4}$ | 1.36 |
| M39 | R28N | G50A L56T | A57N S58Y | L99T A100V | $9.95 \times 10^{-3}$ | 552.8 | $4.25 \times 10^{-4}$ | 2.66 |
| M40 | R28N | G50A L56T | E54K A57L | L99T A100V | 0.36 | 20000.0 | $1.28 \times 10^{-3}$ | 8.00 |
| M41 | R28N | G50A L56T | E54K A57N E64D | L99T A100V | $4.53 \times 10^{-3}$ | 251.7 | $2.10 \times 10^{-4}$ | 1.31 |
| M42 | R28N | G50A L56T | E54K A57N H61F | L99T A100V | $7.52 \times 10^{-3}$ | 417.8 | $4.17 \times 10^{-4}$ | 2.61 |
| M43 | R28N | G50A L56T | E54K A57N S58C | L99T A100V | $4.53 \times 10^{-3}$ | 251.7 | $2.63 \times 10^{-4}$ | 1.64 |
| M44 | R28N | G50A L56T | E54K A57N S58E | L99T A100V | $\underline{6.13 \times 10^{-3}}$ | $\underline{443}$ | $\underline{2.10 \times 10^{-4}}$ | $\underline{2.05}$ |
| M45 | R28N | G50A L56T | E54K A57N S58E E64D | L99T A100V | $\underline{5.58 \times 10^{-3}}$ | $\underline{259}$ | $\underline{2.11 \times 10^{-4}}$ | $\underline{1.85}$ |
| M46 | R28N | G50A L56T | E54K A57N S58E H61F | L99T A100V | $2.94 \times 10^{-3}$ | 163.3 | $5.39 \times 10^{-4}$ | 3.37 |
| M47 | R28N | G50A L56T | E54K A57N S58G | L99T A100V | $8.23 \times 10^{-3}$ | 457.2 | $3.32 \times 10^{-4}$ | 2.08 |
| M48 | R28N | G50A L56T | E54K A57N S58L | L99T A100V | 0.0343 | 1905.6 | $8.42 \times 10^{-4}$ | 5.26 |
| M49 | R28N | G50A L56T | E54K A57N S58Y H61F | L99T A100V | 0.0148 | 822.2 | $5.95 \times 10^{-4}$ | 3.72 |
| M50 | R28N | G50A L56T | E54K A57R | L99T A100V | $5.30 \times 10^{-3}$ | 294.4 | $4.06 \times 10^{-4}$ | 2.54 |
| M51 | R28N | L56I | E54K A57G | L99T A100V | $1.18 \times 10^{-3}$ | 65.6 | $1.31 \times 10^{-4}$ | 0.82 |
| M52 | R28N | L56I | E54K A57N S58A | L99T A100V | $2.29 \times 10^{-3}$ | 127.2 | $2.81 \times 10^{-4}$ | 1.76 |

TABLE 5-continued

Amino acid sequences and binding affinity data for antibody G1 variants determined at 37° C. by Biacore.

| Clone | L1 | L2 | H2 | HC-FW3 | α-rat $k_{off}$ (1/s) | α-rat $K_D$ (nM) | α-human $k_{off}$ (1/s) | α-human $K_D$ (nM) |
|---|---|---|---|---|---|---|---|---|
| M53 | R28N | L56I | E54K A57N S58G | L99T A100V | $1.91 \times 10^{-3}$ | 106.1 | $3.74 \times 10^{-4}$ | 2.34 |
| M54 | R28N T30A | G50A | E54K A57N S58P | L99T A100V | $2.16 \times 10^{-3}$ | 120.0 | $1.79 \times 10^{-3}$ | 11.19 |
| M55 | R28N T30A | L56S | E54K A57N S58E E64D | L99T A100V | $5.85 \times 10^{-3}$ | 325.0 | $4.78 \times 10^{-4}$ | 2.99 |
| M56 | R28N T30D | L56S | E54K A57N H61F | L99T A100V | $9.35 \times 10^{-3}$ | 519.4 | $4.79 \times 10^{-4}$ | 2.99 |
| M57 | R28N T30D | L56S | E54K A57N S58E | L99T A100V | 0.0104 | 1,200 | $3.22 \times 10^{-4}$ | 3.08 |
| M58 | R28N T30D | L56S | E54K A57N S58I H61F | L99T A100V | No binding | n.d. | $1.95 \times 10^{-3}$ | 12.19 |
| M59 | R28N T30D | L56S | E54K A57N S58N H61F | L99T A100V | 0.0123 | 683.3 | $5.24 \times 10^{-4}$ | 3.28 |
| M60 | R28N T30D | L56S | E54K A57N S58R H61F | L99T A100V | 0.0272 | 1511.1 | $9.11 \times 10^{-4}$ | 5.69 |
| M61 | R28N T30G | A51H | E54Q A57N H61F | L99T A100V | $5.21 \times 10^{-3}$ | 289.4 | $4.59 \times 10^{-4}$ | 2.87 |
| M62 | R28N T30G | A51H L56T | E54K A57N S58E | L99T A100V | $5.75 \times 10^{-3}$ | 242 | $5.57 \times 10^{-4}$ | 5.86 |
| M63 | R28N T30G | G50A | E54K A57N S58T | L99T A100V | $2.65 \times 10^{-3}$ | 147.2 | $1.50 \times 10^{-3}$ | 9.38 |
| M64 | R28N T30G | G50A | E54K A57N S58V | L99T A100V | 0.0234 | 1300.0 | $1.32 \times 10^{-3}$ | 8.25 |
| M65 | R28N T30G | G50A | E54K A57C | L99T A100V | $4.07 \times 10^{-3}$ | 226.1 | $8.03 \times 10^{-4}$ | 5.02 |
| M66 | R28N T30G | L56I | E54K A57E | L99T A100V | $5.11 \times 10^{-3}$ | 283.9 | $5.20 \times 10^{-4}$ | 3.25 |
| M67 | R28N T30G | L56I | E54K A57F | L99T A100V | $1.71 \times 10^{-3}$ | 95.0 | $8.20 \times 10^{-4}$ | 5.13 |
| M68 | R28N T30G | L56I | E54K A57N S58D E64D | L99T A100V | $6.76 \times 10^{-3}$ | 375.6 | $4.28 \times 10^{-4}$ | 2.68 |
| M69 | R28N T30G | L56I | E54K A57N S58E | L99T A100V | $1.81 \times 10^{-3}$ | 100.6 | $7.33 \times 10^{-4}$ | 4.58 |
| M70 | R28N T30G | L56I | E54K A57S | L99T A100V | $6.07 \times 10^{-3}$ | 337.2 | $5.59 \times 10^{-4}$ | 3.49 |
| M71 | R28N T30G | L56I | E54K A57Y | L99T A100V | $2.12 \times 10^{-3}$ | 117.8 | $1.28 \times 10^{-3}$ | 8.00 |
| M72 | R28N T30G | L56S | E54K | L99T A100V | $3.95 \times 10^{-3}$ | 219.4 | $4.00 \times 10^{-4}$ | 2.50 |
| M73 | R28N T30G | L56S | E54K A57N S58Y E64D | L99T A100V | $3.00 \times 10^{-3}$ | 166.7 | $2.55 \times 10^{-4}$ | 1.59 |
| M74 | R28N T30G | L56S | E54K A57S | L99T A100V | $6.03 \times 10^{-3}$ | 335.0 | $5.97 \times 10^{-4}$ | 3.73 |
| M75 | R28N T30G | L56S | E54K A57V | L99T A100V | $1.87 \times 10^{-2}$ | 1038.9 | $1.16 \times 10^{-3}$ | 7.25 |
| M76 | R28N T30S | G50A L56T | A57G | L99T A100V | $1.16 \times 10^{-3}$ | 64.4 | $3.64 \times 10^{-4}$ | 2.28 |
| M77 | R28N T30S | G50A L56T | E54K A57D | L99T A100V | 0.0143 | 794.4 | $4.77 \times 10^{-4}$ | 2.98 |
| M78 | R28N T30S | G50A L56T | E54K A57N S58T | L99T A100V | 0.167 | 9277.8 | $1.31 \times 10^{-3}$ | 8.19 |

TABLE 5-continued

Amino acid sequences and binding affinity data for antibody G1 variants determined at 37° C. by Biacore.

| Clone | L1 | L2 | H2 | HC-FW3 | α-rat $k_{off}$ (1/s) | α-rat $K_D$ (nM) | α-human $k_{off}$ (1/s) | α-human $K_D$ (nM) |
|---|---|---|---|---|---|---|---|---|
| M79 | R28N T30S | G50A L56T | E54K A57P | L99T A100V | 0.19 | 10555.6 | $1.29 \times 10^{-3}$ | 8.06 |
| M80 | R28N T30S | L56I | E54K A57N S58V | L99T A100V | 0.0993 | 5516.7 | $2.09 \times 10^{-3}$ | 13.06 |
| M81 | R28N T30S | L56S | E54K A57N S58E | L99T A100V | $4.29 \times 10^{-3}$ | 238.3 | $4.90 \times 10^{-4}$ | 3.06 |
| M82 | R28N T30V | A51H L56T | A57N | L99T A100V | $6.99 \times 10^{-3}$ | 388.3 | $8.77 \times 10^{-4}$ | 5.48 |
| M83 | R28N T30V | A51H L56T | E54K A57N S58M H61F | L99T A100V | No binding | n.d. | $9.33 \times 10^{-4}$ | 5.83 |
| M84 | R28N T30V | A51H L56T | E54N A57N | L99T A100V | $1.76 \times 10^{-2}$ | 977.8 | $1.08 \times 10^{-3}$ | 6.75 |

Figure 6:
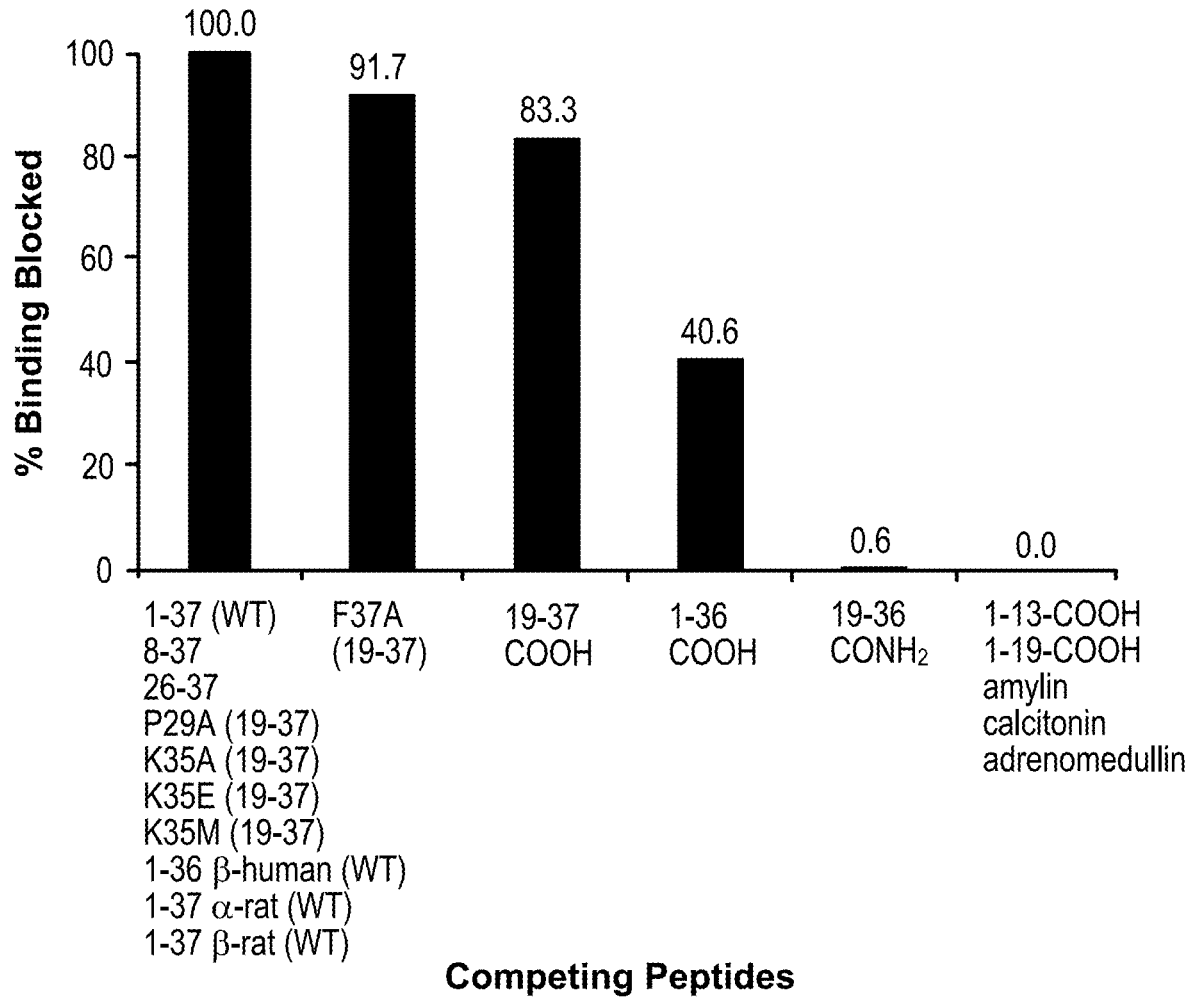
FIG. 6 shows epitope mapping of antibody G1 by peptide competition using Biacore. N-biotinylated human α-CGRP was captured on SA sensor chip. G1 Fab (50 nM) in the absence of a competing peptide or pre-incubated for 1 hour with 10 μM of a competing peptide was flowed onto the chip. Binding of G1 Fab to the human α-CGRP on the chip was measured. Y axis represents percentage of binding blocked by the presence of the competing peptide compared with the binding in the absence of the competing peptide.
Figure 7A:
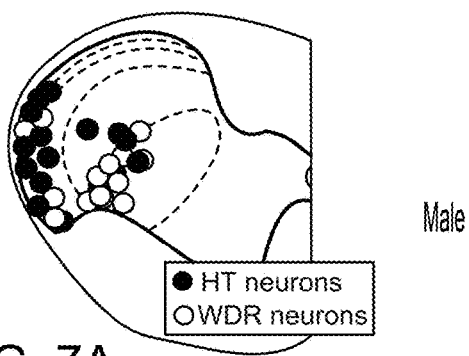
FIGS. 7A, 7B, 7C, 7D, 7E, 7F, 7G, 7H, 7I, and 7J show recording sites (FIGS. 7A and 7F), facial receptive fields (FIGS. 7B, 7D, 7G, and 7I), and dural receptive fields (FIGS. 7C, 7E, 7H, and 7J) of each of the 63 trigeminovascular neurons tested for effects of the CGRP-mAb (FIGS. 7A, 7B, 7C, 7F, 7G, and 7H, n=36) or the isotype-conAb (FIGS. 7D, 7E, 7I, and 7J, n=27) in male and female rats.
Figure 7B:
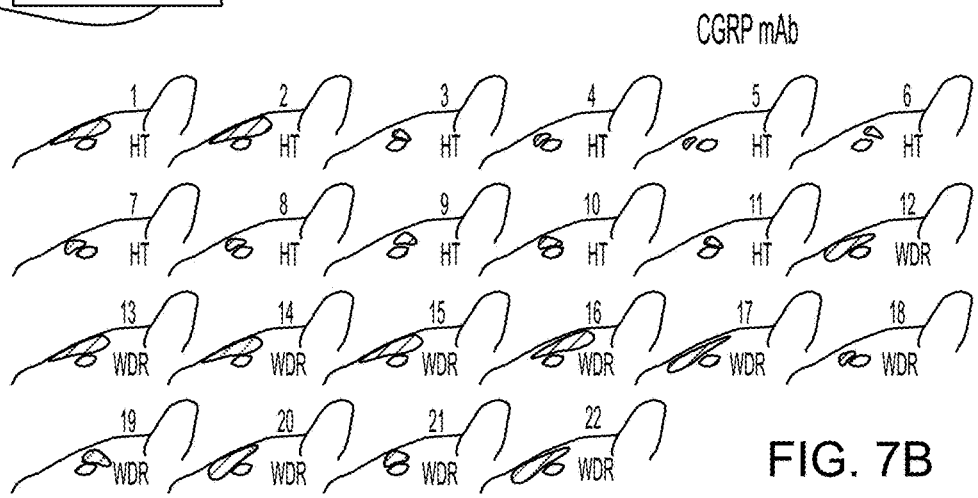
Figure 7C:
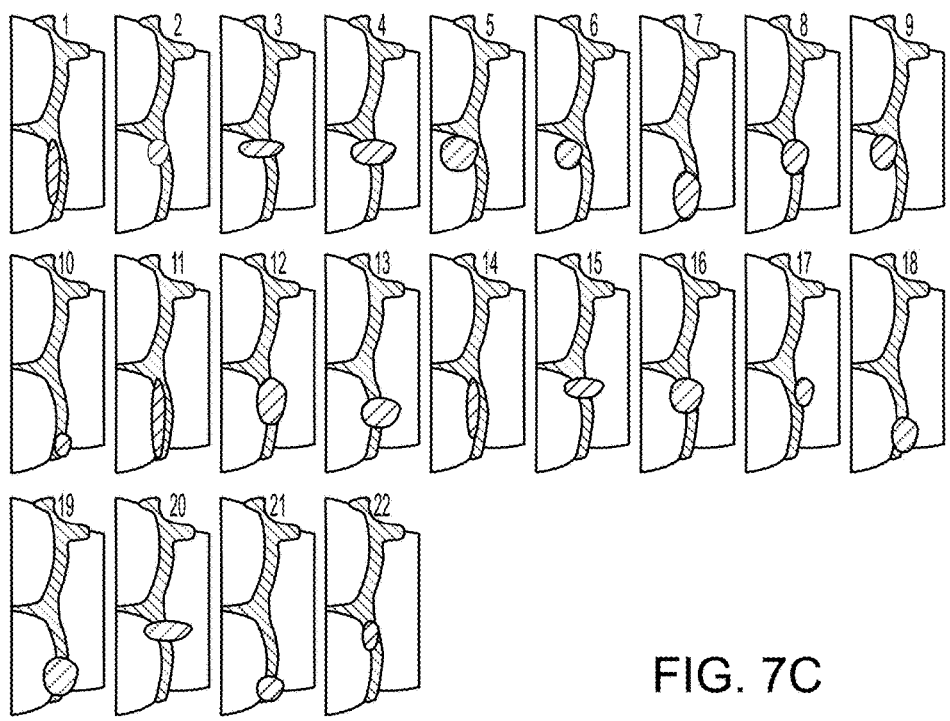
Figure 7D:
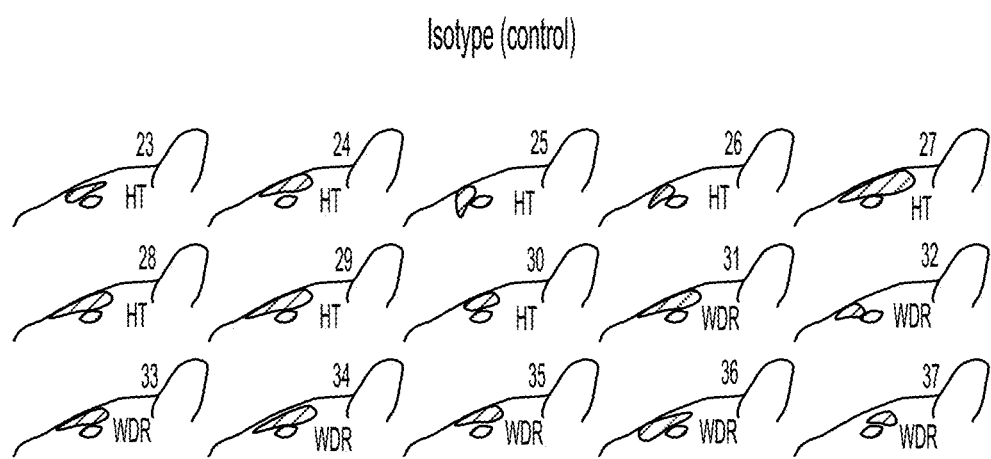
Figure 7E:
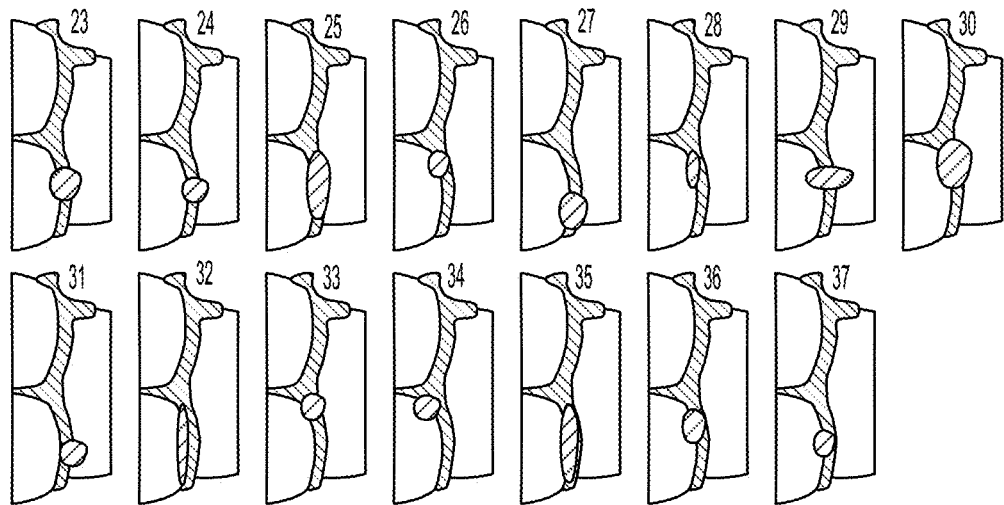
Figure 7F:
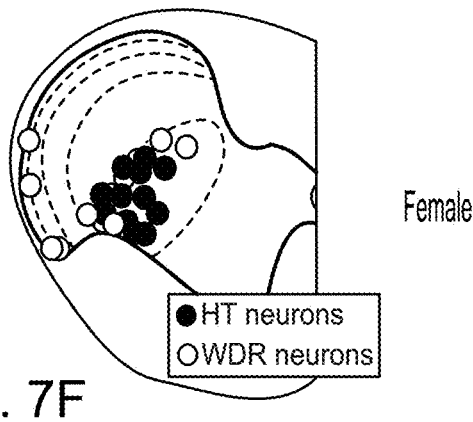
Figure 7G:
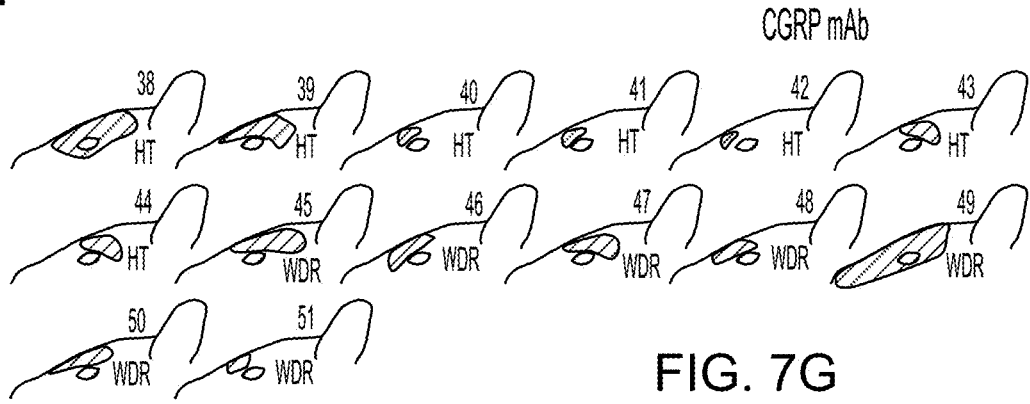
Figure 7H:
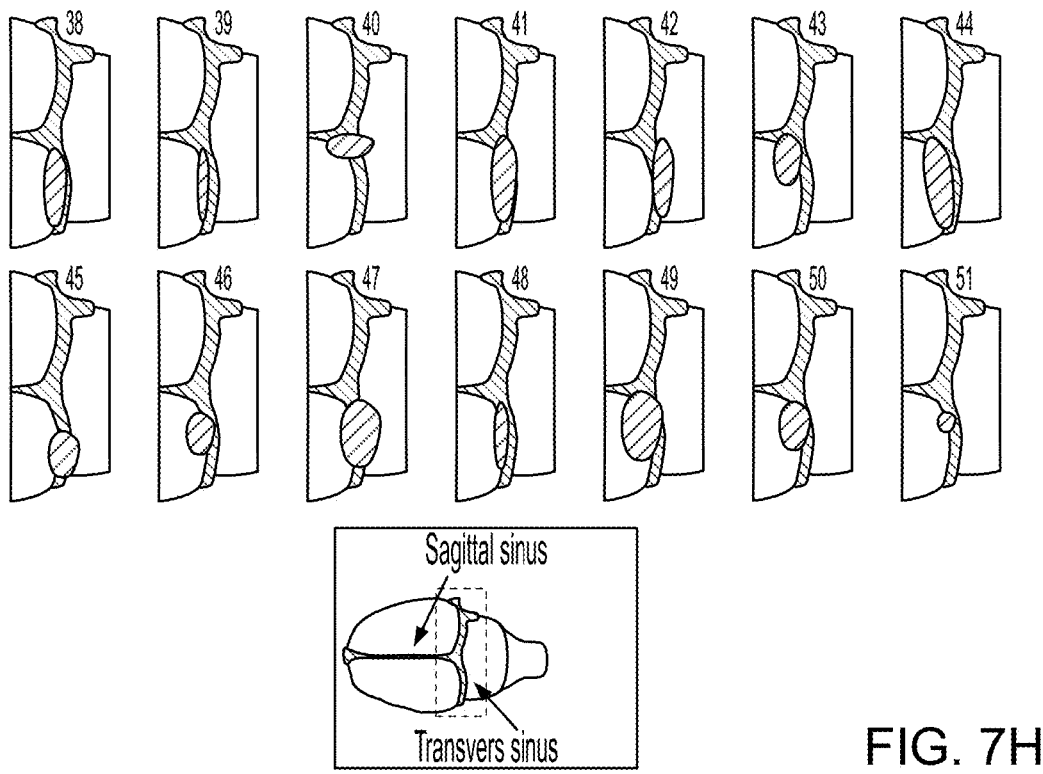
Figure 7I:
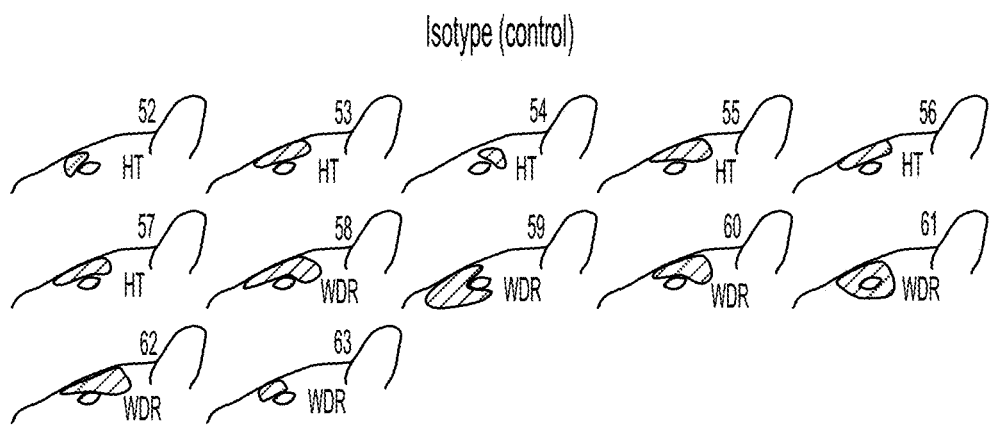
Figure 7J:
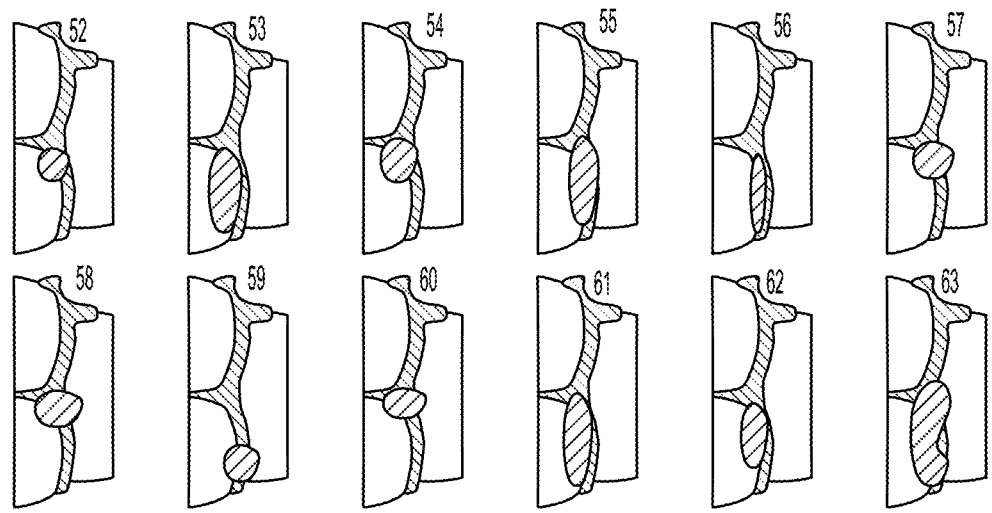

All CDRs including both Kabat and Chothia CDRs. Amino acid residues are numbered sequentially (see FIG. 5). All clones have L3+H1+H3 sequences identical to G1. $K_D=k_{off}/k_{on}$. All $k_{off}$ values were determined in a screening mode except those that are underlined, which were obtained by global analysis of a Fab concentration series (G1 was analyzed in a high-resolution mode). Underlined $K_D$ values were therefore determined experimentally by measuring $k_{on}$. Other $k_{on}$ values were estimated to be the same as M25. n.d.=not determined To determine the epitope on human α-CGRP that is recognized by antibody G1, Biacore assays described above were used. Human α-CGRP was purchased as an N-biotinylated version to enable its high-affinity capture via SA sensor chips. The binding of G1 Fab fragment to the human α-CGRP on the chip in the absence or presence of a CGRP peptide was determined. Typically, a 2000:1 mol peptide/Fab solution (e.g., 10 μM peptide in 50 nM G1 Fab) was injected across human α-CGRP on the chip. FIG. 6 shows the percentage of binding blocked by competing peptide. Data shown in FIG. 6 indicate that peptides that block 100% binding of G1 Fab to human α-CGRP are 1-37 (WT), 8-37, 26-37, P29A (19-37), K35A (19-37), K35E (19-37), and K35M (19-37) of human α-CGRP; 1-37 of β-CGRP (WT); 1-37 of rat α-CGRP (WT); and 1-37 of rat β-CGRP (WT). All these peptides are amidated at the C-terminus. Peptides F37A (19-37) and 19-37 (the latter not amidated at the C-terminus) of human α-CGRP also blocked about 80% to 90% of binding of G1 Fab to human α-CGRP. Peptide 1-36 (not amidated at the C-terminus) of human α-CGRP blocked about 40% of binding of G1 Fab to human α-CGRP. Peptide fragment 19-36 (amidated at the C-terminus) of human α-CGRP; peptide fragments 1-13 and 1-19 of human α-CGRP (neither of which are amidated at the C-terminus); and human amylin, calcitonin, and adrenomedullin (all amidated at the C-terminus) did not compete with binding of G1 Fab to human α-CGRP on the chip. These data demonstrate that G1 targets a C-terminal epitope of CGRP and that both the identity of the most terminal residue (F37) and its amidation is important for binding.

Binding affinities of G1 Fab to variants of human α-CGRP (at 37° C.) was also determined. Table 6 below shows the affinities as measured directly by titrating G1 Fab across N-biotinylated human α-CGRP and variants on the chip. Data in Table 6 indicate that antibody G1 binds to a C-terminal epitope with F37 and G33 being the most important residues. G1 does not bind to CGRP when an extra amino acid residue (alanine) is added at the C-terminal (which is amidated).

TABLE 6

Binding affinities of G1 Fab to human α-CGRP and variants measured at 37° C. (see Table 3 for their amino acid sequences)

| CGRP on chip | $k_{on}$ (1/Ms) | $k_{off}$ (1/s) | $K_D$ (nM) |
|---|---|---|---|
| 1.37 (WT) | $4.68 \times 10^5$ | $7.63 \times 10^{-5}$ | 0.16 (high resolution $K_D = 0.06$) |
| 19-37 | $4.60 \times 10^5$ | $7.30 \times 10^{-5}$ | 0.16 |
| 25-37 | $3.10 \times 10^5$ | $8.80 \times 10^{-5}$ | 0.28 |
| F27A (25-37) | $3.25 \times 10^5$ | $1.24 \times 10^{-4}$ | 0.38 |
| V28A (25-37) | $3.32 \times 10^5$ | $9.38 \times 10^{-5}$ | 0.28 |
| P29A (25-37) | $2.26 \times 10^5$ | $1.78 \times 10^{-4}$ | 0.79 |
| T30A (25-37) | $1.79 \times 10^5$ | $8.41 \times 10^{-5}$ | 0.47 |
| N31A (25-37) | $2.17 \times 10^5$ | $1.14 \times 10^{-4}$ | 0.53 |
| V32A (25-37) | $2.02 \times 10^5$ | $3.46 \times 10^{-4}$ | 1.71 |
| G33A (25-37) | $2.07 \times 10^5$ | 0.0291 | 141 |
| S34A (25-37) | $2.51 \times 10^5$ | $7.64 \times 10^{-4}$ | 3.04 |
| K35A (19-37) | $2.23 \times 10^5$ | $2.97 \times 10^{-4}$ | 1.33 |
| K35E (19-37) | $5.95 \times 10^4$ | $5.79 \times 10^{-4}$ | 9.73 |
| K35M (19-37) | $2.63 \times 10^5$ | $1.34 \times 10^{-4}$ | 0.51 |
| K35Q (19-37) | $1.95 \times 10^5$ | $2.70 \times 10^{-4}$ | 1.38 |
| F37A (25-37) | $8.90 \times 10^4$ | $8.48 \times 10^{-3}$ | 95 (solution $K_D = 172$ nM) |
| 38A (25-38A) | • — | — | No binding detected |

The above data indicate that the epitope that antibody G1 binds is on the C-terminal end of human α-CGRP, and amino acids 33 and 37 on human α-CGRP are important for binding of antibody G1. Also, the amidation of residue F37 is important for binding.

Example 5: Selective Inhibition of Trigeminovascular Neurons by the Humanized Monoclonal Anti-CGRP Antibody (Fremanezumab, TEV-48125)

The purpose of this study was to better understand how the CGRP-mAb fremanezumab (TEV-48125) modulates meningeal sensory pathways. To answer this question single-unit recording was used to determine the effects of fremanezumab (30 mg/kg IV) and a IgG2 isotype control antibody (isotype-conAb) on spontaneous and evoked activity in naïve and CSD-sensitized trigeminovascular neurons in the spinal trigeminal nucleus of anesthetized male and female rats. The study demonstrates that in both sexes fremanezumab inhibited naïve high-threshold (HT) but not wide-dynamic range trigeminovascular neurons, and that the inhibitory effects on the neurons were limited to their activation from the intracranial dura but not facial skin or cornea. Additionally, when given sufficient time, fremanezumab prevents activation and sensitization of HT neurons by cortical spreading depression.

A. Materials and Methods

Surgical Preparation

Experiments were approved by the Beth Israel Deaconess Medical Center and Harvard Medical School standing committees on animal care, and in accordance with the U.S. National Institutes of Health Guide for the Care and Use of Laboratory Animals. Male and female Sprague-Dawley rats (250-350 g) were anesthetized with urethane (0.9-1.2 g/kg i.p.). They were fitted with an intra-tracheal tube to allow artificial ventilation (0.1 L/min of $O_2$), and an intra-femoral-vein cannula for later infusion of drugs. Rats were placed in a stereotaxic apparatus, and core temperature was kept at 37° C. using a heating blanket. End-tidal $CO_2$ was continuously monitored and kept within physiological range (3.5-4.5 $pCO_2$). Once stabilized, rats were paralyzed with rocuronium bromide (10 mg/ml, 1 ml/hr continuous intravenous infusion) and ventilated. For stimulation of the cranial dura later in the experiment, a 5×5-mm opening was carefully carved in the parietal and occipital bones in front and behind the lambda suture, directly above the left transverse sinus. The exposed dura was kept moist using a modified synthetic interstitial fluid (135 mM NaCl, 5 mM KCl, 1 mM $MgCl_2$, 5 mM $CaCl_2$, 10 mM glucose and 10 mM Hepes, pH 7.2). For single-unit recording in the spinal trigeminal nucleus, a segment of the spinal cord between the obex and C2 was uncovered from overlying tissues, stripped of the dura mater, and kept moist with mineral oil.

Neuronal Identification and Selection

To record neuronal activity, a tungsten microelectrode (impedance 3-4 MΩ) was lowered repeatedly into the spinal trigeminal nucleus (STN) in search of central trigeminovascular neurons receiving convergent input from the dura and facial skin.

Trigeminovascular neurons were first identified based on their responses to electrical stimulation of the dura. They were selected for the study if they exhibited discrete firing bouts in response to ipsilateral electrical (0.1-3.0 mA, 0.5 msec, 0.5 Hz pulses) and mechanical (with a calibrated von Frey monofilaments) stimulation of the exposed cranial dura and to mechanical stimulation of the facial skin and cornea. Dural receptive fields were mapped by indenting the dura (with the 4.19 g VFH monofilament) at points separated by 1 mm mediolaterally and rostrocaudally. Points at which dural indentation produced a response in ≥50% of the trials were considered inside the neurons receptive field. Cutaneous receptive fields were mapped by applying innocuous and noxious mechanical stimulation to all facial skin areas and the cornea. An area was considered outside the receptive field if no stimulus produced a response in ≥50% of the trials. Responses to mechanical stimulation of the skin were determined by applying brief (10 s) innocuous and noxious stimuli to the most sensitive portion of the cutaneous receptive field. Innocuous stimuli consisted of slowly passing a soft bristled brush across the cutaneous receptive field (one 5-s brush stroke from caudal to rostral and one 5-s brush stroke from rostral to caudal) and pressure applied with a loose arterial clip. Noxious stimuli consisted of pinch with a strong arterial clip (Palecek et al., 1992, *J. Neurophysiol.* 67:1562-1573; Dado et al., 1994, *J. Neurophysiol.* 71:981-1002; Burstein et al., 1998, *J. Neurophysiol.* 79:964-982). More intense or prolonged stimuli were not used to avoid inducing prolonged changes in spontaneous neuronal discharge or response properties. Responses to mechanical stimulation of the cornea consisted of gentle and slow brushing strokes with a thin paintbrush (about 10 hair-follicles). Two classes of neurons were thus identified: wide-dynamic-range (WDR) neurons (incrementally responsive to brush, pressure and pinch), and high-threshold (HT) neurons (unresponsive to brush). Real-time waveform discriminator was used to create and store a template for the action potential evoked in the neuron under study by electrical pulses on the dura; spikes of activity matching the template waveform were acquired and analyzed online and offline using Spike 2 software (CED, Cambridge, UK).

Induction and Recording of Cortical Spreading Depression

Cortical spreading depression (CSD) was induced mechanically by inserting a glass micropipette (tip diameter 25 µm) about 1 mm into the visual cortex for 10 sec. At a propagation rate of 3-5 mm/min, a single wave of CSD was expected to enter the neuronal receptive field within 1-2 min of cortical stimulation. For verification of CSD, cortical activity was recorded (electrocorticogram) with a glass micropipette (0.9% saline, ~1 megohm, 7 µm tip) placed just below the surface of the cerebral cortex (approximately 100 µm). The electrocorticogram electrode was positioned about 6 mm anterior to the visual cortex.

Treatment with the Monoclonal Anti-CGRP Antibody Fremanezumab (TEV-48125)

Fremanezumab (also known as TEV-48125/LBR-101/RN-307) (TEVA Pharmaceutical Industries Ltd., Israel) is a humanized monoclonal anti-CGRP antibody (CGRP-mAb). It was diluted in saline to a final dose of 30 mg/kg and administered intravenously (bolus injection, total volume 0.6-0.7 ml). A corresponding human IgG2 isotype control antibody (isotype-conAb) was also diluted in saline to a final dose of 30 mg/kg and administered intravenously (bolus injection, total volume 1.6-2.0 ml).

Experimental Protocol

The experimental protocol included two parts. The first part was designed to compare CGRP-mAb vs isotype-conAb effects on spontaneous and induced activity of naïve trigeminovascular neurons, and the second part was designed to test CGRP-mAb vs isotype-conAb effects on the activation and sensitization of trigeminovascular neurons by CSD. Both parts included sampling of WDR and HT neurons in male and female rats. In the first part, the baseline neuronal profile was established by (a) mapping the dural, cutaneous and corneal receptive field; (b) measuring responses (mean spikes/sec) to mechanical stimulation of the dura (with a fixed force), skin (brush, pressure, pinch) and cornea (brush), and (c) measuring spontaneous firing rate (recorded over 30 min prior to treatment). Once the baseline was established, CGRP-mAb or isotype-conAb were administered and receptive fields were remapped, neuronal responses to stimulation of the dura, skin and cornea were re-examined, and the spontaneous activity rate was re-sampled at 1, 2, 3, and 4 hours post-treatment. The resulting values for each measure were then compared with the respective baseline values obtained before treatment. In the second part, CSD was induced 4 hours after administration of CGRP-mAb or isotype-conAb and 2 hours later (i.e., 6 hours after treatment) receptive field size, spontaneous activity rate, and response magnitude to stimulation of the dura, skin and cornea were measured again. The resulting post-CSD values for each measure were then compared with the respective pre-CSD values obtained at the 4-hour post-treatment time. This part was initiated only in cases in which the physiological condition of the rats (heart rate, blood pressure, respiration, end tidal CO2) and the neuronal isolation signal (signal-to-noise ratio ≥1:3) were stable at the 4-hour post-treatment time point.

At the conclusion of each experiment, a small lesion was produced at the recording site (anodal DC of 15 µA for 15 sec) and its localization in the dorsal horn was determined postmortem using histological analysis as described elsewhere (Zhang et al. (2011) *Ann. Neurol.* 69: 855-865). Only one neuron was studied in each animal.

Data Analysis

To calculate the response magnitude to each stimulus, the mean firing frequency occurring before the onset of the first stimulus (30 min for spontaneous activity, 10 sec for mechanical stimulation of the dura, skin and cornea) was subtracted from the mean firing frequency that occurred throughout the duration of each stimulus. In the first part of the study, corresponding values for each measure (determined at 1, 2, 3, 4 hrs after treatment) were compared with the respective baseline values obtained before fremanezumab or isotype-conAb administration. In the second part of the study, resulting values for each measure (determined 2 hours after CSD induction) were compared with the respective values obtained before CSD induction in the 2 treatment groups (fremanezumab and isotype-conAb). A neuron was considered activated when its mean firing rate after CSD exceeded its mean baseline activity by 2 standard deviations of that mean for a period >10 min, which translated to ≥33% increase in activity. A neuron was considered sensitized if 2 hours after occurrence of CSD it exhibited enhanced responses to at least 3 of the following 5 stimuli: dural indentation, brushing, pressuring or pinching the skin, and brushing the cornea. Mean firing rates of respective values were compared using nonparametric statistics (Wilcoxon signed-ranks test). Two-tailed level of significance was set at 0.05.

B. Results

The database for testing CGRP-mAb vs isotype-conAb effects on spontaneous and induced activity of naïve trigeminovascular neurons consisted of 63 neurons. Of these, 31 were classified as WDR and 32 as HT. Of the 31 WDR neurons, 18 (11 in males, 7 in females) were tested before and after administration of the CGRP-mAb, and 13 (7 in males, 6 in females) were tested before and after administration of the isotype-conAb. Of the 32 HT neurons, 18 (11 in males, 7 in female) were tested before and after administration of the CGRP-mAb, and 14 (8 in males, 6 in females) were tested before and after administration of the isotype-conAb.

The database for testing CGRP-mAb vs. isotype-conAb effects on the activation and sensitization of the neurons by CSD consisted of 50 neurons. Of these, 23 were classified as WDR and 27 as HT. Of the 23 WDR neurons, 13 (7 in males, 6 in females) were tested in the CGRP-mAb treated animals and 10 (5 in males, 5 in females) in the isotype-conAb treated animals. Of the 27 HT neurons, 14 (8 in males, 6 in female) were tested in the CGRP-mAb treated animals, and 13 (7 in males, 6 in females) in the isotype-conAb treated animals.

Recording Sites, Receptive Fields and Neuronal Classes

Recording site, maps of dural and cutaneous receptive fields, and cell types did not differ between neurons tested for CGRP-mAb and those tested for the isotype-conAb (FIGS. 7A-7J). All identified recording sites were localized in laminae I-II and IV-V of the first cervical segment of the spinal cord and the caudal part of nucleus caudalis. In all cases, the most sensitive area of the dural receptive field was along the transverse sinus and the most sensitive area of the cutaneous receptive field was around the eye, involving the cornea in more than 90% of the cases.

Spontaneous Activity of Naïve Central Trigeminovascular Neurons

Figure 8A:
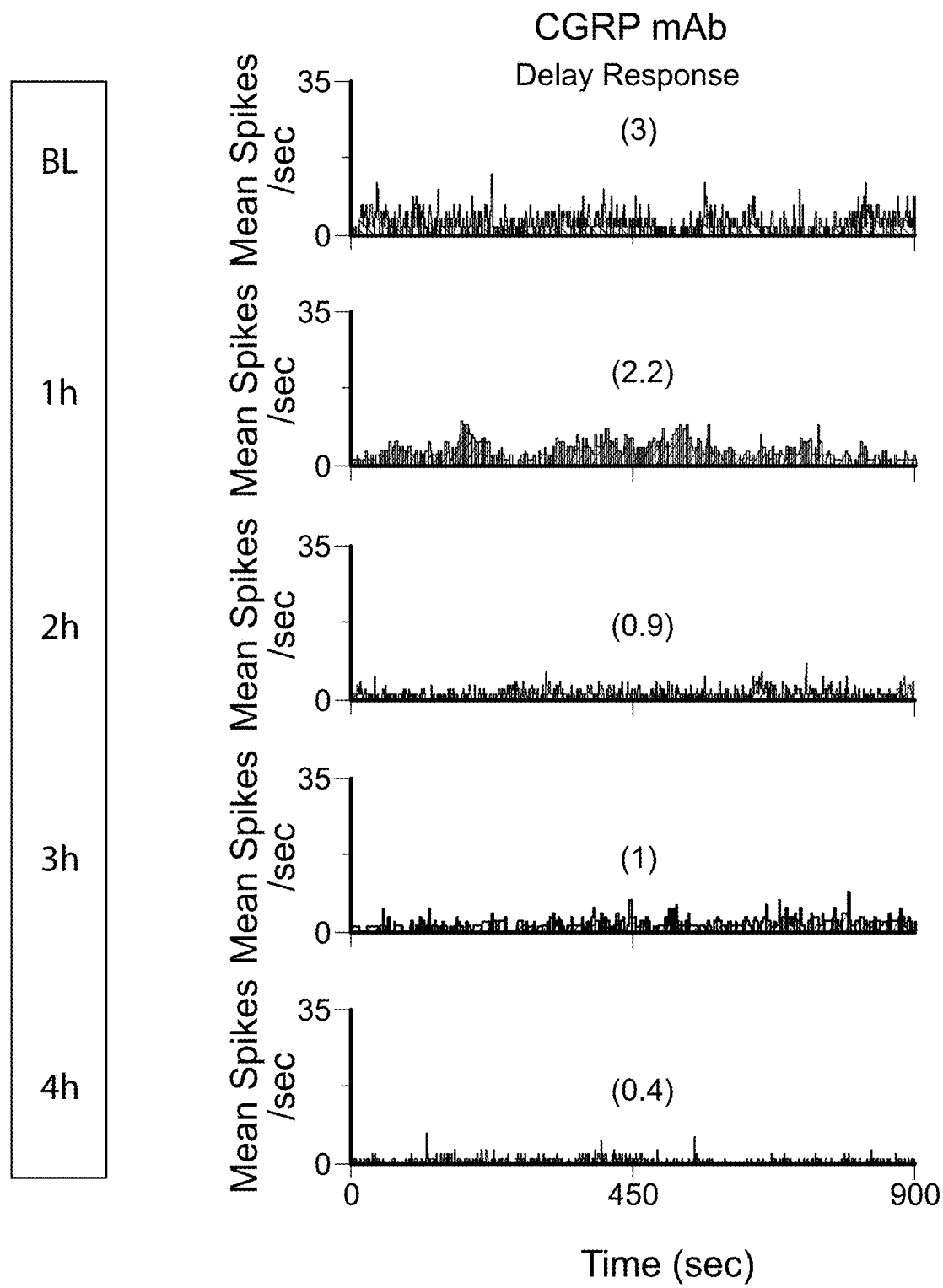
FIGS. 8A, 8B, 8C, 8D, 8E, 8F, and 8G show the effect of CGRP-mAb (FIGS. 8A, 8B, 8C, and 8D) and isotype-conAb (FIGS. 8E, 8F, and 8G) on the spontaneous activity of trigeminovascular neurons in male and female rats.
Figure 8B:
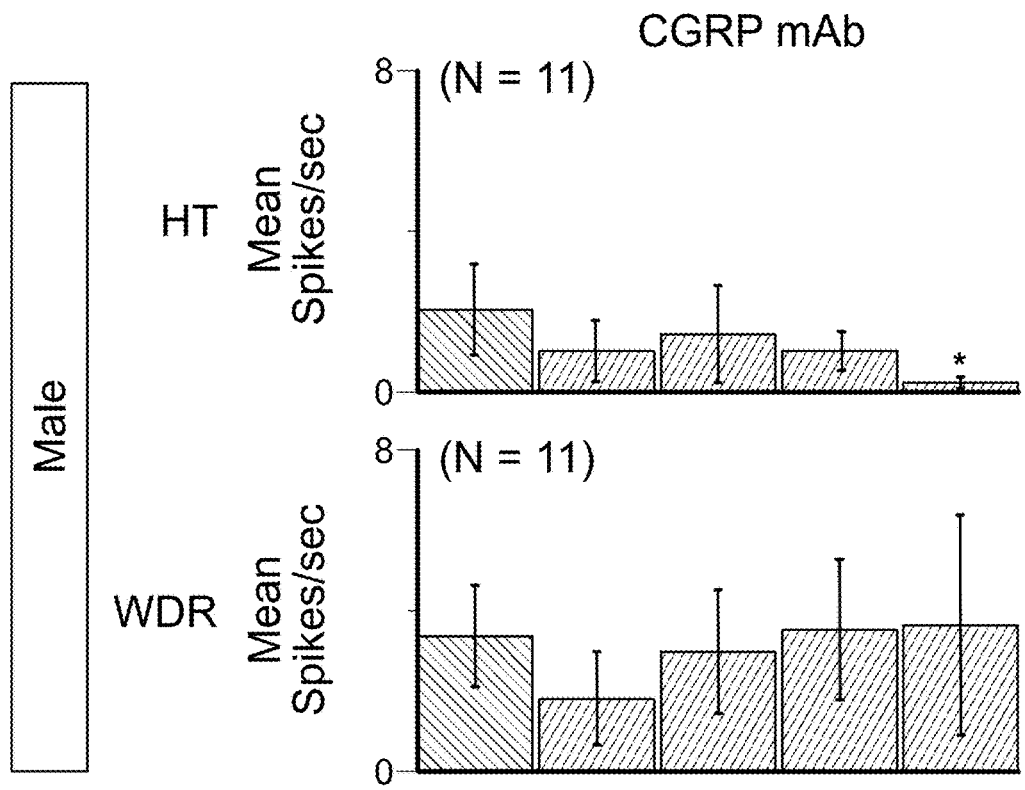
Figure 8C:
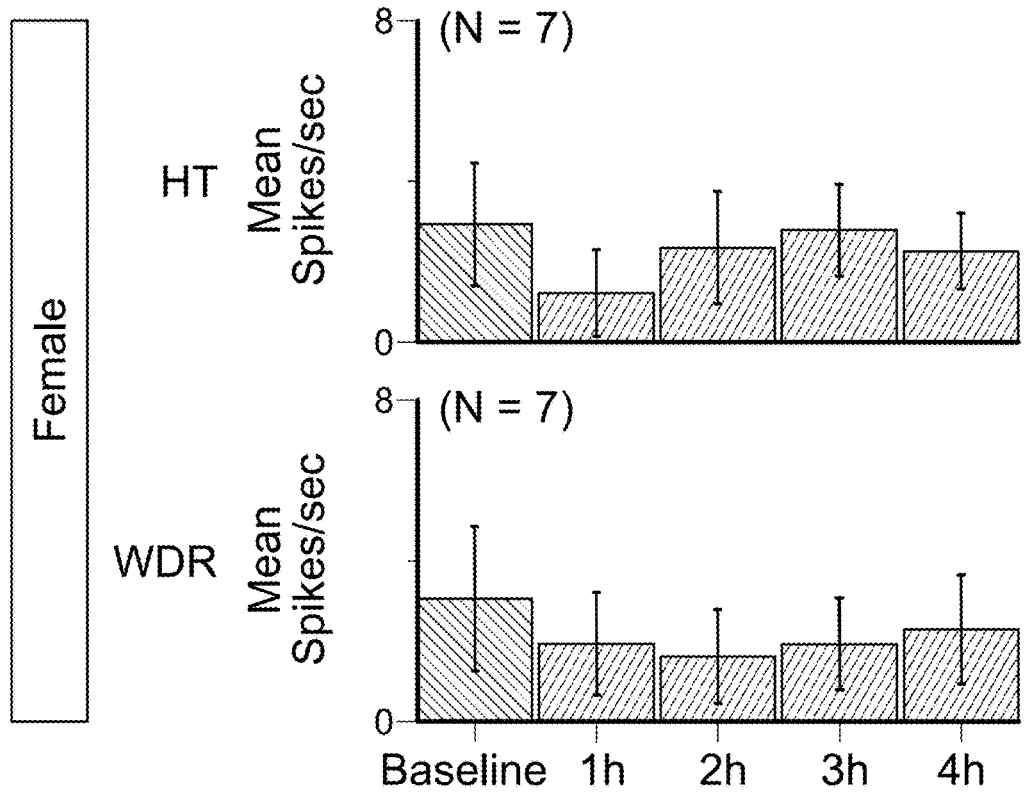
Figure 8D:
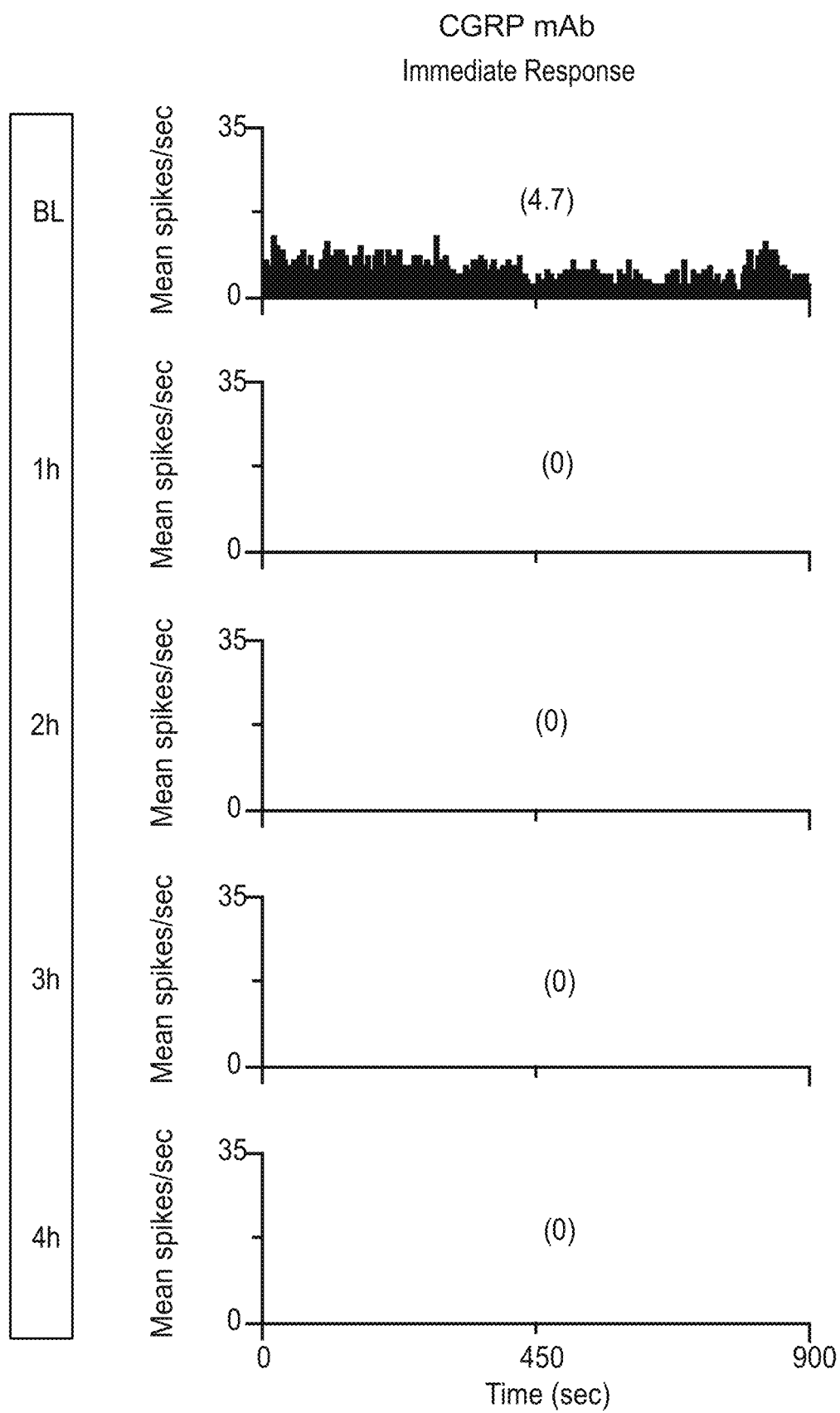
Figure 8E:
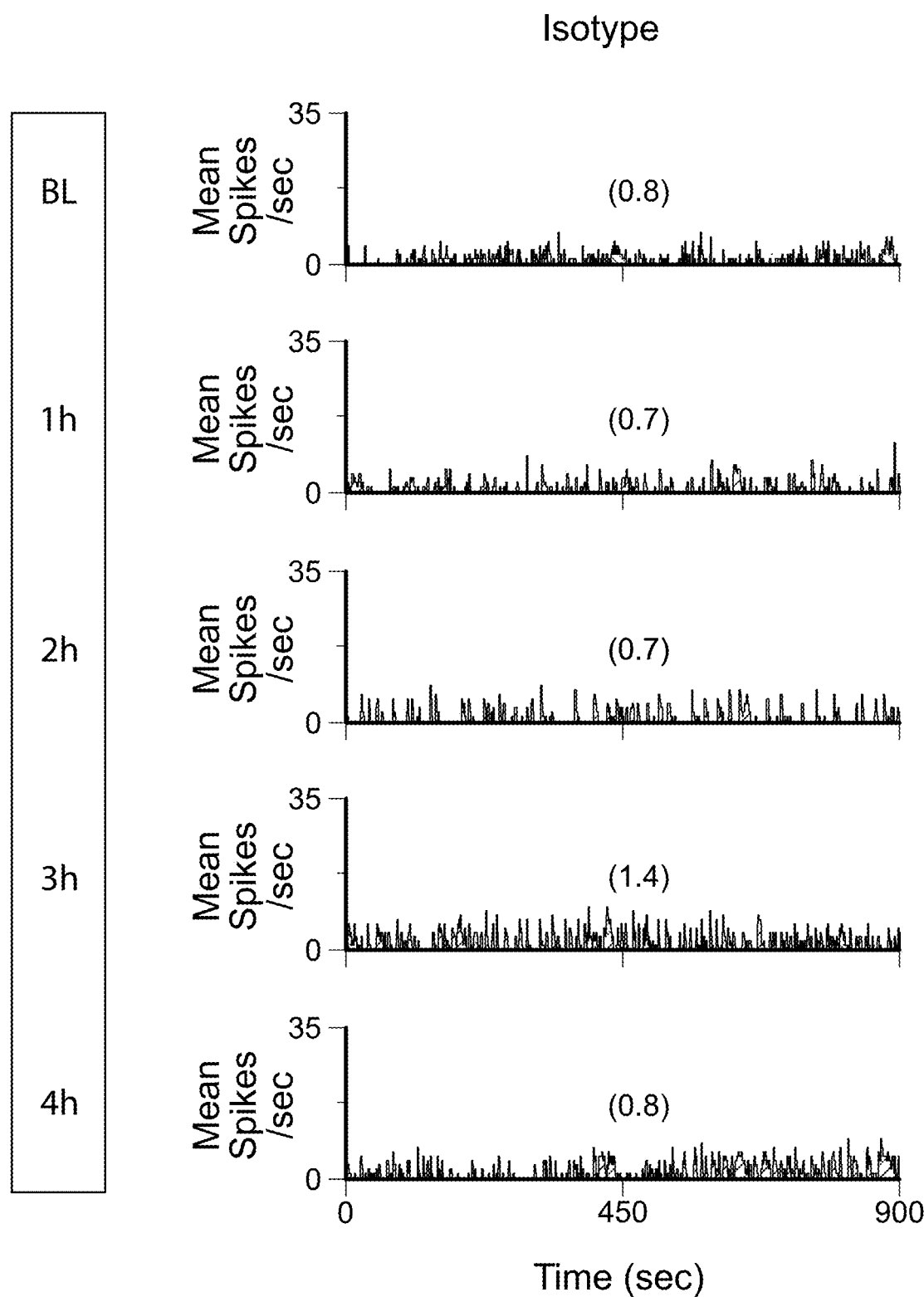
Figure 8F:
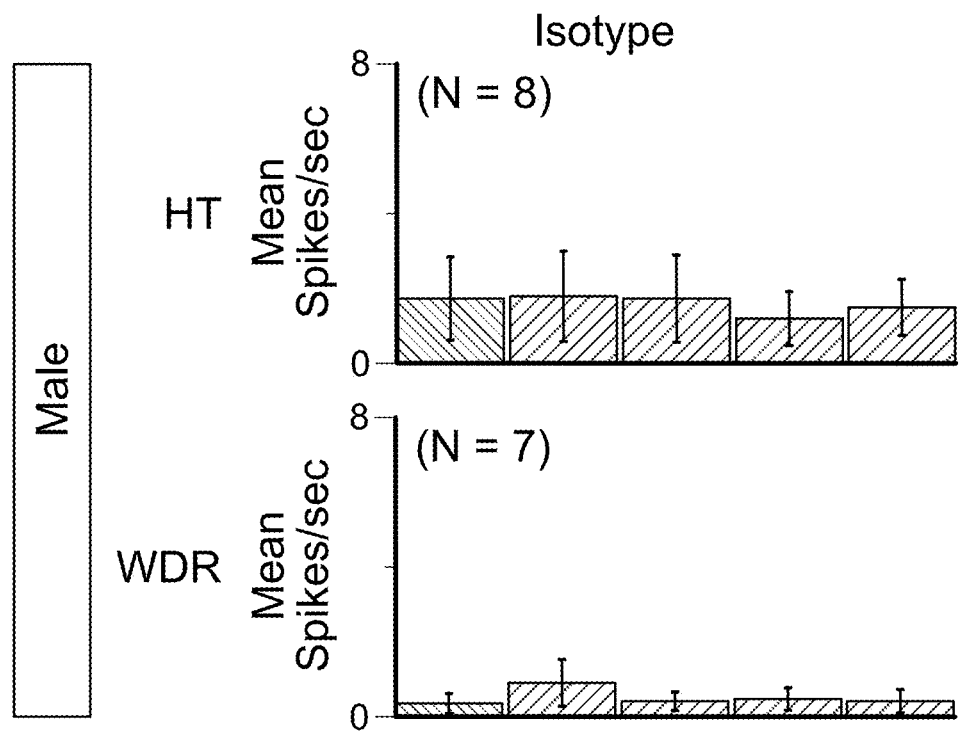

In male rats, intravenous administration of the CGRP-mAb reduced the spontaneous activity of the HT but not the WDR neurons (FIGS. 8A and 8B). In the HT group, neuronal firing decreased within 3-4 hrs by 90% (p=0.040). Occasionally, the firing rate of some HT neurons decreased within 1-2 hours after the intravenous administration of the CGRP-mAb (FIG. 8D). In contrast, intravenous administration of the isotype-conAb did not alter the spontaneous activity of either group of neurons (FIGS. 8E and 8F).

Figure 8G:
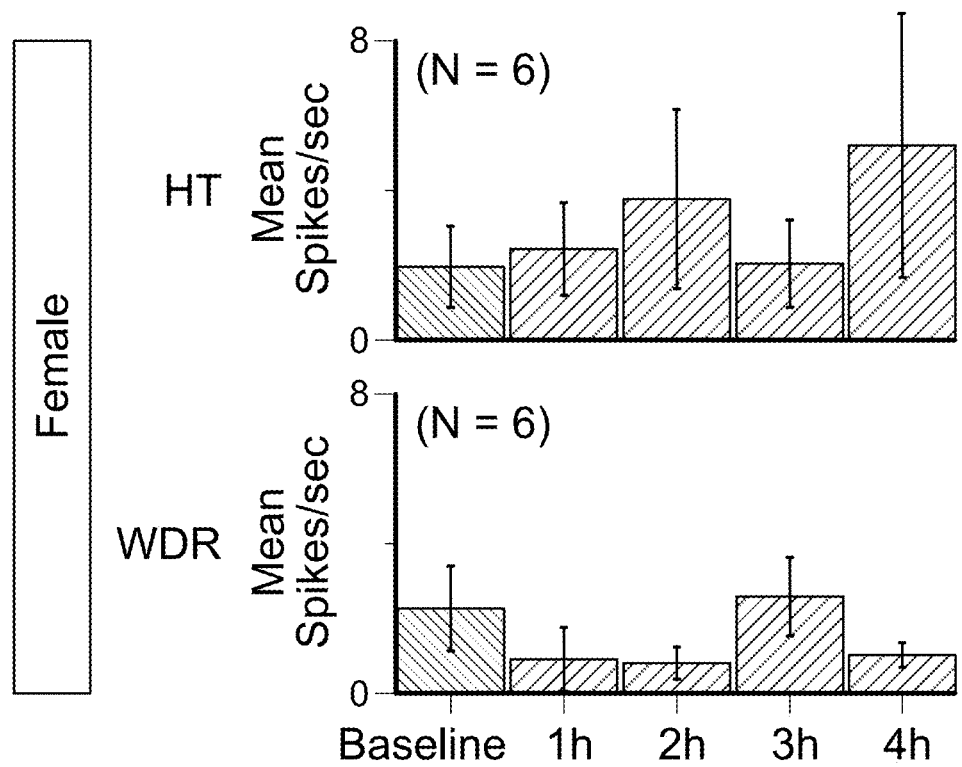

In females, unlike in males, intravenous administration of the CGRP-mAb did not reduce the spontaneous activity of HT or WDR neurons (FIG. 8C) Similarly, intravenous administration of the isotype-conAb did not alter the spontaneous activity of either group of neurons (FIG. 8G). Critically, the baseline (i.e., before any treatment) spontaneous firing rate of HT and WDR neurons did not differ between the male and the female rats (p=0.14). For the HT neurons, mean spikes/sec before any treatment was 1.7±1.1 in the male vs. 1.9±1.0 in the female (p=0.55). For the WDR neurons, mean spikes/sec before any treatment was 0.3±0.6 in the male vs. 2.2±1.1 in the female (p=0.16).

Sensitivity of Naïve Central Trigeminovascular Neurons to Dural Indentation

Figure 9A:
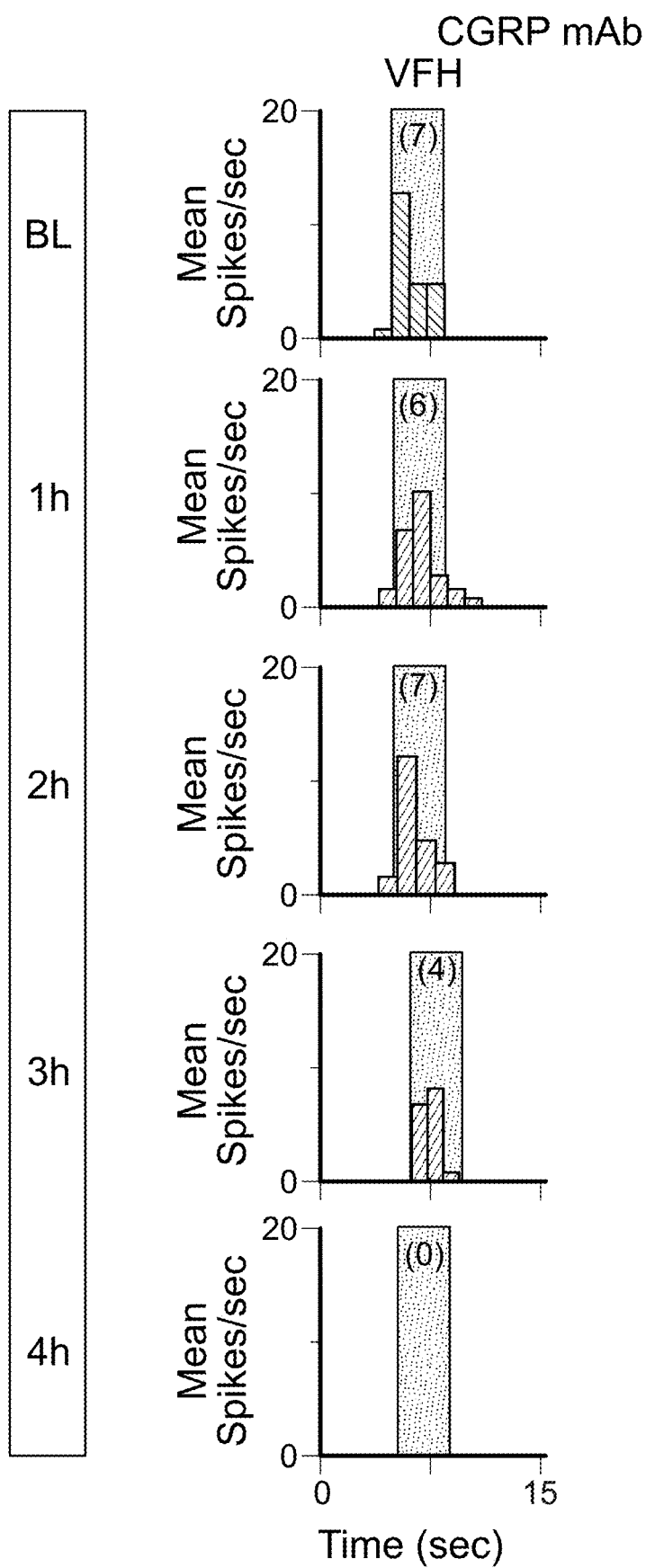
FIGS. 9A, 9B, 9C, 9D, 9E, and 9F are graphs showing the effect of CGRP-mAb (FIGS. 9A, 9B, and 9C) and isotype-conAb (FIGS. 9D, 9E, and 9F) on the response of trigeminovascular neurons to dural indentation in male and female rats.
Figure 9B:
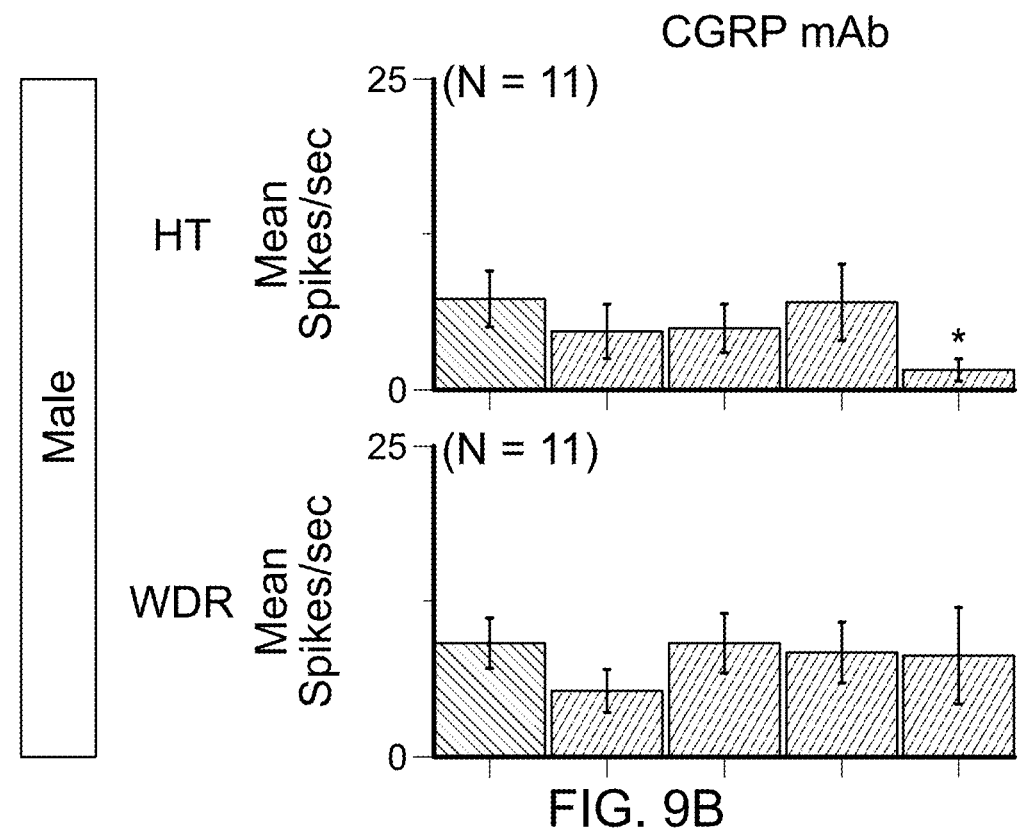
Figure 9C:
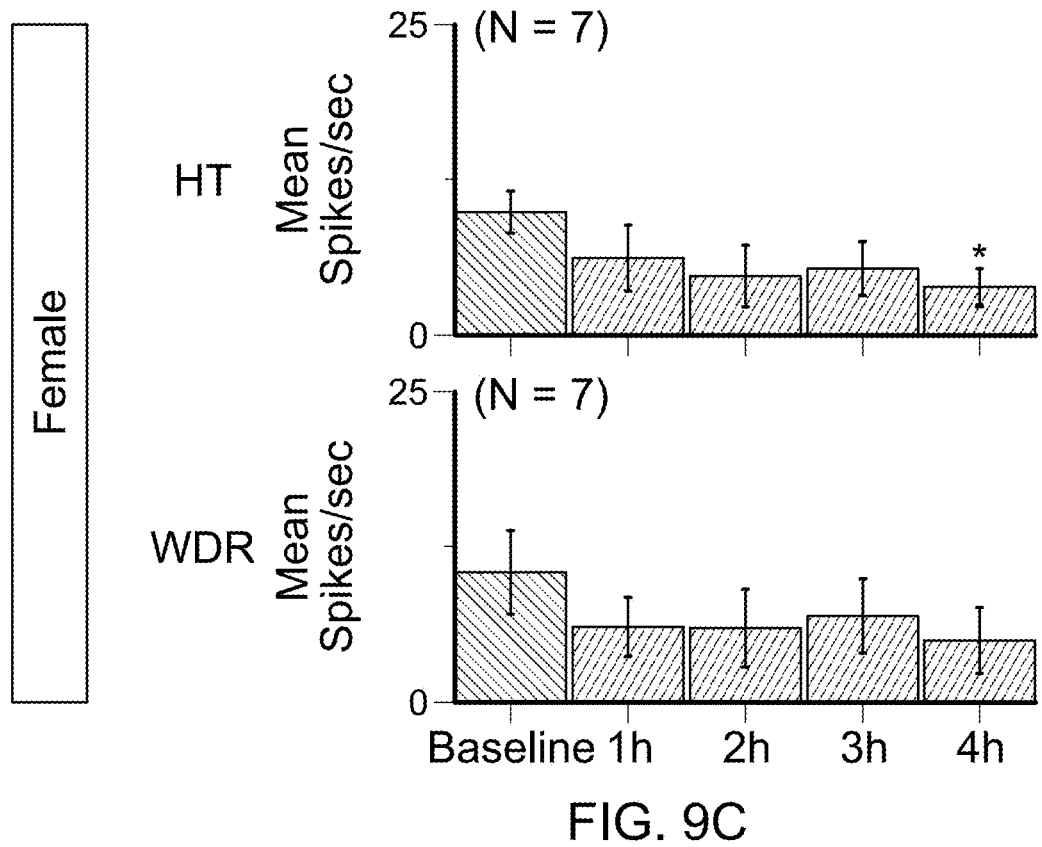
Figure 9D:
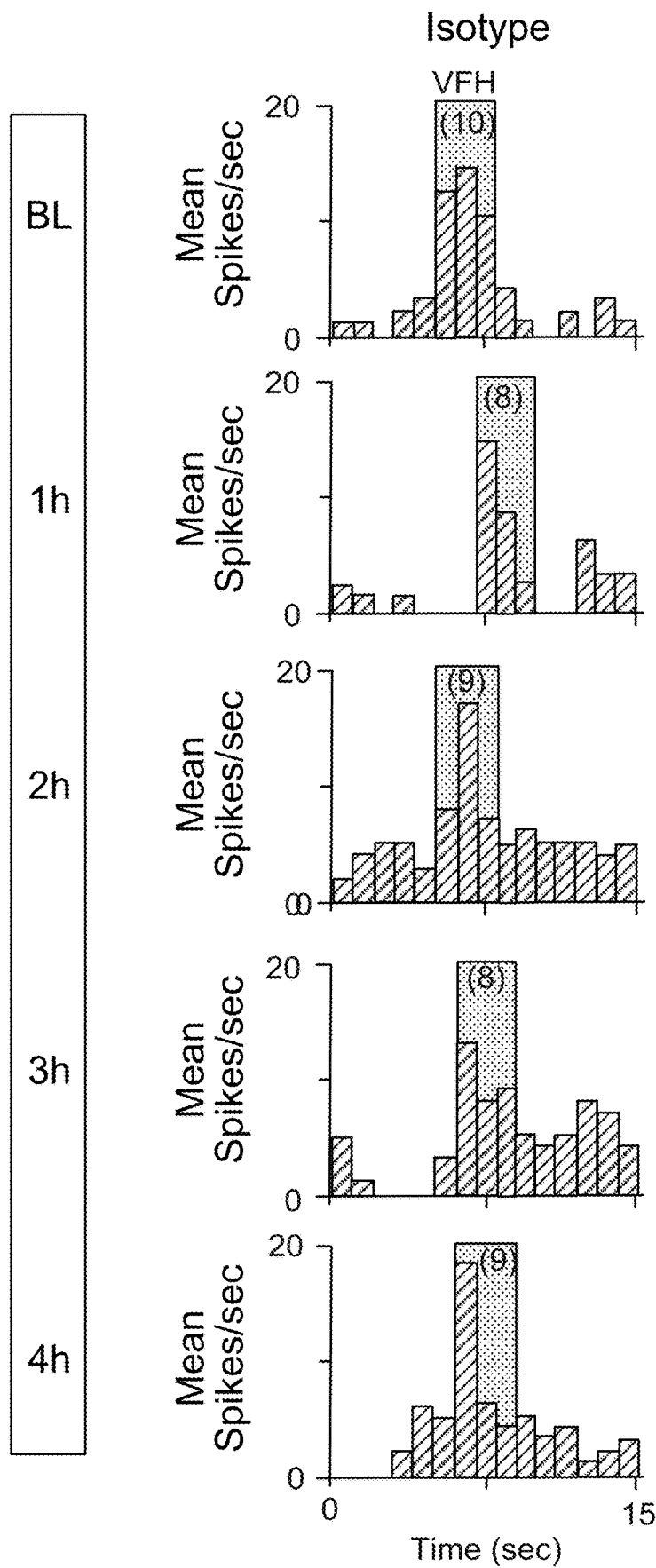
Figure 9E:
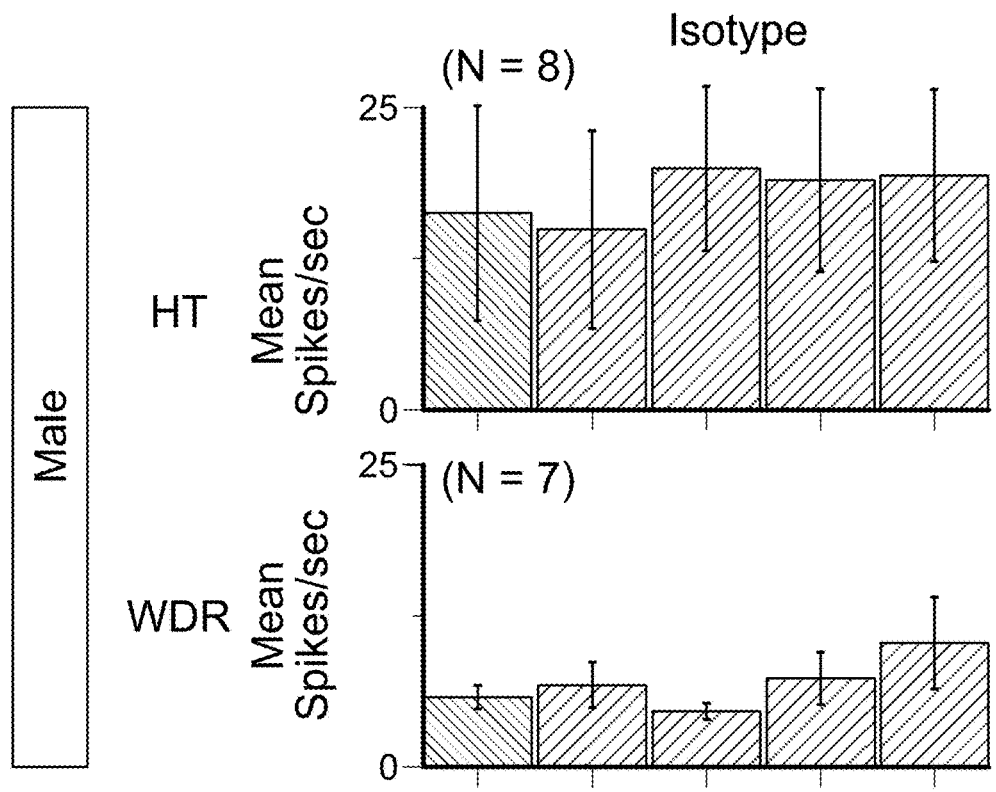
Figure 9F:
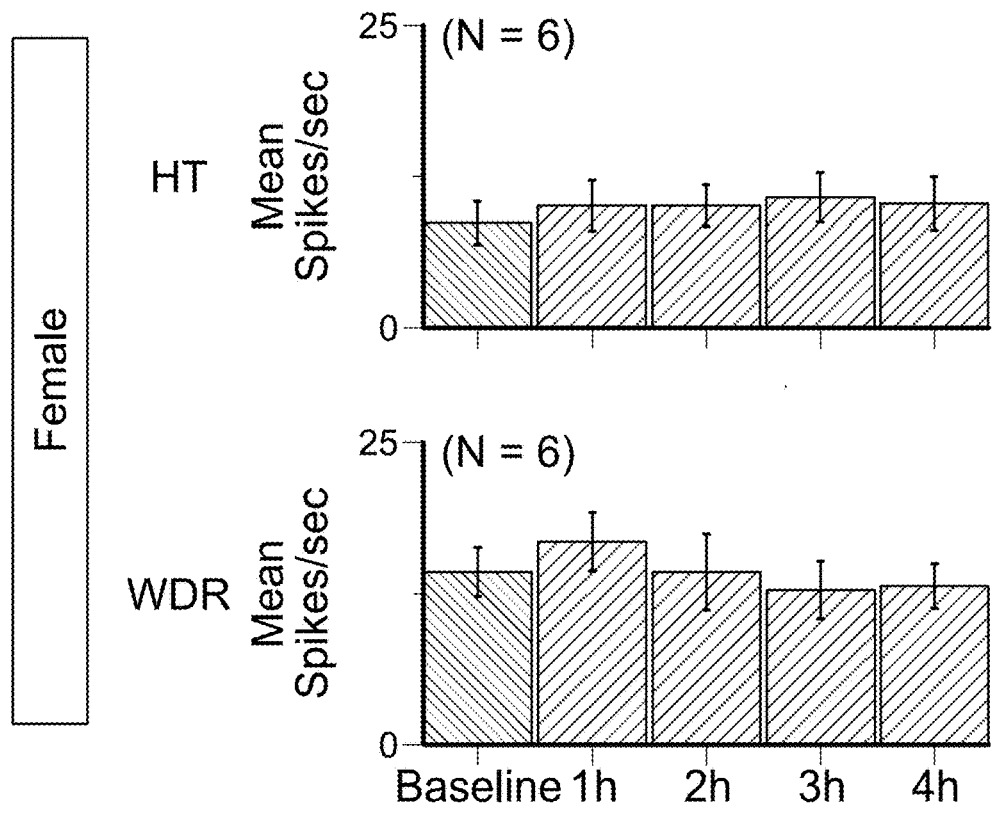
Figure 10A:
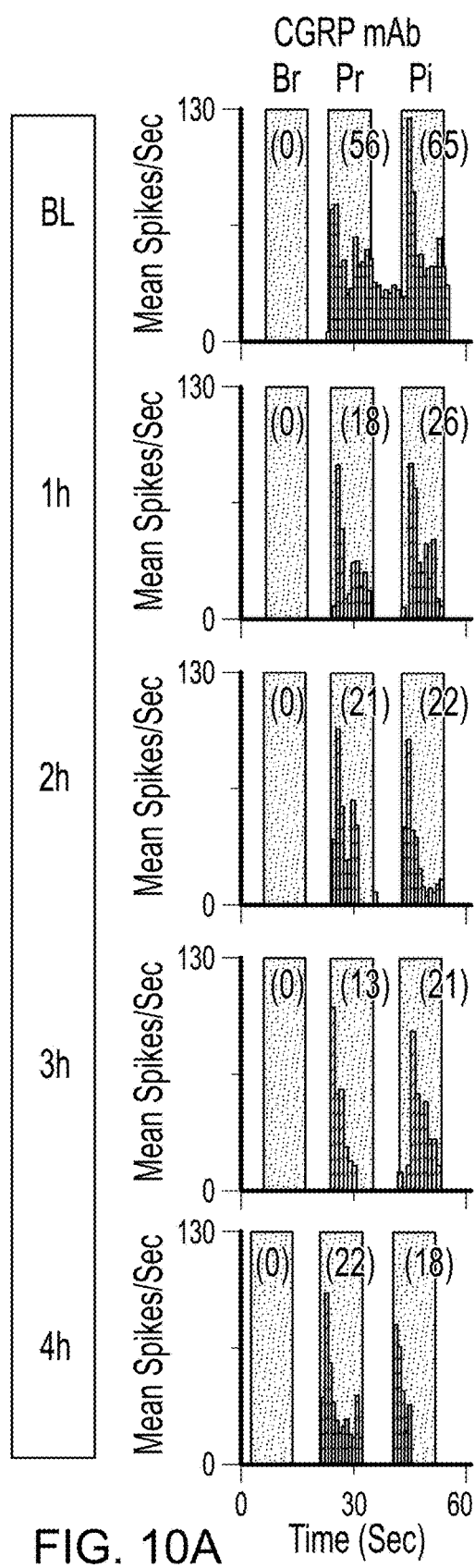
FIGS. 10A, 10B, 10C, 10D, 10E, 10F, 10G, and 10H are graphs showing the effect of CGRP-mAb (FIGS. 10A, 10B, 10C, 10D) and isotype-conAb (FIGS. 10E, 10F, 10G, and 10H) on the response of central trigeminovascular neurons to innocuous and noxious mechanical stimulation of cutaneous receptive fields of male and female rats.
Figure 10B:
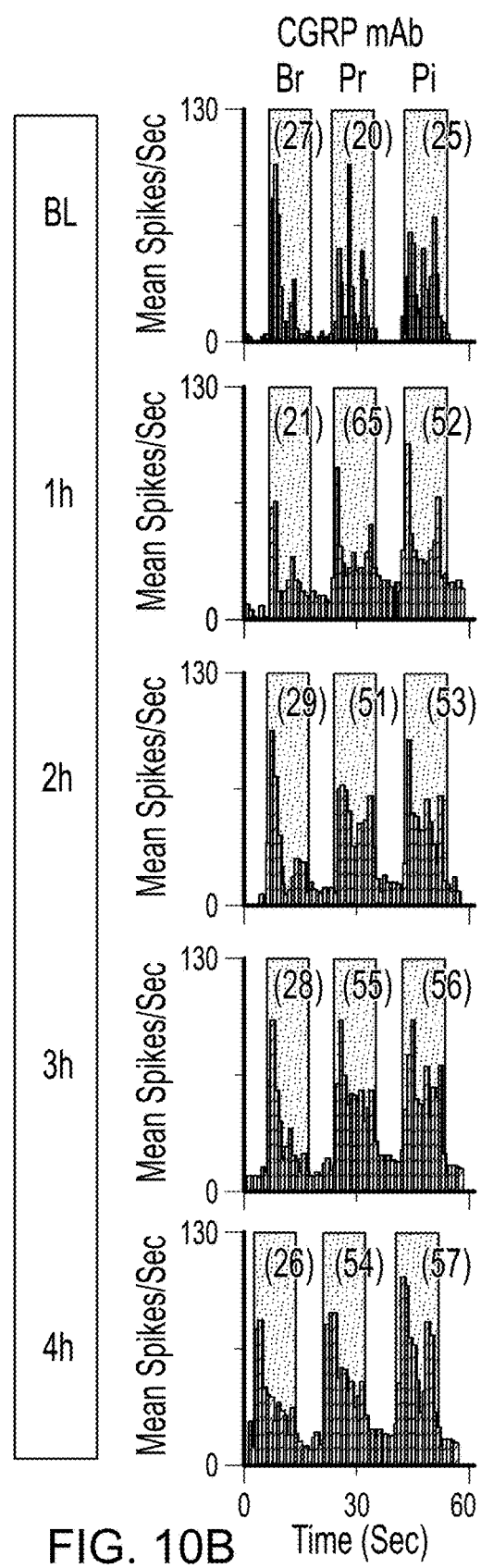
Figure 10C:
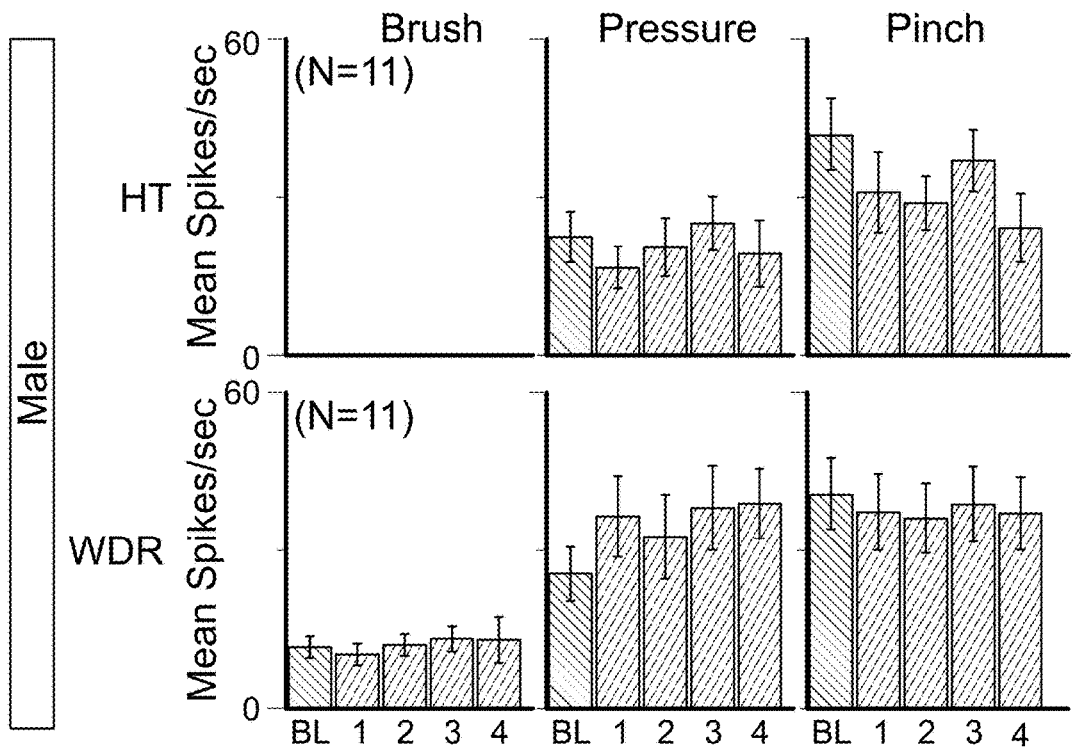
Figure 10D:
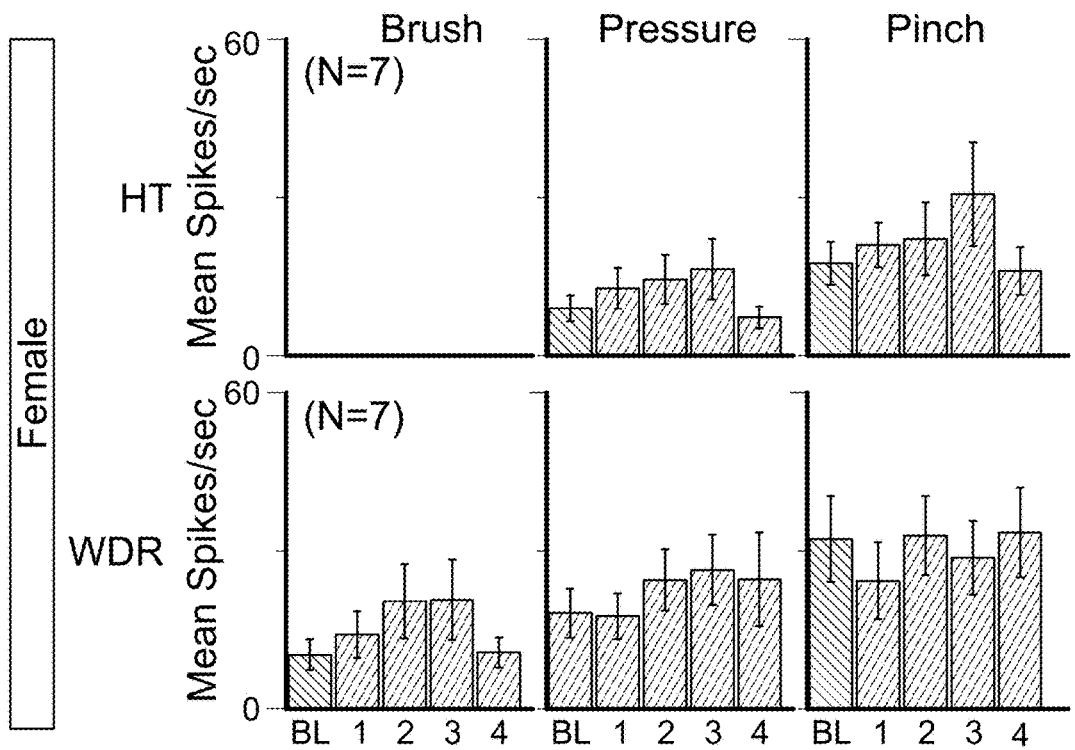
Figure 10E:
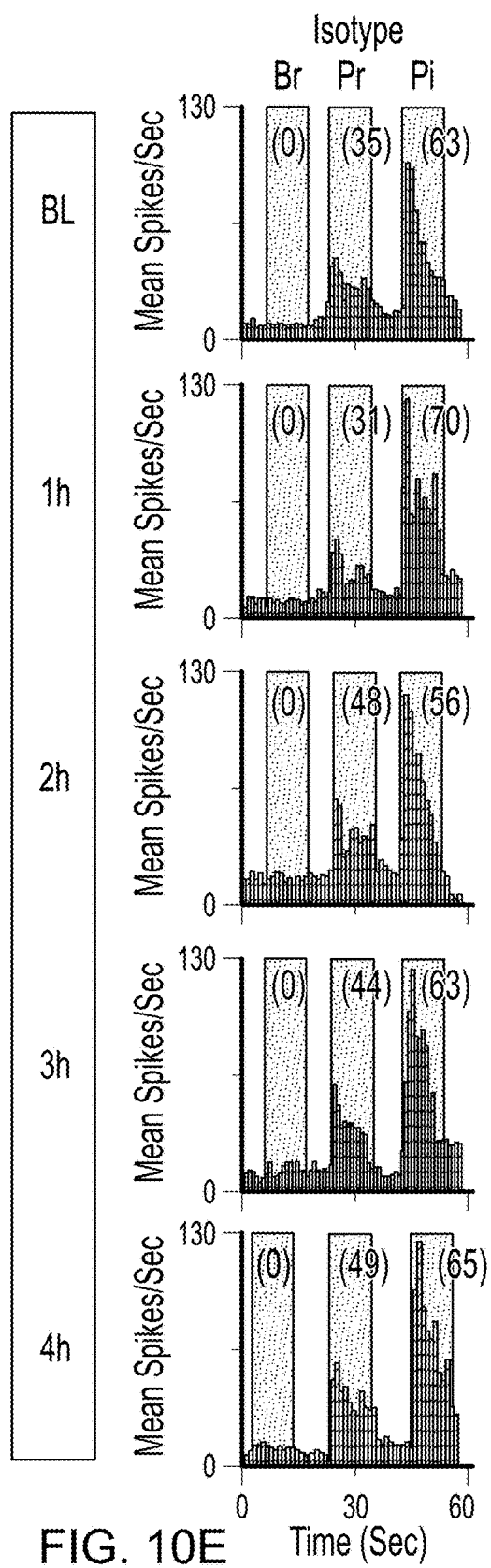
Figure 10F:
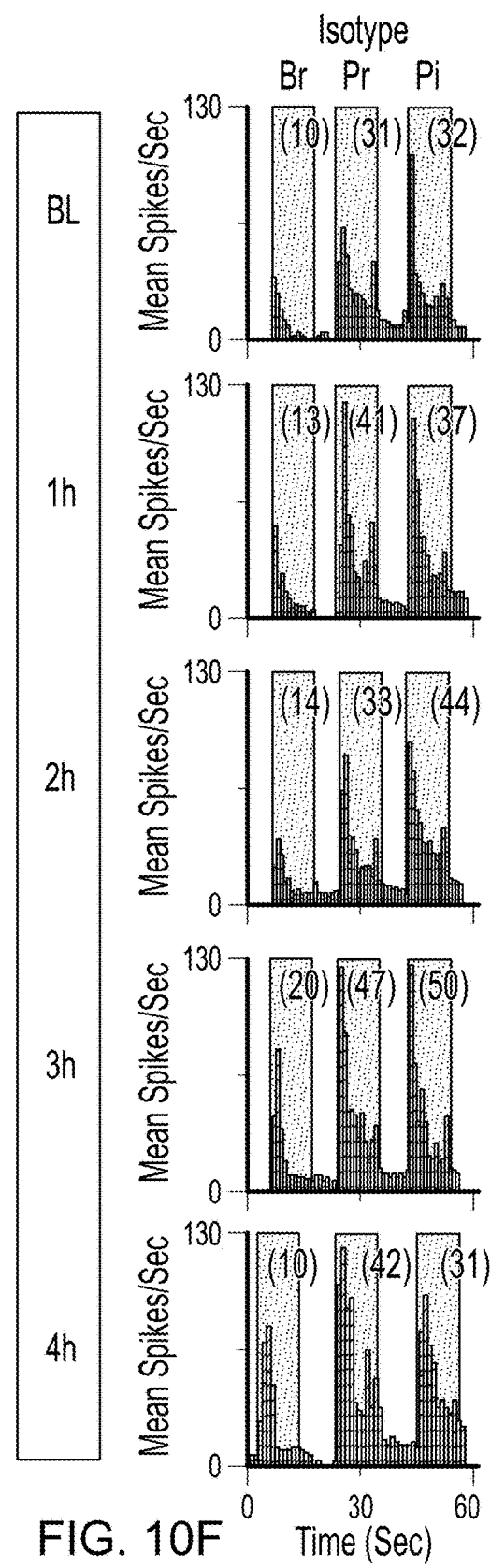
Figure 10G:
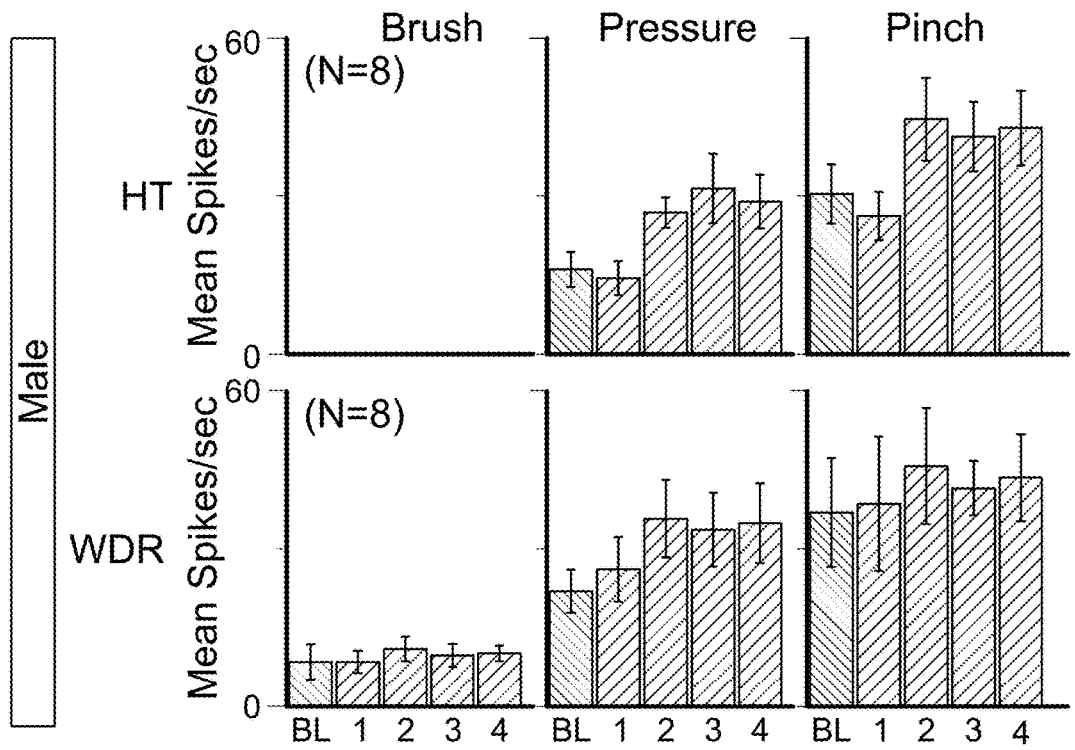
Figure 10H:
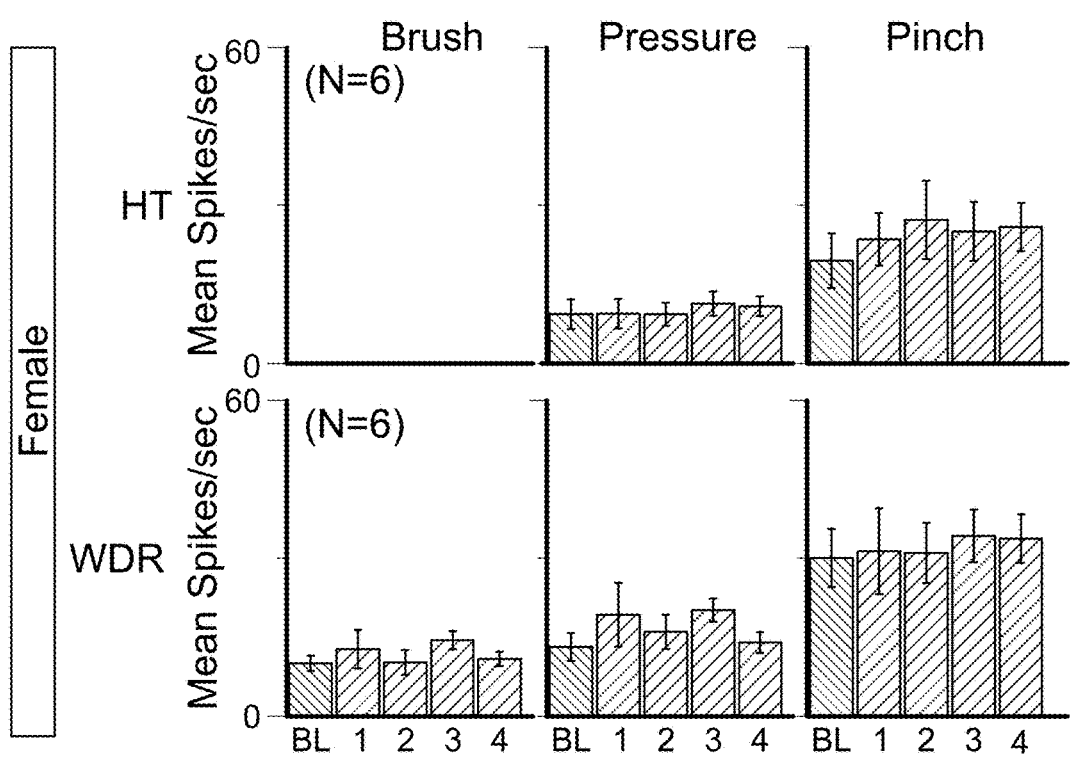
Figure 11A:
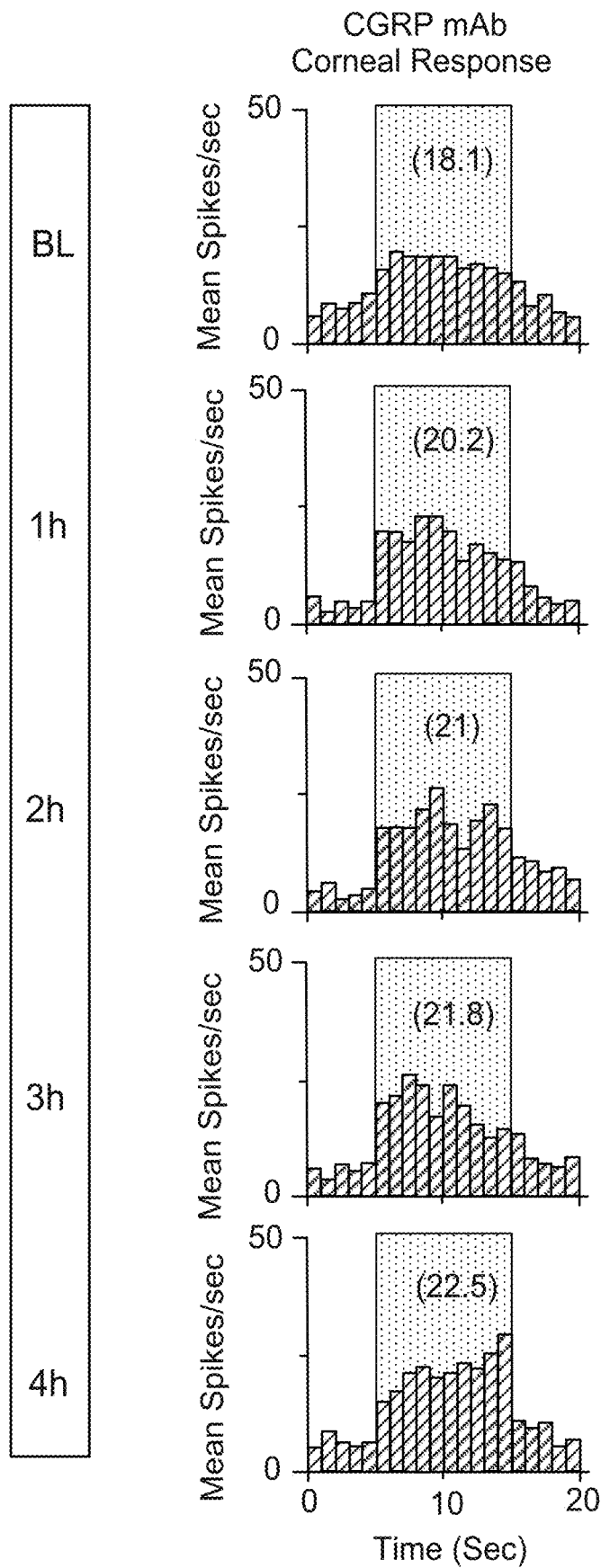
FIGS. 11A, 11B, 11C, 11D, 11E, and 11F are graphs showing the effect of CGRP-mAb (FIGS. 11A, 11B, and 11C) and isotype-conAb (FIGS. 11D, 11E, and 11F) on the response of central trigeminovascular neurons to mechanical stimulation of the cornea in male and female rats.
Figure 11B:
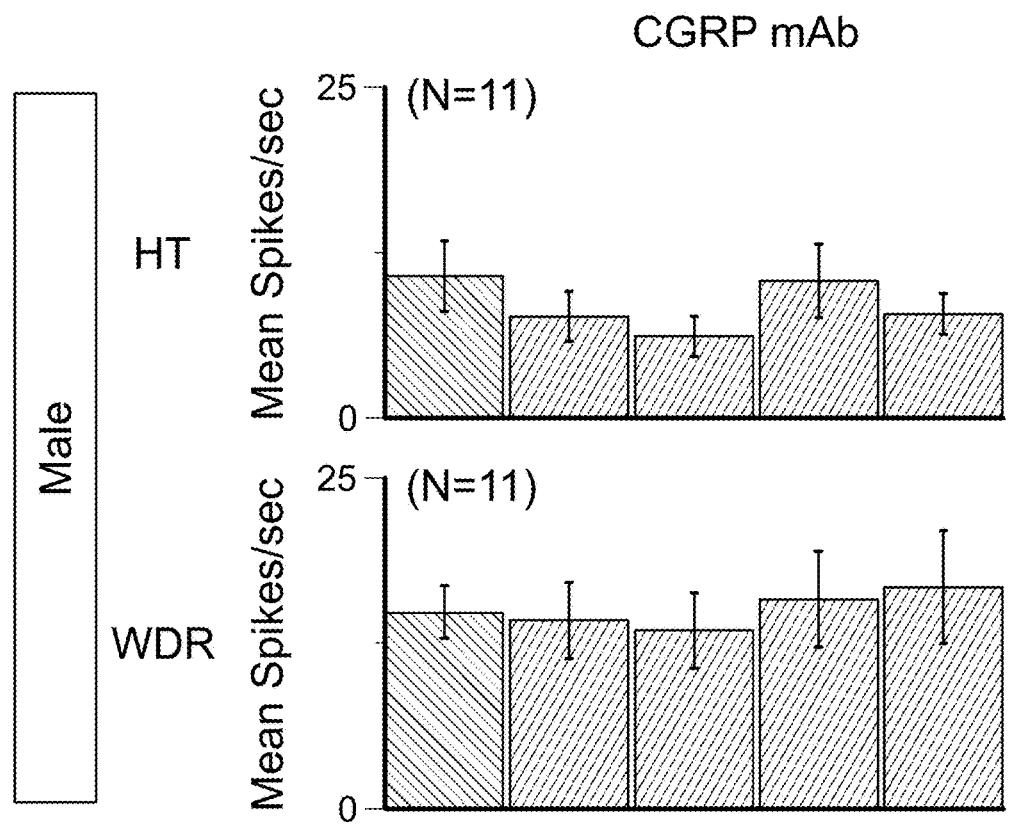
Figure 11C:
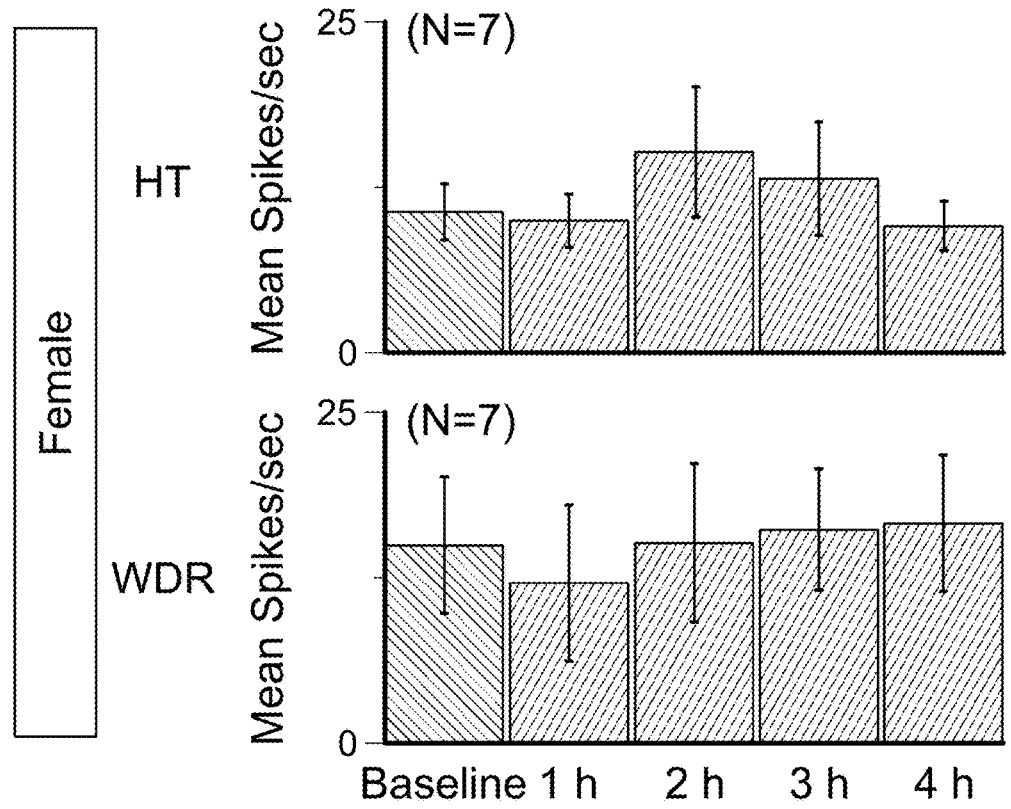
Figure 11D:
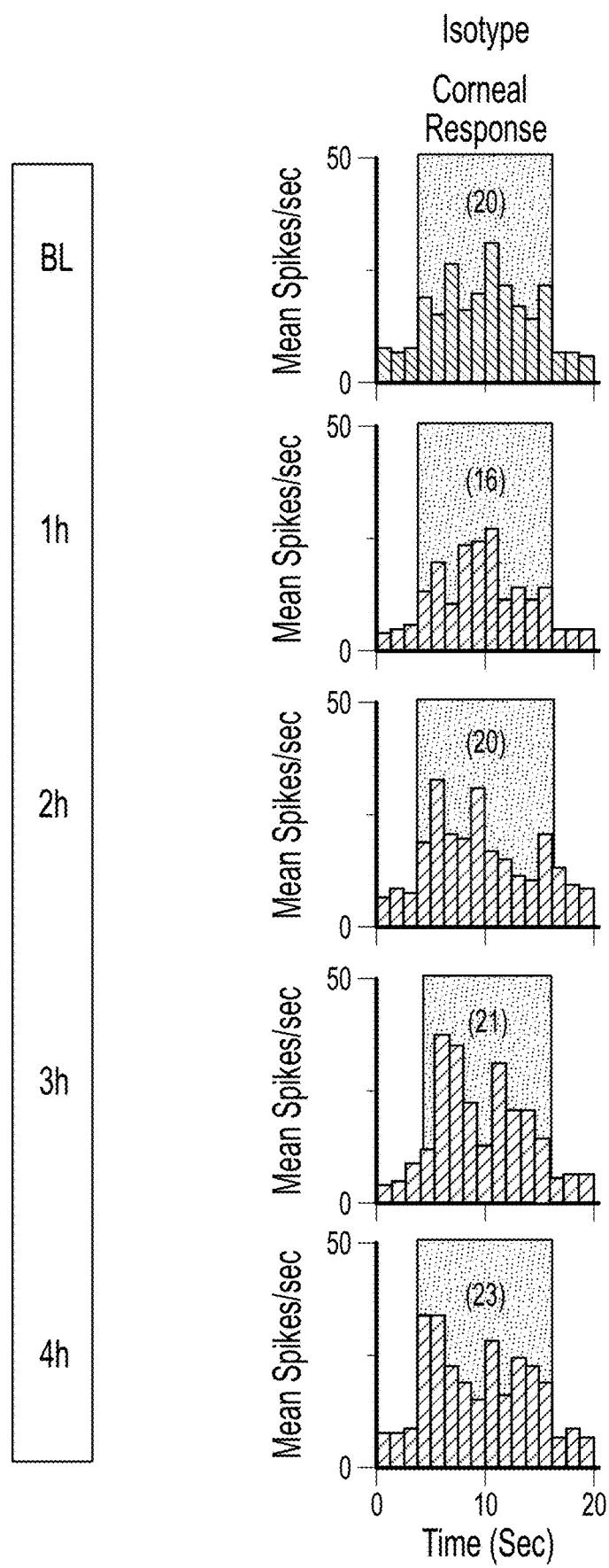
Figure 11E:
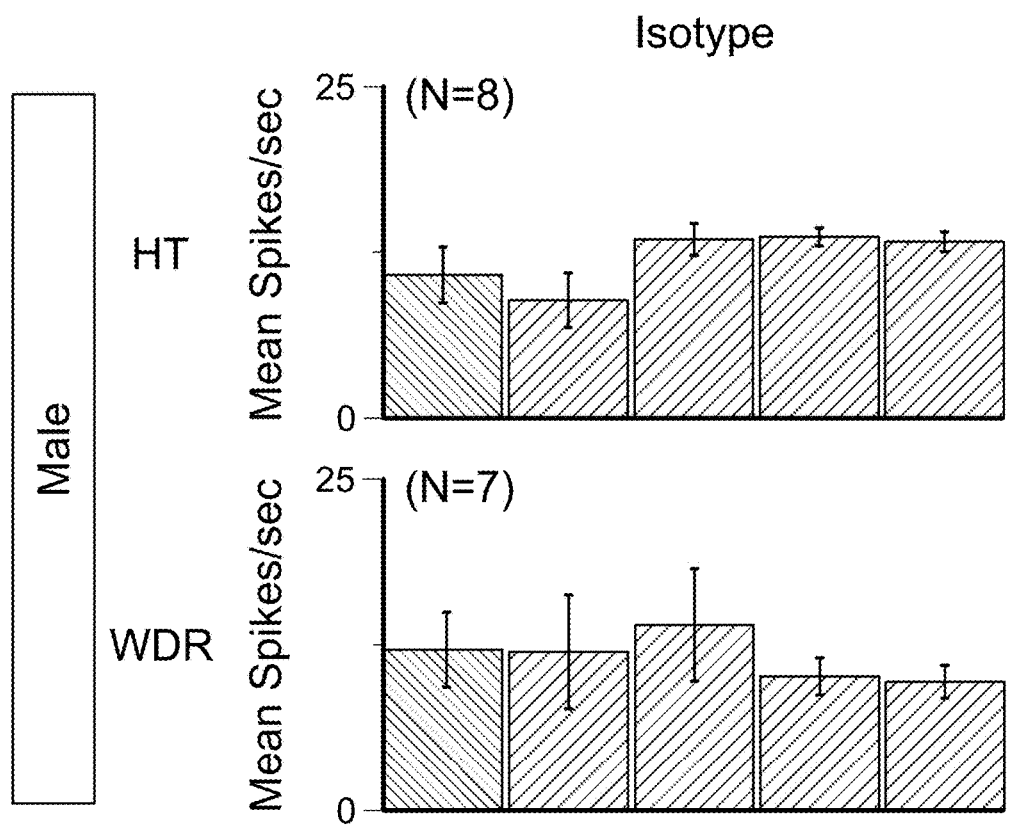
Figure 11F:
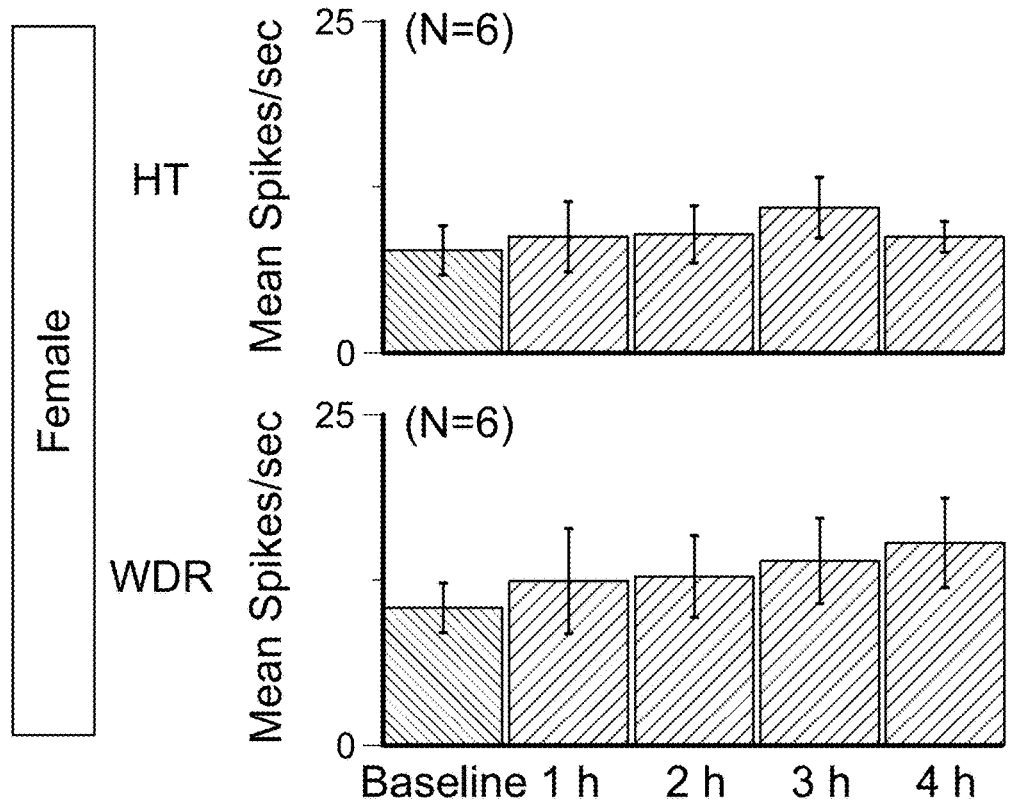

In both male and female rats, intravenous administration of the CGRP-mAb reduced the sensitivity to mechanical stimulation of the dura in the HT but not the WDR neurons (FIGS. 9A-9C). In males, the firing of HT neurons decreased by 75% (p=0.047) whereas in females it decreased by 61% (p=0.017). Regardless of the sex, intravenous administration of the isotype-conAb did not alter the sensitivity to dural stimulation in either group of neurons (FIGS. 9D-9F).

Sensitivity of Naïve Central Trigeminovascular Neurons to Mechanical Stimulation of the Periorbital Skin and the Cornea Intravenous administration of the CGRP-mAb (FIGS. 10A-10D)—or the isotype-conAb (FIGS. 10E-10H) did not alter the responses of HT or WDR neurons to innocuous (brush, pressure) or noxious (pinch) mechanical stimulation of the skin or the cornea FIGS. 11A-11F in male or female rats.

Cortical Spreading Depression

Effects of CGRP-mAb (n=27) or isotype-conAb (n=23) on activation of central trigeminovascular neurons by CSD was tested in 50 neurons in which baseline firing rate (i.e., mean spikes/sec before induction of CSD) was reliable and consistent over hours. At baseline (i.e., before CSD), the spontaneous firing rate of HT and WDR neurons did not differ between the male and the female rats (p=0.14). For the HT neurons, mean spikes/sec before induction of CSD was 1.2±0.6 in the male vs. 3.3±1.7 in the female (p=0.29). For the WDR neurons, mean spikes/sec before induction of CSD was 1.5±0.6 in the male vs. 3.5±2.2 in the female (p=0.37).

CSD-Induced Activity in Central Trigeminovascular Neurons

Figure 12A:
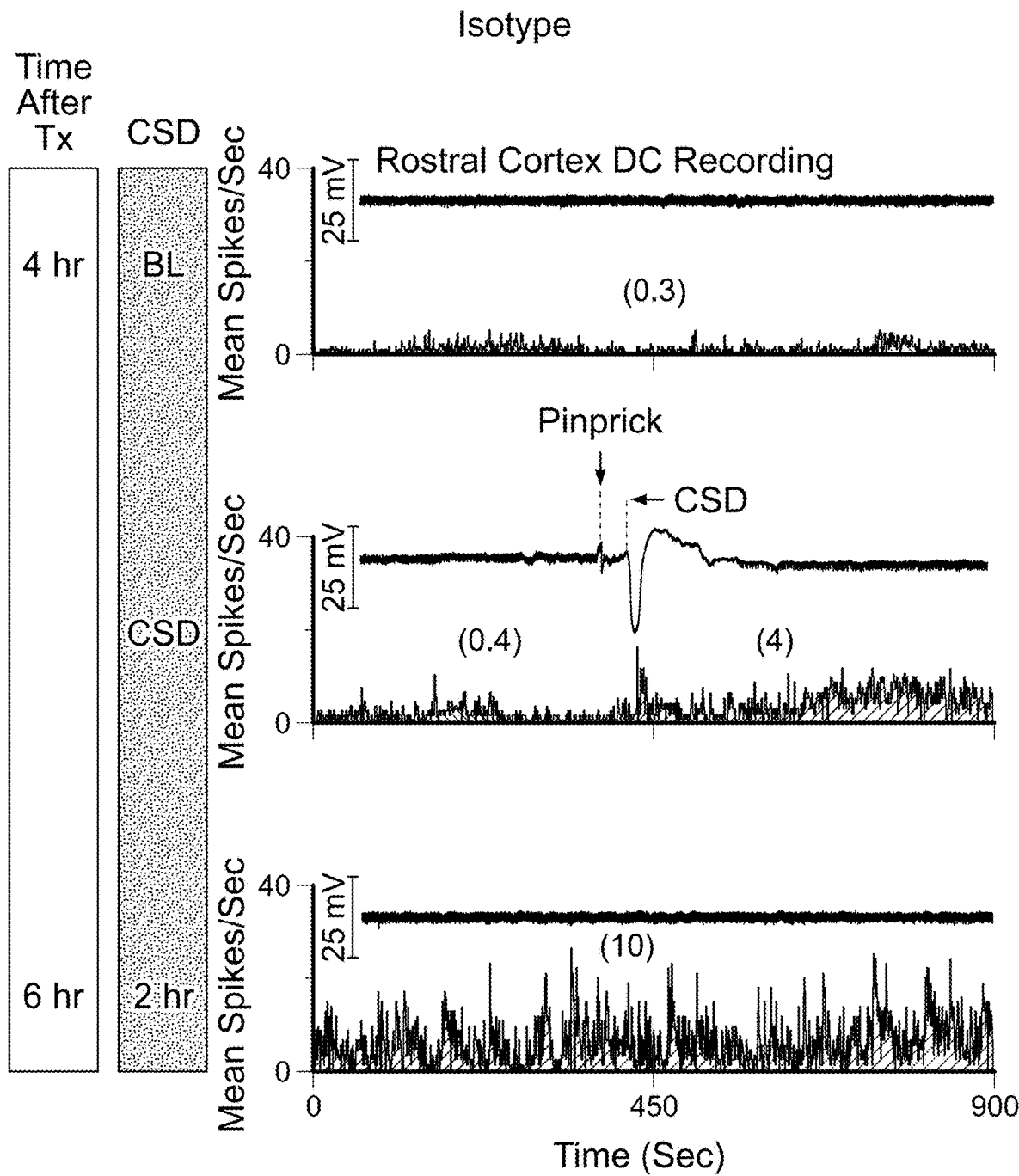
FIGS. 12A, 12B, 12C, 12D, 12E, and 12F are graphs showing the effect of CGRP-mAb (FIGS. 12A, 12B, and 12C) and isotype-conAb (FIGS. 12D, 12E, and 12F) on the activation of trigeminovascular neurons by cortical spreading depression (CSD) induced 4 hours post-drug treatment.
Figure 12B:
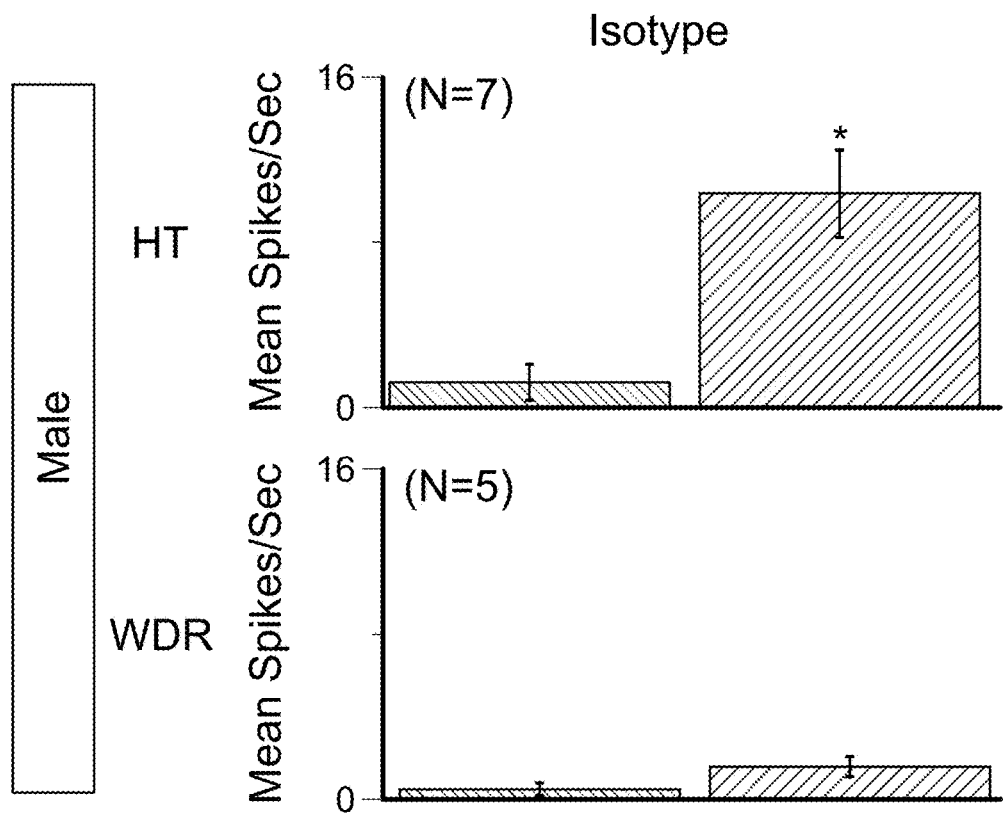

In male rats, two hours after induction of CSD and 6 hours after isotype-conAb administration, the mean firing rate of the 7 HT neurons increased from 1.1±0.8 spikes/sec before CSD to 10.2±2.1 after CSD(p=0.019), whereas the mean firing rate of the 5 WDR neurons did not increase (0.5±0.3 spikes/sec before CSD vs. 1.6±0.5 after CSD; p=0.14) (FIGS. 12A and 12B). In contrast, in the CGRP-mAb treated rats, the response magnitude of the 8 HT neurons remained unchanged 2 hours after induction of CSD and 6 hours after CGRP-mAb administration (1.2±0.6 spikes/sec before CSD vs. 1.9±1.5 after CSD, p=0.29) (FIGS. 12D and 12E). In other words, the expected CSD-induced activation of the HT neurons was prevented by the CGRP-mAb treatment.

Figure 12C:
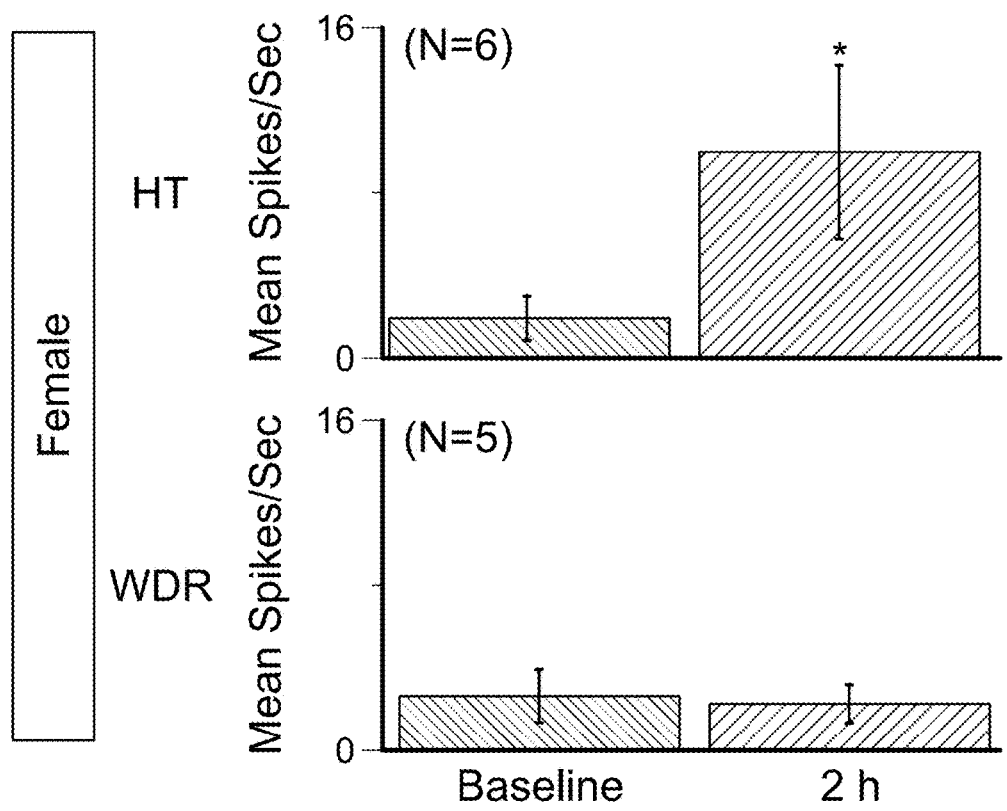
Figure 12D:
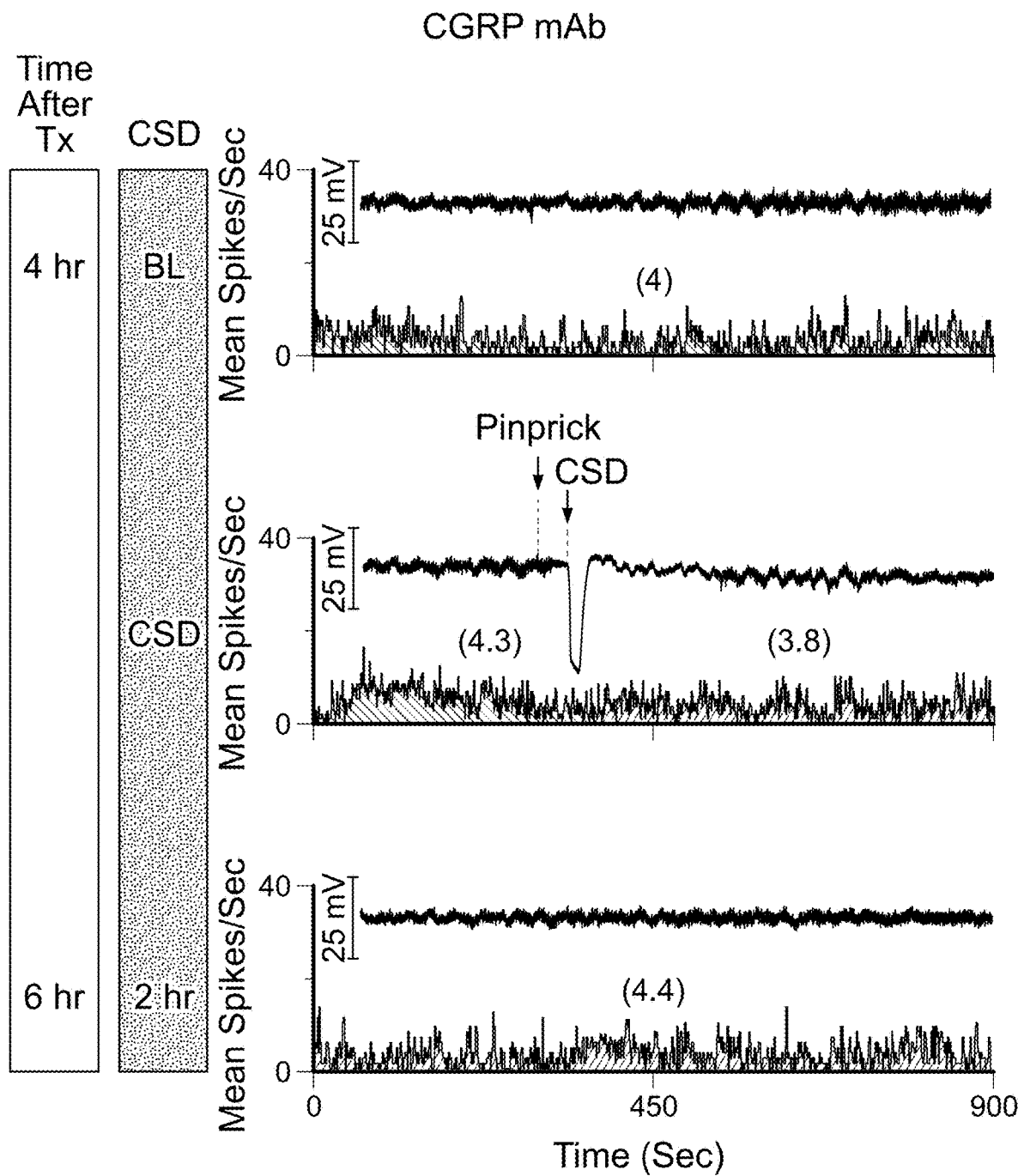
Figure 12E:
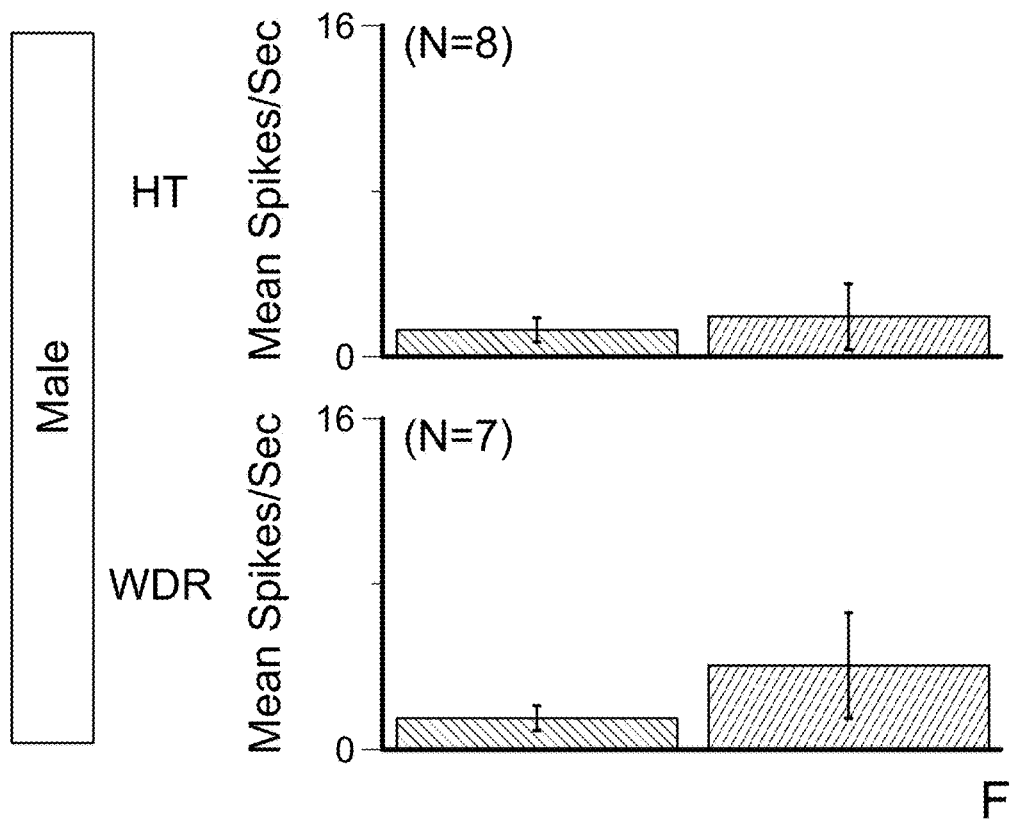
Figure 12F:
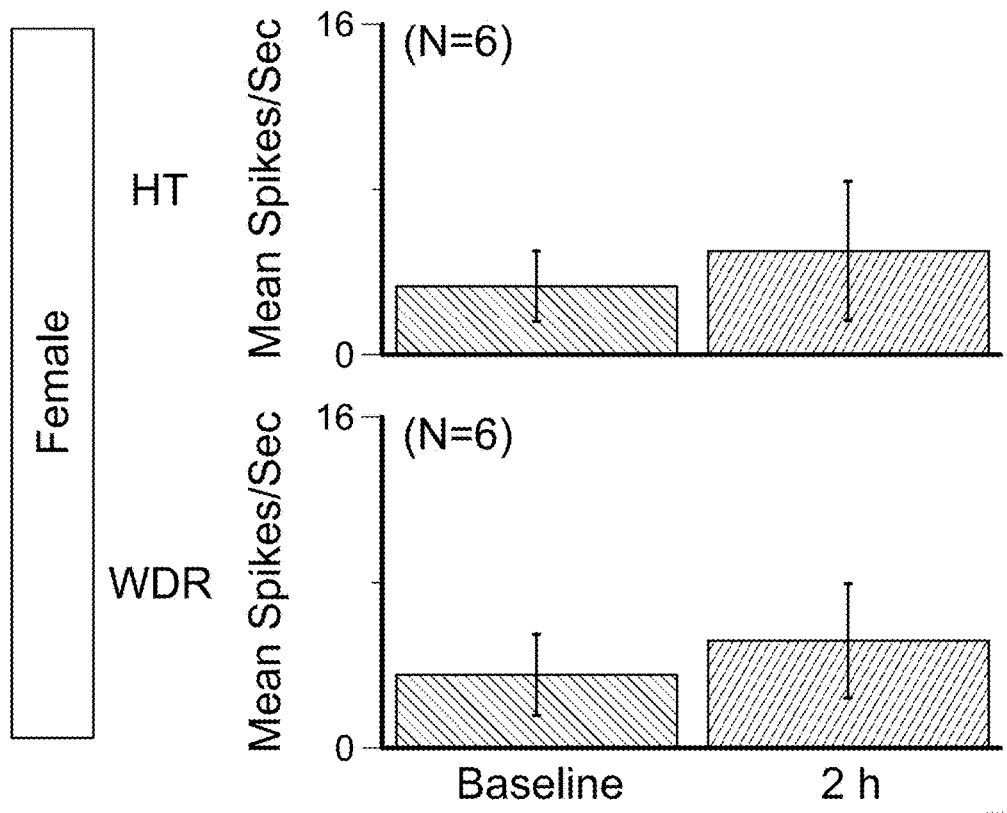

In female rats, two hours after induction of CSD and 6 hours after isotype-conAb administration, the mean firing rate of the 6 HT neurons increased from 1.9±1.0 spikes/sec before CSD to 10.0±4.5 after CSD (p=0.027), whereas the mean firing rate of the 5 WDR neurons remained unchanged (2.6±1.2 spikes/sec before CSD vs. 2.2±0.9 after CSD p=0.73) (FIG. 12C). In contrast, in the CGRP-mAb treated rats, the response magnitude of the 6 HT neurons remained unchanged 2 hours after induction of CSD and 6 hours after CGRP-mAb administration (3.3±1.7 spikes/sec before CSD vs. 5.0±3.4 after CSD, p=0.45) (FIG. 12F). As in the male, the expected CSD-induced activation of the HT neurons was prevented by the CGRP-mAb treatment.

To further examine CGRP-mAb effects on the activation of WDR and HT neurons by CSD, a case-by-case analysis was also performed. Of all CGRP-mAb and isotype-conAb treated WDR neurons, 5/13 and 4/10 were activated by CSD, a mere 2% difference. In contrast, of all CGRP-mAb and isotype-conAb treated HT neurons, 2/14 and 13/13 were activated by CSD, an 86% difference.

CSD-Induced Sensitization

Regardless of activation by CSD, 11/13 HT and none of the WDR neurons fulfilled criteria for the development of sensitization (defined in the data analysis section). Therefore, the CGRP-mAb's ability to interfere with the development of sensitization after CSD is presented for HT but not WDR neurons.

Figure 14A:
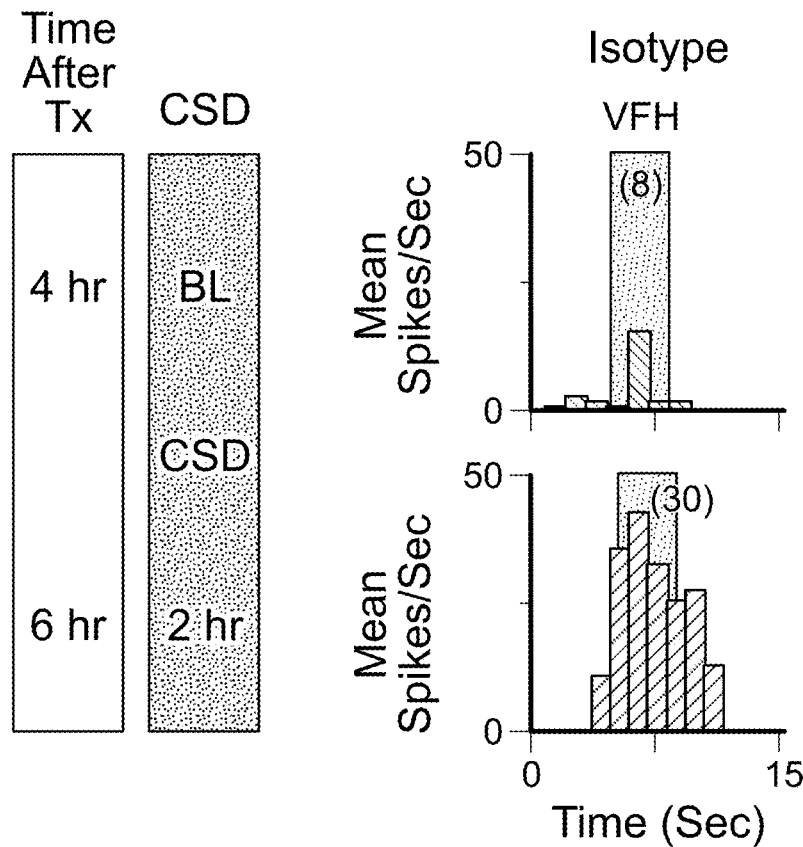
FIGS. 14A, 14B, 14C, 14D, 14E, and 14F are graphs showing that the enhanced responses to mechanical stimulation of the dura following CSD are prevented by the CGRP-mAb.
Figure 14B:
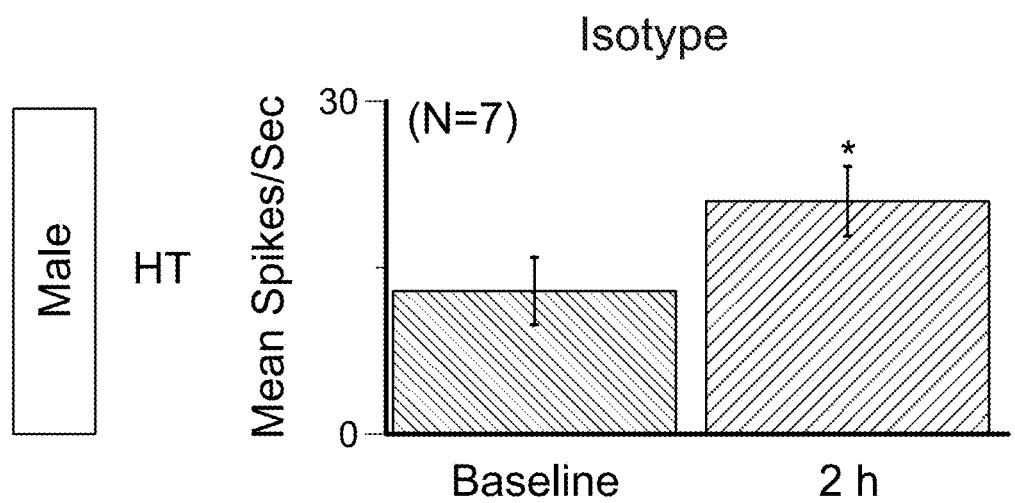
Figure 14C:
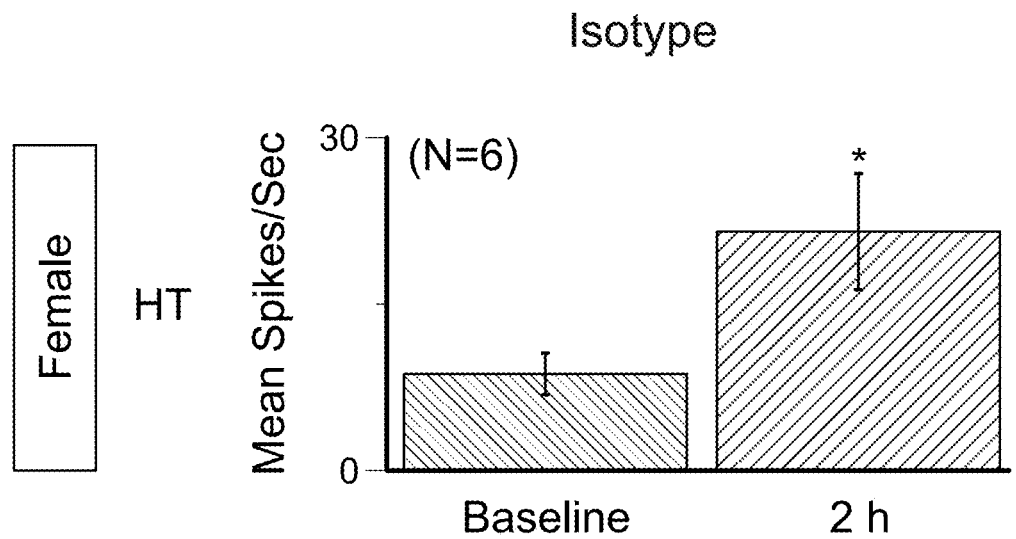

Expansion of Dural Receptive Fields and Enhanced Responses to Mechanical Stimulation of the Dura after CSD In the isotype-conAb treated group, dural receptive fields expanded in 5/7 HT neurons in males and 6/6 HT neurons in females (FIG. 13A). Two hours after induction of CSD (6 hours after isotype-conAb administration), neuronal responses to dural indentation with VFH increased in all 7 HT neurons in the male (12.8±3.9 spikes/sec before CSD vs. 22.0±3.7 after CSD; p=0.026), and all 6 HT neurons in the female (8.5±1.7 before CSD vs. 21.6±5.1 after CSD, p=0.047) (FIGS. 14A-14C).

Figure 14D:
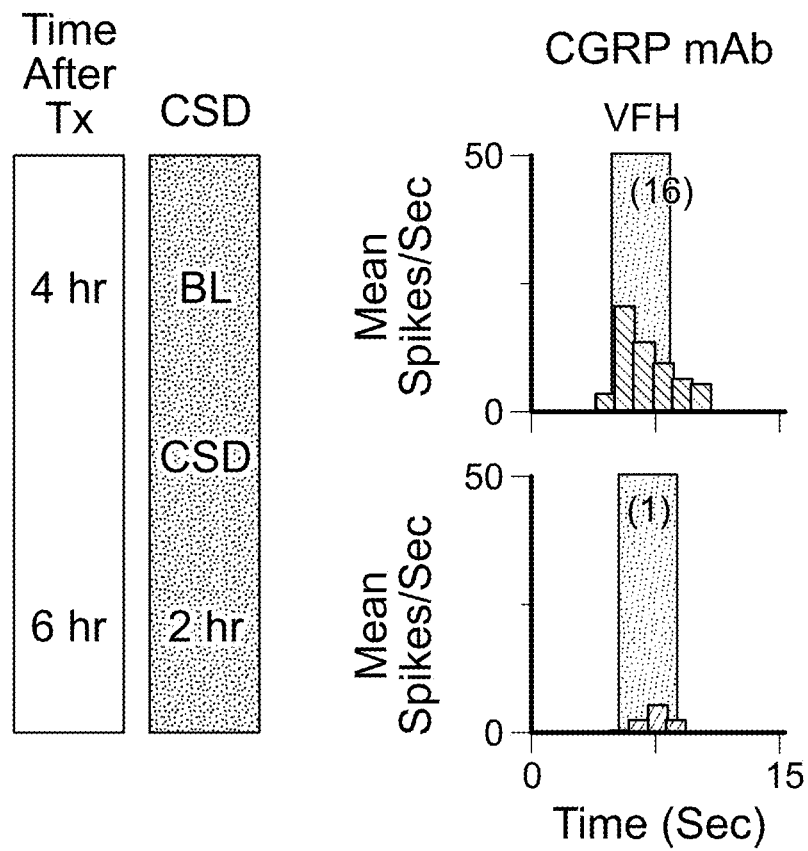
Figure 14E:
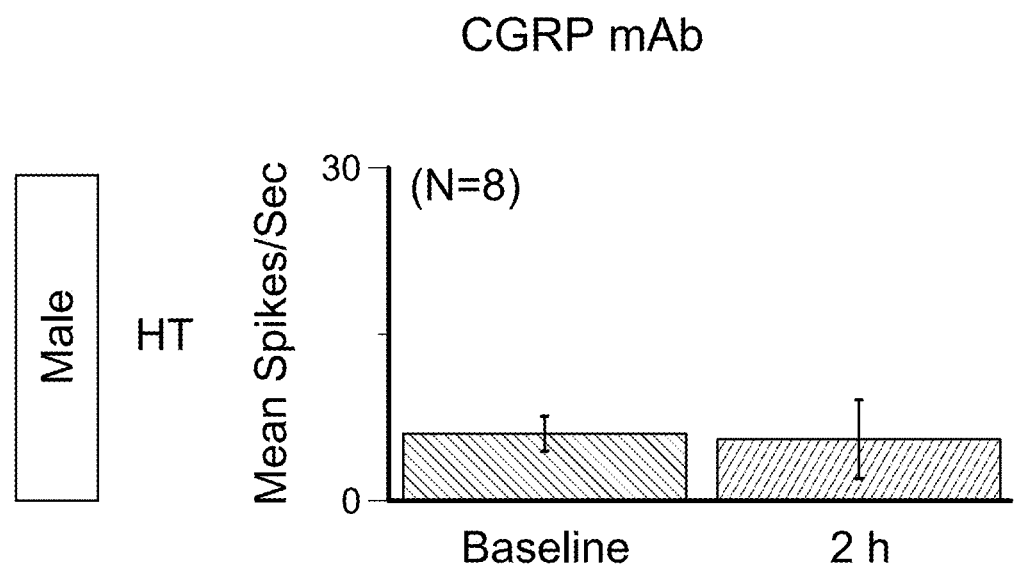
Figure 14F:
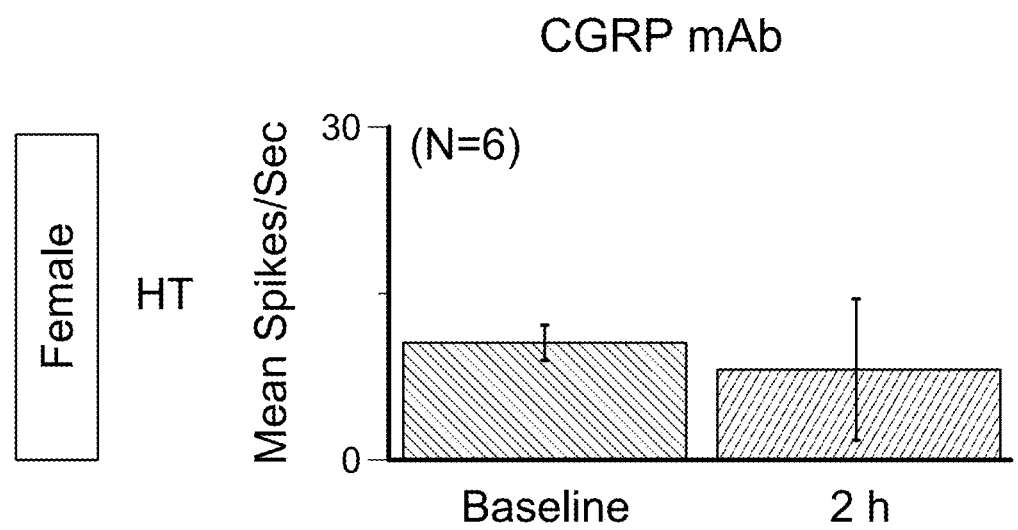

In contrast, in the CGRP-mAb treated group, expansion of dural receptive fields, which was smaller when it occurred, was recorded in only 2/8 HT neurons in the male and 0/6 in the female (FIG. 13B). Two hours after induction of CSD (6 hours after CGRP-mAb administration), neuronal responses to dural indentation with VFH remained unchanged in all HT neurons in both the male (1.8±0.6 before CSD vs. 1.9±1.5 after CSD, p=0.83) and the female (10.5±1.6 before CSD vs. 8.1±6.4 after CSD, p=0.72, FIGS. 14D-14F)—indicative of prevention of sensitization. Thus, the CGRP-mAb prevented the development of intracranial mechanical hypersensitivity in HT neurons in both male and female rats.

Expansion of Cutaneous Receptive Fields and Enhanced Responses to Mechanical Stimulation of the Periorbital Skin after CSD (i.e., Central Sensitization)

Figure 15A:
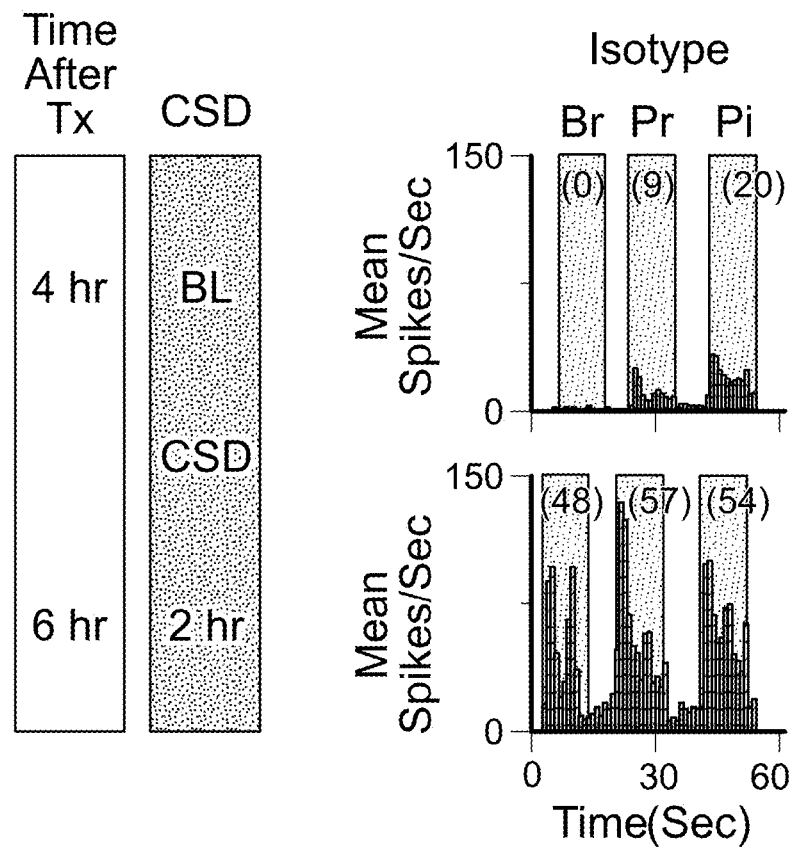
FIGS. 15A, 15B, 15C, 15D, 15E, and 15F are graphs showing the enhanced responses to cutaneous stimulation following CSD are prevented by the CGRP-mAb.
Figure 15B:
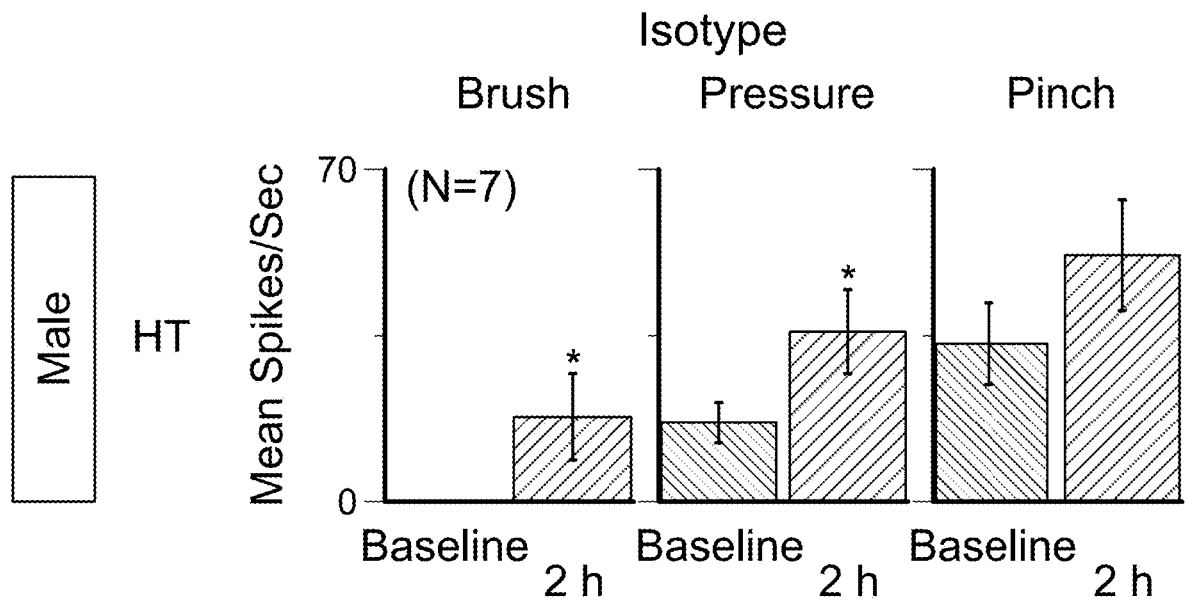
Figure 15C:
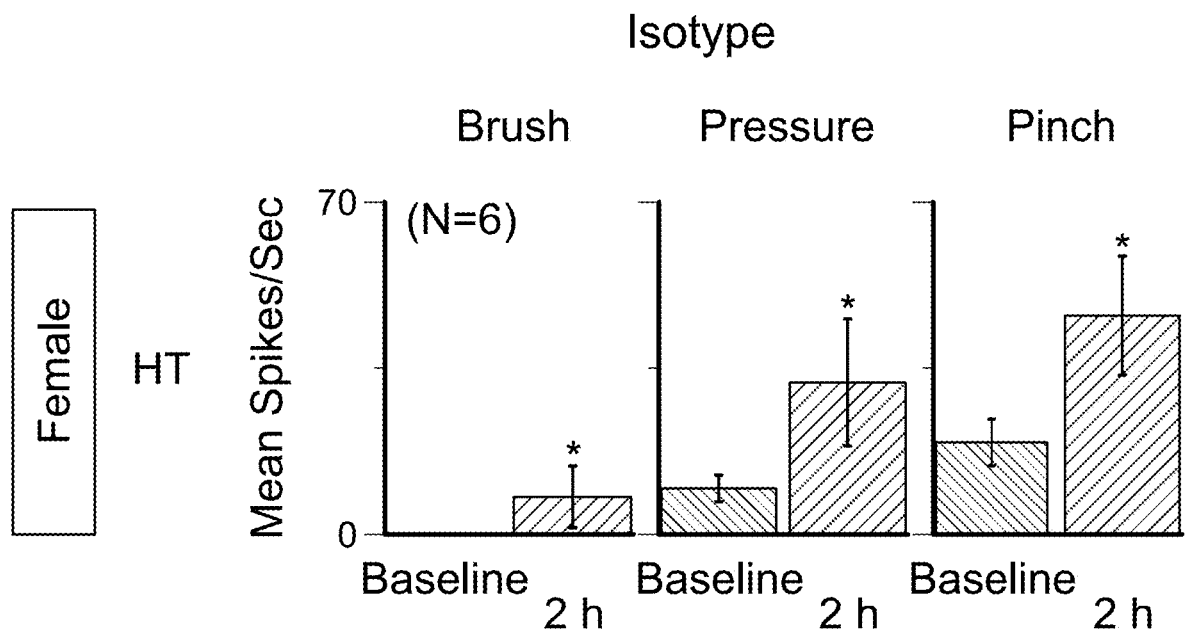

In the isotype-conAb treated group, facial receptive fields expanded in 5/7 HT neurons in males and 6/6 HT neurons in females (FIG. 13A). Two hours after induction of CSD (6 hours after isotype-conAb administration) responses to brush and pressure increased significantly in all 13 HT neurons (7 in males, 6 in females) (FIGS. 15A-15C). In males, responses to brush and pressure increased from 0.0 to 18.2±9.1 spikes/sec (p=0.046) and from 16.6±4.2 to 35.8±9.1 spikes/sec (p=0.045), respectively (FIG. 15B). In females, responses to brush and pressure increased from 0.0 to 8±6.5 spikes/sec (p=0.027) and from 9.3±2.7 to 31.8±13.6 spikes/sec (p=0.016), respectively (FIG. 15C). In contrast, responses to pinch increased significantly in all HT neurons in females (19.3±5.0 spikes/sec before CSD vs. 45.8±12.4 spikes/sec after CSD, n=6, p=0.027) but not in the male (33.8±7.1 spikes/sec before CSD vs. 52.4±10.3 spikes/sec after CSD, n=6, p=0.068) (FIGS. 15B and 15C).

Figure 15D:
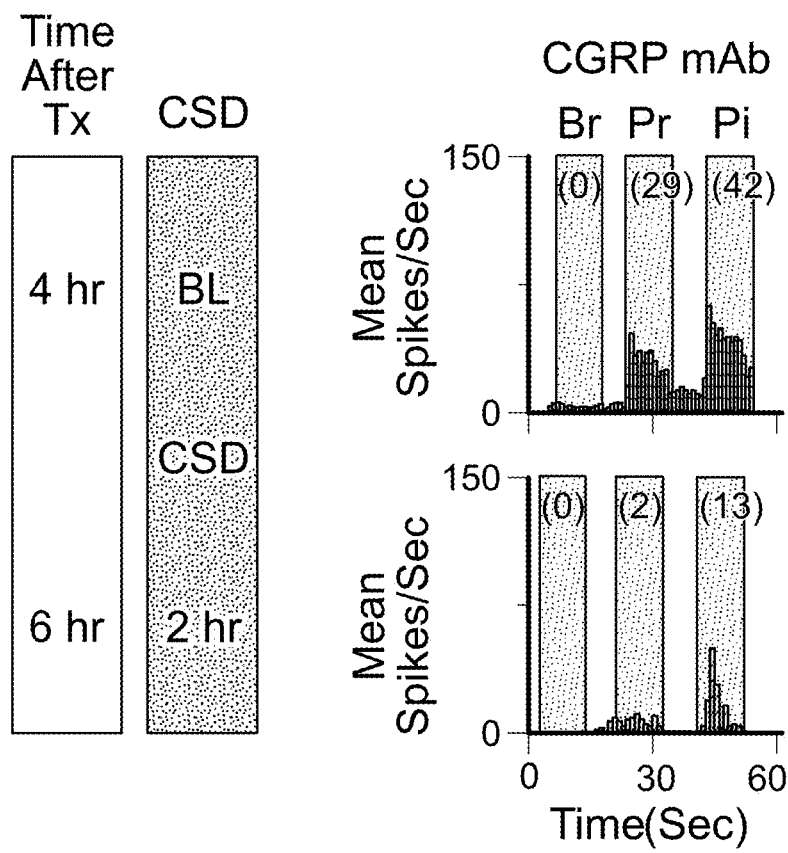
Figure 15E:
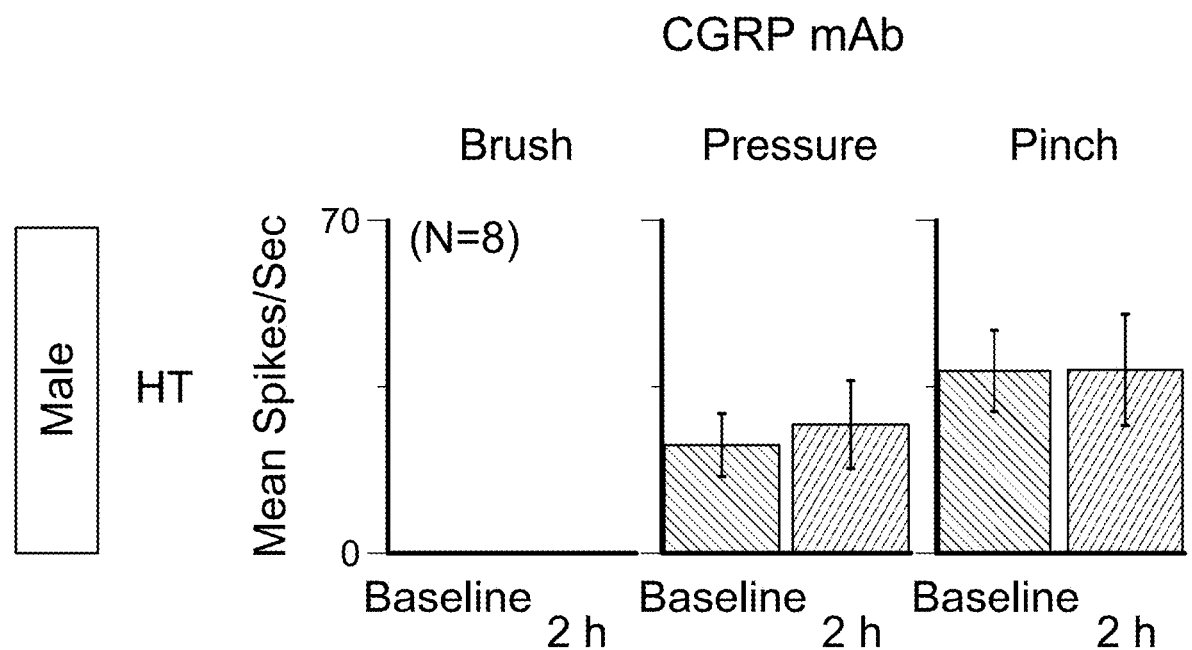
Figure 15F:
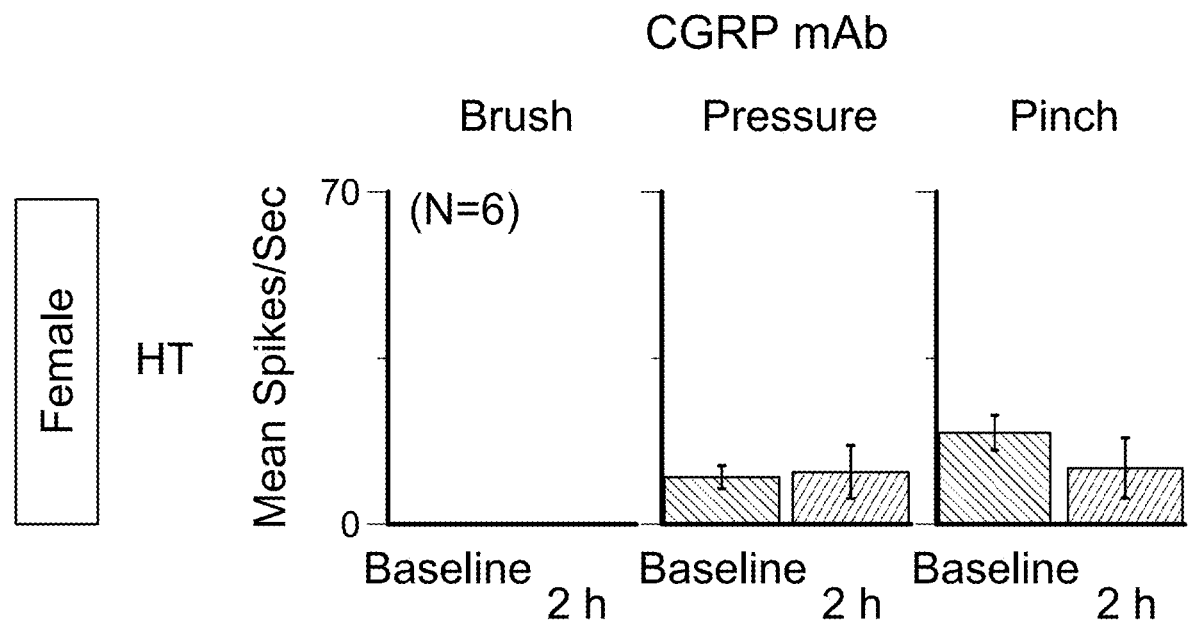

In the CGRP-mAb treated rats, facial receptive fields expanded in only 2/8 HT neurons in males and 0/6 HT neurons in females (FIG. 13B). Two hours after induction of CSD (6 hours after CGRP-mAb administration), neuronal responses to brush (p=0.35), pressure (p=0.63) and pinch (p=0.78) remained unchanged in all HT neurons in both male and female (FIGS. 15D-15F)—suggesting that the CGRP-mAb prevented induction of sensitization.

Enhanced Responses to Corneal Stimulation after CSD

Figure 16A:
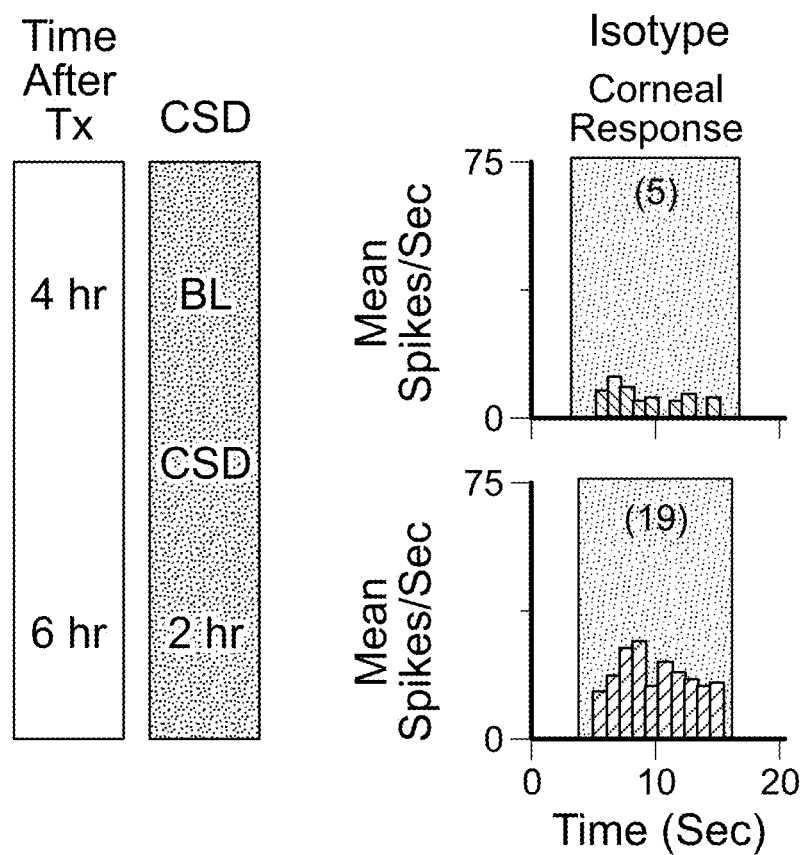
FIGS. 16A, 16B, 16C, 16D, 16E, and 16F are graphs showing the enhanced responses to mechanical stimulation of the cornea following CSD are prevented by CGRP-mAb (female only).
Figure 16B:
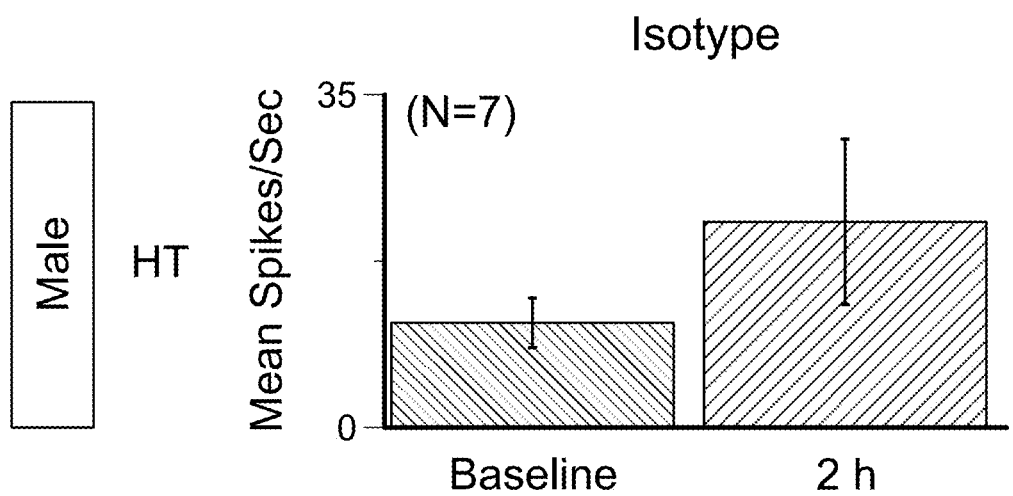
Figure 16C:
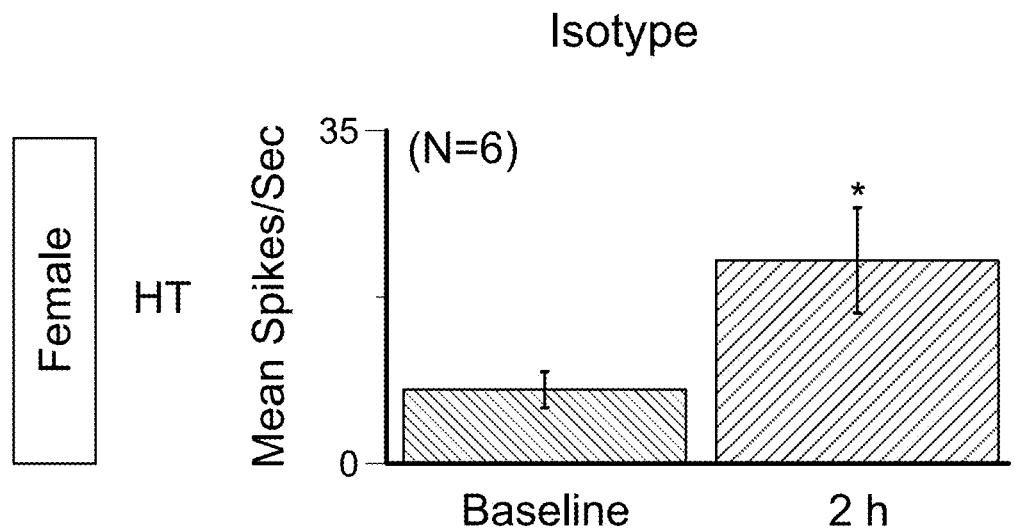

In the isotype-conAb treated rats, responses to corneal stimulation after CSD increased significantly in females (7.6±1.9 spikes/sec before CSD vs. 21.0±6.4 spikes/sec after CSD, n=6, p=0.044) but not in males (11.0±2.6 spikes/sec before CSD vs. 21.6±8.7 spikes/sec after CSD, n=7, p=0.19) HT neurons (FIGS. 16A-16C).

Figure 16D:
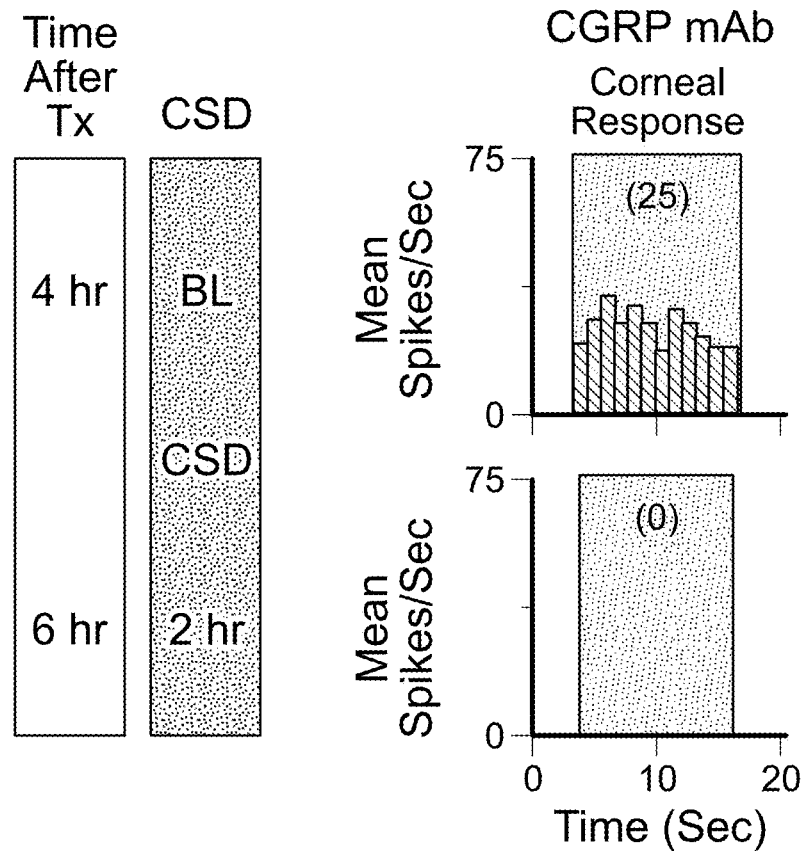
Figure 16E:
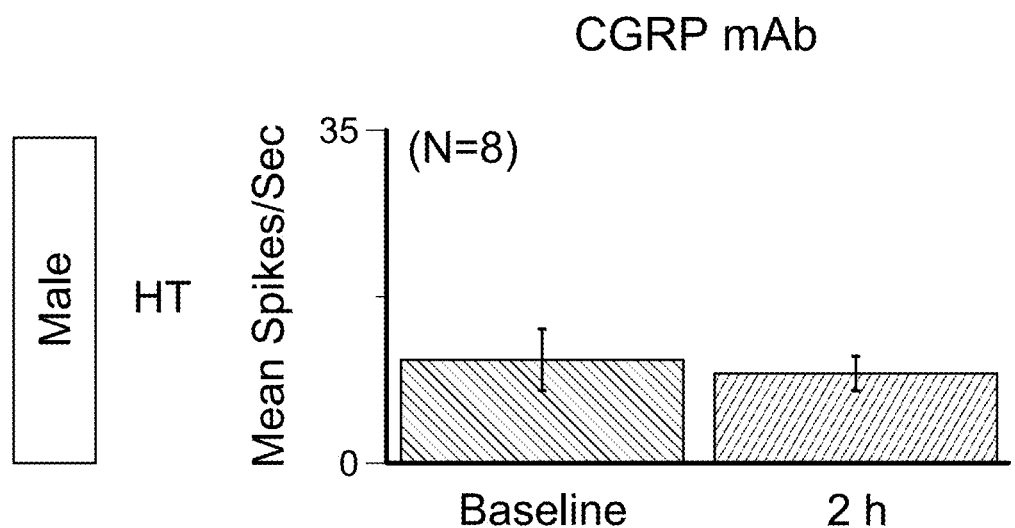
Figure 16F:
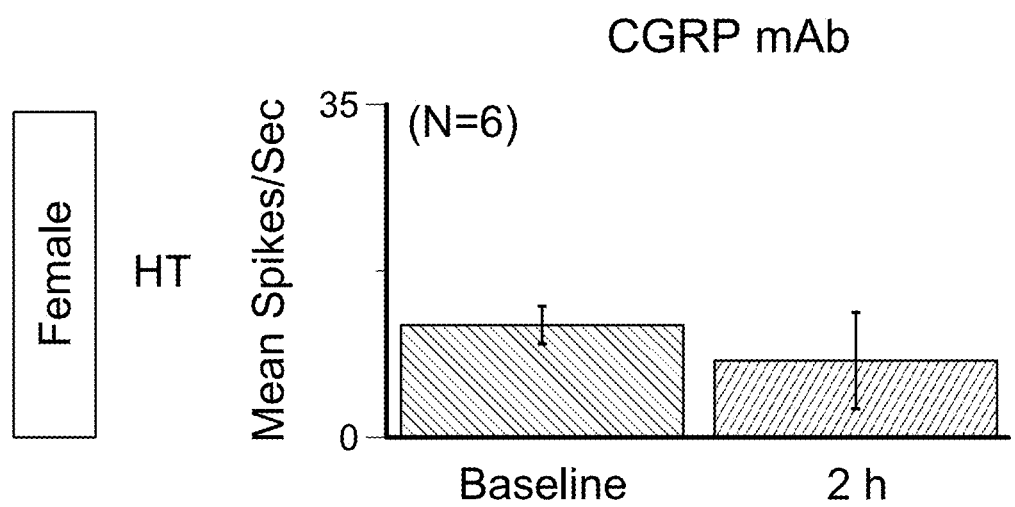
Figure 20A:
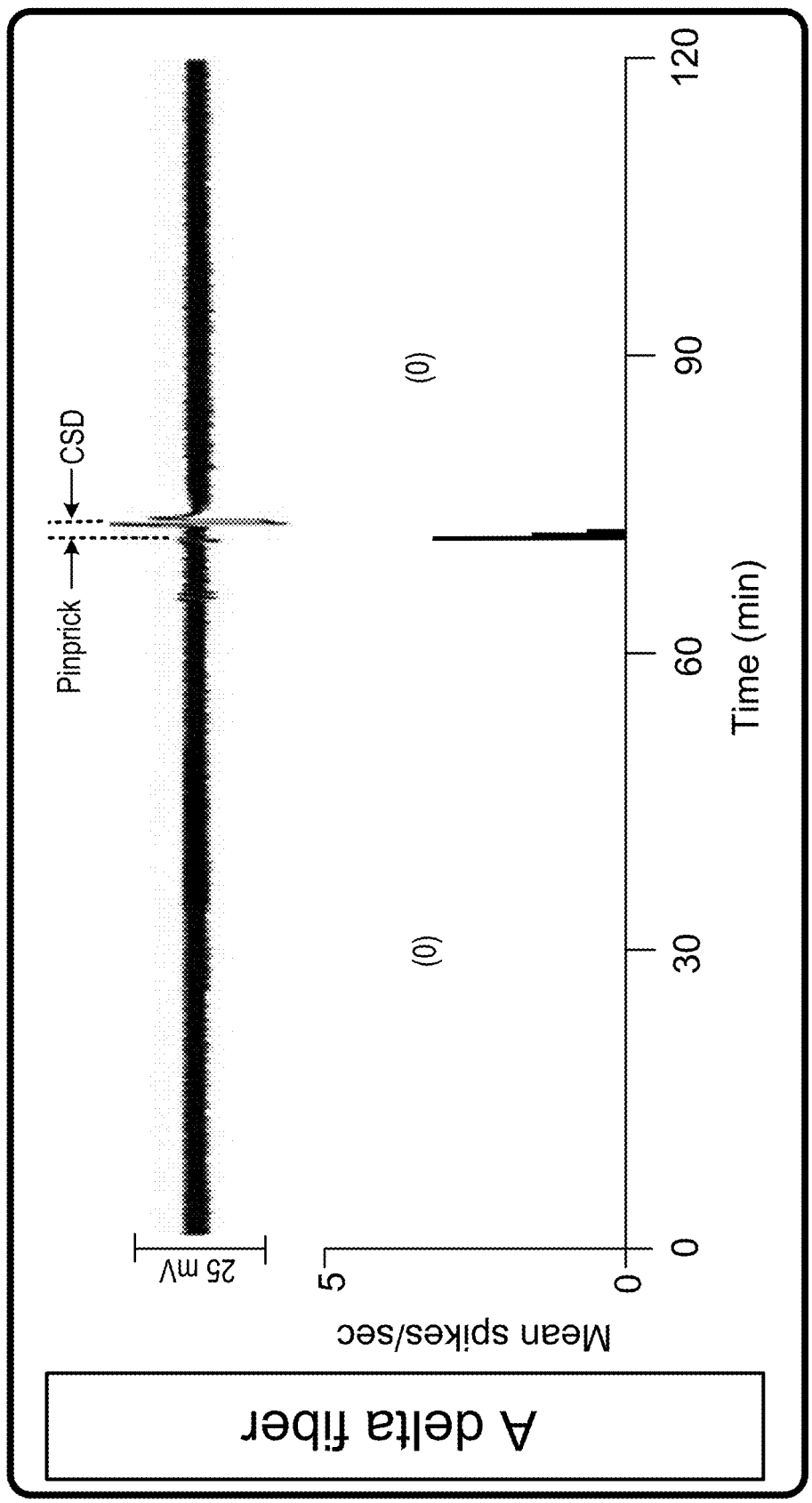
FIGS. 20A and 20B show that fremanezumab prevents the activation of most a-delta and some C-type meningeal nociceptors.
Figure 20B:
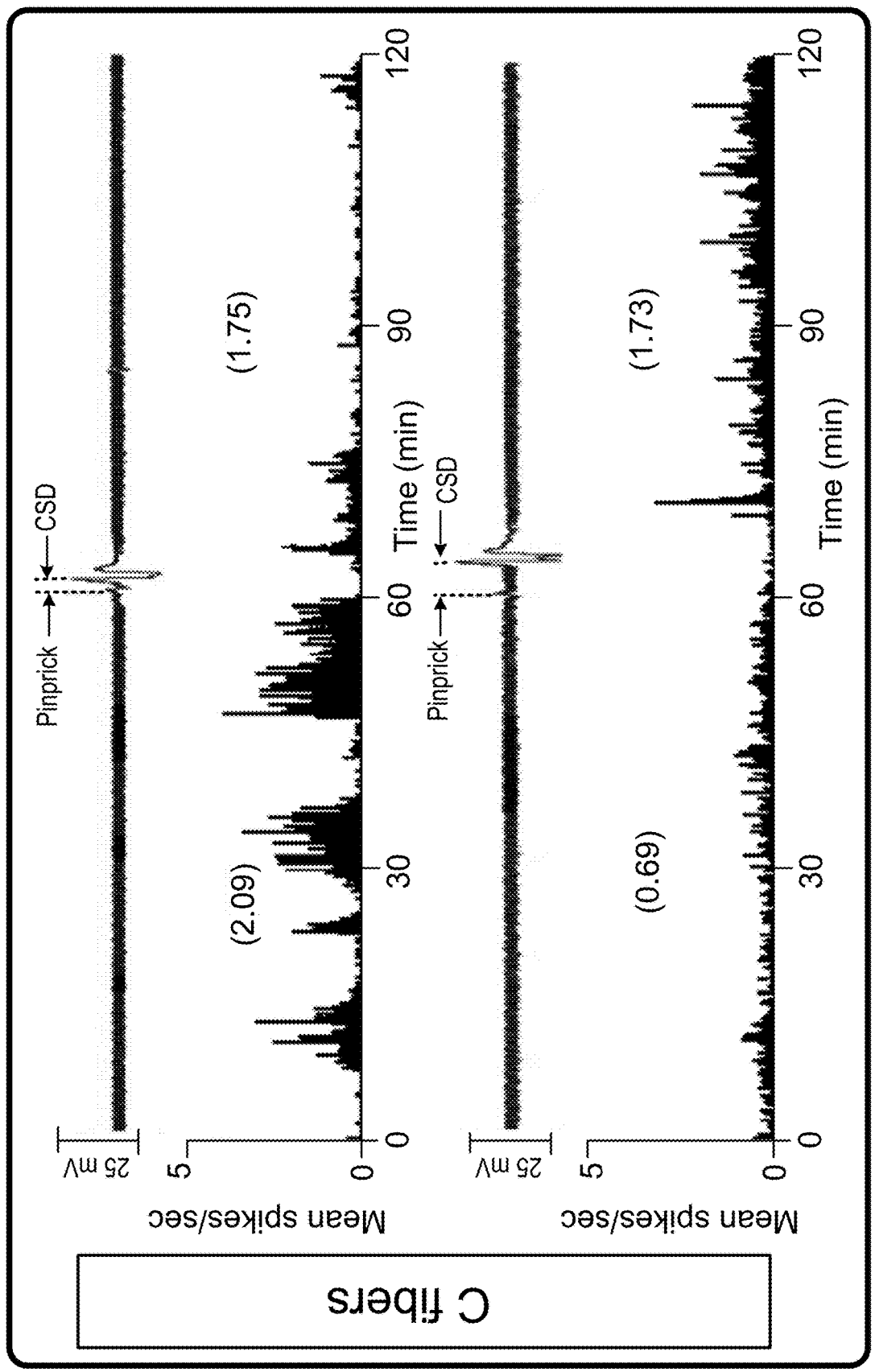
Figure 22C:
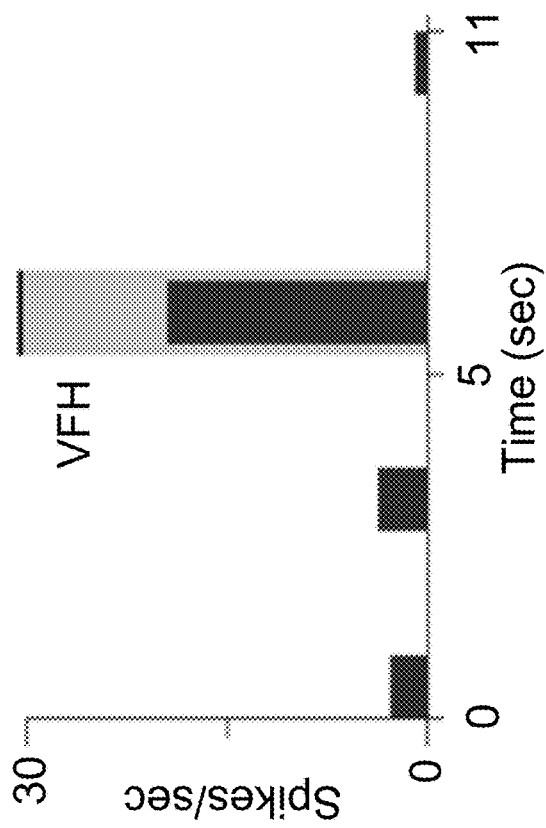
FIG. 22C is a bar graph that shows location of dural receptive field.
Figure 22A:
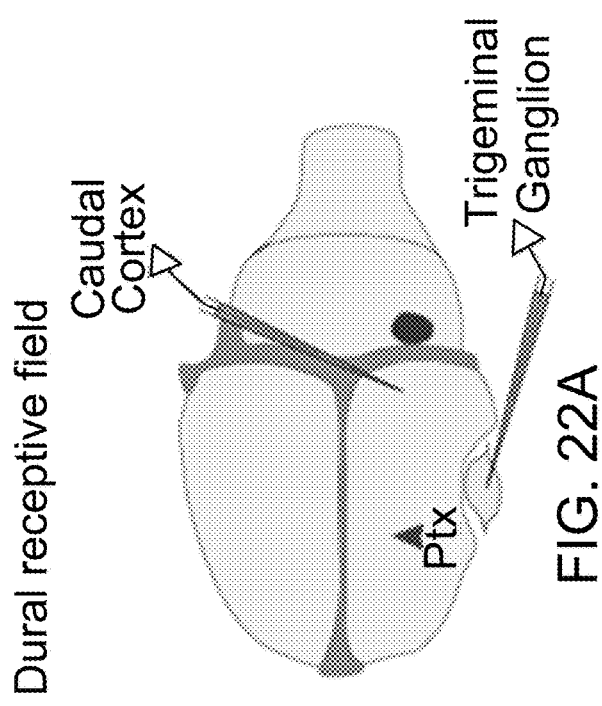
FIG. 22A shows how single-unit recordings were obtained from dural primary afferent nociceptors in the trigeminal ganglion while recording electrocorticogram activity from the caudal cortex. Triangle shows site of picrotoxin administration.
Figure 22B:
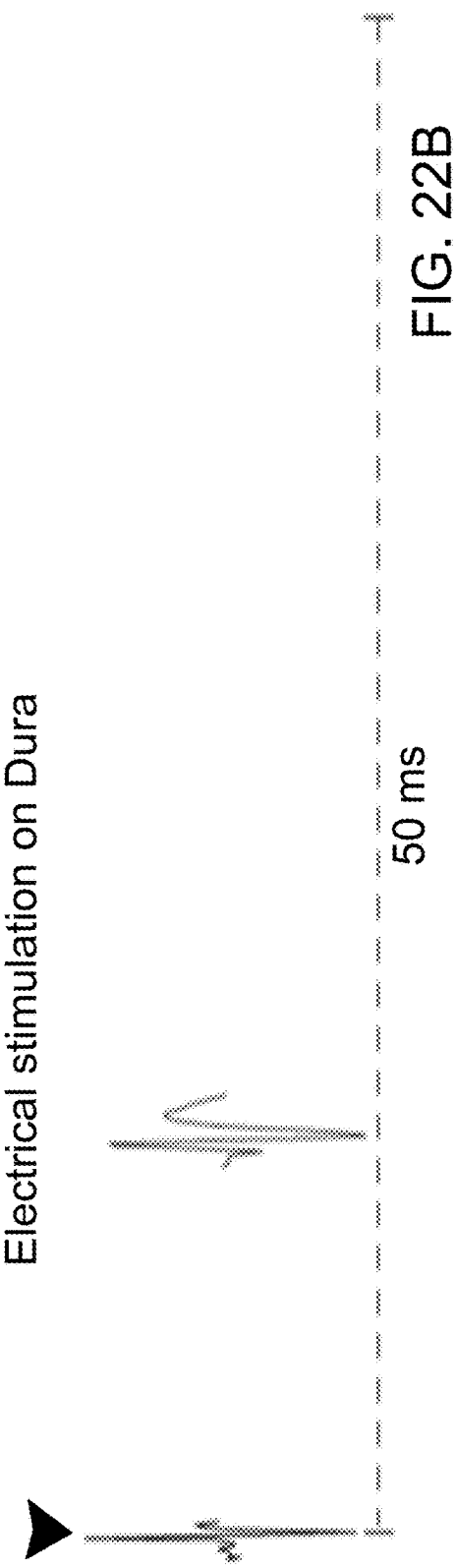
FIG. 22B shows dural afferents were identified by their response to single-shock stimulation applied to the dura overlying the transverse sinus, and were further characterized as mechanosensitive by their response to von Frey (VFH) stimulation of the dura.
Figure 22D:
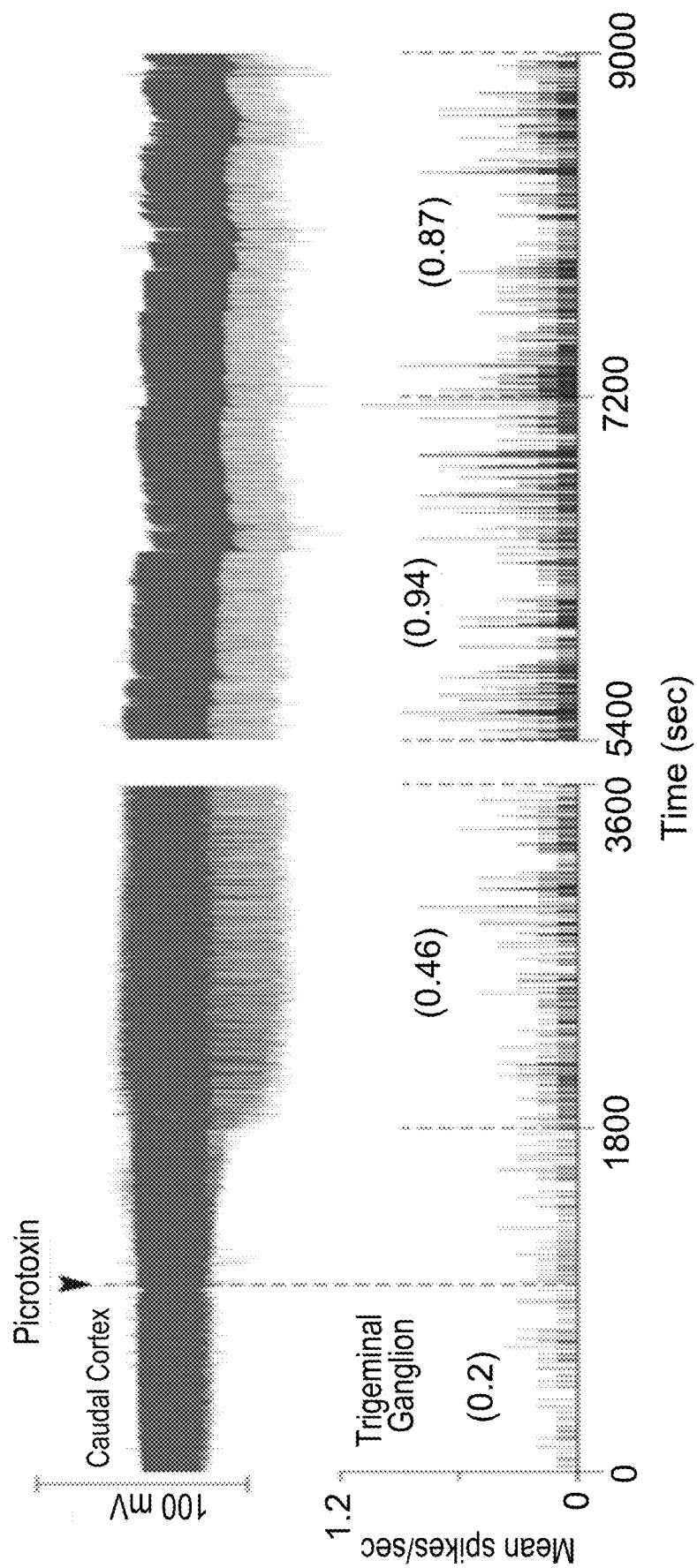
FIG. 22D is an electrocorticogram (upper trace) and firing rate of a dural afferent (lower trace) before and after induction of seizure by picrotoxin. Triangle shows time of picrotoxin administration.
Figure 23C:
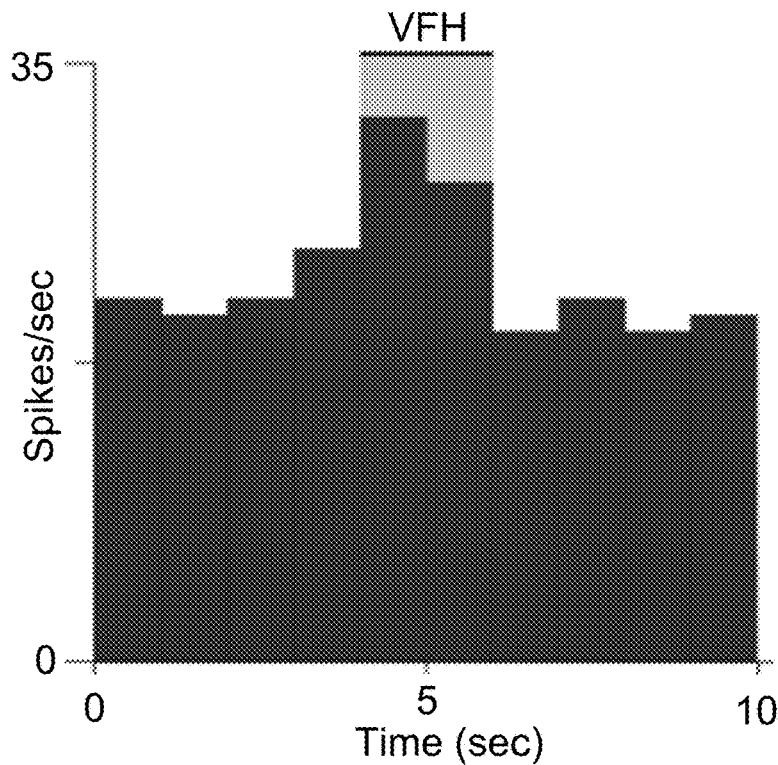
FIG. 23C is a bar graph that shows mechanical stimulation on dura.
Figure 23D:
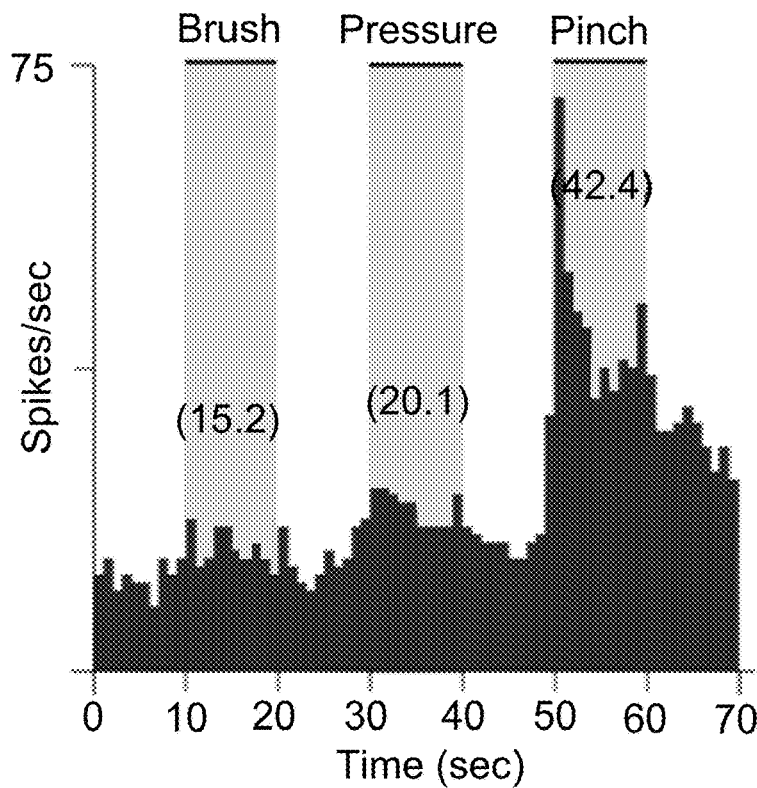
FIG. 23D shows an ECG recording of a neuron characterized as wide dynamic range (WDR) by its responses to graded mechanical stimulation of the facial skin.
Figure 23E:
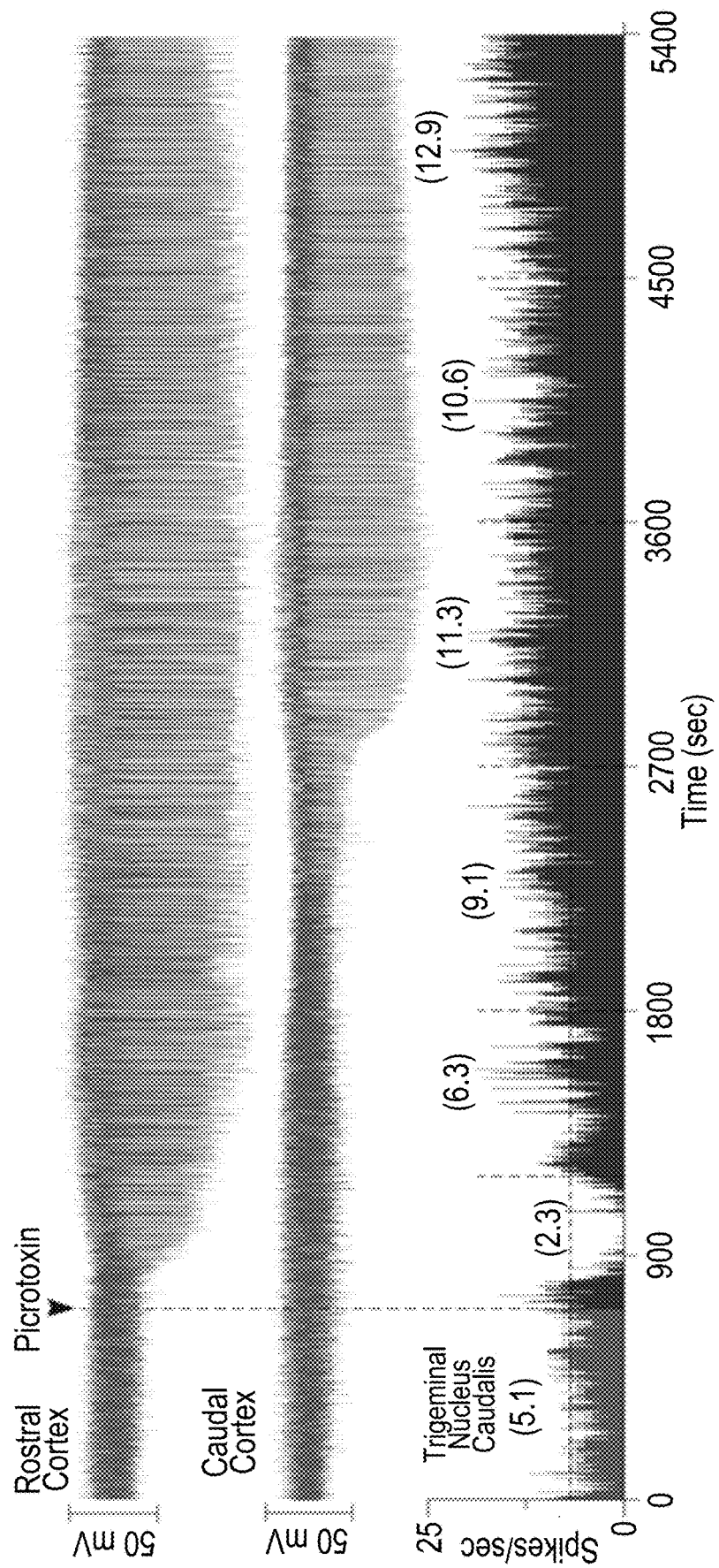
FIG. 23E shows that topical application of picrotoxin to the parietal cortex induced cortical seizure (upper trace) and transient suppression of neuronal firing, which was followed by a prolonged increase above baseline that persisted after the cessation of seizure activity.

In the CGRP-mAb treated female rats, response to brushing the cornea remained unchanged in the 6 HT neurons (p=0.51)—suggesting prevention of sensitization; and as expected, it also remained unchanged in the 8 HT neurons in the males (10.8±3.3 spikes/sec before CSDS vs. 9.4±1.8 (spikes/sec after CSD, p=0.60) (FIGS. 16D-16F). Thus, the CGRP-mAb prevented the development of corneal hypersensitivity in HT neurons in female but not male rats.

C. Discussion

The study demonstrates that the humanized monoclonal anti-CGRP antibody fremanezumab inhibits activation and sensitization of HT but not WDR trigeminovascular neurons (FIG. 17). In males, the CGRP-mAb inhibited the spontaneous activity of naive HT neurons and their responses to stimulation of the intracranial dura but not facial skin or cornea, whereas in females it only inhibited their responses to stimulation of the intracranial dura. When given sufficient time, however, the CGRP-mAb prevented in both sexes the activation and consequential sensitization of the HT neurons by CSD, but not the partial activation of WDR neurons. Mechanistically, these findings suggest that HT neurons play a critical role (not recognized before) in the initiation of the perception of headache and the development of allodynia and central sensitization. Clinically, the present findings may help explain the therapeutic effectiveness of CGRP-mAb in preventing headaches of intracranial origin such as migraine and why this therapeutic approach may not be effective for every migraine patient.

This study tested the effects on CGRP-mAb on the responsiveness of different classes of central trigeminovascular neurons. Previously, Storer and colleagues showed that the CGRP-R antagonist BIBN4096BS inhibits naïve central trigeminovascular neurons responses to electrical stimulation of the superior sagittal sinus and microiontophoretic administration of L-glutamate (Storer et al., 2004, *Br. J. Pharmacol.* 142:1171-1181).

Fremanezumab Effects on HT Vs. WDR

When given intravenously, CGRP-mAb reduced baseline spontaneous activity in HT but not WDR neurons. Considering current and previous evidence that WDR trigeminovascular neurons are activated by a variety of dural stimulation used to study the pathophysiology of migraine (Davis and Dostrovsky, 1988, *J. Neurophysiol.* 59:648-666; Burstein et al., 1998, *J. Neurophysiol.* 79:964-982; Storer et al., 2004, *Brit. J. Pharmacol.* 142:1171-1181; Zhang et al., 2011, *Ann. Neurol.* 69:855-865), it is reasonable to conclude that activation of WDR alone is insufficient to induce the headache perception in episodic migraine patients whose headaches are completely or nearly completely prevented by CGRP-mAb therapy (Bigal et al., 2015, *Lancet Neurol.* 14:1081-1090). Conversely, it is also reasonable to speculate that activation of WDR trigeminovascular neurons alone may be sufficient to induce the headache perception in those episodic migraine patients who do not benefit from CGRP-mAb therapy, as the headache could be unaffected by elimination of the signals sent to the thalamus from HT trigeminovascular neurons.

Outside migraine and the trigeminovascular system, HT and WDR neurons have been thought to play different roles in the processing of noxious stimuli and the perception of pain (Craig A D, 2002, *Nat. Rev. Neurosci.* 3:655-666; Craig A D, 2003, *Trends Neurosci.* 26:303-307; Craig A D, 2003, *Annu. Rev. Neurosci.* 26:1-30). While most HT neurons exhibit small receptive fields and respond exclusively to noxious mechanical stimuli, most WDR neurons exhibit large receptive fields and respond to both mechanical and thermal noxious stimuli (Price et al., 1976, *J. Neurophysiol.* 39:936-953; Price et al., 1978, *J. Neurophysiol.* 41:933-947; Hoffman et al., 1981, *Neurophysiology* 46:409-427; Dubner and Bennett, 1983, *Annu. Rev. Neurosci.* 6:381-418; Bushnell et al., 1984, *J. Neurophysiol.* 52:170-187; Surmeier et al., 1986, *J. Neurophysiol.* 56:328-350; Ferrington et al., 1987, *J. Physiol.* (Lond) 388:681-703; Dubner et al., 1989, *J. Neurophysiol.* 62:450-457; Maixner et al., 1989, *J. Neurophysiol.* 62:437-449; Laird and Cervero, 1991, *J. Physiol.* 434:561-575). Based on these differences, it is generally believed that HT neurons make a greater contribution to the spatial encoding (size, location) of pain and a lesser contribution to the encoding of pain modalities, whereas WDR neurons make a greater contribution to the radiating qualities of the pain. Along this line, it is also reasonable that those patients unresponsive to fremanezumab are the ones whose headaches affect large areas of the head (i.e., frontal, temporal, occipital, bilateral) whereas the ones whose headaches are well localized to small and distinct areas will be among the responders.

Effectiveness in Headache

Fremanezumab reduced responsiveness to mechanical stimulation of the dura (both in males and females) but not to innocuous or noxious stimulation of the skin or cornea. This finding, together with the fact that the CGRP-mAb also prevented the activation of HT trigeminovascular neurons by CSD, provides a scientific basis for fremanezumab's effectiveness in preventing headaches of intracranial origin. Conversely, lack of effects on modulating the processing of sensory and nociceptive signals that arise in the facial skin and cornea predicts that this class of drugs will have little therapeutic effect on treating prolonged trigeminal pain conditions such as dry eye and herpes-induced trigeminal neuralgia. Given that fremanezumab inhibited activation of central trigeminovascular neurons from the dura (mechanical, CSD) but not skin or cornea, and that the size of this molecule is too large to readily penetrate the blood brain barrier, it is reasonable to suggest that the inhibitory effects described above were secondary to (primary) inhibition of responses to dural indentation and CSD in peripheral trigeminovascualr neurons.

Given the wide distribution throughout the body of CGRP fibers (Kruger et al., 1988, *J. Comp. Neurol.* 273:149-162; Kruger et al., 1989, *J. Comp. Neurol.* 280:291-302; Silverman and Kruger, 1989, *J. Comp. Neurol.* 280:303-330), their presence in multiple spinal cord segments (Hansen et al., 2016, *Pain* 157:666-676; Nees et al., 2016, *Pain* 157:687-697), and in multiple sensory dorsal root ganglia (Edvinsson et al., 1998, *J. Auton. Nerv. Syst.* 70:15-22; Edvinsson et al., 2001, *Microsc. Res. Techniq.* 53:221-228; Cho et al., 2015, *J. Korean Med. Sci.* 30:1902-1910; Kestell et al., 2015, *J. Comp. Neurol.* 523:2555-2569; Spencer et al., 2016, *J. Comp. Neurol.* 524:3064-3083), it is surprising that the CGRP-mAb had little or no effect on the responses of the central neurons to noxious stimulation of the skin and cornea. If one accepts the notion that the CGRP-mAb acts mainly in the periphery, it is also reasonable to propose that peripheral aspects of the sensory innervation of the meninges and the way this innervation affects sensory transmission in the dorsal horn differ from those involved in the generation of cutaneous, corneal or other (somatic) pains. Studies on fremanezumab's effects in animal models of other pain conditions should allow for more accurate interpretation of the difference between the CGRP-mAb's effects in the dura vs. extracranial tissues not believed to have a distinct initiating role in migraine.

Inhibition of CSD-Induced Activation and Sensitization

This study demonstrates sensitization of central trigeminovascular neurons by CSD. This sensitization—observed in HT but not WDR neurons in both males and females—was prevented by the CGRP-mAb administration. These findings indicate that cutaneous allodynia in attacks preceded by aura (Burstein et al., 2000, *Ann. Neurol.* 47:614-624) is mediated by HT neurons that are unresponsive to innocuous mechanical stimulation of the skin at baseline (interictally in patients and before induction of CSD in animals), but become mechanically responsive to brush after the CSD. According to this scenario, among migraine aura patients, responders to the prophylactic treatment with CGRP-mAb would show no signs of cutaneous allodynia.

Male v. Female

This study also tested CGRP-mAb's effects in both male and female rats. While the overall analysis-by-sex suggests that the therapeutic benefit of this class of drugs should be similar in male and female migraineurs, it also shows that in the naïve state, CGRP-mAb reduces the spontaneous activity in male, but not female HT neurons, and that after induction of sensitization by CSD, only HT neurons recorded in females exhibited signs of sensitization to noxious stimulation of the skin and cornea. Given that migraine is more common in women than men, the differences may suggest that hyperalgesia (rather than allodynia) is more likely to develop in women than in men during migraine with aura, and that attempts to reduce neuronal excitability by CGRP-mAb in the interictal state (i.e., as a preventative), may also be more challenging in women than men. Mechanistically, the three observed differences could be attributed to greater excitability of female HT neurons, either due to these neurons' internal properties or due to differences in the strength of inputs they receive from peripheral nociceptors. Whereas no data exist to support the first option, it is possible that differences in the activation of dural immune cells and inflammatory molecules in females compared to males (McIlvried et al. (2015) *Headache* 55:943-957) can support the second option. Regarding fremanezumab's ability to reduce spontaneous activity in male but not female rats, one may take into consideration data showing that female rats express fewer CGRP receptors in the trigeminal ganglion and spinal trigeminal nucleus, and higher levels of CGRP-encoding mRNA in the dorsal horn (Stucky et al. (2011) *Headache* 51:674-692).

Finally, the inhibitory effects of CGRP-mAb required only a few hours to reach significance. This relatively short time (hours rather than days) was achieved using intravenous administration.

Example 6. Assessing Anti-CGRP Antibody (TEV-48125) Responders Using Behavioral and Psychophysical Tools The majority of episodic migraineurs seeking secondary or tertiary medical care exhibit signs of cutaneous allodynia and hyperalgesia during the acute phase of migraine, but not when pain-free (Burstein R et al. (2000) *Ann. Neurol.* 47:614-624). In contrast, chronic migraine patients commonly exhibit sign of cutaneous allodynia and hyperalgesia both during acute migraine attacks as well as during the interictal phase. Mechanistically, allodynia and hyperalgesia are thought to be mediated by sensitization of central trigeminovascular neurons in the spinal trigeminal nucleus (Burstein R et al. (1998) *J. Neurophysiol.* 79(2): 964-982; Burstein R et al. (2000) *Ann. Neurol.* 47: 614-624; and Lipton et al. (2008) *Ann. Neurol.* 63(2):148-58). In contrast, chronic migraine patients commonly exhibit sign of cutaneous allodynia and hyperalgesia both during acute migraine attacks as well as during the interictal phase. Mechanistically, allodynia and hyperalgesia are thought to be mediated by sensitization of central trigeminovascular neurons in the spinal trigeminal nucleus (see Burstein (1998)). Example 5 demonstrates that TEV-48125, through its inhibitory action in peripheral meningeal nociceptors, is capable of preventing the activation and sensitization of high-threshold (HT) neurons in the spinal trigeminal nucleus to an extent that is far superior than its ability to inhibit wide-dynamic range (WDR) neurons (see also Melo-Carrillo et al. (2017) *J. Neurosci.* 37(30): 7149-63). Given that HT neurons respond exclusively to noxious (painful) stimuli whereas WDR neurons respond preferentially to noxious stimuli (i.e., their response to noxious stimuli is larger than their response to innocuous stimuli), it is reasonable to hypothesize that the blockade of HT will prevent hyperalgesia more effectively than allodynia.

To date, there are no examples or hints in the literature of examples of drugs that reduce activation and sensitization of only one of these two classes of nociceptive neurons in the spinal trigeminal nucleus. Given that fremanezumab inhibits meningeal Aδ-but not C-fibers, the selective inhibition of the Aδ-fibers potentially explains the antibody's selective inhibition of HT neurons (see Melo-Carillo et al. (2017) *J. Neurosci.* 37(44): 10587-96). Also, since C-fibers may not influence the activity of HT neurons, consequently, fremanezumab may achieve a very selective effect on ascending nociceptive trigeminovascular pathways—those whose activity depends on CGRP release in the periphery.

Without wishing to be bound by any particular theory, it is believed that responders are subjects in which ongoing peripheral input is required to maintain the central sensitization in WDR and HT neurons, whereas non-responders are subjects in which ongoing peripheral input is not required to maintain the central sensitization in WDR and HT neurons. Since fremanezumab blocks activation of the Aδ-fibers, in responders this blockade may be sufficient to render HT neurons completely quiescent (i.e., terminate their sensitization). Fremanezumab may also decrease the overall input that drives the sensitization state of the WDR neurons to the extent that the input that the neurons receive from the unblocked C-fibers only induces excitatory post-synaptic potentials (EPSPs), but not actual action potentials. The sensitization state of both WDR and HT neurons may be reversed by fremanezumab and consequently, the allodynia/hyperalgesia will be reversed in the responders. Conversely, in non-responders, the sensitization of either HT or WDR neurons, or both, is completely independent of the peripheral input, regardless of whether it originates in the Aδ- or C-fibers. Accordingly, the non-responders will be allodynic and/or hyperalgesic after treatment. It is expected that other anti-CGRP antibodies (e.g., an anti-CGRP antibody described herein) will exhibit the same behavior as fremanezumab.

Study Design:

Overall strategy: To determine cutaneous pain thresholds (which test for allodynia), and pain rating in response to repeated suprathreshold mechanical and heat stimuli (which test for hyperalgesia) in chronic migraine patients under 4 different conditions: (a) before treatment while migraine-free, (b) after treatment while migraine-free, and if possible, (c) before and after treatment while in the middle of acute migraine attack. Note: part (c) is not necessary for identifying responders among the CM population. It may be relevant to identifying responders among the high-frequency episodic patients.

Participant selection and recruitment: Individuals with chronic migraine will be considered for participation in this study. Primary inclusion criteria will be (1) age 18-64 years old, (2) history of chronic migraine with or without aura, based on the International Classification of Headache Disorders (3rd edition) for at least 3 years, and (3) ability to communicate in English (in order to understand and follow instructions of testing). Exclusion criteria will include: (1) less than fifteen headache days per month; (2) pregnancy; (3) history of coronary artery bypass surgery, heart attack, angina, stroke, serious gastrointestinal bleeding, peptic ulcer disease; or chronic kidney disease; (5) having medical conditions requiring use of diuretics or daily anticoagulants.

Open-label design: After screening, which will be performed on a pre-scheduled day (visit 1), the migraine history of study participants will be captured using a questionnaire, and quantitative sensory testing for allodynia and hyperalgesia will be performed. Visit 1 will take place at least 30 days prior to visit 2, when the participant is headache-free. Participants will be instructed to maintain a daily headache diary during this period.

Visit 2 will take place when the study participant has migraine, and will include 3 cycles of pain rating and QST for the evaluation of allodynia and hyperalgesia. The first cycle of pain rating will take place prior to treatment and at least 2 hours after attack onset. Patients will be randomized to receive either placebo (isotype control antibody) or 675 mg of fremanezumab subcutaneously. The second cycle of pain rating will take place two hours after treatment. The third cycle of pain rating will take place 4 hours after treatment. Participants will be instructed to maintain a daily headache diary throughout the study.

Visit 3 will take place 1 week after treatment and will include headache diary review, rating of headache intensity, and QST testing for allodynia and hyperalgesia.

Visit 3 will take place 4 weeks after treatment and will include headache diary review, rating of headache intensity, and QST testing for allodynia and hyperalgesia.

In each visit, the baseline headache intensity, pain threshold to quantitative mechanical and thermal stimuli, and headache intensity score in response to suprathreshold mechanical and heat stimuli will be documented.

Quantitative Sensory testing (QST): Testing will be done in a quiet room away from noise and distraction. Patients will be able to choose their most comfortable position (sitting on a chair or laying in bed) during the sensory testing. In each testing session, pain thresholds to hot and mechanical stimulation will be determined in the skin over the site to where the pain is referred to. This site includes most commonly the periorbital and temporal regions. Heat skin stimuli will be delivered through a 30×30 mm$^2$ thermode (Q-Sense 2016, Medoc) attached to the skin at a constant pressure and their pain thresholds will be determined by using the *Method of Limit*.

Allodynia testing: To determine pain thresholds, the skin will be allowed to adapt to a temperature of 32° C. for 5 minutes and then warmed up at a slow rate (1° C./sec) until pain sensation is perceived, at which moment the subject stops the stimulus by pressing a button on a patient response unit. Heat stimuli will be repeated three times each and the mean of recorded temperatures will be considered threshold. Pain threshold to mechanical stimuli will be determined by using a set of 20 calibrated von Frey hairs (VFH, Stoelting). Each VFH monofilament is assigned a scalar number in an ascending order (1=0.0045 g, 2=0.023 g, 3=0.027 g, 4=0.07 g, 5=0.16 g, 6=0.4 g, 7=0.7 g, 8=1.2 g, 9=1.5 g, 10=2.0 g, 11=3.6 g, 12=5.4 g, 13=8.5 g, 14=11.7 g, 15=15.1 g, 16=28.8 g, 17=75 g, 18=125 g, 19=281 g). Because a linear relationship exists between the log force and the ranked number, mechanical pain thresholds are expressed as VFH numbers (#) rather than their forces (g). Each monofilament will be applied to the skin 3 times (for 2 sec) and the smallest VFH number capable of inducing pain at two out of three trials will be considered threshold. Skin sensitivity will also be determined by recording the subject's perception of soft skin brushing, which is a dynamic mechanical stimulus, as distinguished from the VFH, which is a static mechanical stimulus, as distinguished from the VFH, which is a static mechanical stimulus.

Hyperalgesia testing: When a painful stimulus is perceived as more painful than usual, the subject is considered hyperalgesic. To determine whether the subject is hyperalgesic, 3 supra-threshold heat and mechanical stimuli will be applied to the skin. The value of the supra-threshold stimulus will be determined during the allodynia testing above. For example, if the heat pain threshold is 45° C., we will use 46° C. in the hyperalgesia testing. In this test, the skin will be exposed to 3 supra-threshold stimuli (1-above-threshold), each lasting 10 seconds and separated by 10 seconds (i.e., inter-stimulus interval of 10 seconds). At the end of each stimulus, the patient will have 10 seconds to identify the intensity of the pain using a visual analog scale (VAS) of 0-10 (o=no pain, 10=most imaginable pain). Similar test will be administered using supra-threshold mechanical stimulation.

The equipment used for quantitative sensory testing has FDA approval. It is routinely used by neurologists, nurses, and pain specialists throughout the country. It imposes no risk or discomfort, and since it is controlled by the patient, stimuli can be stopped at any time.

Interpretation of QST:

Allodynia: Since the detection of pain thresholds depends on subjective data input, several algorithms have been developed in order to minimize subjective variation, and make the results as objective as possible. These algorithms are incorporated into the software program that controls the thermal and mechanical sensory analyzer (Q-Sense 2016).

In healthy subjects, pain thresholds for heat and mechanical skin stimuli range between 42–47° C. and 75-281 g, respectively (see Lindblom (1994) Analysis of abnormal touch, pain, and temperature sensation in patients. In: Boivie J, Hansson P, Lindblom U, eds. Touch, temperature and pain in health and disease: mechanism and assessments. Vol, 3. Progress in brain research and management. Seattle: IASP press. p 63-84; and Strigo et al. (2000) *Anesthesiology* 92(3): 699-707. Using a more stringent criteria, a subject will be considered to be allodynic if her/his pain threshold is below 41° C. for heat, and below 30 g for skin indentation with the calibrated von Frey hairs. Meeting the criterion for any one modality will be sufficient to determine that the subject is allodynic (Burstein et al. (2004) *Ann. Neurol.* 47(5): 614-24; and Burstein et al. (2004) *Ann. Neurol.* 55(1): 19-26).

Hyperalgesia: Any change in pain rating that is larger than 30% will be considered as evidence for hyperalgesia (e.g., if supra-threshold stimulus #1 is rated 6/10 on a VAS, supra-threshold stimulus #3 will have to be rated at 8/10 or higher).

Data analysis will take into consideration values of mechanical and heat pain thresholds before and after treatment.

Data Analysis:

Data analyses will include subjects who complete all 4 visits and 6 testing sessions.

The primary outcome measure is the presence or absence of allodynia after the intervention (1 month) in responders vs. non-responders. Responders are primarily defined as experiencing a minimal reduction of 50% in monthly headache days; non-responders are defined as experiencing a maximal reduction of less than 50% in monthly headache days. A secondary definition addresses responders as experiencing a minimal reduction of 60% in monthly headache days; non-responders are defined as experiencing a maximal reduction of less than 40% in monthly headache days. An additional secondary definition addresses responders as experiencing a minimal reduction of 75% in monthly headache days; non-responders are defined as experiencing a maximal reduction of less than 25% in monthly headache days.

The primary outcome measure will be examined using a Chi-square ($\chi^2$) test to assess the categorical association between the presence of allodynia (yes/no) and the responsiveness of subjects (yes/no). Secondary outcome measures are migraine duration (hours) before and after the intervention (1 month) and changes in headache intensity at 2 and 4 hours after intervention.

Data of the continuous secondary outcome measures will first be tested for normality so as to determine whether parametric or non-parametric analyses are appropriate. Accordingly, parameters of central distribution (means/medians) will be used to assess differences in these variables between responders and non-responders.

Analyses will also examine the effects the following factors on the primary and secondary outcome measures: number of years with migraine, number of years with CM, family history, associated symptoms (e.g., nausea, vomiting, photophobia, phonophobia, osmophobia, aura, muscle tenderness), common triggers (e.g., stress, prolong wakefulness food deprivation, menstruation), and acute as well as prophylactic treatment history.

Power Analysis:

Power analysis was based on the Chi-square ($\chi^2$) Goodness-of-Fit and Z comparison of proportions tests. Incorporated were a of 5% (significance level), 1-β error probability of 90% (power), w of 0.36 (effect size; $\chi^2$ Goodness-of-Fit test), and allocation ratio of 1:1 (Z comparison of proportions test). Stratification analysis included the variables Group (placebo vs. treatment), Responsiveness (Responder vs. Non-responder; see definition above), and Allodynia (Presence vs. Absence). The primary hypothesis was that post-intervention proportions of Responders (according to the aforementioned definition of the 50% reduction threshold in monthly headache days) in the treatment and placebo groups would be 55% and 25%, respectively (based on published data by Bigal et al. (2015) *Lancet Neurol.* 14(11): 1091-100). This computation yielded a required number of 64 subjects in each of the placebo and treatment groups (df=5; critical $\chi^2$=11.07; noncentrality parameter $\chi$=16.51, FIG. 4). An additional 20% were accounted for potential dropout. Thus, a total of 77 patients are to be enrolled in each group, yielding a total of 144 patients in the entire study.

Example 7. Selective Inhibition of First-Order Trigeminovascular Neurons by Anti-CGRP Antibody (Fremanezumab)

A large body of evidence supports an important role for CGRP in the pathophysiology of migraine. This evidence gave rise to a global effort to develop a new generation of therapeutics that reduces the availability of CGRP in migraineurs. Recently, the second generation of such drugs, CGRP-mAb, was found to be effective in reducing the frequency of chronic or episodic migraine. In order to investigate the neural basis for this therapeutic action, the effect of fremanezumab, a CGRP-mAb, on the activity of first- and second-order neurons in the meningeal sensory pathway was tested. This study shows the effects of fremanezumab on first-order neurons in the trigeminal ganglion (FIGS. 18A-21B).

Design/Methods:

Single-unit extracellular recording techniques were used to determine the effects of fremanezumab (30 mg/kg IV) and its isotype (control) on the activity of first-order trigeminovascular neurons in the trigeminal ganglion evoked by cortical spreading depression (CSD) in urethane-anesthetized male rats. CSD was induced by pinprick 4 hours after drug/isotype infusion.

Results:

CSD induced activation of 40% of neurons tested in isotype-treated animals and 20% of neurons tested in fremanezumab-treated animals. As shown in FIG. 21A (a-delta), in isotype treated animals, CSD activated 54% of all a-delta fibers, which was similar to the percentage of a-delta fibers activated by CSD in untreated animals. In contrast in animals treated with fremanezumab, CSD activated only 14% of all a-delta fibers. This difference was statistically significant (Z test p=0.001). In isotype treated animals (FIG. 21B; C-type), CSD activated 31% of all C-fibers, which was similar to the percentage of C-fibers activated by CSD in untreated animals. Similarly, in animals treated with fremanezumab, CSD activated 23% of all C-fibers. This difference was statistically insignificant (Z test p>0.05).

Thus, the effect of fremanezumab was selective for A-delta neurons: the percentage of A-delta neurons that responded to CSD was reduced significantly (p<0.05) from 54% (isotype) to 14% (fremanezumab) (FIG. 21A), whereas the percentage of C-fibers neurons that responded to CSD showed no significant change (31% vs. 23%, isotype vs. fremanezumab) (FIG. 21B).

The selective action of fremanezumab on A-delta but not C-fiber first-order neurons can help explain the selective inhibition of second-order high-threshold but not wide-dynamic range neurons. For patients whose chronic and episodic migraines are relieved by fremanezumab, the findings raise the possibility that A-delta neurons play a critical role in the initiation and chronification of the perception of headache whereas C-fiber neurons contribute to the associated allodynia and central sensitization.

Without wishing to be bound by any particular theory, a proposed mechanism for the prevention of migraine by anti-CGRP monoclonal antibodies is provided. Briefly, CSD induces brief constriction, brief dilatation, and prolonged constriction of pial arteries, as well as immediate and delayed activation of C-fiber meningeal nociceptors containing CGRP. Upon their CGRP-independent activation, meningeal C-fibers release CGRP in the dura and by doing so, mediate a CGRP-dependent activation of the nearby Aδ-fibers. Once activated, C-fiber meningeal nociceptors converge on and activate WDR neurons in the spinal trigeminal nucleus, whereas Aδ-fibers converge on and activate both WDR and HT neurons that eventually transmit the nociceptive signals from the dura to the thalamus. The absence of CGRP receptors from the meningeal C-fibers renders the activation of the C-WDR pathway CGRP-independent, and thus, unresponsive to the anti-CGRP monoclonal antibodies. In contrast, the presence of CGRP receptors on the meningeal Aδ-fibers renders the activation of the Aδ-HT pathway CGRP-dependent, and thus, responsive to the anti-CGRP monoclonal antibodies.

Example 8: Anti-CGRP Antagonist Antibody Prevents Post-ictal Headaches (PIH)

Single-unit electrophysiological techniques were used to study the response profile of peripheral and central trigeminovascular neurons in the spinal trigeminal nucleus in response to occurrence of seizure in rats treated with fremanezumab (TEV-48125) as compared to untreated rats. Cortical electrodes were used to trace the magnitude, extent and progression of epileptiform seizures.

Surgical preparation and single-unit recording. Single-unit recordings were obtained from neurons in the trigeminal ganglion and dorsal horn as described in previous studies (Burstein et al. (1998) *J. Neurophysiol.* 79: 964-82; Strassman and Levy (2006) *J. Neurophysiol.* 95: 1298-306; Strassman et al. (1996) *Nature* 384: 560-4; Zhang et al. (2010) *J. Neurosci.* 30: 8807-14; and Zhang et al. (2011) *Ann. Neurol.* 69: 855-65). Experiments were done in adult Sprague-Dawley rats (250 g to 350 g). Animals were anesthetized with urethane (1.2-1.5 g/kg), artificially ventilated with oxygen, and paralyzed. Body temperature was controlled, and end-tidal $CO_2$ and oxygen saturation was monitored. For ganglion recordings, four separate craniotomies were made: over the contralateral cortex, to advance the microelectrode; over the ipsilateral parietal cortex, and the ipsilateral occipital cortex, for application of the picrotoxin and recording of electrocorticogram activity; and over the ipsilateral transverse sinus, for electrical and mechanical stimulation of dural afferents, and lidocaine application. For dorsal horn recording, the same craniotomies were made over the ipsilateral cortex and the ipsilateral transverse sinus, but no contralateral craniotomy was made. Instead, a laminectomy was made to expose the upper cervical spinal cord (C1-2) for microelectrode recording. In both the trigeminal ganglion and the dorsal horn recording experiments, the search stimulus for finding dura-sensitive neurons is single-shock electrical stimulation applied to the dura covering the transverse sinus.

Seizure induction and electrocorticogram recording. Seizure was induced by application of picrotoxin to the surface of the cerebral cortex (10 μl, applied on a small piece of gelfoam, at a concentration of either 5 mM or 100 mM, for focal or generalized seizure, respectively). For verification of seizure induction, cortical activity was recorded with a glass micropipette (0.9% saline, ~1 megohm, 7 μm tip) placed just below the surface of the cerebral cortex, at the parietal and the occipital site.

Treatment with the monoclonal anti-CGRP antibody TEV-48125. TEV-48125 (TEVA Pharmaceutical Industries Ltd., Israel) is a humanized monoclonal anti-CGRP antibody (CGRP-mAb). It was diluted in saline to a final dose of 30 mg/kg and administered intravenously (total volume 0.8 ml) four hours before induction of seizure.

Figure 24:
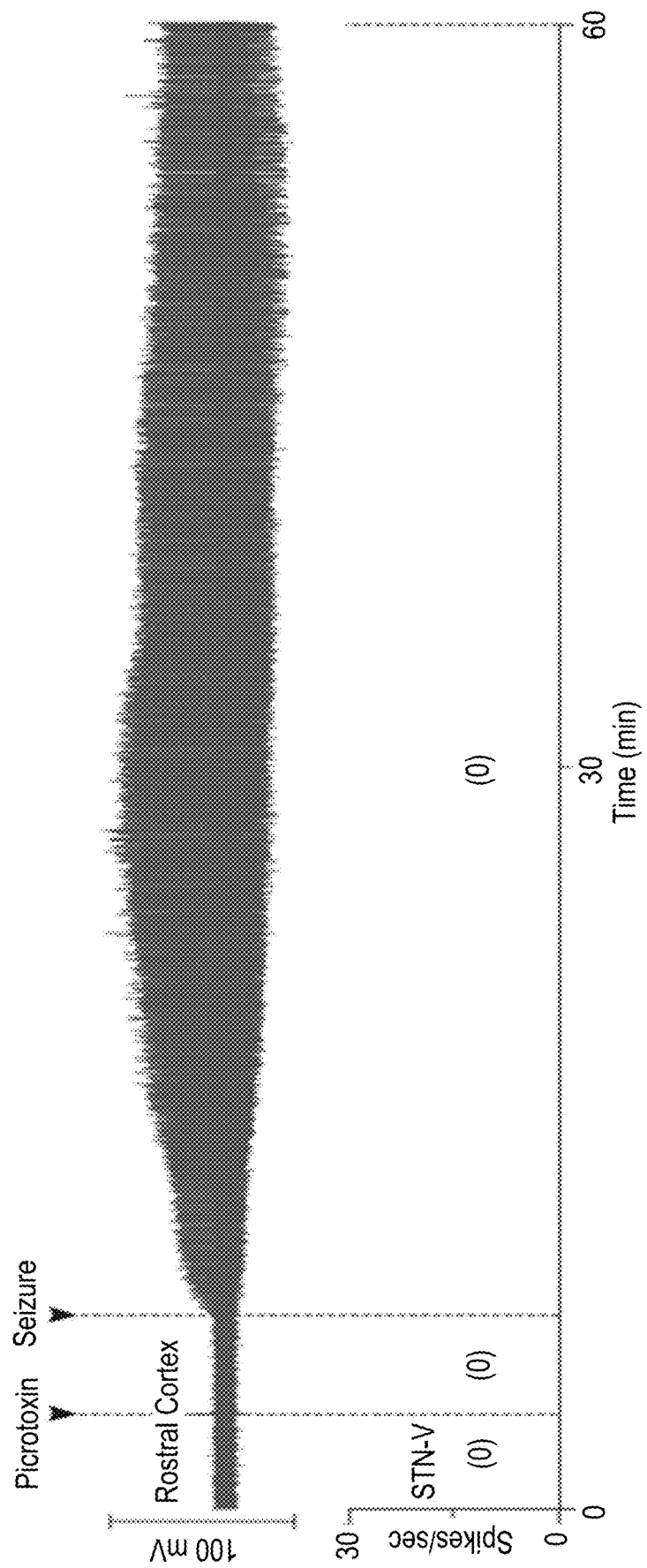
FIG. 24 shows that an anti-CGRP antagonist antibody prevents activation of central trigeminovascular neuron by seizure. When given intravenously (30 mg/kg) four hours before induction of seizure, TEV-48125 prevented the activation of a central trigeminovascular neuron but not the occurrence of a seizure. Top panel shows the seizure activity in the cortex. Bottom panel shows lack of activity in the central neuron.

Results. In untreated animals, the induction of seizure triggered prolonged activation in peripheral and central trigeminovascular neurons. In the ganglion, activity began to increase minutes after the seizure reached their receptive fields and remained elevated for as long the seizure activity continued (FIGS. 22A-22D). In the medullary dorsal horn, 28/30 (93%) neurons were activated for over 2 hours by the seizure (FIGS. 23A-23E). In contrast, in the TEV-48125 treated animals, only 2/13 (15%) neurons were activated by the seizure (FIG. 24).

Conclusions. This example shows activation of the trigeminovascular pathway by seizure and prevention of such activation by TEV-48125. Since the trigeminovascular pathway mediates post-ictal headaches (PIH), the findings demonstrate that TEV-48125 can prevent PIH if given prophylactically. Critically, the results show that in untreated animals, the induction of seizure triggered prolonged activation in 28/30 (93%) neurons whereas in the TEV-48125 treated animals, only 2/13 (15%) neurons were activated by the seizure.

| Antibody Sequences |
| --- |
| G1 heavy chain variable region amino acid sequence (SEQ ID NO: 1) |
| EVQLVESGGGLVQPGGSLRLSCAASGFTFSNYWISWVRQAPGKGLEWVAE |
| IRSESDASATHYAEAVKGRFTISRDNAKNSLYLQMNSLRAEDTAVYYCLA |
| YFDYGLAIQNYWGQGTLVTVSS |
| |
| G1 light chain variable region amino acid sequence (SEQ ID NO: 2) |
| EIVLTQSPATLSLSPGERATLSCKASKRVTTYVSWYQQKPGQAPRLLIYG |
| ASNRYLGIPARFSGSGSGTDFTLTISSLEPEDFAVYYCSQSYNYPYTFGQ |
| GTKLEIK |
| |
| G1 CDR H1 (extended CDR) (SEQ ID NO: 3) |
| GFTFSNYWIS |
| |
| G1 CDR H2 (extended CDR) (SEQ ID NO: 4) |
| EIRSESDASATHYAEAVKG |
| |
| G1 CDR H3 (SEQ ID NO: 5) |
| YFDYGLAIQNY |
| |
| G1 CDR L1 (SEQ ID NO: 6) |
| KASKRVTTYVS |
| |
| G1 CDR L2 (SEQ ID NO: 7) |
| GASNRYL |
| |
| G1 CDR L3 (SEQ ID NO: 8) |
| SQSYNYPYT |
| |
| G1 heavy chain variable region nucleotide sequence (SEQ ID NO: 9) |
| GAAGTTCAGCTGGTTGAATCCGGTGGTGGTCTGGTTCAGCCAGGTGGTTC |
| CCTGCGTCTGTCCTGCGCTGCTTCCGGTTTCACCTTCTCCAACTACTGGA |
| TCTCCTGGGTTCGTCAGGCTCCTGGTAAAGGTCTGGAATGGGTTGCTGAA |
| ATCCGTTCCGAATCCGACGCGTCCGCTACCCATTACGCTGAAGCTGTTAA |
| AGGTCGTTTCACCATCTCCCGTGACAACGCTAAGAACTCCCTGTACCTGC |
| AGATGAACTCCCTGCGTGCTGAAGACACCGCTGTTTACTACTGCCTGGCT |
| TACTTTGACTACGGTCTGGCTATCCAGAACTACTGGGGTCAGGGTACCCT |
| GGTTACCGTTTCCTCC |
| |
| G1 light chain variable region nucleotide sequence (SEQ ID NO: 10) |
| GAAATCGTTCTGACCCAGTCCCCGGCTACCCTGTCCCTGTCCCCAGGTGA |
| ACGTGCTACCCTGTCCTGCAAAGCTTCCAAACGGGTTACCACCTACGTTT |
| CCTGGTACCAGCAGAAACCCGGTCAGGCTCCTCGTCTGCTGATCTACGGT |
| GCTTCCAACCGTTACCTCGGTATCCCAGCTCGTTTCTCCGGTTCCGGTTC |
| CGGTACCGACTTCACCCTGACCATCTCCTCCCTGGAACCCGAAGACTTCG |
| CTGTTTACTACTGCAGTCAGTCCTACAACTACCCCTACACCTTCGGTCAG |
| GGTACCAAACTGGAAATCAAA |
| |
| G1 heavy chain full antibody amino acid sequence (including modified IgG2 as described herein) (SEQ ID NO: 11) |
| EVQLVESGGGLVQPGGSLRLSCAASGFTFSNYWISWVRQAPGKGLEWVAE |
| IRSESDASATHYAEAVKGRFTISRDNAKNSLYLQMNSLRAEDTAVYYCLA |
| YFDYGLAIQNYWGQGTLVTVSSASTKGPSVFPLAPCSRSTSESTAALGCL |
| VKDYFPEPVTVSWNSGALTSGVHTFPAVLQSSGLYSLSSVVTVPSSNFGT |
| QTYTCNVDHKPSNTKVDKTVERKCCVECPPCPAPPVAGPSVFLFPPKPKD |
| TLMISRTPEVTCVVVDVSHEDPEVQFNWYVDGVEVHNAKTKPREEQFNST |
| FRVVSVLTVVHQDWLNGKEYKCKVSNKGLPSSIEKTISKTKGQPREPQVY |
| TLPPSREEMTKNQVSLTCLVKGFYPSDIAVEWESNGQPENNYKTTPPMLD |
| SDGSFFLYSKLTVDKSRWQQGNVFSCSVMHEALHNHYTQKSLSLSPGK |
| |
| G1 light chain full antibody amino acid sequence (SEQ ID NO: 12) |
| EIVLTQSPATLSLSPGERATLSCKASKRVTTYVSWYQQKPGQAPRLLIYG |
| ASNRYLGIPARFSGSGSGTDFTLTISSLEPEDFAVYYCSQSYNYPYTFGQ |
| GTKLEIKRTVAAPSVFIFPPSDEQLKSGTASVVCLLNNFYPREAKVQWKV |
| DNALQSGNSQESVTEQDSKDSTYSLSSTLTLSKADYEKHKVYACEVTHQG |
| LSSPVTKSFNRGEC |
| |
| G1 heavy chain full antibody nucleotide sequence (including modified IgG2 as described herein) (SEQ ID NO: 13) |
| GAAGTTCAGCTGGTTGAATCCGGTGGTGGTCTGGTTCAGCCAGGTGGTTC |
| CCTGCGTCTGTCCTGCGCTGCTTCCGGTTTCACCTTCTCCAACTACTGGA |
| TCTCCTGGGTTCGTCAGGCTCCTGGTAAAGGTCTGGAATGGGTTGCTGAA |
| ATCCGTTCCGAATCCGACGCGTCCGCTACCCATTACGCTGAAGCTGTTAA |
| AGGTCGTTTCACCATCTCCCGTGACAACGCTAAGAACTCCCTGTACCTGC |
| AGATGAACTCCCTGCGTGCTGAAGACACCGCTGTTTACTACTGCCTGGCT |
| TACTTTGACTACGGTCTGGCTATCCAGAACTACTGGGGTCAGGGTACCCT |
| GGTTACCGTTTCCTCCGCCTCCACCAAGGGCCCATCTGTCTTCCCACTGG |
| CCCCATGCTCCCGCAGCACCTCCGAGAGCACAGCCGCCCTGGGCTGCCTG |
| GTCAAGGACTACTTCCCAGAACCTGTGACCGTGTCCTGGAACTCTGGCGC |
| TCTGACCAGCGGCGTGCACACCTTCCCAGCTGTCCTGCAGTCCTCAGGTC |
| TCTACTCCCTCAGCAGCGTGGTGACCGTGCCATCCAGCAACTTCGGCACC |
| CAGACCTACACCTGCAACGTAGATCACAAGCCAAGCAACACCAAGGTCGA |
| CAAGACCGTGGAGAGAAAGTGTTGTGTGGAGTGTCCACCTTGTCCAGCCC |
| CTCCAGTGGCCGGACCATCCGTGTTCCTGTTCCCTCCAAAGCCAAAGGAC |
| ACCCTGATGATCTCCAGAACCCCAGAGGTGACCTGTGTGGTGGTGGACGT |
| GTCCCACGAGGACCCAGAGGTGCAGTTCAACTGGTATGTGGACGGAGTGG |
| AGGTGCACAACGCCAAGACCAAGCCAAGAGAGGAGCAGTTCAACTCCACC |
| TTCAGATGGTGAGCGTGCTGACCGTGGTGCACCAGGACTGGCTGAACGG |
| AAAGGAGTATAAGTGTAAGGTGTCCAACAAGGGACTGCCATCCAGCATCG |
| AGAAGACCATCTCCAAGACCAAGGGACAGCCAAGAGAGCCACAGGTGTAT |
| ACCCTGCCCCCATCCAGAGAGGAGATGACCAAGAACCAGGTGTCCCTGAC |
| CTGTCTGGTGAAGGGATTCTATCCATCCGACATCGCCGTGGAGTGGGAGT |
| CCAACGGACAGCCAGAGAACAACTATAAGACCACCCCTCCAATGCTGGAC |
| TCCGACGGATCCTTCTTCCTGTATTCCAAGCTGACCGTGGACAAGTCCAG |
| ATGGCAGCAGGGAAACGTGTTCTCTTGTTCCGTGATGCACGAGGCCCTGC |
| ACAACCACTATACCCAGAAGAGCCTGTCCCTGTCTCCAGGAAAGTAA |
| |
| G1 light chain full antibody nucleotide sequence (SEQ ID NO: 14) |
| GAAATCGTTCTGACCCAGTCCCCGGCTACCCTGTCCCTGTCCCCAGGTGA |
| ACGTGCTACCCTGTCCTGCAAAGCTTCCAAACGGGTTACCACCTACGTTT |
| CCTGGTACCAGCAGAAACCCGGTCAGGCTCCTCGTCTGCTGATCTACGGT |
| GCTTCCAACCGTTACCTCGGTATCCCAGCTCGTTTCTCCGGTTCCGGTTC |
| CGGTACCGACTTCACCCTGACCATCTCCTCCCTGGAACCCGAAGACTTCG |

| Antibody Sequences |
|---|
| CTGTTTACTACTGCAGTCAGTCCTACAACTACCCCTACACCTTCGGTCAG<br>GGTACCAAACTGGAAATCAAACGCACTGTGGCTGCACCATCTGTCTTCAT<br>CTTCCCTCCATCTGATGAGCAGTTGAAATCCGGAACTGCCTCTGTTGTGT<br>GCCTGCTGAATAACTTCTATCCGCGCGAGGCCAAAGTACAGTGGAAGGTG<br>GATAACGCCCTCCAATCCGGTAACTCCCAGGAGAGTGTCACAGAGCAGGA<br>CAGCAAGGACAGCACCTACAGCCTCAGCAGCACCCTGACCCTGAGCAAAG<br>CAGACTACGAGAAACACAAAGTCTACGCCTGCGAAGTCACCCATCAGGGC<br>CTGAGTTCTCCAGTCACAAAGAGCTTCAACCGCGGTGAGTGCTAA |
| Amino acid sequence comparison of human and rat<br>CGRP (human α-CGRP (SEQ ID NO: 15); human β-CGRP<br>(SEQ ID NO: 43); rat60 -CGRP (SEQ ID NO: 41); and<br>rat β CGRP (SEQ ID NO: 44))<br>NH2-ACDTATCVTHRLAGLLSRSGGVVKNNFVPTNVGSKAF-CONH2<br>(human α-CGRP)<br>NH2-ACNTATCVTHRLAGLLSRSGGMVKSNFVPTNVGSKAF-CONH2<br>(human β-CGRP)<br>NH2-SCNTATCVTHRLAGLLSRSGGVVKDNFVPTNVGSEAF-CONH2<br>(rat α-CGRP)<br>NH2-SCNTATCVTHRLAGLLSRSGGVVKDNFVPTNVGSKAF-CONH2<br>(rat β-CGRP) |
| Light chain variable region LCVR17 amino acid<br>sequence (SEQ ID NO: 58)<br>DIQMTQSPSSLSASVGDRVTITCRASQDIDNYLNWYQQKPGKAPKLLIYY<br>TSEYHSGVPSRFSGSGSGTDFTFTISSLQPEDIATYYCQQGDALPPTFGQ<br>GTKLEIK |
| Heavy chain variable region HCVR22 amino acid<br>sequence (SEQ ID NO: 59)<br>QVQLVQSGAEVKKPGASVKVSCKASGYTFGNYWMQWVRQAPGQGLEWMGA<br>IYEGTGDTRYIQKFAGRVTMTRDTSTSTVYMELSSLRSEDTAVYYCARLS<br>DYVSGFSYWGQGTLVTVSS |
| Light chain variable region LCVR18 amino acid<br>sequence (SEQ ID NO: 60)<br>DIQMTQSPSSLSASVGDRVTITCRASQDIDNYLNWYQQKPGKAPKLLIYY<br>TSEYHSGVPSRFSGSGSGTDFTFTISSLQPEDIATYYCQQGDALPPTFGQ<br>GTKLEIK |
| Heavy chain variable region HCVR23 amino acid<br>sequence (SEQ ID NO: 61)<br>QVQLVQSGAEVKKPGASVKVSCKASGYTFGNYWMQWVRQAPGQGLEWMGA<br>IYEGTGKTVYIQKFAGRVTMTRDTSTSTVYMELSSLRSEDTAVYYCARLS<br>DYVSGFSYWGQGTLVTVSS |
| Light chain variable region LCVR19 amino acid<br>sequence (SEQ ID NO: 62)<br>DIQMTQSPSSLSASVGDRVTITCRASKDISKYLNWYQQKPGKAPKLLIYY<br>TSGYHSGVPSRFSGSGSGTDFTLTISSLQPEDFATYYCQQGDALPPTFGG<br>GTKVEIK |
| Heavy chain variable region HCVR24 amino acid<br>sequence (SEQ ID NO: 63)<br>QVQLVQSGAEVKKPGSSVKVSCKASGYTFGNYWMQWVRQAPGQGLEWMGA<br>IYEGTGKTVYIQKFADRVTITADKSTSTAYMELSSLRSEDTAVYYCARLS<br>DYVSGFGYWGQGTTVTVSS |
| Light chain variable region LCVR20 amino acid<br>sequence (SEQ ID NO: 64)<br>DIQMTQSPSSLSASVGDRVTITCRASRPIDKYLNWYQQKPGKAPKLLIYY<br>TSEYHSGVPSRFSGSGSGTDFTFTISSLQPEDIATYYCQQGDALPPTFGQ<br>GTKLEIK |
| Heavy chain variable region HCVR25 amino acid<br>sequence (SEQ ID NO: 65)<br>QVQLVQSGAEVKKPGASVKVSCKASGYTFGNYWMQWVRQAPGQGLEWMGA<br>IYEGTGKTVYIQKFAGRVTMTRDTSTSTVYMELSSLRSEDTAVYYCARLS<br>DYVSGFGYWGQGTLVTVSS |
| Light chain variable region LCVR21 amino acid<br>sequence (SEQ ID NO: 66)<br>DIQMTQSPSSLSASVGDRVTITCRASQDIDKYLNWYQQKPGKAPKLLIYY<br>TSGYHSGVPSRFSGSGSGTDFTLTISSLQPEDFATYYCQQGDALPPTFGG<br>GTKVEIK |
| Heavy chain variable region HCVR26 amino acid<br>sequence (SEQ ID NO: 67)<br>QVQLVQSGAEVKKPGSSVKVSCKASGYTFGNYWMQWVRQAPGQGLEWMGA<br>IYEGTGKTVYIQKFAGRVTITADKSTSTAYMELSSLRSEDTAVYYCARLS<br>DYVSGFGYWGQGTTVTVSS |
| Light chain variable region LCVR27 amino acid<br>sequence (SEQ ID NO: 68)<br>QVLTQSPSSLSASVGDRVTINCQASQSVYHNTYLAWYQQKPGKVPKQLIY<br>DASTLASGVPSRFSGSGSGTDFTLTISSLQPEDVATYYCLGSYDCTNGDC<br>FVFGGGTKVEIKR |
| Heavy chain variable region HCVR28 amino acid<br>sequence (SEQ ID NO: 69)<br>EVQLVESGGGLVQPGGSLRLSCAVSGIDLSGYYMNWVRQAPGKGLEWVGV<br>IGINGATYYASWAKGRFTISRDNSKTTVYLQMNSLRAEDTAVYFCARGDI<br>WGQGTLVTVSS |
| Light chain variable region LCVR29 amino acid<br>sequence (SEQ ID NO: 70)<br>QVLTQSPSSLSASVGDRVTINCQASQSVYDNNYLAWYQQKPGKVPKQLIY<br>STSTLASGVPSRFSGSGSGTDFTLTISSLQPEDVATYYCLGSYDCSSGDC<br>FVFGGGTKVEIKR |
| Heavy chain variable region HCVR30 amino acid<br>sequence (SEQ ID NO: 71)<br>EVQLVESGGGLVQPGGSLRLSCAVSGLDLSSYYMQWVRQAPGKGLEWVGV<br>IGINDNTYYASWAKGRFTISRDNSKTTVYLQMNSLRAEDTAVYFCARGDI<br>WGQGTLVTVSS |
| Light chain variable region LCVR31 amino acid<br>sequence (SEQ ID NO: 72)<br>QVLTQSPSSLSASVGDRVTINCQASQSVYDNNYLAWYQQKPGKVPKQLIY<br>STSTLASGVPSRFSGSGSGTDFTLTISSLQPEDVATYYCLGSYDCSSGDC<br>FVFGGGTKVEIKR |
| Heavy chain variable region HCVR32 amino acid<br>sequence (SEQ ID NO: 73)<br>EVQLVESGGGLVQPGGSLRLSCAVSGLDLSSYYMQWVRQAPGKGLEWVGV<br>IGINDNTYYASWAKGRFTISRDNSKTTVYLQMNSLRAEDTAVYFCARGDI<br>WGQGTLVTVSS |
| Light chain variable region LCVR33 amino acid<br>sequence (SEQ ID NO: 74)<br>QVLTQTPSPVSAAVGSTVTINCQASQSVYHNTYLAWYQQKPGQPPKQLIY<br>DASTLASGVPSRFSGSGSGTQFTLTISGVQCNDAAAYYCLGSYDCTNGDC<br>FVFGGGTEVVVKR |
| Heavy chain variable region HCVR34 amino acid<br>sequence (SEQ ID NO: 75)<br>QSLEESGGGRLVTPGTPLTLTCSVSGIDLSGYYMNWVRQAPGKGLEWIGVI<br>GINGATYYASWAKGRFTISKTSSTTVDLKMTSLTTEDTATYFCARGDIWG<br>PGTLVTVSS |
| Light chain variable region LCVR35 amino acid<br>sequence (SEQ ID NO: 76)<br>QVLTQSPSSLSASVGDRVTINCQASQSVYHNTYLAWYQQKPGKVPKQLIY<br>DASTLASGVPSRFSGSGSGTDFTLTISSLQPEDVATYYCLGSYDCTNGDC<br>FVFGGGTKVEIKR |
| Heavy chain variable region HCVR36 amino acid<br>sequence (SEQ ID NO: 77)<br>EVQLVESGGGLVQPGGSLRLSCAVSGIDLSGYYMNWVRQAPGKGLEWVGV<br>IGINGATYYASWAKGRFTISRDNSKTTVYLQMNSLRAEDTAVYFCARGDI<br>WGQGTLVTVSS |
| Light chain variable region LCVR37 amino acid<br>sequence (SEQ ID NO: 78)<br>QSVLTQPPSVSAAPGQKVTISCSGSSSNIGNNYVSWYQQLPGTAPKLLIY<br>DNNKRPSGIPDRFSGSKSGTSTTLGITGLQTGDEADYYCGTWDSRLSAVV<br>FGGGTKLTVL |
| Heavy chain variable region HCVR38 amino acid<br>sequence (SEQ ID NO: 79)<br>QVQLVESGGGVVQPGRSLRLSCAASGFTFSSFGMHWVRQAPGKGLEWVAV<br>ISFDGSIKYSVDSVKGRFTISRDNSKNTLFLQMNSLRAEDTAVYYCARDR<br>LNYYDSSGYYHYKYYGMAVWGQGTTVTVSS |

What is claimed is:

1. A method for reducing migraine frequency in a subject suffering from migraine comprising:
   a) determining or having determined whether the subject exhibits allodynia and/or hyperalgesia during an interictal phase of a migraine, and
   b) administering an anti-CGRP antagonist antibody or an anti-CGRP receptor antibody that blocks, inhibits, suppresses, or reduces the calcitonin gene related peptide (CGRP) pathway to the subject that does not exhibit signs of allodynia and/or hyperalgesia during the interictal phase of the migraine.

2. The method of claim 1, wherein the subject suffers from episodic migraine.

3. The method of claim 1, wherein the subject suffers from chronic migraine.

4. The method of claim 1, wherein the subject is known to exhibit allodynia and/or hyperalgesia during an acute phase of the migraine.

5. The method of claim 1, wherein the subject was determined during the interictal phase of the migraine to have a heat pain threshold of above 41° C. and/or a mechanical pain threshold of above 30 g for skin indentation with calibrated von Frey hairs.

6. The method of claim 1, wherein the absence of allodynia and/or hyperalgesia during the interictal phase of the migraine was determined by quantitative sensory testing (QST).

7. The method of claim 1, wherein the absence of allodynia and/or hyperalgesia during the interictal phase of the migraine was determined by questionnaire.

8. The method of claim 1, wherein the anti-CGRP antagonist antibody or the anti-CGRP receptor antibody is a monoclonal antibody, a humanized antibody, or an antigen-binding fragment selected from a Fab, a Fab', a F(ab')2, an Fv, or an ScFv.

9. The method of claim 1, wherein the anti-CGRP antagonist antibody comprises a CDR H1 amino acid sequence as set forth in SEQ ID NO: 3; a CDR H2 amino acid sequence as set forth in SEQ ID NO: 4; a CDR H3 amino acid sequence as set forth in SEQ ID NO: 5; a CDR L1 amino acid sequence as set forth in SEQ ID NO: 6; a CDR L2 amino acid sequence as set forth in SEQ ID NO: 7; and a CDR L3 amino acid sequence as set forth in SEQ ID NO: 8.

10. The method of claim 9, wherein:
    the anti-CGRP antagonist antibody comprises a heavy chain variable region comprising the amino acid sequence as set forth in SEQ ID NO: 1, and a light chain variable region comprising the amino acid sequence as set forth in SEQ ID NO:2; or
    the anti-CGRP antagonist antibody comprises a heavy chain comprising the amino acid sequence as set forth in SEQ ID NO: 11, and a light chain comprising the amino acid sequence as set forth in SEQ ID NO: 12.

11. The method of claim 1, wherein the anti-CGRP antagonist antibody comprises a CDR H1 amino acid sequence as set forth in SEQ ID NO: 87; a CDR H2 amino acid sequence as set forth in SEQ ID NO: 88; a CDR H3 amino acid sequence as set forth in SEQ ID NO:89; a CDR L1 amino acid sequence as set forth in SEQ ID NO:84; a CDR L2 amino acid sequence as set forth in SEQ ID NO:85; and a CDR L3 amino acid sequence as set forth in SEQ ID NO:86.

12. The method of claim 11, wherein:
    the anti-CGRP antagonist antibody comprises a heavy chain variable region comprising the amino acid sequence as set forth in SEQ ID NO: 82, and a light chain variable region comprising the amino acid sequence as set forth in SEQ ID NO: 80; or
    the anti-CGRP antagonist antibody comprises a heavy chain comprising the amino acid sequence as set forth in SEQ ID NO: 83, and a light chain comprising the amino acid sequence as set forth in SEQ ID NO:81.

13. The method of claim 1, wherein the anti-CGRP antagonist antibody comprises a CDR H1 amino acid sequence as set forth in SEQ ID NO:93; a CDR H2 amino acid sequence as set forth in SEQ ID NO:94; a CDR H3 amino acid sequence as set forth in SEQ ID NO:95; a CDR L1 amino acid sequence as set forth in SEQ ID NO:91; a CDR L2 amino acid sequence as set forth in SEQ ID NO:92; and a CDR L3 amino acid sequence as set forth in SEQ ID NO:90.

14. The method of claim 13, wherein:
    the anti-CGRP antagonist antibody comprises a heavy chain variable region comprising the amino acid sequence as set forth in SEQ ID NO: 97, and a light chain variable region comprising the amino acid sequence as set forth in SEQ ID NO: 96; or
    the anti-CGRP antagonist antibody comprises a heavy chain comprising the amino acid sequence as set forth in SEQ ID NO:99, and a light chain comprising the amino acid sequence as set forth in SEQ ID NO:98.

15. The method of claim 1, wherein the anti-CGRP receptor antibody comprises a CDR H1 amino acid sequence as set forth in SEQ ID NO: 103; a CDR H2 amino acid sequence as set forth in SEQ ID NO: 104; a CDR H3 amino acid sequence as set forth in SEQ ID NO: 105; a CDR L1 amino acid sequence as set forth in SEQ ID NO: 100; a CDR L2 amino acid sequence as set forth in SEQ ID NO: 101; and a CDR L3 amino acid sequence as set forth in SEQ ID NO: 102.

16. The method of claim 15, wherein:
the anti-CGRP receptor antibody comprises a heavy chain variable region comprising the amino acid sequence as set forth in SEQ ID NO: 107, and a light chain variable region comprising the amino acid sequence as set forth in SEQ ID NO: 106; or
the anti-CGRP receptor antibody comprises a heavy chain comprising the amino acid sequence as set forth in SEQ ID NO: 109, and a light chain comprising the amino acid sequence as set forth in SEQ ID NO: 108.

17. The method of claim 1, wherein the anti-CGRP antagonist antibody or the anti-CGRP receptor antibody is administered while the patient is migraine-free.

18. The method of claim 1, wherein the allodynia is cutaneous allodynia.

19. A method for reducing migraine frequency in a subject suffering from migraine comprising:
a) determining or having determined whether said subject exhibits, or does not exhibit, allodynia and/or hyperalgesia during an interictal phase of a migraine, and
b) administering to said subject that does not exhibit signs of allodynia and/or hyperalgesia during the interictal phase of the migraine, an anti-CGRP antagonist antibody or an anti-CGRP receptor antibody that blocks, inhibits, suppresses, or reduces the calcitonin gene related peptide (CGRP) pathway.

20. A method of treating migraine in a subject comprising:
a) determining or having determined whether the subject exhibits allodynia and/or hyperalgesia during the interictal phase of a migraine, and
b) administering an anti-CGRP antagonist antibody or an anti-CGRP receptor antibody that blocks, inhibits, suppresses, or reduces the calcitonin gene related peptide (CGRP) pathway to the subject that does not exhibit signs of allodynia and/or hyperalgesia during the interictal phase of the migraine.

* * * * *

SEQUENCE LISTING

<160> NUMBER OF SEQ ID NOS: 109

<210> SEQ ID NO 1
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Ile Ser Trp Val Arg Gln Ala Pro Gly Lys Gly Leu Glu Trp Val
        35                  40                  45

Ala Glu Ile Arg Ser Glu Ser Asp Ala Ser Ala Thr His Tyr Ala Glu
    50                  55                  60

Ala Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Leu Ala Tyr Phe Asp Tyr Gly Leu Ala Ile Gln Asn Tyr Trp
            100                 105                 110

Gly Gln Gly Thr Leu Val Thr Val Ser Ser
        115                 120

<210> SEQ ID NO 2
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Glu Ile Val Leu Thr Gln Ser Pro Ala Thr Leu Ser Leu Ser Pro Gly
1               5                   10                  15

Glu Arg Ala Thr Leu Ser Cys Lys Ala Ser Lys Arg Val Thr Thr Tyr
            20                  25                  30

Val Ser Trp Tyr Gln Gln Lys Pro Gly Gln Ala Pro Arg Leu Leu Ile
        35                  40                  45

Tyr Gly Ala Ser Asn Arg Tyr Leu Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Ser Gln Ser Tyr Asn Tyr Pro Tyr
                85                  90                  95

Thr Phe Gly Gln Gly Thr Lys Leu Glu Ile Lys
            100                 105

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 3

Gly Phe Thr Phe Ser Asn Tyr Trp Ile Ser
1               5                   10

<210> SEQ ID NO 4
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Glu Ile Arg Ser Glu Ser Asp Ala Ser Ala Thr His Tyr Ala Glu Ala
1               5                   10                  15

Val Lys Gly

<210> SEQ ID NO 5
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Tyr Phe Asp Tyr Gly Leu Ala Ile Gln Asn Tyr
1               5                   10

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Lys Ala Ser Lys Arg Val Thr Thr Tyr Val Ser
1               5                   10

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Ala Ser Asn Arg Tyr Leu
1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ser Gln Ser Tyr Asn Tyr Pro Tyr Thr
1               5
```

<210> SEQ ID NO 9
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9

```
gaagttcagc tggttgaatc cggtggtggt ctggttcagc caggtggttc cctgcgtctg     60
tcctgcgctg cttccggttt caccttctcc aactactgga tctcctgggt tcgtcaggct    120
cctggtaaag gtctggaatg ggttgctgaa atccgttccg aatccgacgc gtccgctacc    180
cattacgctg aagctgttaa agtcgtttc accatctccc gtgacaacgc taagaactcc     240
ctgtacctgc agatgaactc cctgcgtgct gaagacaccg ctgttttacta ctgcctggct    300 tactttgact acggtctggc tatccagaac tactggggtc agggtaccct ggttaccgtt    360
tcctcc                                                               366
```

<210> SEQ ID NO 10
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10

```
gaaatcgttc tgacccagtc cccggctacc ctgtccctgt ccccaggtga acgtgctacc     60
ctgtcctgca agcttccaa acgggttacc acctacgttt cctggtacca gcagaaaccc    120
ggtcaggctc tcgtctgct gatctacggt gcttccaacc gttacctcgg tatcccagct    180
cgtttctccg gttccggttc cggtaccgac ttcaccctga ccatctcctc cctggaaccc    240
gaagacttcg ctgttttacta ctgcagtcag tcctacaact accctacac cttcggtcag    300 ggtaccaaac tggaaatcaa a                                              321
```

<210> SEQ ID NO 11
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Ile Ser Trp Val Arg Gln Ala Pro Gly Lys Gly Leu Glu Trp Val
        35                  40                  45

Ala Glu Ile Arg Ser Glu Ser Asp Ala Ser Ala Thr His Tyr Ala Glu
    50                  55                  60

Ala Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Leu Ala Tyr Phe Asp Tyr Gly Leu Ala Ile Gln Asn Tyr Trp
            100                 105                 110
```

Gly Gln Gly Thr Leu Val Thr Val Ser Ser Ala Ser Thr Lys Gly Pro
            115                 120                 125

Ser Val Phe Pro Leu Ala Pro Cys Ser Arg Ser Thr Ser Glu Ser Thr
        130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Asn Phe Gly Thr Gln Thr Tyr Thr Cys Asn Val Asp
        195                 200                 205

His Lys Pro Ser Asn Thr Lys Val Asp Lys Thr Val Glu Arg Lys Cys
    210                 215                 220

Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Phe Arg Val Val
    290                 295                 300

Ser Val Leu Thr Val Val His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Thr Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Met Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 12
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Glu Ile Val Leu Thr Gln Ser Pro Ala Thr Leu Ser Leu Ser Pro Gly
1               5                   10                  15

Glu Arg Ala Thr Leu Ser Cys Lys Ala Ser Lys Arg Val Thr Thr Tyr
            20                  25                  30

Val Ser Trp Tyr Gln Gln Lys Pro Gly Gln Ala Pro Arg Leu Leu Ile
            35                  40                  45

Tyr Gly Ala Ser Asn Arg Tyr Leu Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Ser Gln Ser Tyr Asn Tyr Pro Tyr
                 85                  90                  95

Thr Phe Gly Gln Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
210

<210> SEQ ID NO 13
<211> LENGTH: 1347
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
gaagttcagc tggttgaatc cggtggtggt ctggttcagc caggtggttc cctgcgtctg      60
tcctgcgctg cttccggttt caccttctcc aactactgga tctcctgggt tcgtcaggct     120
cctggtaaag gtctggaatg ggttgctgaa atccgttccg aatccgacgc gtccgctacc     180
cattacgctg aagctgttaa aggtcgtttc accatctccc gtgacaacgc taagaactcc     240
ctgtacctgc agatgaactc cctgcgtgct gaagacaccg ctgtttacta ctgcctggct     300
tactttgact acggtctggc tatccagaac tactggggtc agggtaccct ggttaccgtt     360
tcctccgcct ccaccaaggg cccatctgtc ttcccactgg ccccatgctc cgcagcacc     420 tccgagagca cagccgccct gggctgcctg gtcaaggact acttcccaga acctgtgacc     480
gtgtcctgga ctctggcgc tctgaccagc ggcgtgcaca ccttcccagc tgtcctgcag     540
tcctcaggtc tctactccct cagcagcgtg gtgaccgtgc catccagcaa cttcggcacc     600
cagacctaca cctgcaacgt agatcacaag ccaagcaaca ccaaggtcga caagaccgtg     660
gagagaaagt gttgtgtgga gtgtccacct tgtccagccc ctccagtggc cggaccatcc     720
gtgttcctgt tccctccaaa gccaaaggac accctgatga tctccagaac cccagaggtg     780
acctgtgtgg tggtggacgt gtcccacgag gacccagagg tgcagttcaa ctggtatgtg     840
gacggagtgg aggtgcacaa cgccaagacc aagccaagag aggagcagtt caactccacc     900
ttcagagtgg tgagcgtgct gaccgtggtg caccaggact ggctgaacgg aaaggagtat     960

```
aagtgtaagg tgtccaacaa gggactgcca tccagcatcg agaagaccat ctccaagacc   1020
aagggacagc caagagagcc acaggtgtat accctgcccc catccagaga ggagatgacc   1080
aagaaccagg tgtccctgac ctgtctggtg aagggattct atccatccga catcgccgtg   1140
gagtgggagt ccaacggaca gccagagaac aactataaga ccaccccctcc aatgctggac   1200 tccgacggat ccttcttcct gtattccaag ctgaccgtgg acaagtccag atggcagcag   1260
ggaaacgtgt tctcttgttc cgtgatgcac gaggccctgc acaaccacta cccagaag     1320 agcctgtccc tgtctccagg aaagtaa                                       1347
```

<210> SEQ ID NO 14
<211> LENGTH: 645
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14

```
gaaatcgttc tgacccagtc cccggctacc ctgtccctgt ccccaggtga acgtgctacc    60
ctgtcctgca aagcttccaa acgggttacc acctacgttt cctggtacca gcagaaaccc   120
ggtcaggctc ctcgtctgct gatctacggt gcttccaacc gttacctcgg tatcccagct   180
cgtttctccg gttccggttc cggtaccgac ttcaccctga ccatctcctc cctggaaccc   240
gaagacttcg ctgtttacta ctgcagtcag tcctacaact accccctacac cttcggtcag   300 ggtaccaaac tggaaatcaa acgcactgtg gctgcaccat ctgtcttcat cttccctcca    360
tctgatgagc agttgaaatc cggaactgcc tctgttgtgt gcctgctgaa taacttctat    420
ccgcgcgagg ccaaagtaca gtggaaggtg gataacgccc tccaatccgg taactcccag    480
gagagtgtca cagagcagga cagcaaggac agcacctaca gcctcagcag cacc ctgacc    540 ctgagcaaag cagactacga gaaacacaaa gtctacgcct gcgaagtcac ccatcagggc    600
ctgagttctc cagtcacaaa gagcttcaac cgcggtgagt gctaa                     645
```

<210> SEQ ID NO 15
<211> LENGTH: 37
<212> TYPE: PRT
<213> ORGANISM: Homo sapiens

<400> SEQUENCE: 15

```
Ala Cys Asp Thr Ala Thr Cys Val Thr His Arg Leu Ala Gly Leu Leu
1               5                   10                  15

Ser Arg Ser Gly Gly Val Val Lys Asn Asn Phe Val Pro Thr Asn Val
            20                  25                  30

Gly Ser Lys Ala Phe
        35
```

<210> SEQ ID NO 16
<211> LENGTH: 30
<212> TYPE: PRT
<213> ORGANISM: Homo sapiens

<400> SEQUENCE: 16

```
Val Thr His Arg Leu Ala Gly Leu Leu Ser Arg Ser Gly Gly Val Val
1               5                   10                  15

Lys Asn Asn Phe Val Pro Thr Asn Val Gly Ser Lys Ala Phe
            20                  25                  30
```

```
<210> SEQ ID NO 17
<211> LENGTH: 19
<212> TYPE: PRT
<213> ORGANISM: Homo sapiens

<400> SEQUENCE: 17

Ser Gly Gly Val Val Lys Asn Asn Phe Val Pro Thr Asn Val Gly Ser
1               5                   10                  15

Lys Ala Phe

<210> SEQ ID NO 18
<211> LENGTH: 19
<212> TYPE: PRT
<213> ORGANISM: Homo sapiens

<400> SEQUENCE: 18

Ser Gly Gly Val Val Lys Asn Asn Phe Val Ala Thr Asn Val Gly Ser
1               5                   10                  15

Lys Ala Phe

<210> SEQ ID NO 19
<211> LENGTH: 19
<212> TYPE: PRT
<213> ORGANISM: Homo sapiens

<400> SEQUENCE: 19

Ser Gly Gly Val Val Lys Asn Asn Phe Val Pro Thr Asn Val Gly Ser
1               5                   10                  15

Ala Ala Phe

<210> SEQ ID NO 20
<211> LENGTH: 19
<212> TYPE: PRT
<213> ORGANISM: Homo sapiens

<400> SEQUENCE: 20

Ser Gly Gly Val Val Lys Asn Asn Phe Val Pro Thr Asn Val Gly Ser
1               5                   10                  15

Glu Ala Phe

<210> SEQ ID NO 21
<211> LENGTH: 19
<212> TYPE: PRT
<213> ORGANISM: Homo sapiens

<400> SEQUENCE: 21

Ser Gly Gly Val Val Lys Asn Asn Phe Val Pro Thr Asn Val Gly Ser
1               5                   10                  15

Met Ala Phe

<210> SEQ ID NO 22
<211> LENGTH: 19
<212> TYPE: PRT
<213> ORGANISM: Homo sapiens

<400> SEQUENCE: 22

Ser Gly Gly Val Val Lys Asn Asn Phe Val Pro Thr Asn Val Gly Ser
1               5                   10                  15

Gln Ala Phe
```

<210> SEQ ID NO 23
<211> LENGTH: 19
<212> TYPE: PRT
<213> ORGANISM: Homo sapiens

<400> SEQUENCE: 23

Ser Gly Gly Val Val Lys Asn Asn Phe Val Pro Thr Asn Val Gly Ser
1               5                   10                  15

Lys Ala Ala

<210> SEQ ID NO 24
<211> LENGTH: 14
<212> TYPE: PRT
<213> ORGANISM: Homo sapiens

<400> SEQUENCE: 24

Asn Asn Phe Val Pro Thr Asn Val Gly Ser Lys Ala Phe Ala
1               5                   10

<210> SEQ ID NO 25
<211> LENGTH: 13
<212> TYPE: PRT
<213> ORGANISM: Homo sapiens

<400> SEQUENCE: 25

Asn Asn Phe Val Pro Thr Asn Val Gly Ser Lys Ala Phe
1               5                   10

<210> SEQ ID NO 26
<211> LENGTH: 13
<212> TYPE: PRT
<213> ORGANISM: Homo sapiens

<400> SEQUENCE: 26

Asn Asn Ala Val Pro Thr Asn Val Gly Ser Lys Ala Phe
1               5                   10

<210> SEQ ID NO 27
<211> LENGTH: 13
<212> TYPE: PRT
<213> ORGANISM: Homo sapiens

<400> SEQUENCE: 27

Asn Asn Phe Ala Pro Thr Asn Val Gly Ser Lys Ala Phe
1               5                   10

<210> SEQ ID NO 28
<211> LENGTH: 13
<212> TYPE: PRT
<213> ORGANISM: Homo sapiens

<400> SEQUENCE: 28

Asn Asn Phe Val Ala Thr Asn Val Gly Ser Lys Ala Phe
1               5                   10

<210> SEQ ID NO 29
<211> LENGTH: 13
<212> TYPE: PRT
<213> ORGANISM: Homo sapiens

<400> SEQUENCE: 29

Asn Asn Phe Val Pro Ala Asn Val Gly Ser Lys Ala Phe
1               5                   10

```
<210> SEQ ID NO 30
<211> LENGTH: 13
<212> TYPE: PRT
<213> ORGANISM: Homo sapiens

<400> SEQUENCE: 30

Asn Asn Phe Val Pro Thr Ala Val Gly Ser Lys Ala Phe
1               5                   10

<210> SEQ ID NO 31
<211> LENGTH: 13
<212> TYPE: PRT
<213> ORGANISM: Homo sapiens

<400> SEQUENCE: 31

Asn Asn Phe Val Pro Thr Asn Ala Gly Ser Lys Ala Phe
1               5                   10

<210> SEQ ID NO 32
<211> LENGTH: 13
<212> TYPE: PRT
<213> ORGANISM: Homo sapiens

<400> SEQUENCE: 32

Asn Asn Phe Val Pro Thr Asn Val Ala Ser Lys Ala Phe
1               5                   10

<210> SEQ ID NO 33
<211> LENGTH: 13
<212> TYPE: PRT
<213> ORGANISM: Homo sapiens

<400> SEQUENCE: 33

Asn Asn Phe Val Pro Thr Asn Val Gly Ala Lys Ala Phe
1               5                   10

<210> SEQ ID NO 34
<211> LENGTH: 13
<212> TYPE: PRT
<213> ORGANISM: Homo sapiens

<400> SEQUENCE: 34

Asn Asn Phe Val Pro Thr Asn Val Gly Ser Lys Ala Ala
1               5                   10

<210> SEQ ID NO 35
<211> LENGTH: 12
<212> TYPE: PRT
<213> ORGANISM: Homo sapiens

<400> SEQUENCE: 35

Asn Phe Val Pro Thr Asn Val Gly Ser Lys Ala Phe
1               5                   10

<210> SEQ ID NO 36
<211> LENGTH: 19
<212> TYPE: PRT
<213> ORGANISM: Homo sapiens

<400> SEQUENCE: 36

Ser Gly Gly Val Val Lys Asn Asn Phe Val Pro Thr Asn Val Gly Ser
1               5                   10                  15

Lys Ala Phe
```

```
<210> SEQ ID NO 37
<211> LENGTH: 18
<212> TYPE: PRT
<213> ORGANISM: Homo sapiens

<400> SEQUENCE: 37

Ser Gly Gly Val Val Lys Asn Asn Phe Val Pro Thr Asn Val Gly Ser
1               5                   10                  15

Lys Ala

<210> SEQ ID NO 38
<211> LENGTH: 36
<212> TYPE: PRT
<213> ORGANISM: Homo sapiens

<400> SEQUENCE: 38

Ala Cys Asp Thr Ala Thr Cys Val Thr His Arg Leu Ala Gly Leu Leu
1               5                   10                  15

Ser Arg Ser Gly Gly Val Val Lys Asn Asn Phe Val Pro Thr Asn Val
            20                  25                  30

Gly Ser Lys Ala
        35

<210> SEQ ID NO 39
<211> LENGTH: 19
<212> TYPE: PRT
<213> ORGANISM: Homo sapiens

<400> SEQUENCE: 39

Ala Cys Asp Thr Ala Thr Cys Val Thr His Arg Leu Ala Gly Leu Leu
1               5                   10                  15

Ser Arg Ser

<210> SEQ ID NO 40
<211> LENGTH: 13
<212> TYPE: PRT
<213> ORGANISM: Homo sapiens

<400> SEQUENCE: 40

Ala Cys Asp Thr Ala Thr Cys Val Thr His Arg Leu Ala
1               5                   10

<210> SEQ ID NO 41
<211> LENGTH: 37
<212> TYPE: PRT
<213> ORGANISM: Rattus sp.

<400> SEQUENCE: 41

Ser Cys Asn Thr Ala Thr Cys Val Thr His Arg Leu Ala Gly Leu Leu
1               5                   10                  15

Ser Arg Ser Gly Gly Val Val Lys Asp Asn Phe Val Pro Thr Asn Val
            20                  25                  30

Gly Ser Glu Ala Phe
        35

<210> SEQ ID NO 42
<211> LENGTH: 19
<212> TYPE: PRT
<213> ORGANISM: Rattus sp.
```

<400> SEQUENCE: 42

Ser Gly Gly Val Val Lys Asp Asn Phe Val Pro Thr Asn Val Gly Ser
1               5                   10                  15

Glu Ala Phe

<210> SEQ ID NO 43
<211> LENGTH: 37
<212> TYPE: PRT
<213> ORGANISM: Homo sapiens

<400> SEQUENCE: 43

Ala Cys Asn Thr Ala Thr Cys Val Thr His Arg Leu Ala Gly Leu Leu
1               5                   10                  15

Ser Arg Ser Gly Gly Met Val Lys Ser Asn Phe Val Pro Thr Asn Val
                20                  25                  30

Gly Ser Lys Ala Phe
            35

<210> SEQ ID NO 44
<211> LENGTH: 37
<212> TYPE: PRT
<213> ORGANISM: Rattus sp.

<400> SEQUENCE: 44

Ser Cys Asn Thr Ala Thr Cys Val Thr His Arg Leu Ala Gly Leu Leu
1               5                   10                  15

Ser Arg Ser Gly Gly Val Val Lys Asp Asn Phe Val Pro Thr Asn Val
                20                  25                  30

Gly Ser Lys Ala Phe
            35

<210> SEQ ID NO 45
<211> LENGTH: 32
<212> TYPE: PRT
<213> ORGANISM: Homo sapiens

<400> SEQUENCE: 45

Cys Gly Asn Leu Ser Thr Cys Met Leu Gly Thr Tyr Thr Gln Asp Phe
1               5                   10                  15

Asn Lys Phe His Thr Phe Pro Gln Thr Ala Ile Gly Val Gly Ala Pro
                20                  25                  30

<210> SEQ ID NO 46
<211> LENGTH: 37
<212> TYPE: PRT
<213> ORGANISM: Homo sapiens

<400> SEQUENCE: 46

Lys Cys Asn Thr Ala Thr Cys Ala Thr Gln Arg Leu Ala Asn Phe Leu
1               5                   10                  15

Val His Ser Ser Asn Asn Phe Gly Ala Ile Leu Ser Ser Thr Asn Val
                20                  25                  30

Gly Ser Asn Thr Tyr
            35

<210> SEQ ID NO 47
<211> LENGTH: 52
<212> TYPE: PRT
<213> ORGANISM: Homo sapiens

<400> SEQUENCE: 47

Tyr Arg Gln Ser Met Asn Asn Phe Gln Gly Leu Arg Ser Phe Gly Cys
1               5                   10                  15
Arg Phe Gly Thr Cys Thr Val Gln Lys Leu Ala His Gln Ile Tyr Gln
            20                  25                  30
Phe Thr Asp Lys Asp Lys Asp Asn Val Ala Pro Arg Ser Lys Ile Ser
        35                  40                  45
Pro Gln Gly Tyr
    50

<210> SEQ ID NO 48

<400> SEQUENCE: 48

000

<210> SEQ ID NO 49

<400> SEQUENCE: 49

000

<210> SEQ ID NO 50

<400> SEQUENCE: 50

000

<210> SEQ ID NO 51

<400> SEQUENCE: 51

000

<210> SEQ ID NO 52

<400> SEQUENCE: 52

000

<210> SEQ ID NO 53

<400> SEQUENCE: 53

000

<210> SEQ ID NO 54

<400> SEQUENCE: 54

000

<210> SEQ ID NO 55

<400> SEQUENCE: 55

000

<210> SEQ ID NO 56

<400> SEQUENCE: 56

000

<210> SEQ ID NO 57

<400> SEQUENCE: 57

000

<210> SEQ ID NO 58
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asp Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Glu Tyr His Ser Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asp Ala Leu Pro Pro
                85                  90                  95

Thr Phe Gly Gln Gly Thr Lys Leu Glu Ile Lys
            100                 105

<210> SEQ ID NO 59
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Gly Asn Tyr
            20                  25                  30

Trp Met Gln Trp Val Arg Gln Ala Pro Gly Gln Gly Leu Glu Trp Met
        35                  40                  45

Gly Ala Ile Tyr Glu Gly Thr Gly Asp Thr Arg Tyr Ile Gln Lys Phe
50                  55                  60

Ala Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Leu Ser Asp Tyr Val Ser Gly Phe Ser Tyr Trp Gly Gln Gly
            100                 105                 110

Thr Leu Val Thr Val Ser Ser
        115

<210> SEQ ID NO 60
<211> LENGTH: 107
<212> TYPE: PRT
<213> ORGANISM: Artificial Sequence
<220> FEATURE:

<223> OTHER INFORMATION: Description of Artificial Sequence: Synthetic
     polypeptide

<400> SEQUENCE: 60

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asp Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Glu Tyr His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asp Ala Leu Pro Pro
                85                  90                  95

Thr Phe Gly Gln Gly Thr Lys Leu Glu Ile Lys
            100                 105

<210> SEQ ID NO 61
<211> LENGTH: 119
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 61

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Gly Asn Tyr
            20                  25                  30

Trp Met Gln Trp Val Arg Gln Ala Pro Gly Gln Gly Leu Glu Trp Met
        35                  40                  45

Gly Ala Ile Tyr Glu Gly Thr Gly Lys Thr Val Tyr Ile Gln Lys Phe
    50                  55                  60

Ala Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Leu Ser Asp Tyr Val Ser Gly Phe Ser Tyr Trp Gly Gln Gly
            100                 105                 110

Thr Leu Val Thr Val Ser Ser
        115

<210> SEQ ID NO 62
<211> LENGTH: 107
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 62

Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Asp Ile Ser Lys Tyr
            20                  25                  30

```
Leu Asn Trp Tyr Gln Gln Lys Pro Gly Lys Ala Pro Lys Leu Leu Ile
            35                  40                  45

Tyr Tyr Thr Ser Gly Tyr His Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asp Ala Leu Pro Pro
                85                  90                  95

Thr Phe Gly Gly Gly Thr Lys Val Glu Ile Lys
                100                 105

<210> SEQ ID NO 63
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Gly Asn Tyr
                20                  25                  30

Trp Met Gln Trp Val Arg Gln Ala Pro Gly Gln Gly Leu Glu Trp Met
            35                  40                  45

Gly Ala Ile Tyr Glu Gly Thr Gly Lys Thr Val Tyr Ile Gln Lys Phe
        50                  55                  60

Ala Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Ser Asp Tyr Val Ser Gly Phe Gly Tyr Trp Gly Gln Gly
                100                 105                 110

Thr Thr Val Thr Val Ser Ser
        115

<210> SEQ ID NO 64
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Asp Ile Gln Met Thr Gln Ser Pro Ser Ser Leu Ser Ala Ser Val Gly
1               5                   10                  15

Asp Arg Val Thr Ile Thr Cys Arg Ala Ser Arg Pro Ile Asp Lys Tyr
                20                  25                  30

Leu Asn Trp Tyr Gln Gln Lys Pro Gly Lys Ala Pro Lys Leu Leu Ile
            35                  40                  45

Tyr Tyr Thr Ser Glu Tyr His Ser Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asp Ala Leu Pro Pro
                85                  90                  95
```

Thr Phe Gly Gln Gly Thr Lys Leu Glu Ile Lys
            100                 105

<210> SEQ ID NO 65
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Gly Asn Tyr
            20                  25                  30

Trp Met Gln Trp Val Arg Gln Ala Pro Gly Gln Gly Leu Glu Trp Met
        35                  40                  45

Gly Ala Ile Tyr Glu Gly Thr Gly Lys Thr Val Tyr Ile Gln Lys Phe
    50                  55                  60

Ala Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Leu Ser Asp Tyr Val Ser Gly Phe Gly Tyr Trp Gly Gln Gly
            100                 105                 110

Thr Leu Val Thr Val Ser Ser
        115

<210> SEQ ID NO 66
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asp Lys Tyr
            20                  25                  30

Leu Asn Trp Tyr Gln Gln Lys Pro Gly Lys Ala Pro Lys Leu Leu Ile
        35                  40                  45

Tyr Tyr Thr Ser Gly Tyr His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asp Ala Leu Pro Pro
                85                  90                  95

Thr Phe Gly Gly Gly Thr Lys Val Glu Ile Lys
            100                 105

<210> SEQ ID NO 67
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Gly Asn Tyr
            20                  25                  30

Trp Met Gln Trp Val Arg Gln Ala Pro Gly Gln Gly Leu Glu Trp Met
        35                  40                  45

Gly Ala Ile Tyr Glu Gly Thr Gly Lys Thr Val Tyr Ile Gln Lys Phe
    50                  55                  60

Ala Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Ser Asp Tyr Val Ser Gly Phe Gly Tyr Trp Gly Gln Gly
            100                 105                 110

Thr Thr Val Thr Val Ser Ser
        115

<210> SEQ ID NO 68
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Gln Val Leu Thr Gln Ser Pro Ser Ser Leu Ser Ala Ser Val Gly Asp
1               5                   10                  15

Arg Val Thr Ile Asn Cys Gln Ala Ser Gln Ser Val Tyr His Asn Thr
            20                  25                  30

Tyr Leu Ala Trp Tyr Gln Gln Lys Pro Gly Lys Val Pro Lys Gln Leu
        35                  40                  45

Ile Tyr Asp Ala Ser Thr Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Val Ala Thr Tyr Tyr Cys Leu Gly Ser Tyr Asp Cys Thr
                85                  90                  95

Asn Gly Asp Cys Phe Val Phe Gly Gly Gly Thr Lys Val Glu Ile Lys
            100                 105                 110

Arg

<210> SEQ ID NO 69
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Glu Val Gln Leu Val Glu Ser Gly Gly Gly Leu Val Gln Pro Gly Gly
1               5                   10                  15

Ser Leu Arg Leu Ser Cys Ala Val Ser Gly Ile Asp Leu Ser Gly Tyr
            20                  25                  30

```
Tyr Met Asn Trp Val Arg Gln Ala Pro Gly Lys Gly Leu Glu Trp Val
            35                  40                  45

Gly Val Ile Gly Ile Asn Gly Ala Thr Tyr Tyr Ala Ser Trp Ala Lys
 50                  55                  60

Gly Arg Phe Thr Ile Ser Arg Asp Asn Ser Lys Thr Thr Val Tyr Leu
 65                  70                  75                  80

Gln Met Asn Ser Leu Arg Ala Glu Asp Thr Ala Val Tyr Phe Cys Ala
             85                  90                  95

Arg Gly Asp Ile Trp Gly Gln Gly Thr Leu Val Thr Val Ser Ser
             100                 105                 110
```

```
<210> SEQ ID NO 70
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70
```

```
Gln Val Leu Thr Gln Ser Pro Ser Ser Leu Ser Ala Ser Val Gly Asp
1               5                   10                  15

Arg Val Thr Ile Asn Cys Gln Ala Ser Gln Ser Val Tyr Asp Asn Asn
             20                  25                  30

Tyr Leu Ala Trp Tyr Gln Lys Pro Gly Lys Val Pro Lys Gln Leu
            35                  40                  45

Ile Tyr Ser Thr Ser Thr Leu Ala Ser Gly Val Pro Ser Arg Phe Ser
 50                  55                  60

Gly Ser Gly Ser Gly Thr Asp Phe Thr Leu Thr Ile Ser Ser Leu Gln
 65                  70                  75                  80

Pro Glu Asp Val Ala Thr Tyr Tyr Cys Leu Gly Ser Tyr Asp Cys Ser
             85                  90                  95

Ser Gly Asp Cys Phe Val Phe Gly Gly Gly Thr Lys Val Glu Ile Lys
             100                 105                 110

Arg
```

```
<210> SEQ ID NO 71
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71
```

```
Glu Val Gln Leu Val Glu Ser Gly Gly Gly Leu Val Gln Pro Gly Gly
1               5                   10                  15

Ser Leu Arg Leu Ser Cys Ala Val Ser Gly Leu Asp Leu Ser Ser Tyr
             20                  25                  30

Tyr Met Gln Trp Val Arg Gln Ala Pro Gly Lys Gly Leu Glu Trp Val
            35                  40                  45

Gly Val Ile Gly Ile Asn Asp Asn Thr Tyr Tyr Ala Ser Trp Ala Lys
 50                  55                  60

Gly Arg Phe Thr Ile Ser Arg Asp Asn Ser Lys Thr Thr Val Tyr Leu
 65                  70                  75                  80

Gln Met Asn Ser Leu Arg Ala Glu Asp Thr Ala Val Tyr Phe Cys Ala
             85                  90                  95
```

Arg Gly Asp Ile Trp Gly Gln Gly Thr Leu Val Thr Val Ser Ser
            100                 105                 110

<210> SEQ ID NO 72
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Gln Val Leu Thr Gln Ser Pro Ser Ser Leu Ser Ala Ser Val Gly Asp
1               5                   10                  15

Arg Val Thr Ile Asn Cys Gln Ala Ser Gln Ser Val Tyr Asp Asn Asn
            20                  25                  30

Tyr Leu Ala Trp Tyr Gln Gln Lys Pro Gly Lys Val Pro Lys Gln Leu
        35                  40                  45

Ile Tyr Ser Thr Ser Thr Leu Ala Ser Gly Val Pro Ser Arg Phe Ser
50                  55                  60

Gly Ser Gly Ser Gly Thr Asp Phe Thr Leu Thr Ile Ser Ser Leu Gln
65                  70                  75                  80

Pro Glu Asp Val Ala Thr Tyr Tyr Cys Leu Gly Ser Tyr Asp Cys Ser
                85                  90                  95

Ser Gly Asp Cys Phe Val Phe Gly Gly Gly Thr Lys Val Glu Ile Lys
            100                 105                 110

Arg

<210> SEQ ID NO 73
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Glu Val Gln Leu Val Glu Ser Gly Gly Gly Leu Val Gln Pro Gly Gly
1               5                   10                  15

Ser Leu Arg Leu Ser Cys Ala Val Ser Gly Leu Asp Leu Ser Ser Tyr
            20                  25                  30

Tyr Met Gln Trp Val Arg Gln Ala Pro Gly Lys Gly Leu Glu Trp Val
        35                  40                  45

Gly Val Ile Gly Ile Asn Asp Asn Thr Tyr Tyr Ala Ser Trp Ala Lys
50                  55                  60

Gly Arg Phe Thr Ile Ser Arg Asp Asn Ser Lys Thr Thr Val Tyr Leu
65                  70                  75                  80

Gln Met Asn Ser Leu Arg Ala Glu Asp Thr Ala Val Tyr Phe Cys Ala
                85                  90                  95

Arg Gly Asp Ile Trp Gly Gln Gly Thr Leu Val Thr Val Ser Ser
            100                 105                 110

<210> SEQ ID NO 74
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Gln Val Leu Thr Gln Thr Pro Ser Pro Val Ser Ala Ala Val Gly Ser
1               5                   10                  15

Thr Val Thr Ile Asn Cys Gln Ala Ser Gln Ser Val Tyr His Asn Thr
            20                  25                  30

Tyr Leu Ala Trp Tyr Gln Gln Lys Pro Gly Gln Pro Pro Lys Gln Leu
        35                  40                  45

Ile Tyr Asp Ala Ser Thr Leu Ala Ser Gly Val Pro Ser Arg Phe Ser
    50                  55                  60

Gly Ser Gly Ser Gly Thr Gln Phe Thr Leu Thr Ile Ser Gly Val Gln
65                  70                  75                  80

Cys Asn Asp Ala Ala Ala Tyr Tyr Cys Leu Gly Ser Tyr Asp Cys Thr
                85                  90                  95

Asn Gly Asp Cys Phe Val Phe Gly Gly Thr Glu Val Val Val Lys
            100                 105                 110

Arg

<210> SEQ ID NO 75
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Gln Ser Leu Glu Glu Ser Gly Gly Arg Leu Val Thr Pro Gly Thr Pro
1               5                   10                  15

Leu Thr Leu Thr Cys Ser Val Ser Gly Ile Asp Leu Ser Gly Tyr Tyr
            20                  25                  30

Met Asn Trp Val Arg Gln Ala Pro Gly Lys Gly Leu Glu Trp Ile Gly
        35                  40                  45

Val Ile Gly Ile Asn Gly Ala Thr Tyr Tyr Ala Ser Trp Ala Lys Gly
    50                  55                  60

Arg Phe Thr Ile Ser Lys Thr Ser Ser Thr Thr Val Asp Leu Lys Met
65                  70                  75                  80

Thr Ser Leu Thr Thr Glu Asp Thr Ala Thr Tyr Phe Cys Ala Arg Gly
                85                  90                  95

Asp Ile Trp Gly Pro Gly Thr Leu Val Thr Val Ser Ser
            100                 105

<210> SEQ ID NO 76
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Gln Val Leu Thr Gln Ser Pro Ser Ser Leu Ser Ala Ser Val Gly Asp
1               5                   10                  15

Arg Val Thr Ile Asn Cys Gln Ala Ser Gln Ser Val Tyr His Asn Thr
            20                  25                  30

Tyr Leu Ala Trp Tyr Gln Gln Lys Pro Gly Lys Val Pro Lys Gln Leu
        35                  40                  45

Ile Tyr Asp Ala Ser Thr Leu Ala Ser Gly Val Pro Ser Arg Phe Ser
            50                  55                  60

Gly Ser Gly Ser Gly Thr Asp Phe Thr Leu Thr Ile Ser Ser Leu Gln
65                  70                  75                  80

Pro Glu Asp Val Ala Thr Tyr Tyr Cys Leu Gly Ser Tyr Asp Cys Thr
                85                  90                  95

Asn Gly Asp Cys Phe Val Phe Gly Gly Gly Thr Lys Val Glu Ile Lys
            100                 105                 110

Arg

<210> SEQ ID NO 77
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Glu Val Gln Leu Val Glu Ser Gly Gly Gly Leu Val Gln Pro Gly Gly
1               5                   10                  15

Ser Leu Arg Leu Ser Cys Ala Val Ser Gly Ile Asp Leu Ser Gly Tyr
            20                  25                  30

Tyr Met Asn Trp Val Arg Gln Ala Pro Gly Lys Gly Leu Glu Trp Val
        35                  40                  45

Gly Val Ile Gly Ile Asn Gly Ala Thr Tyr Tyr Ala Ser Trp Ala Lys
    50                  55                  60

Gly Arg Phe Thr Ile Ser Arg Asp Asn Ser Lys Thr Thr Val Tyr Leu
65                  70                  75                  80

Gln Met Asn Ser Leu Arg Ala Glu Asp Thr Ala Val Tyr Phe Cys Ala
                85                  90                  95

Arg Gly Asp Ile Trp Gly Gln Gly Thr Leu Val Thr Val Ser Ser
            100                 105                 110

<210> SEQ ID NO 78
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Thr Thr Leu Gly Ile Thr Gly Leu Gln
65                  70                  75                  80

Thr Gly Asp Glu Ala Asp Tyr Tyr Cys Gly Thr Trp Asp Ser Arg Leu
                85                  90                  95

Ser Ala Val Val Phe Gly Gly Gly Thr Lys Leu Thr Val Leu
            100                 105                 110

<210> SEQ ID NO 79
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Phe
                20                  25                  30

Gly Met His Trp Val Arg Gln Ala Pro Gly Lys Gly Leu Glu Trp Val
            35                  40                  45

Ala Val Ile Ser Phe Asp Gly Ser Ile Lys Tyr Ser Val Asp Ser Val
        50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Arg Asp Arg Leu Asn Tyr Tyr Asp Ser Ser Gly Tyr Tyr His Tyr
            100                 105                 110

Lys Tyr Tyr Gly Met Ala Val Trp Gly Gln Gly Thr Thr Val Thr Val
        115                 120                 125

Ser Ser
130

<210> SEQ ID NO 80
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Gln Val Leu Thr Gln Ser Pro Ser Ser Leu Ser Ala Ser Val Gly Asp
1               5                   10                  15

Arg Val Thr Ile Asn Cys Gln Ala Ser Gln Ser Val Tyr His Asn Thr
                20                  25                  30

Tyr Leu Ala Trp Tyr Gln Gln Lys Pro Gly Lys Val Pro Lys Gln Leu
            35                  40                  45

Ile Tyr Asp Ala Ser Thr Leu Ala Ser Gly Val Pro Ser Arg Phe Ser
        50                  55                  60

Gly Ser Gly Ser Gly Thr Asp Phe Thr Leu Thr Ile Ser Ser Leu Gln
65                  70                  75                  80

Pro Glu Asp Val Ala Thr Tyr Tyr Cys Leu Gly Ser Tyr Asp Cys Thr
                85                  90                  95

Asn Gly Asp Cys Phe Val Phe Gly Gly Gly Thr Lys Val Glu Ile Lys
            100                 105                 110

Arg

<210> SEQ ID NO 81
<211> LENGTH: 219
<212> TYPE: PRT
<213> ORGANISM: Artificial Sequence
<220> FEATURE:

<223> OTHER INFORMATION: Description of Artificial Sequence: Synthetic
polypeptide

<400> SEQUENCE: 81

Gln Val Leu Thr Gln Ser Pro Ser Leu Ser Ala Ser Val Gly Asp
1               5                   10                  15

Arg Val Thr Ile Asn Cys Gln Ala Ser Gln Ser Val Tyr His Asn Thr
            20                  25                  30

Tyr Leu Ala Trp Tyr Gln Gln Lys Pro Gly Lys Val Pro Lys Gln Leu
        35                  40                  45

Ile Tyr Asp Ala Ser Thr Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Val Ala Thr Tyr Tyr Cys Leu Gly Ser Tyr Asp Cys Thr
                85                  90                  95

Asn Gly Asp Cys Phe Val Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 82
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Glu Val Gln Leu Val Glu Ser Gly Gly Gly Leu Val Gln Pro Gly Gly
1               5                   10                  15

Ser Leu Arg Leu Ser Cys Ala Val Ser Gly Ile Asp Leu Ser Gly Tyr
            20                  25                  30

Tyr Met Asn Trp Val Arg Gln Ala Pro Gly Lys Gly Leu Glu Trp Val
        35                  40                  45

Gly Val Ile Gly Ile Asn Gly Ala Thr Tyr Tyr Ala Ser Trp Ala Lys
    50                  55                  60

Gly Arg Phe Thr Ile Ser Arg Asp Asn Ser Lys Thr Thr Val Tyr Leu
65                  70                  75                  80

Gln Met Asn Ser Leu Arg Ala Glu Asp Thr Ala Val Tyr Phe Cys Ala
                85                  90                  95

Arg Gly Asp Ile Trp Gly Gln Gly Thr Leu Val Thr Val Ser Ser
            100                 105                 110

<210> SEQ ID NO 83
<211> LENGTH: 441
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 83

```
Glu Val Gln Leu Val Glu Ser Gly Gly Gly Leu Val Gln Pro Gly Gly
1               5                   10                  15

Ser Leu Arg Leu Ser Cys Ala Val Ser Gly Ile Asp Leu Ser Gly Tyr
            20                  25                  30

Tyr Met Asn Trp Val Arg Gln Ala Pro Gly Lys Gly Leu Glu Trp Val
        35                  40                  45

Gly Val Ile Gly Ile Asn Gly Ala Thr Tyr Tyr Ala Ser Trp Ala Lys
    50                  55                  60

Gly Arg Phe Thr Ile Ser Arg Asp Asn Ser Lys Thr Thr Val Tyr Leu
65                  70                  75                  80

Gln Met Asn Ser Leu Arg Ala Glu Asp Thr Ala Val Tyr Phe Cys Ala
                85                  90                  95

Arg Gly Asp Ile Trp Gly Gln Gly Thr Leu Val Thr Val Ser Ser Ala
            100                 105                 110

Ser Thr Lys Gly Pro Ser Val Phe Pro Leu Ala Pro Ser Ser Lys Ser
        115                 120                 125

Thr Ser Gly Gly Thr Ala Ala Leu Gly Cys Leu Val Lys Asp Tyr Phe
    130                 135                 140

Pro Glu Pro Val Thr Val Ser Trp Asn Ser Gly Ala Leu Thr Ser Gly
145                 150                 155                 160

Val His Thr Phe Pro Ala Val Leu Gln Ser Ser Gly Leu Tyr Ser Leu
                165                 170                 175

Ser Ser Val Val Thr Val Pro Ser Ser Ser Leu Gly Thr Gln Thr Tyr
            180                 185                 190

Ile Cys Asn Val Asn His Lys Pro Ser Asn Thr Lys Val Asp Ala Arg
        195                 200                 205

Val Glu Pro Lys Ser Cys Asp Lys Thr His Thr Cys Pro Pro Cys Pro
    210                 215                 220

Ala Pro Glu Leu Leu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
        275                 280                 285

Gln Tyr Ala Ser Thr Tyr Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320

Ala Leu Pro Ala Pro Ile Glu Lys Thr Ile Ser Lys Ala Lys Gly Gln
                325                 330                 335

Pro Arg Glu Pro Gln Val Tyr Thr Leu Pro Pro Ser Arg Glu Glu Met
            340                 345                 350

Thr Lys Asn Gln Val Ser Leu Thr Cys Leu Val Lys Gly Phe Tyr Pro
        355                 360                 365
```

Ser Asp Ile Ala Val Glu Trp Glu Ser Asn Gly Gln Pro Glu Asn Asn
        370                 375                 380

Tyr Lys Thr Thr Pro Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
            420                 425                 430

Lys Ser Leu Ser Leu Ser Pro Gly Lys
            435                 440

<210> SEQ ID NO 84
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Gln Ala Ser Gln Ser Val Tyr His Asn Thr Tyr Leu Ala
1               5                   10

<210> SEQ ID NO 85
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Asp Ala Ser Thr Leu Ala Ser
1               5

<210> SEQ ID NO 86
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Leu Gly Ser Tyr Asp Cys Thr Asn Gly Asp Cys Phe Val
1               5                   10

<210> SEQ ID NO 87
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Gly Tyr Tyr Met Asn
1               5

<210> SEQ ID NO 88
<211> LENGTH: 15
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 88

Ile Gly Ile Asn Gly Ala Thr Tyr Tyr Ala Ser Trp Ala Lys Gly
1               5                   10                  15

<210> SEQ ID NO 89
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Gly Asp Ile
1

<210> SEQ ID NO 90
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Gln Gln Gly Asp Ala Leu Pro Pro Thr
1               5

<210> SEQ ID NO 91
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Arg Ala Ser Lys Asp Ile Ser Lys Tyr Leu
1               5                   10

<210> SEQ ID NO 92
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Tyr Thr Ser Gly Tyr His Ser
1               5

<210> SEQ ID NO 93
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Gly Tyr Thr Phe Gly Asn Tyr Trp Met Gln
1               5                   10
```

<210> SEQ ID NO 94
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 94

```
Ala Ile Tyr Glu Gly Thr Gly Lys Thr Val Tyr Ile Gln Lys Phe Ala
1               5                   10                  15

Asp
```

<210> SEQ ID NO 95
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 95

```
Leu Ser Asp Tyr Val Ser Gly Phe Gly Tyr
1               5                   10
```

<210> SEQ ID NO 96
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 96

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Asp Ile Ser Lys Tyr
            20                  25                  30

Leu Asn Trp Tyr Gln Gln Lys Pro Gly Lys Ala Pro Lys Leu Leu Ile
        35                  40                  45

Tyr Tyr Thr Ser Gly Tyr His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asp Ala Leu Pro Pro
                85                  90                  95

Thr Phe Gly Gly Gly Thr Lys Val Glu Ile Lys
            100                 105
```

<210> SEQ ID NO 97
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 97

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Gly Asn Tyr
            20                  25                  30
```

-continued

```
Trp Met Gln Trp Val Arg Gln Ala Pro Gly Gln Gly Leu Glu Trp Met
        35                  40                  45

Gly Ala Ile Tyr Glu Gly Thr Gly Lys Thr Val Tyr Ile Gln Lys Phe
    50                  55                  60

Ala Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Ser Asp Tyr Val Ser Gly Phe Gly Tyr Trp Gly Gln Gly
            100                 105                 110

Thr Thr Val Thr Val Ser Ser
            115

<210> SEQ ID NO 98
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Asp Ile Ser Lys Tyr
            20                  25                  30

Leu Asn Trp Tyr Gln Gln Lys Pro Gly Lys Ala Pro Lys Leu Leu Ile
        35                  40                  45

Tyr Tyr Thr Ser Gly Tyr His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asp Ala Leu Pro Pro
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 99
<211> LENGTH: 445
<212> TYPE: PRT
<213> ORGANISM: Artificial Sequence
<220> FEATURE:
```

<223> OTHER INFORMATION: Description of Artificial Sequence: Synthetic
polypeptide

<400> SEQUENCE: 99

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Gly Asn Tyr
            20                  25                  30

Trp Met Gln Trp Val Arg Gln Ala Pro Gly Gln Gly Leu Glu Trp Met
        35                  40                  45

Gly Ala Ile Tyr Glu Gly Thr Gly Lys Thr Val Tyr Ile Gln Lys Phe
    50                  55                  60

Ala Asp Arg Val Thr Ile Thr Ala Asp Lys Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Ser Asp Tyr Val Ser Gly Phe Gly Tyr Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400
```

```
Gly Ser Phe Phe Leu Tyr Ser Arg Leu Thr Val Asp Lys Ser Arg Trp
                405                 410                 415
Gln Glu Gly Asn Val Phe Ser Cys Ser Val Met His Glu Ala Leu His
            420                 425                 430
Asn His Tyr Thr Gln Lys Ser Leu Ser Leu Ser Leu Gly
        435                 440                 445

<210> SEQ ID NO 100
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Ser Gly Ser Ser Ser Asn Ile Gly Asn Asn Tyr Val Ser
1               5                   10

<210> SEQ ID NO 101
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Asp Asn Asn Lys Arg Pro Ser
1               5

<210> SEQ ID NO 102
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Gly Thr Trp Asp Ser Arg Leu Ser Ala Val Val
1               5                   10

<210> SEQ ID NO 103
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Ser Phe Gly Met His
1               5

<210> SEQ ID NO 104
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Val Ile Ser Phe Asp Gly Ser Ile Lys Tyr Ser Val Asp Ser Val Lys
1               5                   10                  15
```

Gly

<210> SEQ ID NO 105
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Asp Arg Leu Asn Tyr Tyr Asp Ser Ser Gly Tyr Tyr His Tyr Lys Tyr
1               5                   10                  15

Tyr Gly Met Ala Val
            20

<210> SEQ ID NO 106
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Thr Thr Leu Gly Ile Thr Gly Leu Gln
65                  70                  75                  80

Thr Gly Asp Glu Ala Asp Tyr Tyr Cys Gly Thr Trp Asp Ser Arg Leu
                85                  90                  95

Ser Ala Val Val Phe Gly Gly Gly Thr Lys Leu Thr Val Leu
            100                 105                 110

<210> SEQ ID NO 107
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Phe
            20                  25                  30

Gly Met His Trp Val Arg Gln Ala Pro Gly Lys Gly Leu Glu Trp Val
        35                  40                  45

Ala Val Ile Ser Phe Asp Gly Ser Ile Lys Tyr Ser Val Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                    85                  90                  95

Ala Arg Asp Arg Leu Asn Tyr Tyr Asp Ser Ser Gly Tyr Tyr His Tyr
                100                 105                 110

Lys Tyr Tyr Gly Met Ala Val Trp Gly Gln Gly Thr Thr Val Thr Val
            115                 120                 125

Ser Ser
    130

<210> SEQ ID NO 108
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Met Asp Met Arg Val Pro Ala Gln Leu Leu Gly Leu Leu Leu Leu Trp
1               5                   10                  15

Leu Arg Gly Ala Arg Cys Gln Ser Val Leu Thr Gln Pro Pro Ser Val
                20                  25                  30

Ser Ala Ala Pro Gly Gln Lys Val Thr Ile Ser Cys Ser Gly Ser Ser
            35                  40                  45

Ser Asn Ile Gly Asn Asn Tyr Val Ser Trp Tyr Gln Gln Leu Pro Gly
    50                  55                  60

Thr Ala Pro Lys Leu Leu Ile Tyr Asp Asn Asn Lys Arg Pro Ser Gly
65                  70                  75                  80

Ile Pro Asp Arg Phe Ser Gly Ser Lys Ser Gly Thr Ser Thr Thr Leu
                85                  90                  95

Gly Ile Thr Gly Leu Gln Thr Gly Asp Glu Ala Asp Tyr Tyr Cys Gly
            100                 105                 110

Thr Trp Asp Ser Arg Leu Ser Ala Val Val Phe Gly Gly Gly Thr Lys
        115                 120                 125

Leu Thr Val Leu Gly Gln Pro Lys Ala Asn Pro Thr Val Thr Leu Phe
    130                 135                 140

Pro Pro Ser Ser Glu Glu Leu Gln Ala Asn Lys Ala Thr Leu Val Cys
145                 150                 155                 160

Leu Ile Ser Asp Phe Tyr Pro Gly Ala Val Thr Val Ala Trp Lys Ala
                165                 170                 175

Asp Gly Ser Pro Val Lys Ala Gly Val Glu Thr Thr Lys Pro Ser Lys
            180                 185                 190

Gln Ser Asn Asn Lys Tyr Ala Ala Ser Ser Tyr Leu Ser Leu Thr Pro
        195                 200                 205

Glu Gln Trp Lys Ser His Arg Ser Tyr Ser Cys Gln Val Thr His Glu
    210                 215                 220

Gly Ser Thr Val Glu Lys Thr Val Ala Pro Thr Glu Cys Ser
225                 230                 235

<210> SEQ ID NO 109
<211> LENGTH: 478
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Met Asp Met Arg Val Pro Ala Gln Leu Leu Gly Leu Leu Leu Leu Trp
1               5                   10                  15

Leu Arg Gly Ala Arg Cys Gln Val Gln Leu Val Glu Ser Gly Gly Gly
            20                  25                  30

Val Val Gln Pro Gly Arg Ser Leu Arg Leu Ser Cys Ala Ala Ser Gly
        35                  40                  45

Phe Thr Phe Ser Ser Phe Gly Met His Trp Val Arg Gln Ala Pro Gly
    50                  55                  60

Lys Gly Leu Glu Trp Val Ala Val Ile Ser Phe Asp Gly Ser Ile Lys
65                  70                  75                  80

Tyr Ser Val Asp Ser Val Lys Gly Arg Phe Thr Ile Ser Arg Asp Asn
                85                  90                  95

Ser Lys Asn Thr Leu Phe Leu Gln Met Asn Ser Leu Arg Ala Glu Asp
            100                 105                 110

Thr Ala Val Tyr Tyr Cys Ala Arg Asp Arg Leu Asn Tyr Tyr Asp Ser
        115                 120                 125

Ser Gly Tyr Tyr His Tyr Lys Tyr Tyr Gly Met Ala Val Trp Gly Gln
    130                 135                 140

Gly Thr Thr Val Thr Val Ser Ser Ala Ser Thr Lys Gly Pro Ser Val
145                 150                 155                 160

Phe Pro Leu Ala Pro Cys Ser Arg Ser Thr Ser Glu Ser Thr Ala Ala
                165                 170                 175

Leu Gly Cys Leu Val Lys Asp Tyr Phe Pro Glu Pro Val Thr Val Ser
            180                 185                 190

Trp Asn Ser Gly Ala Leu Thr Ser Gly Val His Thr Phe Pro Ala Val
        195                 200                 205

Leu Gln Ser Ser Gly Leu Tyr Ser Leu Ser Ser Val Val Thr Val Pro
    210                 215                 220

Ser Ser Asn Phe Gly Thr Gln Thr Tyr Thr Cys Asn Val Asp His Lys
225                 230                 235                 240

Pro Ser Asn Thr Lys Val Asp Lys Thr Val Glu Arg Lys Cys Cys Val
                245                 250                 255

Glu Cys Pro Pro Cys Pro Ala Pro Pro Val Ala Gly Pro Ser Val Phe
            260                 265                 270

Leu Phe Pro Pro Lys Pro Lys Asp Thr Leu Met Ile Ser Arg Thr Pro
        275                 280                 285

Glu Val Thr Cys Val Val Val Asp Val Ser His Glu Asp Pro Glu Val
    290                 295                 300

Gln Phe Asn Trp Tyr Val Asp Gly Val Glu Val His Asn Ala Lys Thr
305                 310                 315                 320

Lys Pro Arg Glu Glu Gln Phe Asn Ser Thr Phe Arg Val Val Ser Val
                325                 330                 335

Leu Thr Val Val His Gln Asp Trp Leu Asn Gly Lys Glu Tyr Lys Cys
            340                 345                 350

Lys Val Ser Asn Lys Gly Leu Pro Ala Pro Ile Glu Lys Thr Ile Ser
        355                 360                 365

Lys Thr Lys Gly Gln Pro Arg Glu Pro Gln Val Tyr Thr Leu Pro Pro
    370                 375                 380

Ser Arg Glu Glu Met Thr Lys Asn Gln Val Ser Leu Thr Cys Leu Val
385                 390                 395                 400

```
Lys Gly Phe Tyr Pro Ser Asp Ile Ala Val Glu Trp Glu Ser Asn Gly
            405                 410                 415

Gln Pro Glu Asn Asn Tyr Lys Thr Thr Pro Pro Met Leu Asp Ser Asp
        420                 425                 430

Gly Ser Phe Phe Leu Tyr Ser Lys Leu Thr Val Asp Lys Ser Arg Trp
        435                 440                 445

Gln Gln Gly Asn Val Phe Ser Cys Ser Val Met His Glu Ala Leu His
    450                 455                 460

Asn His Tyr Thr Gln Lys Ser Leu Ser Leu Ser Pro Gly Lys
465                 470                 475
```